(12) United States Patent
Nolte et al.

(10) Patent No.: US 12,673,984 B2
(45) Date of Patent: Jul. 7, 2026

(54) VHH-CONTAINING HEAVY CHAIN ANTIBODY AND PRODUCTION THEREOF

(71) Applicant: Universitätsklinikum Hamburg-Eppendorf, Hamburg (DE)

(72) Inventors: Friedrich Nolte, Hamburg (DE); Thomas Eden, Hamburg (DE); Janusz Wesolowski, Hamburg (DE); Stephan Menzel, Hamburg (DE)

(73) Assignee: Universitätsklinikum Hamburg-Eppendorf, Hamburg (DE)

( * ) Notice: Subject to any disclaimer, the term of this patent is extended or adjusted under 35 U.S.C. 154(b) by 808 days.

(21) Appl. No.: 16/467,398

(22) PCT Filed: Dec. 8, 2017

(86) PCT No.: PCT/EP2017/082074
§ 371 (c)(1),
(2) Date: Jun. 6, 2019

(87) PCT Pub. No.: WO2018/104528
PCT Pub. Date: Jun. 14, 2018

(65) Prior Publication Data
US 2020/0062833 A1 Feb. 27, 2020

(30) Foreign Application Priority Data
Dec. 9, 2016 (EP) .................................... 16203240

(51) Int. Cl.
*C12N 15/00* (2006.01)
*A01K 67/0275* (2024.01)
(Continued)

(52) U.S. Cl.
CPC .......... *C07K 16/18* (2013.01); *A01K 67/0275* (2013.01); *A01K 67/0278* (2013.01);
(Continued)

(58) Field of Classification Search
CPC ........ C12N 15/00; C12N 15/09; C12N 15/63; C12N 15/8509; C12N 2015/8518;
(Continued)

(56) References Cited

FOREIGN PATENT DOCUMENTS

CN      105777894 A    7/2016
EP      1978032    * 10/2008
(Continued)

OTHER PUBLICATIONS

Janssens et al, PNAS 103(41): 15130-15135, 2006.*
(Continued)

*Primary Examiner* — Kevin K Hill
(74) *Attorney, Agent, or Firm* — Hovey Williams LLP; Crissa A. Cook

(57) ABSTRACT

The present invention contemplates isolated polynucleotide for the production of a VHH-containing heavy chain antibody in a mammal and vectors comprising said isolated polynucleotide. Moreover, the invention relates to a transgenic mammal comprising the vector for the production of a VHH-containing heavy chain antibody. Further, the invention relates to VHH-containing heavy chain antibodies as well as methods for the production and cloning of VHH-containing heavy chain antibodies.

6 Claims, 12 Drawing Sheets

Specification includes a Sequence Listing.

(51) Int. Cl.

| | | |
|---|---|---|
| *A01K 67/0278* | (2024.01) | |
| *C07K 16/00* | (2006.01) | |
| *C07K 16/18* | (2006.01) | |
| *C12N 15/63* | (2006.01) | |
| *C12N 15/64* | (2006.01) | |

(52) U.S. Cl.
CPC ........ *C12N 15/64* (2013.01); *A01K 2217/072* (2013.01); *A01K 2227/105* (2013.01); *A01K 2267/01* (2013.01); *C07K 2317/22* (2013.01); *C07K 2317/569* (2013.01); *C12N 2800/204* (2013.01); *C12N 2800/24* (2013.01); *C12N 2800/90* (2013.01)

(58) Field of Classification Search
CPC .......... C12N 2800/204; A01K 67/0275; A01K 2267/01; C07K 16/00; C07K 2317/22
See application file for complete search history.

(56) References Cited

FOREIGN PATENT DOCUMENTS

| WO | 2002085944 A2 | 10/2002 |
|---|---|---|
| WO | 2002085945 A2 | 10/2002 |
| WO | WO 02/085945 | * 10/2002 |
| WO | 2007096779 A2 | 8/2007 |

OTHER PUBLICATIONS

GenBank AM773729.1, Lama pacos, germline IgH gene, 2008.*

Janssens et al. Generation of heavy-chain-only antibodies in mice, PNAS 103(41): 15130-15135, 2006.*

Achur et al, Tetrameric and Homodimeric Camelid IgGs Originate from the Same IgH Locus, J. Immunol. 181: 2001-2009, 2008.*

Zou et al, Expression of a Dromedary Heavy Chain-Only Antibody and B Cell Development in the Mouse, J. Immunol. 175: 3769-3779, 2005.*

Murphy et al, Mice with megabase humanization of their immunoglobulin genes generate antibodies as efficiently as normal mice, PNAS 111(14): 5153-5158, 2014.*

GenBank CAQ53179.1, Lama pacos IgM heavy chain variable region, 2008.*

GenBank 4KRPB, Lama glama VHH nanobody 9g8, 2013.*

Klein et al, Germinal centres: role in B-cell physiology and malignancy, Nature Reviews 8: 22-33, 2008.*

Van der Linden et al, Induction of immune responses and molecular cloning of the heavy chain antibody repertoire of Lama glama, J. Immunol. Methods 240: 185-195, 2000.* www.calculator.net/exponent-calculator; last visited May 7, 2025.*

Janssens, R., et al., "Generation of heavy-chain-only antibodies in mice," The National Academy of Sciences, vol. 103, No. 41, Oct. 10, 2006, pp. 15130-15135.

Achour, I., et al., "Tetrameric and Homodimeric Camelid IgCs Originate from the Same IgH Locus," Journal of Immunology, 2008. vol. 181, pp. 2001-2009.

Bolotin DA, et al. MiXCR: software for comprehensive adaptive immunity profiling. Nat Methods. 2015;12(5):380-381.

Gu et al. "Independent control of immunoglobulin switch recombination at individual switch regions evidenced through Cre-loxP-mediated gene targeting" Cell 73(6):1155-1164 (1993).

International Searching Authority. International Search Report and Written Opinion for application PCT/EP2017/082074. Mailed on Mar. 29, 2018.

Ménoret et al. (2010) "Characterization of immunoglobulin heavy chain knockout rats" Eur. J. Immunol 40: 2932-2941.

Parrish et al. (2011) "BAC modification through serial or simultaneous use of CRE/Lox technology" J Miomed Biotechnol 2011:924068.

Pinaud et al., (2001) "Localization of the 3' IgH locus elements that effect long-distance regulation of class switch recombination" Immunity 15:187-199.

Schirrmann et al. "Transient Production of scFv-Fc Fusion Proteins in Mammalian Cells" in Antibody Engineering vol. 2. (eds. R. Kontermann & S. Dubel) 387-398 (Springer-Verlag, Berlin Heidelberg; 2010).

Warming et al. "Simple and highly efficient BAC recombineering using galk selection." Nucleic Acids Res.33(4):e36 (2005).

Zhang et al. "Production of chimeric heavy-chain antibodies" Methods Mol Biol 525, 323-336 (2009).

Wesolowski, J. Klonierung des Lama glama (Linnaeus, 1758) Schwereketten-Antikörper-Genlokus und Herstellung von Konstrukten für Lama Antikörper produzierende transgene Mäuse. 2012. See p. 6 for English language abstract.

European Patent Office. Office Action for application 17829150.6. Mailed on Sep. 9, 2020.

Shugay M. et al., "VDJtools: Unifying Post-analysis of T Cell Receptor Repertoires," Nov. 25, 2015; PLoS Comput. Biol. 11(11):e1004503.

Teng, et al., "Diverse human VH antibody fragments with biotherapeutic properties from the Crescendo Mouse", New Biotechnology, 2020, 55, pp. 65-76.

Belanger, et al., "High-efficacy, high-manufacturability human VH domain antibody therapeutics from transgenic sources", Protein Engineering, Design and Selection, 2021, 34, 7 pages.

Drabek, et al., "Expression Cloning and Production of Human Heavy-Chain-Only Antibodies from Murine Transgenic Plasma Cells," Frontiers in Immunology, Dec. 19, 2016, 7:619, pp. 1-10. doi: 10.3389/fimmu.2016.00619.

* cited by examiner

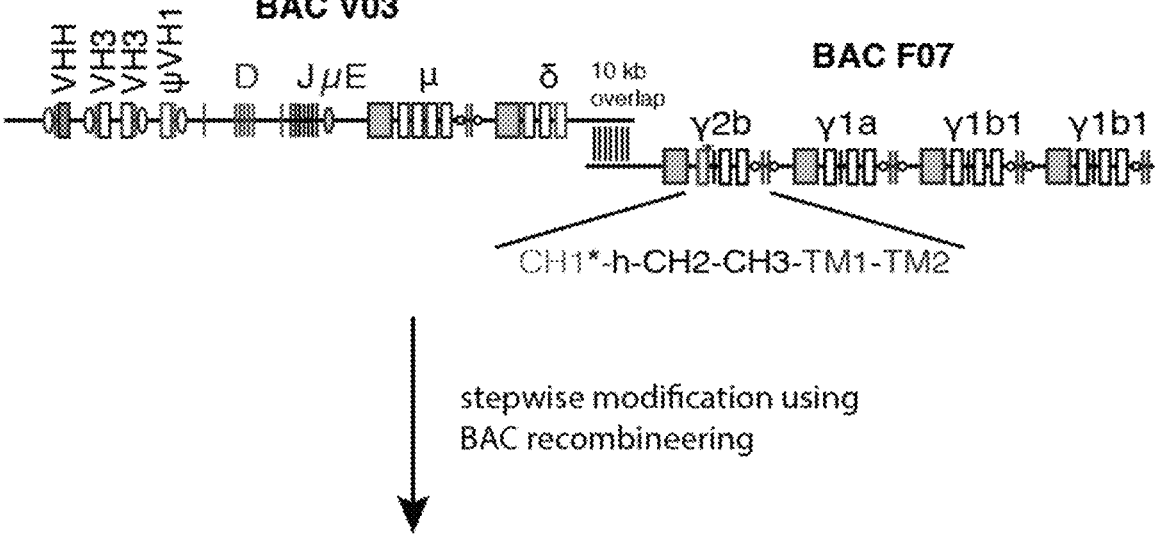
Fig. 1

A   Llama IgH transgene TE-01
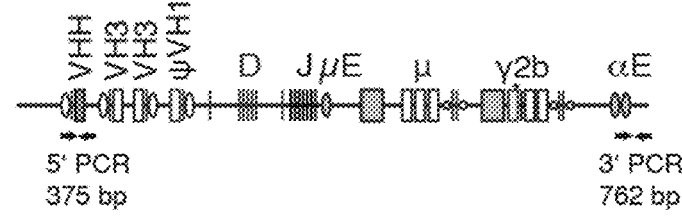
B
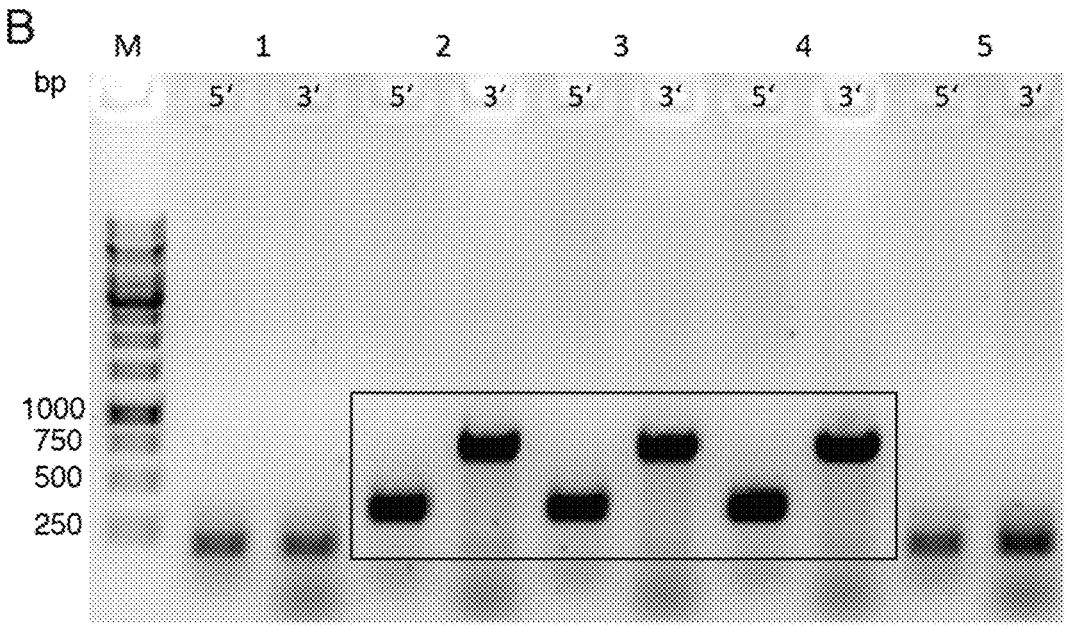
Fig. 2

Fig. 5

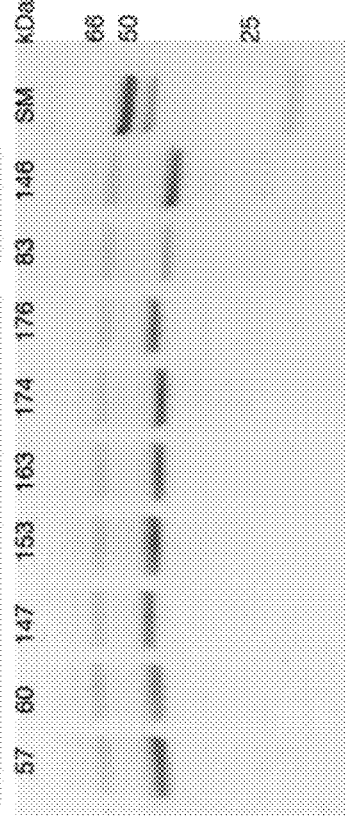
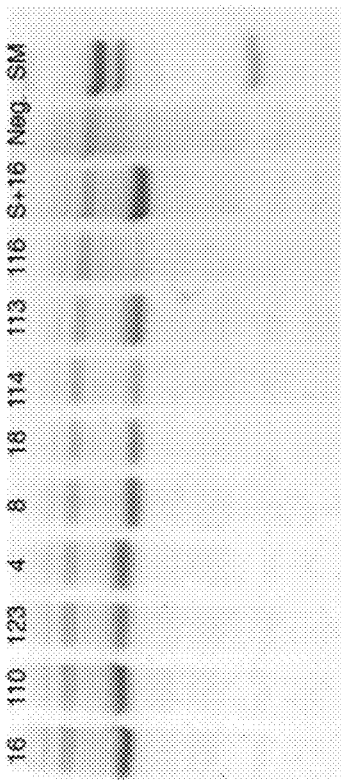
Fig. 8

VHH - D3 - J4

```
          10        20*       30        40        50 a      60        70        80 abc     90*
10-01  GLVQAGGSLRLSCAASGRTFSSYAMGWFRQAPGKEREFVASISWNGGSTIYADSVKGRFTISRDNAKNTVYLQMNSLKPEDTAVYYCAADSTNWVFYDYWGQGTQ
10-02  GLVQAGGSLRLSCAASGRTFSSYAMGWFRQAPGKEREFVASISWNGGSTIYADSVKGRFTISRDNAKNTVYLQMNSLKPEDTAVYYCAADSTNWVFYDYWGQGTQ
10-03  GLVQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-04  GLVQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-05  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-06  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-07  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-08  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-09  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-10  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-11  GLKQAGGSLRLSCAASGRTFSSYAMWFRQAPGKEREFVASISWNGGSTIYADSVKGRFTISRDNAKNTVYLQMNSLKPEDTAVYYCAADSTNWVFYDYWGQGTQ
10-12  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-13  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-14  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-15  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-16  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-17  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-18  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-19  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-20  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-21  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ
10-22  GLKQAGGSLRLSCAASGRTFSSYAMWFRQAPGKEREFVASISWNGGSTIYADSVKGRFTISRDNAKNTVYLQMNSLKPEDTAVYYCAADSTKWVFYDYWGQGTQ

*      ><CDR1><   FR2    >< CDR2 ><         FR3            *  >< CDR3 >< FR4
       FR1
```

Fig. 10

SEQUENCE LISTING

```
<160> NUMBER OF SEQ ID NOS: 105

<210> SEQ ID NO 1
<211> LENGTH: 47
<212> TYPE: DNA
<213> ORGANISM: Lama glama

<400> SEQUENCE: 1
cttcccccat tgctggggca cctgggcacc tgggcaccgt gtcctca                    47

<210> SEQ ID NO 2
<211> LENGTH: 53
<212> TYPE: DNA
<213> ORGANISM: Lama glama

<400> SEQUENCE: 2
gctacaggta tctcgaagtt tggggccagg gcaccctggt cactgtctcc tca            53

<210> SEQ ID NO 3
<211> LENGTH: 49
<212> TYPE: DNA
<213> ORGANISM: Lama glama

<400> SEQUENCE: 3
caatgctttg gacgcatggg gccaggggac cctggtcact gtctcctca                 49

<210> SEQ ID NO 4
<211> LENGTH: 47
<212> TYPE: DNA
<213> ORGANISM: Lama glama

<400> SEQUENCE: 4
atgagtatga ctactggggc caggggaccc aggtcaccgt ctcctca                   47
```

-continued

<210> SEQ ID NO 5
<211> LENGTH: 47
<212> TYPE: DNA
<213> ORGANISM: Lama glama

<400> SEQUENCE: 5 accccccagtt tgaatactgg ggccagggca ccctggtcac tgtctca                47

<210> SEQ ID NO 6
<211> LENGTH: 59
<212> TYPE: DNA
<213> ORGANISM: Lama glama

<400> SEQUENCE: 6
ctgactttgg ttcctggggc caggggaccc aggtcaccgt ctcctcgggt gagtcctca      59

<210> SEQ ID NO 7
<211> LENGTH: 53
<212> TYPE: DNA
<213> ORGANISM: Lama glama

<400> SEQUENCE: 7
attactacgg catggactac tggggcaaag ggaccctggt caccgtctcc tca            53

<210> SEQ ID NO 8
<211> LENGTH: 29
<212> TYPE: DNA
<213> ORGANISM: Lama glama

<400> SEQUENCE: 8
tattgcgctt attggcttgg agatgctgg                                       29

<210> SEQ ID NO 9
<211> LENGTH: 30
<212> TYPE: DNA
<213> ORGANISM: Lama glama

<400> SEQUENCE: 9
acatactata gtggtagtta ctactacacc                                      30

<210> SEQ ID NO 10
<211> LENGTH: 34
<212> TYPE: DNA
<213> ORGANISM: Lama glama

<400> SEQUENCE: 10
gtattactac tgctcaggct atgggtgtta tgac                                 34

<210> SEQ ID NO 11
<211> LENGTH: 19
<212> TYPE: DNA
<213> ORGANISM: Lama glama

<400> SEQUENCE: 11
ttactatagc gactatgac                                                  19

<210> SEQ ID NO 12
<211> LENGTH: 19
<212> TYPE: DNA
<213> ORGANISM: Lama glama

<400> SEQUENCE: 12
agactacggg ttggggtac                                                  19

-continued

```
<210> SEQ ID NO 13
<211> LENGTH: 19
<212> TYPE: DNA
<213> ORGANISM: Lama glama

<400> SEQUENCE: 13
gtacggtagt agctggtac                                                    19

<210> SEQ ID NO 14
<211> LENGTH: 11
<212> TYPE: DNA
<213> ORGANISM: Lama glama

<400> SEQUENCE: 14
ctaactggag c                                                            11

<210> SEQ ID NO 15
<211> LENGTH: 307
<212> TYPE: DNA
<213> ORGANISM: Lama glama

<400> SEQUENCE: 15
gtgtccaggc tcaggtgcag ctggtagagt ctggggagg attggtgcag gctgggggct        60
ctctgagact ctcctgtgca gcctctggac gcaccttcag tagctatgcc atgggctggt      120
tccgccaggc tccagggaag gagcgtgagt ttgtagcagc tattagctgg agtggtggta      180
gcacatacta tgcagactcc gtgaagggcc gattcaccat ctccagagac aacgccaaga      240
acacggtgta tctgcaaatg aacagcctga aacctgagga cacggccgtt tattactgtg      300
cagcaga                                                                307

<210> SEQ ID NO 16
<211> LENGTH: 304
<212> TYPE: DNA
<213> ORGANISM: Lama glama

<400> SEQUENCE: 16
gtgtccaggc tcaggtgcag ctggtggagt ctgggggagg cttggtgcag cctggggggt       60
ctctgagact ctcctgtgca gcctctggaa gcatcttcag tatcaatgcc atgggctggt      120
accgccaggc tccagggaag cagcgcgagt tggtcgcagc tattactagt ggtggtagca      180
caaactatgc agactccgtg aagggccgat tcaccatctc cagagacaac gccaagaaca      240
cggtgtatct gcaaatgaac agcctgaaac tgaggacac ggccgtctat tactgtaatg       300
caga                                                                   304

<210> SEQ ID NO 17
<211> LENGTH: 304
<212> TYPE: DNA
<213> ORGANISM: Lama glama

<400> SEQUENCE: 17
gtgtccaggc tcaggtgcag ctggtggagt ctgtgggagg cttggtgcag gatggggggt       60
ctctgagact ctcctgtgca gcctctggac gcacattcag tagatctgcc atgaggtggt      120
tccgccaggc tccagggaag gagcgcgagt gggtctcatg tattagtagt agtgatggta      180
gcacaaacta tgcagactcc gtgaaggccc gattcaccat ctccagagac aacgccaaga      240
acacgctgta tctgcaaatg aacagcctaa aacctgagga cacggccgtg tattactgtg      300
cgca                                                                   304
```

```
<210> SEQ ID NO 18
<211> LENGTH: 296
<212> TYPE: DNA
<213> ORGANISM: Artificial Sequence
<220> FEATURE:
<223> OTHER INFORMATION: Synthetic- VHH element

<400> SEQUENCE: 18
caggtgcagc tggtggaatc tggcggagga ctggtgcagc ctggcggctc tctgagactg      60
tcttgtgccg ccagcggcag aaccttcagc agctacgcta tgggctggtt cagacaggcc     120
cctggcaagg gcctggaagc cgtggctgct atctcttgga tcggcggcag cacctactac     180
gccgacagcg tgaagggcag attcaccatc agcagagaca acagcaagaa caccctgtac     240
ctgcagatga acagcctgag agccgaggac accgccgtgt actactgcgc agcaga         296

<210> SEQ ID NO 19
<211> LENGTH: 304
<212> TYPE: DNA
<213> ORGANISM: Lama glama

<400> SEQUENCE: 19
gtgtccaggc tcaggtgcag ctggtggagt ctgggggagg cttggtgcag gctgggggct      60
ctctgagaca ctcctgtgca gcctctggac tcaccttcgg tagctatgcc atgggctggt     120
accgccaggc tccagggaag gagcgcgagt tggtcgcagc tattagtagt ggtggtagca     180
catactatgc agactctgtg aagggccgat tcaccatctc cagagacaac gccaagaaca     240
cgctgtatct gcaaatgaac agcctgaaac tgaggacacg gccgtgtat tactgtgcaa      300 aaga                                                                  304

<210> SEQ ID NO 20
<211> LENGTH: 307
<212> TYPE: DNA
<213> ORGANISM: Lama glama

<400> SEQUENCE: 20
gtgtcctggc tcaggtgcag ctcgtggagt ctgggggagg cttggtgcag cctggggggt      60
ctctgagact ctcctgtgca gcctctggat tcactttgga ttattatgcc ataggctggt     120
tccgccaggc cccagggaag gagcgcgagg gggtctcatg tattagtagt agtgatggta     180
gcacatacta tgcagactcc gtgaagggcc gattcaccat ctccagagac aacgccaaga     240
acacggtgta tctgcaaatg aacagcctga aacctgagga cacggccgtt tattactgtg     300
cagcaga                                                               307

<210> SEQ ID NO 21
<211> LENGTH: 87
<212> TYPE: DNA
<213> ORGANISM: Lama glama

<400> SEQUENCE: 21
aacccaagac accaaaacca caaccacaac cacaaccaca accacaaccc aatcctacaa       60
cagaatccaa gtgtcccaaa tgtccag                                          87

<210> SEQ ID NO 22
<211> LENGTH: 330
<212> TYPE: DNA
<213> ORGANISM: Lama glama
```

-continued

```
<400> SEQUENCE: 22
cccctgagct cctgggaggg ccctcagtct tcatcttccc cccgaaaccc aaggacgtcc      60
tctccatttc tgggaggccc gaggtcacgt gcgttgtggt agacgtgggc caggaagacc     120
ccgaggtcag tttcaactgg tacattgatg gcgctgaggt gcgaacggcc aacacgaggc     180
caaaagagga acagttcaac agcacgtacc gcgtggtcag cgtcctgccc atccagcacc     240
aggactggct gacggggaag gaattcaagt gcaaggtcaa caacaaagct ctcccggccc     300
ccatcgagaa gaccatctcc aaggccaaag                                      330

<210> SEQ ID NO 23
<211> LENGTH: 326
<212> TYPE: DNA
<213> ORGANISM: Lama glama

<400> SEQUENCE: 23
ggcagacccg ggagccgcag gtgtacgccc tggccccaca ccgggaagag ctggccaagg      60
acaccgtgag cgtaacctgc ctggtcaaag gcttctaccc acctgatatc aacgttgagt     120
ggcagaggaa cggtcagccg gagtcagagg gcacctacgc caccacgcca ccccagctgg     180
acaacgacgg gacctacttc ctctacagca agctctcggt gggaaagaac acgtggcagc     240
ggggagaaac cttcacctgt gtggtgatgc acgaggccct gcacaaccac tacacccaga     300
aatccatcac ccagtcttcg ggtaaa                                          326

<210> SEQ ID NO 24
<211> LENGTH: 134
<212> TYPE: DNA
<213> ORGANISM: Lama glama

<400> SEQUENCE: 24
agccactcct ggaggaggag agctgtgccg aggcccagag cggggagctg gacgggctgt      60
ggaccaccat ctccatattc atcaccctct tcctgctcag cgtgtgctac agcgccacag     120
tgaccctctt caag                                                       134

<210> SEQ ID NO 25
<211> LENGTH: 81
<212> TYPE: DNA
<213> ORGANISM: Lama glama

<400> SEQUENCE: 25
gtgaagtgga tcttctcctc ggtgttggag ctgaagcaga cgatcgtccc agactacaga      60
aacatgatcg ggcagggggc c                                                81

<210> SEQ ID NO 26
<211> LENGTH: 333
<212> TYPE: DNA
<213> ORGANISM: Lama glama

<400> SEQUENCE: 26
tgattttaga tctgcccccc agcgtgacac tcttcatgcc cccccgagac ggcttctctg      60
gcacttccaa acgcacgtcc aagctcatct gtcaggccac agacttcagc cccagggaga     120
tctccgtgtc ctggtttcgt gagggcaagc ggctggtgtc tggcttcatt acggaagatg     180
tggaagcctc aaagtccaat ccagggacct tcagtgtcat cagcatgctg accatcaccg     240
acggcgactg gttcagccag gctgtgtaca cctgccaggt ggagcacaga gggatggtca     300
tcgagaagaa cgtgtcttcc cagtgcaacc cca                                   333
```

-continued

```
<210> SEQ ID NO 27
<211> LENGTH: 318
<212> TYPE: DNA
<213> ORGANISM: Lama glama

<400> SEQUENCE: 27
gtccttcccc cggcatcgag gtcttcgcca ttccccctc cttctccgac atcttcctca      60
acaagtcagc caagctcacc tgcctggtca caggcctggt cacctacgac agcctgagaa     120
tttcctggac ccgccagggt gaaaaggctg tggattccca gatcattgac tccacgatcc     180
tccccaacgg caccttcagc gccacgtgtg tggcgtcagt ctgcgtggag gactgggagt     240
caggagacag gttcacgtgc acggtgaccc acctggatct gccctcaccc ctgaagcgga     300
gcatcttcaa gcccacag                                                   318

<210> SEQ ID NO 28
<211> LENGTH: 398
<212> TYPE: DNA
<213> ORGANISM: Lama glama

<400> SEQUENCE: 28
aagtgcacaa gcacatgcct tccgtctacg tgctgccgcc ggcccgggag cagctgagcc      60
tgcgggagtc agcctccatc acctgcctgg tgaagggctt ctcccctccg gacgtgtttg     120
tgcagtggct gaagaagggg gagcaggagc ccctgtcccc tgacaactac gtgaccagtg     180
ccccagtgcc cgagcccaac agcccgggct actactttgt ccacagcgtc ctgacggtga     240
gcgagaagga ctggagtgcc ggggcgacct acacctgcgt cgtgggccat gaggccctgc     300
cccacttggt gaccgagagg accgtggaca agtccaccgg taaacccacc ctgtacaacg     360
tgtccctggt catgtccgac acggccagca cctgctac                             398

<210> SEQ ID NO 29
<211> LENGTH: 116
<212> TYPE: DNA
<213> ORGANISM: Lama glama

<400> SEQUENCE: 29 aggggggaggt gagcgcggat gaggaaggct tcgagaacct gaacaccatg gcctccacct      60
tcatcgtcct cttcctcctg agcctcttct acagcaccac cgtcaccctg ttcaag         116

<210> SEQ ID NO 30
<211> LENGTH: 137870
<212> TYPE: DNA
<213> ORGANISM: Artificial Sequence
<220> FEATURE:
<223> OTHER INFORMATION: T01 construct
<220> FEATURE:
<221> NAME/KEY: misc_feature
<222> LOCATION: (126799)..(126799)
<223> OTHER INFORMATION: n is a, c, g, or t

<400> SEQUENCE: 30
agcttcaata taaattttat ttaaataaag gagtacgagt ctcattttgg tctttgcagc      60
agccttggat acctggttca attctaagtg cagatggcaa catggggatt tatgccccaa     120
gagtgatgac gttgactggg tggaaaatga ctgtgaggag actacaaggt cagggggatt     180
ctgagcaggc tgtctccagg ggactcttga tacaggaggt cagggtggtc agatgttccc     240
tgaagatcat aggttagggg aattggatca aatattgagg gtgatcagat ttccaaggta     300
```

-continued

```
aggaatctca ctaacctgac tcagcaggtt tcctgataaa actgggacat gcagagatgg      360
acacagaatc ctgcaggccc agacctcggg gagaaaacca tctcaaggag cctgagtgat      420
gaatgttcag agggtcattg tcgcttccag agtcagggtt cttatcttca ctgacatgat      480
tctctgagag cagaaggttt aatccgaagg gacacggact ccttctggtc attcctcctc      540
ttggtggttc gtctcagctg tgagcacctc ctgggtctga ggaacactga cctctgtgga      600
tggtgctgtg aagtgagtgt gtctctgtgt ttccagtccc caggtgtcct gtcatgggtg      660
ctggtgtagg agttggtcaa agactattga agactctccc ccgcacctgc tctgtctctg      720
ggaccacccc atcacacaca gtggttactg tgggatctgt cacaccccag ggaaagcact      780
gggtaactca cctgctttgg gtgtacggtc tatgtctctt aaaaggcgcc tccatctcca      840
cagacatagt ggagatgagt tttccctgca gcgcagctct ggggtctccg agggcacagc      900
catgtgtcac tctcacagga gggagagtga gtgaggggag gccagtgtgg cccacatgaa      960
accagccctg cagggagggc tcaggccacc agggggcacc cagggtcatg aggaaacaag    1020
agggacagtt tcagagcagg tgcaggagaa gccatggggg gtttcctccc agagactgtg    1080
gatgctccac tggaccatca ccttccctgg gagcccaccc ataatgattc caggcaaaca    1140
tcttgtttct gaacttgagc ttttttcatg gagtcagaat tgtctgtctt cttttcctca    1200
tttgttgtag gaccagacac agaagaaaca tttcttcatg ggactttcgt ttgaaattta    1260
gtcactaccc acacttttag ttgtcaggtt tacagatact taatgacaca aatgaaactt    1320
ctgtggagcc tcgagtctgc cctccaccct caatgtattt ccagtcattt catcctcaag    1380
tgtgtcccca gtcctgtttc ctgcagtgcc tttccctaga aaagcacgag gaatgttgta    1440
tatttgggaa ttgatgtctg tgtgacactg gagtcattct gtcccccaga ggacacatgg    1500
aagtgtctag agccaggctg ggctgtcaca tgtggggtgg gctgcaggca cccagttacc    1560
tagtgggcag agtccttcaa tgtggccgtg catcccacac tgcacacggc agctcccaca    1620
aaaggaaatt agcctcagat gtcagtaatg cggaaaaact ctgagagaaa gctttgtatc    1680
tcatcaactt cataaaaatg tagacatgca gaaggtaaat ttctctatgt gaatcatcat    1740
caatgaatga aaagatgaac aaacaccaac cctgagtctt cagttcactc acaggcacct    1800
tacaccctat tcacccctgt gctggttgtg ggtcggaggg tcctgagcac agacctgcaa    1860
gggaagagga cagtggaaca gagagcctgc actggggagg ggccgtgtct ctgcttcacc    1920
tgagtcccca aacaagacag ggcaaggctg aacctggttg tgataatatt cactaaaatc    1980
caacctatat cagctatttt aggtttctac tttacattaa taattaatct caatattaac    2040
tgatatttaa catgcttgtc ttatatctag aatagttttg aatgtaattt ttcaattctt    2100
gctaatatat ccaaacatgc catttgtgtc acagacacat ggtgacagaa acagcaagac    2160
cttcaccagc atccacacac cctcccacag gggctcacag ctagtctgca aatcccctca    2220
cctcctgcaa gctagacacg gcccccttgct gtctcccaca cagggttgct ggtaggaatg    2280
tctgtgaagg taggaacaca tgtgcatccc agtgacctgc tcagaaaatt gcaagatata    2340
aaaagtaaat aaaataaata aaataaaaag tgttacggga agtaaagatt gttaacataa    2400
ataaatgacc acttacttca aaggcaaaac tgggtttatt tgggaacaac agagaattac    2460
agtttggggt ctgccgtcct ggtgagccac atgcaagtcc ccagtgaaaa cagagacatg    2520
actcttttac agaatgaaag gggaggtgag agggctcctg tgaacaggag ttcatggatt    2580
ttcattggct gagtccttac caggaaagaa gaggaggcct tgcttctccc tgtttgggctc    2640 agacatgaag ttcccagctt acaagatgga agcctcagtc ctcctgcctg agagccactg    2700
```

-continued

```
tgaaaaggct gcttagaggg gcttcgcgta ggtgatcagg agtcaagagg tggtcactcc      2760
gtgtgacgca gtcacgaggg acttcattgc tgacgaaggg gagaagcgta gatgtgctga      2820
ggttgagaca acaaagcaca gctctgtgag gaccagggag caaaagggca gcatgttagg      2880
aagggaggca tctgactgag acatgttgac tgtgatgcgt ggacctgaac aaagggtcag      2940
aggccgtgag gaccccaaga cagtgggagt ctccctgtgc cacagcatcc ggctcacggc      3000
tataaaaccc tagaggtctg cggaggcccc tgtgaatttg gtcaacacct caagacagcc      3060
ccttgctttc ataccaaacg gagaaagggg tctggtaatc aggttgccca caaaaggacg      3120
ggctcttcaa acgctccttt aaggacttga atctgtgtct tctggttcct cccttaaaat      3180
ggagtcggga ttgccagtgt tgagaaaact tcatctaggt tttccttgag agagaagtgt      3240
tgaatccgtc tcagcagtaa tcagctagct gtccacagtc cctcacattt ggcaattagt      3300
gttgcattta ggaagcagaa aaacaccatg gatgtacgta gaaccttgtt ctgacgtcag      3360
atgccctaga catcaaatat gatgctggga aactgcacat tttctgtagc cacatttagt      3420
cccttagagg ctaaatgttt gtaacgagtg aattctgtct tcctgcaaga ttgtttgaga      3480
agatgagcaa agaggcaaat tatccacata ttgcagccca gcagaaacac tagaaacttt      3540
gcatcatcca gaccagcctt ccagtggctc cagaaatgag aagggctctc aatgtcctag      3600
tgagctttac tcttcccact gaaggttaaa aggtaacggc ttcctccatc ggctggagga      3660
gtaaccaggg cacagtggac accagttaca gtaaaggcct cacttccagt gggagtggat      3720
gttagcacca caggagggtt agggacgaca gggtgataag gattaaagtg cactttacta      3780
ttgttattat ctttgcaatt attttgcttt ttattgaagt gtgtttgatt tacaatgtta      3840
gtttttggtg catagcaaac agattcagtt atgcatatac atatatattt tttcagactt      3900
tttcccacga tatgatatta taagacatgg aacacagttc cctgcactat acagcagctc      3960 tttgtttttat atctgtgtta cataaggtca tgtgtatctg tgaatcccaa actcttaatt      4020
tatccctccc ctgccctatg cactttggtg aacatagttt gttttcaacg tccgtgagtc      4080
tacttttgtc ttgtgagtaa aatctttttt catttttttaa ttccacgtat cagtgagatc      4140
atgggataag tgttctgcta tttgacttaa ctcacttaat atgattgtgt ttttatccat      4200
ctgtgttgct gccgatggca ttatttaacc cttttttaaac tacacgtgga acacatacgt      4260
gatgaagtat tgctcagcca tatttcaatg cagtttgcta atctgaggtc tggacaccac      4320
tccccccttg gcatagggt tttctctcca ggaaaacaag agtatcagaa acacctacaa      4380
gggccagtga agccttcagc cttggaatct gctcttctgg gcttcatggc ctgaagggct      4440
tcctcccttg caggacattg attaatcctg ggatggtgtt aaattctgtt ttaattttga      4500
aggaggctgc actctgaagt ttgccaaaat gttttgggga ttttgcccga aaagggtgg      4560 taactaacta agtaggaaaa atggtcgctg cttctacaat tagctgtagt atcatcagag      4620
acaaaacaag taaagtgtc tcaggccac ttaattaatt tcacacatac tttgatggct      4680
gctctaacat gccggaatca tttcccctt tggggagac agaaactata gcaggatgct      4740
ccactgtgaa gtctcattca gtaaacagat aggagttgaa taagtaagga gtaaatggtg      4800
tacatcgctc aaagggccta aataaaaggg ggaggtccag aggcagagac ccctggaggc      4860
tcatcacagg tccccactgg gtgagctgct gtagttccct gagcctgggc tgccttcagt      4920
agctcgggtg agcagggaga gtccggctcc agtgcccaat atgactgggg gagacacact      4980
tccaatctgg agaaatgctt gtccaagcct attgagagaa aagactgaca agagcccagc      5040
```

-continued

```
tattccctca gagcctgtca ctgggatcag gaggatgtga gaaggctggt ctgagggctg   5100
atggtgcctg aagtgcacac gtttgtgaca atctctgtcc cggtgtcctg gctgttggga   5160
aacaatagca gaaactaagg gggtttggtt tgtattctgg ggttttattt gctggaattc   5220
aagtttaaga atttaaacat tcttccttca ggtgactctc ctgtagtgtg agagacatgg   5280
tttgtcagct taaggaaacc tggagaggac acggtttcca ccctgttcct ctgtgaatag   5340
aatggaaagg ccctgaagga gccaggctga aggctgctca gcacaggccc agcagaacag   5400
cccctattcc cacgggctgt gaagaagacc agccaatgcc tctggaacaa tctgacatca   5460
aactcagact gaatgccaag taagaccttg catacagtac acggtctcac ctacgaagga   5520
caaaccttac aatagttctc agacaaagcc tgcagagctt cctactgcac agatgtggaa   5580
ggtgggctcc aggagaatga tttagactca aactccaggg tagttgagaa acacagggtg   5640
cagccatggg cccagtgtgg gtcccacacc tgtttgctca tcagacccac actcatacgg   5700
ggtcttgtct gattccataa gggccttgaa actgttgacc tgaaacaaag agatggccag   5760
ttatttctcc agcaaaaaga agtgtttcca tctgggatca acaacaattt gcgttcaggg   5820
cctggaatga cagttagcca cctgcagctc ctagcataca cggggataag aacttttttg   5880
cagatgggaa tggatgttgg aggaggggtt gtagtgaaca aggcacccag ggcttctcac   5940
tggctgatat gtgaccaccc ctcactgcct gagtccttgc caggagggaa cagggcgtct   6000
ttcttcttca cacagctgga ctcgtctatc ctggtaggac atgagagccc accgtgctgt   6060
caccaaactc tatttaactg aggtttctct gtactcagaa ttattgttat ttttcccact   6120
ttgggagatt ggatcatttt tgtttcagaa gccaggatac cctagtcagg caatgctggg   6180
tttatgagtt caacttcatg gtgaaataaa agtgaatcat gtggatgaca aaaaatgact   6240
tcacttatta gagacactca ttggtaggaa actccagagc agatctggat tatgcaggtt   6300
tttgtattta agcctggaga tgtagcacag atcagactgt gtctaaaccc agaaccgaga   6360
gagaaattgt gctgttccca gcatattcag atattaagaa caaagagcta tatgcacatg   6420
agactgtgtt atcaagacgt ctccccatga ctgaagaata agggataaag aatgtgataa   6480
ttttctaata taaagagaat atagaaacaa accaaaattc tgctgatggc acaaaaatat   6540
tggagccccc aacgtggaaa actgctactt tcttacaagg tttaggacca actcaccatg   6600
aaaccagcca tttcaatact aggtgtatct ctaggtgaat ttcaagctca cgttcactga   6660
aaacactgtg tgcaggtgct cgtggggcct tcacacatgc tgtaaagtgg aaacaagggc   6720
taaacccaga gctcagtgca gggccgtgta ctgatggcgt ctgaggtact aagtcctgca   6780
ttgtagccct tgtcatggga tccaagaaaa cagagtcact cagtcaacac tggaaaatac   6840
aggtcctcca tgtttcctca gatgccagca gtttcctgtc ccaggattat gtcttgtgtg   6900
tgtgtaagac aatactttga cagaggaggg tttggatgca gatatgatac aagagtgtgg   6960
gtctctgcat atgtgcatgt gcacctgtgt gtccacgtgt gtgtgcatgt ccctgcagac   7020
agacgggagc cctggttaca tgtgtgatga tagctttctg gacttccatc atccttctga   7080
atttggaaaa tatcagctaa ttttctttat caaaatcacc caattctata aagaaatatc   7140
taatgggatt atttattaaa atcaatgtct tccccatcat caatggaatc tatacccagg   7200
attctgactt ccctgcggct gagggctcag tgccagtttc atcacccact tcccccctgg   7260
tcatgctttc ctacttctgg cagctaagac cctcgcctgt atggatgagt ctagaccaga   7320
atccttcagt tgctgcaggt ctgtggtcag aggacagcac agctgggtgg ggagtgcttg   7380
tggtgcaaga agcagtttga aataatgagc ctgaatcagg atgggaatga ccctcagtct   7440
```

-continued

```
tcacacctgg cagttcacac tctgaagttt aacacctggg attttgcagt tcatccaaga    7500
gttccagttg gacctttttcc cagctctcat cccacctgga gacgtcaaat tcaggtacag    7560
tgaggcttgg tcacatttcc cacgtcacat agtgtttcta tcccgctatg tgaagatttc    7620
aacctgcaac actgaggtga gatttatacc acattacaca gattataact tacataaaaa    7680
taaaatgaca aagtatataa caagcattta ttacagcaca atcacaagta aagagatttt    7740
cttgaatgca attatttata gaaagacatt aaaatattga cactgttaaa aaaaattctc    7800
aagaacactg cttacatact actggtaaac acagtaacac tcaaaatcat catgatctca    7860
tcaccgaacg gggtctggga aacctgacca atcttgtcca aaactctctt gatgctgact    7920
ctgcatcact tatgtccaag aggaggagca caggtgaaaa tgctggacaa actctcacct    7980
aacatgtgtc cctgctcaga ccacatgcgc tccccatctg ggggctgcgt acatcaccaa    8040
cgtgggagga actctggcac caacatcaca gaatcggtgt gccattgtaa aaaataattc    8100
aggttttaag ggtttaccct gaaatctcac acaataaaca tgatgtttcc aaatgctacc    8160
aacaccagca aaccacagac actcacagct gctcaggggc ctagccctct ctgaggccag    8220
caaggccccg acttttttata tagtgagatg acatgcaaat agggcctccc tctgaggata    8280
aagccaccca gccctggccc tacagctctg ggagaggagg cccagcccag gattcccagc    8340
tgctcccgtt ctctgatcag gactgagcac agacgactca ccatggagct ggggctgagc    8400
tgggtggtcc tggctgctct actacaaggt aattcatgga gaacaagagc tactgaggat    8460
gtgggtggtt gtgagtgagg gaatcaggac gtgtgacagt ctcctgacca ggatgtcttt    8520
gtgtttgcag gtgtccaggc tcaggtgcag ctggtagagt ctgggggagg attggtgcag    8580 gctggggggct ctctgagact ctcctgtgca gcctctggac gcaccttcag tagctatgcc    8640
atgggctggt tccgccaggc tccagggaag gagcgtgagt ttgtagcagc tattagctgg    8700
agtggtggta gcacatacta tgcagactcc gtgaagggcc gattcaccat ctccagagac    8760
aacgccaaga acacggtgta tctgcaaatg aacagcctga acctgagga cacggccgtt    8820 tattactgtg cagcagacac agtgagggga agtcattgtg ggcccagaca aaaaccttgc    8880
tccctggggc acccacagac cccagggggt gctcacgacc caccaagggc agggctgagc    8940
cccagagcag ttgcagaggt gtgggaggag attgcagtta gaatccttgg tttccttttc    9000
ccgcccatca actctactac agaccctctg ctggattcta aattttcatt gttgaggtat    9060
gtgttgctgt ctgacaataa tatttgtaat caggatgtat ttttacaact gaaaaaaagc    9120
tccaaacaat gataaactgt agtataattt taaaggtgac tcagaaattt tcaaacctga    9180
cgaataccct gagaaggcac aggcaccgat aaaacacgtg taaacagtta cacatctttg    9240
tctctgctcc cggggcagga ggctgcacac cctgcatctt tctgccaaag gcacacagg    9300 gtttgcagtg agcaggatgc acgtcacaga cgccagctcc agactgccca ggactgcgtg    9360
tgcagggatc atcattgctc acggagtccg ggctctacag atcacatctg ggcaaaattt    9420
gtttccagcc tcaaaagaaa aatgttgcat tttctgaact cctggacatt tacaacgtgg    9480
gcagcacttt gaatccccaa cactcgaaca ttcccacctg aggtcggtcg gggtgatgct    9540
ctgccctctt gtttcaagtc ccatcacgta aatgagtctc cttccaggtc cagttagtgc    9600 catgttttttg acactttctg ggatatgtag gaaattttcc tgtttaaatt ggcccatgtg    9660
cagtcctgaa gtgcggtcca gtgtccctga gcacaaagtg ctgtgagctg acttaaggag    9720
aaaatatctg ttgcagacaa gctccattca ggcatgaact atactgatgg gggctgtgag    9780
```

```
cttgatgata ctgtttaaaa aataaacatt atttttctaa atgtaataga tatctcactt   9840
tgggtatttg tgtcagcctt aaaaccttgg ctcaattcca aacacagacg gtaaaatgga   9900
gatttatggc caagaagatg gcactgctga ccgggtggaa aacctctgtg aggagacttc   9960
aaggtcgggg gattctgggc agattgtctc cagaggattc gtggtgcagg aggcgggggt  10020
ggttaaaaat tccctggggg gtgataggtg tagtgaattg gatcacatat tgagggtgat  10080
cagagttcca ggtgaggatt cccactaaca cgactcagca ggtttcttga taagactggg  10140
acatgcagag atggacgcag aatcccgcag gcccagaact aactgaggaa agcatttcaa  10200
ggaacttcac tggtgtgtgg tcaaacggtc agtgtcagct tcagagtcag ggttcttatc  10260
ttcactgaca cgattctctg agagccgaaa actaaatccg aagaacatga aacctctggg  10320
cattcctcct cctgatggca ctgccacctt tcagaagaag aaatcagatg cacagaagca  10380
tcatggatgc acagacacgg gaggaaagtg catctgaggc tcagtgagga cggggcccct  10440
gcgagcaaag gagaaaggcc tcagaagaac ccgaacctct gggcaccttg atcttggact  10500
tccggcctcc agatctgaga gaaatgcatt tctgctgttt gagctgccca gtctgttatc  10560
tgtaacggga cctctaccca agtgatacac aaatgatgag cctttcaggt atacatggga  10620
aagtaagtgt cgtaccgcag aggaaaaatc acctgttctg cacagatgtc ctatgatcac  10680
ctccaagagt cacatgaact tctactgaaa aatggttttg gcctcacggg agtgggtaga  10740
atgatcctga acatattaat gtccagtatc tatcagtttt ggtgtaattt ggaaatcacg  10800
atataaaatg tactcaaatt gagaaccaac caaacctcag agcagcaagg aatggacgtc  10860
ttaaagtctg ttcatgattt ctaggggggtc tctgagtaac acactgtaga cacaggatgt  10920
gaggtgaaga attgaggaac agattaagaa attaacaaaa catgtgctgt tgaactgagt  10980
tcactacttt gtaataaatg ccaacacggt ggcaggaaat gtgcaaaaac tttggtgtga  11040
cgtacaggaa agagcacagc ttttgtttca caagcagctg agagtcagag cagagatgca  11100
gagcaggtga gcagggagca gaggggaccg ggggggctggg gggcacgaga ggaggaggga  11160
aagtaagccc tgctctgctt acggtcactc ccctgccctc cgactctcct tggactgaac  11220
tccctgctct gggaggagag cagctgtggt cagtgagcag aaggggggtc caccctggat  11280
ataagccagc accgcctccc aagcccagag acacggcctc acctggccct ctatgttcat  11340
gcggaaacac gaccccacgt gcatgcgaac cacacgcagg gctcagggcc atcacagcac  11400
ctgtgccacc cgggggccagg gtctcctctt cacttacgtc atcctctgag ggccaaaggc  11460
ttggctgaca aggacataaa ccccccctctg cactgcacca cacacagtgc cgtctggtgg  11520
gtctgggtcc atcctccccc agggagagcc cagcagaacc tggggtgctt gggtctggga  11580
gctggacagc atacaccctg cctccccccca aattcccccc catctccaga gacacactga  11640
aggccccgtg accctgtagc tcagctctgg ggtccctgag gaaacagccg tgtgcttttg  11700
tcactggaag gagagtgagt gaggggacat cagggtgacc cagacacaaa ggtccctgca  11760
gggagggctc aggccaccag gggtcaccca gggccgtgag gaaaccagag gacctggttc  11820
agagcaggtg cagaagcagc cgtggacgag ttccctccca taaaaagaag attctacgct  11880
ggctcaccgt gtcccctggg agcccatcca taatgtttcc agggaaactt tctgatctga  11940
acttgggcct ttttcacgga gtcaggcttg tctgtttat tcctcatcta acttaggaac  12000
agactcacag aaatatttct ccatgggact ttacttgata tttattcact aactatactt  12060
tctagtcatc aactttacag atacttaatg acaaaaacga ttcttctgtg catccttgag  12120
tttaccttcc acccttggtg tatttccagg catttcatcc tcgagagggt ccccaggcct  12180
```

```
ttttcctgca gtgcctttcc ctagaatagc atgaggaatg ctgtatactt ggaaaatgat   12240
gtctgtgaga cactggagtc attttgtccc ccagaggaca tgtggaaatg tctggggaca   12300
ggttgggctg tcacatgtgg ggtgggctgc aggcgtccag ttccctagtg ggcagagtcc   12360
ctcaaagctg ctcaacactc cacgatgcac acggcctctc ccacagcaag aaacagcctc   12420
aaatgtcaat aatgttgtaa agctgtgaca gaatgctgta catccaggca aattcatacc   12480
actgttgcca cgcagaagat gaatctgctt tatgtaagtt attctcacta aatgaaaaag   12540
acagacagac agacaccaga attagccttc ggttcactca gagtccccat tacacactat   12600
tcacacaggt ctctaggtct gtgggcagaa gggcccggag caggatccta taagcagacg   12660
gggcagcaga gcagggaccc agaactgggg aggggggccca tgcctctgtg tcagtgagtc   12720
cccagaaaca aaacacggcc caggctggac atcattgttt caacatttac aacttcctac   12780
ctgtaattgt atcaatctta atgtttgcag aattttacgt ctgaacaata atttattcta   12840
atattaacag attttttcaca tatggaacat gtcacaaatt attatttatt ttacatctac   12900
aataacattg cttgtaattg tggaacacta tcaatatata caagacacat gcgactgtat   12960
ccctgccccg ctgtggccca ccctgacaga aatcactaga ccttccccag cacccacatc   13020 ccctcccct caggagctac agctcacctt ctcctcccct caccccctgc aggctgctgg   13080
gggccacctt ctctcctctg agcatggatg tgaccaggaa tgtgtgtgga ggtgggagct   13140
cacgtccagc ccagtgacct cctcagcaaa ttacaagaaa attgaaagaa agtaagggag   13200
ataaaagtca acattctcat gggaagttag ctttttttga tgtaaaacaa ttagacgagc   13260
agttgtttca atagcgaaag tgggcttact ctggaccagt aaacagcttc agtatggggt   13320
ctgcaaccct gaagagccac atgtacatct ccagtaaaag gagaacgcct ccttcatcaa   13380
ggggggaagg gagctgagag agcctgaggg aaccagagac catgcatttc tctcggctga   13440
gtcctgccca ggaaagacgg ggaagccttg cttcccccag ctgggctctg aggccatcaa   13500
agggcatgag agctccccc gttcacccag ttttactaaa ctgagatttt cgttatattt   13560 tacctttgc catttgatca aggttgagat ctttctcgca aaacatcact gatgaagact   13620
taggatttct gggctttttc acgtttttgt ctgtcagtgc caggaaggaa ctcctctggg   13680
tgtaatgtct catgtcagat ggaaagcgct cttattgagg tcacattcca gtaacatgca   13740
ggagtaagag ggagagctcg caggctctct caccgtaagt ccctgtggta tcaacaccag   13800
aggctgcaga tcacctgaca cgttatattc tcatcagaga cttggcagga agttgtccaa   13860
taggtctggc acagatacct tgggaagctg tctcagcaga tgttgccctc aattctgaga   13920
cgtctccaca gtcgggtcac cagatgagca gcaatgtcca gggcccagct gccttcatag   13980
gtgtgtcacg tgaacccaag ttctaactct cgggagactg gtggcacaag ggctgcttag   14040
cagcacctgc tggagccctt tccattgagg ttgaggagtt cttctggaag tatctttcc   14100 tgtaggtaag atatccaggt tgcaaggtgt gacgcttgca tctctgtctc ctgagaggta   14160
ctgtgaagag acggcttctg aggagaatct tggagacgac caggaggcgg aaagtggtcc   14220
gtcagtgttc agcaatcatg agggacgtca gtggtggagc aggggagccg agaggcttca   14280
gtacaggttt tgctgttgag cgaatcatgc tgaggtcggg ccatatgaac aaatttggat   14340
gcaggtctcg gcagtgttca gatagctgag agagtctcac atttagcccg tagatcaggg   14400
tgttgataaa ccgagacccg atggagccca tccgcgtgga ggtacacctg gatttaagtg   14460
gagccctggt tctgatgtca ggcgtcctaa acattgagtc tgcatttggg taaactgcag   14520
```

-continued

```
ttttcctcaa gaaaacgatt gccactgaaa taataagaac tgtagcaagt ggtagatgtc   14580
ttccttcaag gaggattgag aaggagataa aggaaacaaa ttacccacaa actagaactt   14640
ccagaagatg ttgcatcatc caagccagcc tccaggctta cccagaatta gaggggctct   14700
caataaatcc ctggaacagt aatgacccgg taagtctaat gctccccatt gaaggcaaaa   14760
agggactggc cagctctagc aactgggatg ataaagaatg cagtacacta atcaattgca   14820
gtaaggaatt caggaacacg gggtggctgt tagccttgtg tgagtgttag cgacaacaca   14880
gtgctgctgc gtttactgtg cagtttcctg ccccgagggc ctgacgcggc tgcacccgtg   14940
gccccgaggt tgtctcctca ggaaaccgag gaaccacagg gacaagttca aggaatcatg   15000
acgccttgag ccttgcaacc ttctcttttg ggctctatgg cttgaaggat ttcttcactt   15060
gtaggatatt gattaatcct gggaagatgt ttccgagaat atatttgaac cttgaaggaa   15120
ggtgcactgt gaattttgca aacaccagtg tgaggctttg tcaacatgga aggtgacagc   15180
tgattcaatg ggagaaaaaa tcaattcctc cagaacttgc tttagtacca tcagagacag   15240
aatgaatgaa agtgctttca gttcatttca tttaatgtct tccatcaagc tctagaatga   15300
cttctctttg cagatacact aattctccca taatagttca ctgaacagtc ttaaccgtga   15360 aatgacaaa gctggaggaa tgaatgaatg aactgtgtgc atctctcaaa gggcctaaat   15420
acgaggggag gctcagggcg cagacctgtc gaggctcgtc acaggtcccc acgtgggaac   15480
tgctctagtt ccctgagccc gggctgctct cagccgttcc gctgagcagg gagagagcgg   15540
ctccttgacc gttaggacgg aaggaacctc atcatcaacc gcgaggaact tctgttgaga   15600
gaagggactg gggagactcc gtgtgttccc tcagagccac tggggaccag gaggacatca   15660
ggggggctgc tcagagggcg gacggtgccc gagtgcatgc agttacaaga gtctcttttt   15720
caaagtcctg gatcttggca ataatagcag aaccaggagg ggtttcggtt ttttctgcag   15780
ccttcattcg ctgtaaatga agtttaagaa tcagcatgtg tccttctagg tgtctcacct   15840
acactgtgac agagatggtt tgccacatta agaaaataag aggtggacac agtttcccat   15900
tccatcctgc acctctgccc tacaattgaa atgtcctgtg tcagcttgtt tgtaaactag   15960
gtttaaaagt ggcccaggtg gaatgaacat atgaagcaaa actgtaattt tcttttaaaa   16020
tgatttgcag ttgattgaaa taaacatgaa cagattcaac agattttcat gggaaacctg   16080
aatttttatt ccaaatgaaa gtgttgagaa agtctcagaa attgcccaat gaatttgcct   16140
agttgctgct agagaatttt tatataacaa gttcatggac tcttctcctg gctcaaattc   16200
taaacacctt ttaggattct cccagtaagc ggtttacaaa agtgctaggt gtgacttcaa   16260
caactgcagg accaggacga tgtaagtcag agaagccggg ctgaagactc tgaggggcca   16320
cattaaatta ctctgtgagg aacgttggtt tggaaaatct ttgactacag ttcagtttta   16380
gtccagaaaa aaagaaatga ggagatggtc ctctgggtcc tcatatggat gaagtttaag   16440
ataacaagac ctgacaagtt ggaggaatag aatatgggga gaatttcaga ggaagtggga   16500
agtttgtgga gacactgact gtggaagacc tgagggtaca ggggaggtgc aggagtaaga   16560
ggggagggag gcattggtgc tggagggaag cctgagacac acagcccagg gaaggggagc   16620
ccgggcttca gaggcccagg tttctttcct tagtccctgt ttgcctcgtt aatcttatga   16680
tcacgtttga ggacaggtaa cttaaggttc ctaaacatgt ttctaaggca cagaataatg   16740
agggaaatag gttttccatt aaattttgaa gatttgtcat atttcaccaa cttggtttta   16800
agaaaagtaa gtttgaggtt ttctaaagtc ccccataatg accattgaca tgtacattta   16860
atggaagcat gaatcgcctt tcgccaggtc tgtccatttc actacaaatt tccttaagggg  16920
```

-continued

```
aggaccctgg gtttaaaaca aaaactcagc tgtggttcct actgcagaag tgacctcaaa   16980
gcacttagat aacttggacc ccatttctca aggtgatttc tggagaataa aggaataatt   17040
tccaagcagc ctaaagggtc aaacagcgca aatagccagc agggctaaca ccagtcaggt   17100 ctaaagggatc agtctggttg tgaaggagcc aggctgaagg ctgctcagca caggctcagt   17160
agatcagccc ctattcccaa ggagtgggag gaaggccggc cacttccagc tggaacaacc   17220
tgatttcaaa ctcagactga atgccaaata agtacttgca tacagtacaa ggtcttacct   17280
atgaaggaca caccttacaa tagttctcag acaaagcctg cagagcttcc tactgcacag   17340
atgtggaagc tgggatccag gagaatgatt tagactcaaa ctccagggtc ggggagaatc   17400
acagggtgca gccatgggcc cagtgtgggt cccacacctg tttgctcagc agcctcacag   17460
tcatacgggg tcttatctga ttccatcagg gccgtgaaaa tgttgacctg aaacaaagag   17520
atggccagtt atttctccag cgaaaagaag tgttttcatc tgggatcaac aacgatttgc   17580
gttcagtgcc tggaatcaca gtgagccacc tgcagctcct agcatccacg gggataagac   17640
tcttttgcag acgggaatgg atgttggagg aggggctgta gtgaacaagg cacccagggc   17700
ttctcactgc ctgagctgtg accacccctc actgcctgag tccttgccag gagggatcag   17760
ggcatctttc tgcttctaaa agctggactc tgctctcctg gtaggacatg agagcccact   17820
gtgctgtcac caaactctat ttaactgagg tttctgtgta ttcagaatta ttgtgatttt   17880
tcctgctttt tgagattgga tcatttttgt ttcagaagcc aggataccct agtcaggcaa   17940
tgctgggttt atgagttcaa cttcatggtg aaatacaagt gaatcatgtg tataacaaaa   18000
aatgtcttca cgtattagag acactcattg gaaggaaact ccacaccaga tctggattat   18060
gcatgttttt gtatttaagc ctggagatgg agcagagatc agacagtggc taatctgaga   18120
atccagagag caattatgtt gttcccacat gttcagatgt tctgaacacg gagctacatg   18180
cagatgagac tgtgttatca agacccgtcc ccataactga agaatatggga taaggaatgt   18240 gataattttg taatataaag aggatattgg agcaaagcag aattctgctg atgggactaa   18300
aaactggagc cccgactaca aaaaagtgac aaacttttaca atttttagca tcaactcacc   18360
atgaaaccaa ctattccaat actacgtatc tgactgggtg aaattaaagc tctcgttcac   18420
tggaaacaca gtgtgcaggt gctcgtggag ccttcacaca tgctgtaaag tggaaacaag   18480
ggctaaaccc agagctcagt gcagggccgt gtgctgatgg cgtctgaggt actgttaagc   18540
cctgcattgc agcccttgtc gtgggatcca agaaaacaga gtcgctcatt cattactgga   18600
caatacgggt cctccatgtt tcctcagatg ccagcagttt cctgtcccag gattatgtct   18660
tgtgtgtgtg taagacaata ccttggacag aggagggttt ggatggagat atgatacaag   18720
agtgtgggtc cctgaatgta tgtgcatgtg cacctgtgtg tgcatgtgtg tgtgtgcatg   18780
tccctgcaca cagacgggag ccctggttac ttgtgtgatg atggatatgt ggacttccat   18840
catccttctg aattggaaca atatcagcta attttcttta tcaaaatcac ccaattctat   18900
aaagaaatgt ctaataggat tatttattca aatcaatgtc ttccccatct tcagtggaat   18960
ctatacccag gattctgaca ttaatattct cagaagcgtg tgaacctcgg tgcagcccag   19020
cccttctgag gacagtgctg caaagtcagg atgaagcctt ggattctgaa cccacatccc   19080
aagtctttct tggctcctga cagaacttcc ctgtggctga gggctcagtg cctgtttcat   19140
catccacctt ccctctcagtc gtgcttccct acttctggca gctaagaccc tcgcctgtat   19200
ggatgcgtct agaccagaat ccttcaggtg ctgcaggtct gcgatgtgag gacagcacag   19260
```

-continued

```
ctgggtgggg agtggttgtg gtgcaagaag cagtttgaaa tgatgagcct gaaaggggtg   19320
ggaatggccc tcagtcttca cacctggcag ttcacactct gaagtttaac acctgggata   19380
ttgcagttca tccacgaatt ccagttggac cttctcccag ctctcatgcc acctggagac   19440
gtcaaactca ggtagggtga ggcttggtca catttctcat atcacataaa ctttctattc   19500
cactatgtgt agatttcaat gtgcaacact gaggtgagat ttatagcaca ttgtgtagtt   19560
tgtaacttgc ataaaaataa aattacaaag tatataaaaa gtgttcatta cagcccaatc   19620
acaagtaaag aaattttctt gaatgttatt attgatagaa agacatcgat atgttagtga   19680
cttttgaaaa caatcctcat gaactctgct tacagattac tggtcaacac agtaactgtc   19740
aaaatcatca tgaactcatc accgaagggg gtcttgtcca aaactctctt gatgctgact   19800
ctgcatcact tatgtccaag aggaggagca caggtgaaaa tgctggacaa actctcacct   19860
aacatgtgtc cctacacaga ccacaatgcg gtacccgtct gggggctgcg tacatcacca   19920
acgagggacg aactctggca ccgacatcac agaatccatg tgcacacgta aaaaaaattc   19980
aggttctaag tgtttaccct gaaaactcac acaataaaca tgacatttcc aaatgctacc   20040
aacaccagca aaccacagac actcacagct gctcaggggc ctggccctct ctgaggccag   20100
caaggccctg acttgctatg tactgagatg acatgcaaat agggcctccc tctgaggata   20160
aagccaccca gccctggccc tgcagctgtg ggagaggagc cccagtccgg gattcccagc   20220
tgctcccgtt ctctgatcag gactgagcac agacgactca ccatggagct ggggctgagc   20280
tgggtggtcc tggttgctct tctacaaggt aattcatgga gaacaagagc tactgaggat   20340
gtgggtggtc gtgagtgagg gaatcagagg acgtgtgaca gtctcctgac caggatgtct   20400
ttgtgtttgc aggtgtccag gctgaggtgc agctggtgga gtctggggga ggcttggtgc   20460
agcctggggg gtctctgaga ctctcctgtg cagcctctgg attcactttt gatgattatg   20520
ccatgagctg ggtccgacag gctccaggga aggggctgga gtgggtctca gctattagct   20580
ggaatggtgg tagcacatac tatgcagaat ccatgaaggg ccgattcacc atctccagag   20640
acaacgccaa gaacacgctg tatctgcaaa tgaacagtct gaaatctgag gacacggccg   20700
tgtattactg tgcaaaagac acagtgaggg aaagtcggtg tgagcccaga cacaaacctc   20760
cctgcagggt cacagacggt gtgcagggtc acaggggaca cttaagaccc cccagggcac   20820
tcaggactcc ccagttgtgc ccttcagccc caggggcagg tgcaggaggc agctggtttc   20880
acggtttcct gtcaggctct ggagtttcct ctccacagtg caggaacccc tctggatccg   20940
agaatctggg cttgcacatt tagtctccca attagaaagt tttttctaa aaggaaaaac   21000 aacgtttaaa aaaaatcctc tcctgcacaa gaggcagagt ttctcttgca tttatgtact   21060
catgttggcc cctgtccaaa tcgggtcaac gtggagcact gtaaaaccat catggtggat   21120
ttacggacag ttagacacac tctaccctcc cctgtgaact ctcagcccca ccctactgat   21180 ggggcacgt gtccctgcca ggtggggggct ccttgctgac gtcctccatg agaagcccgg   21240
tgaggctggc agcccccag gaccacgagc gggtcacagg gaacgaggcc agtgagaggg   21300
aatgggtggg gccatggcca cgtgggctcc tcctccaggt ccagagaatc cctgcagaac   21360
agaggctcct gctccctgtt ccctgtgcag gtcacgttgg gtcacgagct cattgatcaa   21420
ttatcaccga tgaacgcaca gataattggg agggagctgt tacagacagg tgggcactga   21480
cgtgtgaaat ttcagaaacc actgcagacg cgctgcggga cgctttcttc accaggcacg   21540
cccggctcgt ccaggatctc cttcaggcg gtcaggtccc gtgcttacaa gcccaggtct   21600
gggcaggagg gctctggccc cctgctgtgt gctccccggc accctgcacg cacgccaggc   21660
```

```
tgcacggtgc agctcacacc tgggaaagca ggtaaagctg gtaccgcat cacacgccgg   21720 ctgtgccgag gtaaacacaa acaccgcaac acacaccaag tgcggggtcc agggcgttcc   21780
ccccagcacg tgccccagtg ccatgccgac tgcttggact tacagtggct taaggagcag   21840
ccaccacaag agggaccctc ggaccttccc tctgtctccc agcgcaagac tcacggctct   21900
cctgtgaacg gcgcactccc tgcgtctgga ggtggaagga cccccatcac cccacgtggg   21960
gatccagcct ggcagctcct ggcagcgac tctgctcctt ctgatgcgct aaccccaca    22020 caagctcctc tcaggttctt cactaagtga gccccaaacc acagatttct tcaccctgtc   22080
agttccccag gatattgtgt gtctttgtcc aaaggtatgc gagctgcccg ctttggtctc   22140
ttctcgtcca tttctgtgcc acgtccaaga gcatgataaa tatttactac ttttctccca   22200
ggaatctaat catagaacag cctatgagta aacgacccct gtgccctccg ggactaagag   22260
gagactacgg taaagagttt cagacacgac cttgtcacca gtgccccaga atatcctgtt   22320
gcagttcaga aaccagcctc tatactaccc ctctgtctgc aatcgcagcc gcaaggcctg   22380
agccagaggg agccacccca ggcctggctg gagtcctctt ctgaggtccc cctttgatcc   22440
atttactctg ccactggctg gccgttccat cctcgtattt tgtcaattca ggctgtaaaa   22500
agaccacaca gggacaccta gagcttgtcc aggccagcgg agcttcaggg actgctgcct   22560
aacgtgaaac cctaactcac tagcaggact tgcagccaaa cagataaata ttaggcccag   22620
tgaggcagtg ggctttttga gaacttcact gttttgagg agtaaaaaaa aaagaaaaac    22680
aaaaaaaact ggtactgggg tcacagtctg tggtgccaga agcagaccca tcctataggc   22740
cataaaacct gtcaaccgat catgggagcc tcaaaatcaa agccgacagt tctggactgc   22800
acgattcaaa atttcaaaaa gggtttctca ggagactatg ggattaaatt gtccccagaa   22860
aaactgcaca ggttgtgcaa gttagagtga cccaccttca gagtgggatg gccctcagga   22920
gtcacacttg acctgccaac tatccgggcc atgtacagag taattgccag gacccccaggg  22980 caccccaacc aattcccata tattgacccc tggctaacag tcgcccaaac cttgcccccca  23040 tgggcctggt tctgcacaaa tgatcaggga aagtgtagga tcctcgtggc ccagacagta   23100
aaaataaaaa aggaaggtgc aacgaagcca attcttcagg gggaccctga agaagaacca   23160
gcgatgcccc cgccatgtgt ccttccctct gtggctccac cacagccacc tccacctgat   23220
agccctcctc catccgtgtc cccaccgcca caacccccagg ctccatgcca ggaaccctta   23280
gggaagagac tgttcagccc aactagccag ccagccagcg gccaccctcc agatgcctct   23340
cccggaggcc caagggcccc aacatgttaa cgacaatggc tccgtgcagc ccagacactc   23400
cgtcctgtac caccagcctt tcagtacaac agacctcctg aactggcgac accacactcc   23460
tccgtattca gaaaaacccc aggccatgat tgccctccta gagtccatct tccagaccca    23520
ccggccagct tgggacgaca tccgtcagct gctcctgacg cttcaatgct gaagaaagaa   23580
agctggtcct gacagaaact aaaagttggc tacaagagca gaccccagag ggaaccatgg   23640
acgcagaagg gtcagcccta aatgcagccc cagaaagaag gccaaactgg gactttaaca   23700
cccaagatgg atgagaggct ctgcagatgt atcagagagc cctcccgcat gggctgcgag   23760
ccggggcaaa gaaaccaacc aacgtgactt agaccatcac ggtgatccaa aagccggacg   23820
ggtctccatg gactcctatg agaggctatg cgaagctttc ggatctacac cccatttgac   23880
cccgaagccc ctgaaaccca gcggatggtc agtgctgctt ctgtggccca atcctacacc   23940
ggcatccacc aaaaaacttca aaaactgaaa ggttttgctg gaatgaattc cactcaactg   24000
```

-continued

```
ctggaggtgg ccaacaaagt cttcataaat caaggccacg aagcccgaca agaagcaggc   24060
agatgaacaa aacagaaagc acgcctgctg gcgaaaaggg gggacccgtg tggggccccc   24120
ggaggcaaga ccaacgtgca tactgtaaga aggttggtca ctgggaaaat gaatgtcatc   24180
gcggagaagc aaaaaaccta ccgaagagaa aacctccagc cagcgaagga aagtaccggc   24240
ccgagcctcc tctgaggaac ctggtcgggt tggtcaggct ggactcagcc tagggggagac   24300 tgcgtccctg ctcctgggcc caggggagcc cgcagtcaag atgttggcgg ggggccaacc   24360
gatgacattt acagcagaca cggtggtaat caaagctgtg gccccttga ccgagaaaac   24420 ggcaattatc acaggagcca ccggggacca ggcctctcgc ccgttttgcc atccacgatc   24480
atgccagctc gggggacatt tagtcactca tgagtttctc tacctaccag aatgccccat   24540 cccctttttgg gaagagactt tgtaaactgg gggcccggat aacactctct cctggaaagc   24600
aatcacatct aactctgagg gggaaggaag ccttgctcat gatggtgacc gtgccccgag   24660
aagaagaatg gcgcctatac caaacagaaa gcgcccagac aaaccctgac tctctgtgag   24720
gaagctcccc tccgtctggg cagaagggggg accccccaga ctggcccgat tggtaataga   24780
cctgcgactg ggtgcaaccc catccaggct gcgagagtac cccatacca gagaagcccg   24840 tctgggaatt cagaagcaca tccagcgttt gcgtgatgag ggagttctca aagagggcca   24900
gtctccatgg aacatgcccc tcctgcccgt cagaaaggtg ggagtaatag actgaaggcc   24960
agtgcaggat ctgcgagtag ttaacaatgc cgtgaccaca atacacccag tggtcctgaa   25020
tccacacgct cttctcagac tcctaccggc ccaggccaaa tggttcacct gcctagacct   25080
caaagacgct tccttctgcc tcaggctggc accagtcagt caaccaatat ttgccttcga   25140
atgggaggac ccccacacgg gcaggaaaac tcagttaacc tggcctcgct taccacaggg   25200
ttttaaaaac tcacccaccc tgtttggaga agcactggcc acggatttga ctgccttcct   25260
gggagaagct ctaaactgtg cctgctgccg tgcgcagacg gcctgttatc aggcagcccc   25320
aggcaagagg gctgttggga gggaacccag gccctgttag cgctgctgtc ggatgctggc   25380
tataaggtct cctggaaaaa ggcacaaatt tataaaaaga cagttgagta tctcaggttc   25440
tttgtctcag aaggacaccg agctttgggc ccagagtgaa aacaagccat ttgtgcaata   25500
ccacagccag gcaccaagag agagatccga gaattcctgg gggcagcagg gttctgccga   25560
atctggatcc ctggtttctc agacatagac aagtccctat gtgaagccac cgctggatct   25620
gggaaagaac cctcagactg gggacccaag caggaagaag catttaatga ggtcaaaaga   25680
ctgctaacca gggcccagc cctgggacta ccagacgtga caagagaatt cagcttgttc   25740
gtccatgaga agagtcatac agccctagag gttctcaccc aagcagtggg ggcctggcag   25800
tggcccatgg cctatttgtc aaagaatctg gacccagtag cttcagggtg gccaccatgc   25860
ttacgagcac cggctgctac agtaacccta cggtcaagga agcaggcacg ctcacccttg   25920
gagagactgc cagcgtgaag gttccacacg cagtccccac cctgacgcac agccaggggc   25980
gccgatggct gaccaacact agaatgacac gttgcccagg gctcctctgt gaaaaccgca   26040
ggatctgcct ggagacagtg cggaccttga gcccagccac cttcctgccc gagggagagg   26100
gcccagccga ccacgactgt gaggacatag tagaagtctc aagcaggcgt gagctgtctg   26160
atgttccgct ccagaaccct gaacttgaac ttttacagac gggagcagct ccatgcagga   26220
cggacaacat acggcaggaa acacggtgac cgcagcacac gatgtaataa aagccgaatc   26280
tctaccactg ggatggtcgg catagagggc agaaacatag gtgctcatcc aggcgtcacg   26340
agagggaaga ggaaagcagg tcaacgtcca cacggactct aagcacgcct ttgctaccct   26400
```

-continued

```
gcacacacat ggccctgtac ataaagaagg gggtctgtta acagctggag aaaaggagat   26460
caagaataaa ggcgagatag tgcaactgtt agaggcagtc tgggagcctg cgggggggtca   26520 gtcatccact gcgaggggcc ccgaagggag acgaccctgt aagcagagga agccgactgg   26580
cagaccaggc tgtgtgagaa gcagcaagtc agtctggcca cgccagagat cctgggaccg   26640
tggcgaagtt tccaccagca cccgaactgc caacgcctct ggaacacagc cgagaggaaa   26700
gctcatgggc caggaccgaa ggaggaacca aaagaaagga gggatggtgg gcgatgcctg   26760
acaaatggat atacgtacct gaacacttag cccatcacgt ggtcctccag cagcaggagc   26820
tcacccacgt ggacagacgg cctcagaggc cctgctggat cgatactacc tgatggctca   26880
acttccaccc ctctgtgcct cagtctcaca gcactgcctt gtgcgtgccc agaacaatgc   26940
agaacggggg ccgactggac caaaaggagg ctccttctga agacacggaa gcggatttca   27000
cagaaatagg gcctggcaga ggacacagga cgcactggct tttgtctgca ccttttcagg   27060
gtgggtggac acacacccag cacggactga gaaggcaagg gaagtaacaa aggccttact   27120
cagaggcacc gttcccggat tcgggatgcc actgaccaca ggggcagaca acggatctgc   27180
atttgtggca gaggcgctac acagccactg gagtccacgt gcagccgacg ggcccccgag   27240
ctcagggaga gcagagcgcg ggacccgggc cctgaagcaa gttacggcga agcgcagtcc   27300
ggaaactcag ctgccttggg ctgacactct gccccggct cttctgcggg tacgctgtgc   27360
cgctcggtcc aagacggggc tctcccttct gggggcctgt acgggaggcc cgctcctta   27420 attagactag gggaaagtat tacagaagtg gggagcgtag accttcataa gcaaatacag   27480
ggcctcagaa aggctatgcg agaaatccac aggtggggaa ctgacaggat cccagtgtca   27540 ctggaacaa tgtgataccc atatgacctg gggaccaagt ctgggcaaga gattggcaaa   27600
gggagccact cagacccgcc tggaagggcc cctacccagt tgtgttagcc accccaacag   27660
ctctaaagtt gcagatatcg cccccccggat tcatcacgca gagtaaagag agcagcgcca   27720
ccacgagacg aggatgtctg gagcgtcgcc cagatcccca gagagcctct taaatcagga   27780 tccagacg cccgcctcgc ctgccagaga gcacagagcc ttgctctagc cacacccgga   27840
agccttccgt ggcggaagcc tgaggaaccg ccgatcaaga cagaaaatga actgctgccc   27900
cgctttattt taggactgag tactgtctct gtattgcgag ttgtaggact gatggccact   27960
gcaccccagg attgaaacat gggccagaga ctaacaccag ctgtgctccg ttcctccaca   28020
gtaggaagcc caacggtcag tcagggtctg ctggaggaac catacctccc tgtgagaaat   28080
ggtgagaccc caagcccttc ttctgcttgt gaaaggagtt gctgacttat ctctttccat   28140
gacggaggtt ccaatgggac ccattcacca aattgcagaa gaaaccccgg cccacacgct   28200
cagggccctt ctacagacct agcaagggtt gggaaaagaa aaatagacct aggtccatgc   28260
cttataacca ggacccccaa ttaagtccct tatgaagcaa gtccatcacc ttcttcatgc   28320
tactaaccca caactagcaa gtgcttgctg gctctgcctg catcccggcc cctccagcat   28380
gcggccagcc cgatgggccg ctcagatcta accaagttca atggctgccc tgggtggtcc   28440
ccagactctg ggaaatctgg ccactgccca gtgtgcccaa acccataact gcacacctgt   28500
ttacagttgt atgcctgcca agccctggtg cgacactgag cccaggaacc tttttgtttg   28560
cggagcacac tcctacggtg ctgccagcca gttggacagg tacttgcaca ctggccttcc   28620
ttacccctca gatggacata acacctgata accagagcct tcccgtaccc ctgatggccc   28680
atactagatc aaaaaagggc catccagtta ataccactac tccttgggct ggaatagcga   28740
```

-continued

```
ctggagtggg caaaggaata ggaggaacag cctcatcttc ccactgttac cagcagttat   28800
ctgctgaggt cactgaaggt ttaaaacagg tggctgagtc ctgaatgact ctacaaaacc   28860
agttggactc cctagtggca tttgtcctac agaacaggag gggtttagaa ctgctcactg   28920
ccaaaaaggg gggactctgt ctcttcctaa atgaggaatg ctgtttctac gttaatcaat   28980
cagcaattgt cagaaatacg gtccaacaac tacgagatcg agctgaatgc agaaaccagg   29040
aatcagcaaa ctcctgggca caggggacta acgcctggag ttgggcctcc tgcctcccc   29100 ccagcaggcc ccctccttat gatccttcca gcgctgctgt ttggtccctg catccttaac   29160
ctcattaccc gtttcattag ctcatggata gagtcactga gacggcagct actagtcact   29220
cagtacaggc ccctggacca gaagaaccca atggtgaata aggggcacca ctgtaaggct   29280
gatgctcgct gcagatgttg aagagagcat caaagtgggg aatgaggcgg gaagccccat   29340
agaaagacca gcaggacccc caagcagggc cactactctg ctgccggcac catccagttc   29400
cctggcccag aaacggctta cttatcccta aaaccctatt ggttccctga gctcactcct   29460
gattggttat ttccttcact cctgattggt ccatttccct aacttctgat tggtccattt   29520
gtagtgcttc atttgcatgg agctcactcc tgactggtta tctctccctc ctgatttgtc   29580
catttctgca aagcttgttc ctaattagtc aactttcatt atacctcatt tgcatgtgat   29640
gttgcaaagt gtacactggc agcctatgaa atcctgtgta aacctacaga cggggtccag   29700
agcttggagt gctgactcct ctgggcccgc tggcgtagta aacctgagtt ctccagctct   29760
ccgagtgctg cttggtctcc cgcctggacc caggttgctg acacaactga gctgtaacac   29820
cgagctgtag cacatttttc cacaacaatg taatagttct catctgagta ttttgagaaa   29880
tccccatact gttttccaca gtggctgctc caatttacat ccccaacaac agtgtacagg   29940
ggttcccttt tctccacatc ctcgacaaca tttgtcattt gtgttctttt tgatagcagc   30000
cattctgata ttttattgtt agtggaaaga aatgcagccg atttctctgt gctaatcctg   30060
tgttctgctg ccttgccgaa ttccttcatc agctccagtc gttttgcgtg gagccttagg   30120
gcttctacgt aaagtgccac gccatctgca tgtggtgacc actttcctgc aaatttcccc   30180
agtgacgttt gtttgcaggg aggttttttgt tgctgattct ggtcacttct agtgatcatt   30240
ctgttcaaag gatctatttt ttcttgattc agtttggtag actttatgtt tccagaacct   30300
tgtccgtttc ctttagggtg tccaatctgt tgccatatag ttgttcatag tgttctctag   30360
tggtcttttg aatgtctgtg gtattggctg taatttctcc attttccttt cttattttgt   30420
tcacttgtat cctctctttc cttcttggtg aagctggcca gaggtttgtt gatttttttt   30480
tcactcttta aaaaaaaaca gctcttggtt tgattgattt ttttctattg tttttttttt   30540
tccggtctct attttattca gttcctccct aattttattt atttctttcc tgatgctgac   30600
ttcaggtttt gctcactctt ctttctctaa ttctttcagg tggcaggtta ggtggtttat   30660
ttgaggtcat tctttttttga ggaaggtctg taccgctgtg ctcttccctc ttaggatggc   30720
tttgtctgcg tcctgtagat tttgtgtggt tgtgtttttca ttgtcatttg tctcagggta   30780 tttttttaatt tttccttttga tgttttttgtc gacacattgg tttttagcag catgttgttt   30840
agtctccgtg cagtttgttt tcttattttt ctttctgtga ttgatttcta gtttcatgac   30900
attgtggtca aaactgatgc tcaaaataaa ttctatcctc ttaaatctgt tgaggcttct   30960
ttcgtgccga gtatgtggtc tatccttgag aagtttccat gcacacttga aaaggaagta   31020
tatactattg gggggtaatg taacatctta aaatatcagc tgagcccaac tgttcctttg   31080
tgccatttgg tatctcggtt gcctcgttag ttttctgcct gggagttctg tccagggcgt   31140
```

-continued

```
tagtgggtgt tgcagtccct gctgtcactg tgctcacatc agctttcccc tttcagtctg   31200
tttgtattag tttcatatat tcagaggctc ctatgctggg tgcatgtatg ttaacaaatg   31260
caatatcctc gtcttgtatt tctacttttta ttattacata atgtcatttt ttcctgttta   31320
tggcctttgt tttaaagcct cttttgtctg ataggagtat tgctactcct gctttcttgc   31380
catttctgtt tgcatggaat accttttttcc accctctcac tttcaaacta tgtgtgtcct   31440
tcaccctcaa gtgggtctct tgcaggcagc atattgtagg cttttgtttt attatctggt   31500
ttgctgctct gtgtctttttg actggagcat tgacatccat gataattatt gatagacgtg   31560
tgtttattgg cattttaaac tatgtttttct ggttaatttg gcatttcttc tttgttcttt   31620 tcttttttgtt tttgtttcct tttctggttt gacaacttttc ttttgtgtca gcttggtttc   31680
tttttgatgt atgtgactct actgtatgct tttgatttgt ggttaccctg tttttcaagt   31740
atgttaaccc attactgtat ctgtttgctt tagactggtg gtcatgcagg ctcaaacaca   31800
tcctaagaag aatgaaaaga aaattgtttt cctgttcccc tctcccacaa cttgattttt   31860
atgtcctctt tcacatttttc atgtttattc tcttagttct ctgatatttt catgcttcaa   31920
ttatggcttt ccataattga agaaagtagc ttcctgcttc ttctctattt acagcagacc   31980
ttccaccatt tcctgtagcg tgggtttagt gttgctgaac tcttctagtt tttgcttgcc   32040
tgtgaagctc tttatctctc ctcctatcct aaaggatagc cctgctggat agagtatcct   32100
aggctgcagc ttcttctcac tcaggactgt gaatgtatgc tgcccctccc ttctggcctg   32160
cagtgtttgt gcagtggagt cggctgaaag ccttatgggg ggacccctgt aactcactct   32220 ttttttttctc ttgcagcctt tagaatcttt tctttatctt taactttggc catcttaatt   32280
ataatatgtc ttggtgtaga cctgttaagg ttcttcttgt ttggggccct ctctgcttcc   32340
tgtacctgga tatctgtttc cttcttgaag ttcgggaagt tttcggtcat gacttcttca   32400
agtacctgtt tgatcccttt cccctttctt ctccttccgg gacccctgtt atgtggaggt   32460
tggcctgctt tatatcaccc cataggtccc tcatgttgct ttcgttggtc tccgtttgct   32520
cttctgcctg ctgctttgat gtgatcgggt ggtttccatt atcccgtcat ctaagtcact   32580
tattcgttct tctgtattat ttagtctgct gttgactgcg tttggctcag ctttatctca   32640
gcaactgagt tttccgattt taattggctc ctctttacag tttctatttc catttttagaa   32700 aaccctgtat tctacatttc tgttgatggt cttttcttatt tccttagtgc tttttgtcgt   32760 ctccttttttg aattaggctc tagcagactg tcgggtctgt tttattgttt gttctttcag   32820
ggaacttctc tggtgccttt actcgggagc agctccccct cacgttgctt gcacctctct   32880
ggctgtgggt gtagacgtgt cagttacctg ctgtgtctga agggctgttt ttttcaaatg   32940
ggtagactgt gcaaatctaa caattttgtc gcaaggacag ttttttagtgt ctttcctgca   33000 tgtgtgctgg ttttttgtccc cttgatcagg ggtgtggctg gtgttgtgac cagagcctgc   33060
cctggctgtt gaactgggcc tcctctttgc tctgtggttg tcagagccgg gcctgctccc   33120
ctactgtagg agtcgaagag tccagacccg tttctgagct gcagtgtgtg gcaggcggga   33180
ttggagcact tctgctggaa gacgagcccc agaatactcc tccacaggag acgaccgctg   33240
gcaagggccc ttgtgctgtc gcccaccact agttacttgg gcttccaaag tgcactctgc   33300
ggttgctgcc cttgtccccc ctcagccagg ggaatatcag caacccactc tggtgtcccc   33360
aggttctgcc ctgcagagcc accagtgcag atccactgac atcaggcact gggacctgga   33420
tccaccatga gccacgggtc agccccgacc tcagcccat gtccacgtcg ggtacgcagg   33480
```

-continued

```
gccactgtca gcaccaggct tgccccacat caagcaccag aagcccacta ggttacctca   33540
gaagtgtggg tccacaaagg caccagctat gcaaatctgc caccacagcc tggggcttga   33600
aacaagtctc agtcccacct gcaaagtcac aggaccctgg acatggattc aggtgtcagc   33660
cccacctctg ccccggagcc tcgctgcagg gacggtgccc cccagagaac gctgagaggc   33720
ctgcggtttc tgagccccac ccctcttcta gggcaatgtg tgccacaacg gtgctgagca   33780
gtgccctctg ggctcatgat gacgactgct ggggctgggc tgctttgcac ccctccccac   33840
gtgccccagc agtggtgctg tcgtgggggt tgacccagcc tgttttgcac acttctaccc   33900
gcagcctgca ccgcactctg cctactgtgg ctgcctatgc acactcagca ccagccctct   33960
gcccgggatc atccacggga gcctgagctc cagcagcccc acccagccca ccctcactgg   34020
ctcacaccta gagctaggga tggcagagac cctctgtgct ggtttgtccc agttctgtct   34080
gccaagtcgc tatgaatttt ccctccaagc ttctgaagct ccttttctat ccctgctgac   34140
cttcctgctg gagagggggc ctcctggagt gagcgcactt ttcctccttc tccactccct   34200
ccccaggggg cagctcctgc actgattttt tttttttccca tccggttttg tgagtatttc   34260
cttgtgtttc caattgtaag agatactctg ccaaagttca gtaggcagtc tgtgagattt   34320
gctccatttg cagatgcggt ttttgtggta ttcggggggag agggtgagca cggcctcctt   34380
ctacacctcc atcttggctg tctcccagtt ttgctgtttt tgatatgtca tttttcttct   34440
aaaacctgtt ttaagcagtg cactcccctt tcaacaccgt gtaggtctct gtcctcaccg   34500
ctgaggttcg ttacggaacc tcactctgtc tggcatctgg tggaggttct gggaatagtg   34560
agaaggactc cagccccgga aagcccacgg tctaggagag atttagtgag aatttgggca   34620
gagggagcca gcaggcagtg ctgaggtggg ctttgtgaga caatcaacag acagcagagg   34680
gcagggaggg ggtaggtctc tgtccggctg gttctcgata tctgtgcaga ttgtctatgt   34740
ggaaactgag atgcttctta gaacatggcc cctcgaactg cttcagaga cctgcccaga   34800 acatggccca gcgctgctgt aaagggcaca cgtcccttcg cttgttgtcc tgcagtattc   34860
acgtggaaac ctgagagctg caccttgtag atgggctgtg tctacacccc ggagactcag   34920
ggacaggcac agaaggaggg cacctgtgat catcagtgcc caccacagtg acaacgtgtg   34980
aggggggaac gcgtggcggg aggacgagcc gcctggggca agtgtcccgg cgggattctc   35040
acaggcgtgg agtcagtgtg cgcctggaac acgagagcag ctcacagggt gactgggctc   35100
cgctggtgct tctcacagat gatgaaagcc ctcaggaagc cctcttgtca ggacagaagg   35160
ggagggacag gagcctggag aggggacagc cctcctcact ggtggtggct catctctaaa   35220
cagacagtgt cacttccttc tctgtcggct gcgctgagaa gatgagaaat tagggctacg   35280
tggagcacaa cacaaaatgt cctgggggga ggctgtagag gaaatccctg acagagacag   35340
gaagcccctt tccacccgcc tctgcacttg ctcctggggc tggtctttct gttctgtgag   35400
tcttgcacac cccctggtgg acccacacac ttcttaggag ggaaggtttg cgtctgggct   35460
cacaccggct tcccctcact gtgcctgtgg cacagtaata cacggccgtg tcctcaggtt   35520
tcaggctgtt catttgcaga tacagcgtgt tcttggcgtt gtctctggag atggtgaatc   35580
ggcccttcac ggagtctgca tagtatgtgt tactactgta actataaata ctggacaccg   35640
actccagccc cttccctgga gcctggcgga cccagctcat gtagtagcta ctgaaggtga   35700
gtccagaggc tgcacaggag agtctcagag aaccccagg ctgcaccaag cctcccccag   35760
actccaccag ctgcacctga gcctggcac ctgcaaacac aaagacatcc tggtcaggag   35820
actgtcacac gtcctctgat tccctcactc acgaccaccc acatcctcag tatctctcct   35880
```

-continued

```
tctccatgaa ttaccttgta gaagagcagc caggaccacc cagctcagcc ccagctccat   35940
ggcgagtcgt ctgtgctcag tcctgctcag agaatgggag cagctggaat cctgggctgg   36000
gcctcctctc ccagagctgc agatccaggg ctgggtggct ttatccccag agggaggccc   36060
tatttgcatg tcatctcact acatagcaag cctggagttt gagcaagggc agtaccccag   36120
agcaggagtg agtgtattgg atttggtggt tttgatagaa ttctggaaaa tacgattttc   36180
cactatgtgt tttttccaga gtaaacacct gtcacccatg tgtattttgt tttcacatat   36240
ggacacaaac cctgtgatgt aagtttcact gtttcccgca gagtagagat gtgaactaca   36300
gccaaaatgt agtgggcttg ttgcgtgtcc aaggacacgc ctgtggggag ggccagtccc   36360
agctcctaca cctgtgctca tccccactag acccagctgc ccctgcgtca agtcccggaa   36420
aacaggaccg tgcttgtgag gtttgtgcac cccctccctg aagtgagacg tgaggacttt   36480 gctgcccct agcgtcgagg gtctgagttc agaagctgtg ttttcagcgg tctccagcat   36540
tgcagcgtct gtccaccacg tcttcccccg caggcagcca ctctctgttg gtaacagcct   36600
taataagcgt cgcgcatgta gcaagctgca cgtgctggaa tgcgctcttt ggtacacact   36660
cacgcaagca tcagcgtaat cgagagtgag cggagtgctt cccttccatc tattcgctgg   36720
tttctggagc tcctccttcc tctgcctcct cttttccacg ctgttgcttc aggttagctt   36780
tcttttccca gaattaccca gggggggccat attgcgcgca cggccgcccg tacggcttgt   36840
ttccctcagc gcagatgccg tcaatagcgc cattctgctg cgtgtatcga gaatccttgg   36900
ttttaacaac atgtgtcatt cccagtaagg atcacagtct gtctgtctct taagctgttg   36960
tgcggtgttg gaattatttc tagtttctgg gtgttgcagt aaagctggtg cccatctcgg   37020
agcggtgaga actaagaagc tgggaaacga ctctcttttt cacgttccta caacaaccgt   37080
acgagtgggc aagttgcaga ttatcaggtt ttcattcata tatcagatca ctgtggtcgt   37140
aaaacaaatg aaactgaaaa cttagaagca aatgctcaca gagtaaccaa gaactagact   37200
gtaagcttaa ttggggcaga agctgctgac tggaataaga accgctacag aatcacactg   37260
gaaacggctg gcttgaggac gcgcgcggtg cagctgtgac agcgtcccag ccgtccccta   37320
actaactcct ctgcgagtgt ctacggtgga agccaggcga cgctgcctcc cttcacgcgg   37380
gtgcctctct cctaccagga cggctgggag ctcctgcctg ggaccgcagg ccctcccgct   37440
tcacgggaag gaaggccttg ggctctgggt gcgacctggg gctgtttccc agcacctcca   37500
cctaacagtt cgatgtttgt ccagtcatct caccaaactg caccatgtac ttcccgcaca   37560
cgaggtgggg aagcaggttc tgtgcggaag tagataatga agttctaggt gttgaccgat   37620
gcacaaaaat actgccacag ctcttgccag cttcaagtga caagagccac tgactttgtt   37680
caccctctct gattcggagg ggcttgagga agtccctcct ggcccatgt ggggtcactg   37740 tctctgagat gcacactcac acctacatga agctgccctt gaacacaggc tgggagctca   37800
gcaggctgag ggctgggcct ggtgtccgcc ctgtgcagac atcctcttgg gccctgaccc   37860 cacccagca tggtgactgc ggcagccgat gggtccctgc tccagagacc ttcctcaggg   37920
caacatctca cagacctaga gtttgataca cgaccccagt actcgcgccc ctaagcactc   37980
acccacccga cttgagactt atgtctccat cataaacgca cgtgagttct cgtagcttca   38040
cgtgtaattg agaaaactgg atgcaacaaa ggcattcttc ttaaatgaat aaatgagcaa   38100
tgcatgatgt atccatgcag tggaattcca ttcagcaatt taaatgttaa attatcatag   38160
catgaaaagg caaggatgaa tccaaaatta gcgtattgct acttttaaag ccagtctgaa   38220
```

-continued

```
actgtatgat ttcacctatt tggaattctg ggaaaggcaa gactgtatac atagtaagca   38280
ggtcagtatt tactggaatt tggggacaag gcatttagtg agtgaaacag agacaatatt   38340
taagtgtggt gagattgttc tctatgaagc tgcagtgttg gaaacgtggc actaagaacc   38400
tgtcagaaca catagaacta ttagcgcaaa gagtgaacct tactgagtag aaatataaag   38460
ggcatttgga agttcagagg ctcaaagatg gaacttgtag gctgtgtaga taatacctca   38520
gatcattatg aatcaacttg actgaagaag gtgacaacac atttctgacc aaagtcactg   38580
tgtgactgag tggagtctga ggacaagggt ccaaggacac tgcacagaag ctctggagcc   38640
tggctgacaa ggatgtttcc agcacgggcc aggctagcaa ctccatcact actgtgcacg   38700
tggggttgca ccagcaggta catggatggc acgggcggtg ccgggtttct cactggcgga   38760
gtgcaagtgg caggagcggg tgggtagact gaccccgtgg tggtgcactg gggctgggga   38820
cgtaagaatg ttctcacatt caccttaaag caggtcagaa ggtcagatac agagttagtt   38880
gtagaaatgt gtgtgtgtgc atgtgggaa atgcacatag agatgtttct aaggcctgtt   38940
agctgattgg ctccagaggc aatacccaa ataatgagaa agcaccaaca tcagtatctg   39000
ctccccagca tcttgagtac tgacagtatt ctgcggaaca ggagccacac tgcgtctgag   39060
gaatggctaa ttctagggct ggaatgcagg tgattggcct gcaggtcctt gtggtgctag   39120
acagcaagga aatgttcaga taaatggctg ggggcaggtt aatggacata ggagccaacg   39180
gattgagctc ccagtggcca gcaagctgta acaactacag gagctaaagg gataacttag   39240
tattaccttg atacatagtg tgaaaatata cccatgatgt atgctgacat acggagactg   39300
gatacataaa tctaatgggg gaggaagggc aaaagtcccc gaaggattaa caccaggtaa   39360
tttgttgtga ttacccttcc tctaagaagg tgaaacttaa cacctcatcc ctgaatgtgc   39420
ctggcctcag agtcatggca ggaattgtgg gcgaccttga gtttcacagc gagtgtgtag   39480
acagactacc cgtgacgtga ttcatgcaac ttttctgcat ctgaattaaa agccatgttc   39540
tgtgaacaac agcagctcag caagaacact gagggcgcac agacaggcca cgaggcggag   39600
aacacgctct cagacgccgt gtctggtgaa gggcttctgt cacgagcaca cgtgaaactt   39660
acagctgagc gacagcaacg aaagcagcca gtcagaactg ggcccatggc ccgagagggg   39720
agacaaagaa gagagacaag gtttgcaact tggtttttca tgagggaaac aggaaacagc   39780
gtgatgatga gactctgcta ctgatctgct acaaaacact gaaagagtag aacttcgggc   39840
atagagtgga ccgaaatcac ctctcttcag ctttctggaa ggaatgtgca tagcgacaag   39900
tctggaaggc ccctgacagt ctcccggggg taagacagac accatgggat gaggaggggc   39960
cgcccagtgt ttatctaaat actttggata tttatgttcc caccagtgtc tgcgtgggaa   40020
ggtttctgtc accttcacac atccgtcttt gacactcctt ggatttgctc acagagcagg   40080
gtttcatggc agcttcgatg tcattaggat gtatgcgttt ctattgttcc tttttaacga   40140
tcacttggcc ccactttcta gggcagcagc cacctaaatg gctttgtcat catctcatcc   40200
cagccctgcc tcccagtccc tcagggtttc tgacacactc aggacatgag tggtcacact   40260
gtgtctctca cacagtaaca cacggccgtg tcctcagatc tcagactgct cagctccacg   40320
taggctgtgc tggtggacgt gtctgcagtc aaggtgactc tgccctggaa cttctgtgca   40380
taatttgtgc caccgtcttc agggtcaatt cttcccaccc acccaagccc ttgtccaggg   40440
gcctgtcgca cccaagcatg tagtagctgg tgaaggtgta tccagaagcc ttgcaggaga   40500
ccttcagcaa agcccaggc ttcctcagct cagcccctgg ctacaccagc tggacctgcg   40560
agtgggcacc tggcgacaag agacacaact ggatgagata cccatcgact ggttcccgat   40620
```

-continued

```
cccccctcat cccagagcct ggggagcccc tgacctgcag ccactgccac caggaagagg    40680
gctccccagc tccagtccat ggtgagggct gtgcgctggg gcatctgtgg gggagaggga    40740
ggggctgagt ggtgctccca gggctcagaa tgtccatgtt taacaccgga cacctcggct    40800
tgtttgcatg ttcatgaggc tgaaaacttt atgctgatga cctggaccag cttgggaggg    40860
agcaggtggg ggccgaaagg gccctcccga gtaggaggct gagggtccac accctcacct    40920
cgctggagga tgtgtgtgcc tgccacctcc ctgagctctg taaagggagc gcctcccgtc    40980
aggagccatt ctcacctggc cgggtcctcg tcgcgaaccc accctcgagc gactcggaga    41040
ccctgagcct gctctgggct ttcatagctg agcgacgtac tcctgggatc agacagcctt    41100
ccactctgcc tttttgaatt aataaagctg tccctgcctc ccagatcctt tctactgaga    41160
tattaggagc ctgaaaattc tcttttaaat gtggttccca cggactcact gagtcgtgta    41220
aatgcctccg atacttgaag acacaccagc agtccttgtc gaattcacag tatagacgga    41280
attttgaaaa aagaacccag gtgctcatag gaaacccctc acacccttc tgcacctgcc     41340 accgggtctg tgggcgtgag ggggctcccg agcgccctg cagccctacc ctcactgtgc     41400
agggcaggga cccatctggg ctcgcaggag acgcgtctcc cagggcctct ggtccagtgt    41460
tcagttcctc tgccatgatg tcagaggaca ctttcagaga cactaagctt ttgatctctt    41520
ctttcagtta atgaactggc cgcaccaggc tggcatgctc tgcaggatgg ggccctcctt    41580
ccctggagct gccagatgca ctgacgcagt caacacgcaa ggcgactccg gggagaactg    41640
gaggggtggg ggcctcttac tccttcaggc tcgtctgtat gaaggtcaca gctgactatg    41700
tctgcgggta taaacccagg tagcttagag cccactccac acgtacctgt tcagcaatgc    41760
acccggacac acacacacgc acacgcacac acacacgtat gcgcacacaa accacgcaca    41820
cacacatgca cgcacacgca cgcgcacgca cacgcacgca cacgcacatg cgcgcgcaca    41880
cctacacacc cacgcacaca ccccacgcac acacacatgc acgcacacgc acacccacac    41940
acatgtgcac atgcacacgc acacacgtgc acacacgcac acaccccacg cgcgcacaca    42000
cgcacaccca catacatgca cacacgcaca cacgcgtgcg cacacacaca catgcgcaca    42060
cacccatgca cgcacatgca cgcacacaca taggcacaca cgtgcacaca cacacgcaca    42120
cactatggct ggtatttaca gctctggccg cagatttgcc ctcctccctg tatgtgactt    42180
gctttctcac aaggaagaga agaaatgtga ttcaaccaga gagctggaaa gcgcgctggc    42240
ttacctgttc ccgcagcacc aggagccttg tagatgcctg ggtggaagtg tccaggcttc    42300
cttgtgaggg ttagaccccc tggcccagcc acgccctgtc catgcagcca gcactgaccc    42360
ccgacgtggg gagggtcccc ctagaccac agccccagct ggtccccatt gcagaggcac     42420
agccaggagg ctgagggca ggaccttgaa ggacactgga cagggcggtc tcccagcaga     42480
agagcccctc atgcaagggg cacctggcca gctgggggct tttctgtgga gtcgtcctgc    42540
ccctcaggct ctcatgctcc ggcccggcct cacctgctgg ggatttatca gagcaccacc    42600
aacctgggga agccaacacc tggcctcacc cccagtccag ccctcctgtc tcaccccagg    42660
gaggggaggc ctgagaagct ctcatggggg tcaaggctca gtacaaggaa ggccaattgt    42720
ggggccacag acacgtcacc tgccgcatac ctgcccgcac atcgatgggg tctggttgac    42780
aacagggtgt gtgtctgact tctcactggg atgggagagc cttccaggag tcttccttcc    42840
ccccagactt agggagatgt gactgacaga gagcccccat gcgcgtaagg tgtgcaatgt    42900
ggtcctttga caggtgtctg agctgtgaca tgtttaccac catcaggtga gcttgcacac    42960
```

```
ccttcacctc gcatgacccg cgacgtcttg ttgctcctct tgctgtggtg ggcgtgatac   43020
agctcagccc tcagagcgac tccagagcac caaacacagc acttggaacc ctagtctcgg   43080
ggctgcgcca tctcctgacc gccagcatct ccccactggc tctgcctcag ccctgggccc   43140
gccctctgct ctgcgctctg ctggggacgt ggagggcctt tccacgcctc tgctggccat   43200
tcacgtgtct tctttgccca ggtgtcggct caagcctctg cctgcctgtc cttggggtgg   43260
gctgggccac ttgctggctt gcttctgagg agcaggagct ctccgtcatg cttttagatgt   43320 tagcctctca tcagacgtgc cttttgcaaa cacatttccc cgttccgcaa gggccttttt   43380
actccgttgg ttcctccttt tctgtgcaga agctttttag gttggtgtgg tcacgctcgg   43440
tgatgttcac ttttgttgct tgtgccttgg ggtcatgccc ccaaaaaatc aaggcaagat   43500
attcaggagt tttcatccta atattctgca tttaagtcct taatcaagtt tgcattcgtt   43560
gttgtgaatg gaggaagagg gggtccagct taactcttgg acacatggac attagtttcc   43620
tcaacaccat ttattcaaat gaatactatt tccccattga gcattcttga gattcttgcc   43680
aaatgtgcgc tgaccctgca cacgtgagtg tgtcctgggc tctctgcccc gttggtctgt   43740
gtctgtgtct gcaccagccc cactctgtgc ggacatggct ttgcagtgag cttcaaacca   43800
agagctgtga cgcctccagg gccgttctca ctcaaggttg ctctgtttgg ggtcttctgt   43860
ggtctttgtg gttcggcaca aatgtcaagg atctcttttg ttgttgaaat cccgttggcg   43920
gtttgcaggg acggcgctgc aggtccaggt ggctggtgtg gagccgacgg cacggcagcg   43980
ctgactcgcc tcgtccgtgg cgcggggctt cgttccgctg actcatgtct tcttcggctt   44040
ctcctcaggg ttttacaggt ttggggtccg aagcctgtgc ttcttgatca agtgtgtgtc   44100
taagggttta ctgtttctga tgctgttgta aaagtaactg tatcctttaa ttccttttta   44160
gaaagtttac tgtgtgttca gaaatgcagc tgacttttgt gtgttgaggt tttgtcctga   44220
agcctcactt aggtcattat ctctagtgtt tatctggtgg cgcctgtagg gttctccgta   44280
tacaaggtcg tgtgcgatca gcagacgaag gcggcttcgc ttcttccttt ccgatttgga   44340
gcccttcatt tcttcttctt gcctggttgc ctggctgtgg aaccctgagt cccggcacga   44400
cgaggggtgg tgcgcgtggg tgcccctgac ctgatcctga ccttagaggc aagggtgcaa   44460
cctctcaggg tcgcagtctc agctccggtt ctgtcttgcg tggccttcct cacgctggcg   44520
tggcttcctt ctatttgtct ggagttctta ctgtgaaaga aggcgaactt cggtcaaacg   44580
ctgtccctgc ctctgctgaa atggtcacaa gactttttgt cttttgtttc attgatctgg   44640
tgtattgcgc ttattggctt ggagatgctg gcaccctctt cgtccacggg acaaatcgca   44700
gctgaccctg gcgtgcgctg tgtctagtgt gctgctgagc tcagtgcgct gctgttttgc   44760
tgagagttgc tgcgtctgtg ttcaccaggg tcactgatca gtagttctcc cggcacactt   44820
tcatctggtt gtggtgttgg ggtaacgctg cccttgtgca gtgagcctgg gagtgttcgc   44880
tcctcctcag tctttttggga gaggctgagg tgaactggca tcacttctcc ttcagcgttg   44940
ggggagttca gtagcgaagc ctcctggtcc tgggcttctt gtggagacgg ctctgatgac   45000
tgttccagcc ccttacgttt ggttggtcta ctcagactct ccgtttcctc acctttcaga   45060
cttggtgctg cagtgcagct ccctgatgct agtcctttga ctgattggtc actcatccgt   45120
cttgaacgaa cacagtgccc gctgcgtgaa gcacgcccgg agaaacgcgc agatgaggag   45180
ccgggctgct gtgccgctga gcccctgcg aggaagccct cgctaactga ccgctcgggt   45240
cggaccctgc ttccctcttc cctccagtcc cggccttcct cctcgcgctc atgctttaag   45300
tttgtgatga agcatgaaaa ctagaaaccc tggacacccc gccccagat tctaagtcag   45360
```

```
gccgagcccg ggccaggcct gtgcccctcg accacgacct cgtgctgtgg ccctgggcgc   45420
gcggtgtgcc ctgccttgtc ctgtcagctc agtgctgctt tcccagttcc cagaaaggcc   45480
ggtgctgagg tgcattctgc agtcacgatg agaaccgcag ggctggtcca gccacgatgc   45540
tgggtgtggg gtggggcgc ttggaggcgg ggctggctag ctttctcttg ggtgagtgcc    45600
tcaggcatcc tagccaaggt ctccatcaat gggcagagca tcttctgttc tgcctgtagt   45660
tttacagggg ttggaaggct gacgtttctt ccccaggctc ataatatgtc acttccttaa   45720
tttggtggtc ctgtgagatc tcacatctgt ggctcctcct gagaggcgtg caccagcagg   45780
catggagacg accagagacc aagcgcaaat gcagcactga ccatcggctt ttgctgctgt   45840
ccccgtgctc cttggcttct tggaggaggt ccgctgccta cactccacca gcgcccagtt   45900
gcaggcgctg cggcgcgtcc caggcacatg gcaatggcag cggcttcccc tggtgcagac   45960
ccctctacgc ctgcgtttct caggtgcacc gaatacccg gagcagccaa ggtgccgccg    46020
caccaggcgt cgccacggag ctttccggga gcaggcgggc cgccaggtct cgcacaacca   46080
ccatcttttg ttcctgctgg gggctcctgc agccccagac accggacccc cgagatcgga   46140
gactgatgga gggcagcatg agcccccagg caggtaggca agtggcgtca gccttctgca   46200
caggacaccc gctgctgccc agcctgggag tggatggagt gctcatctct cctgcggggt   46260
ccgacaggca aaggcaagtc cctttaggcc cgtatgggga gaccccctca tccgatgatt   46320
ttggaaacaa tgaggaggga gtgaaacagc ctatggctgt cccagggtta cagggagagg   46380
ctggcaacac gaggaagaac ccaccagtca tgaagtggcc aaggcggagg ggaggaacaa   46440
ggggcagcag gacccgaggc tctcacagcg tccgcgctcc tgcgcggcct ccggacggcc   46500
ggccactgga gggacgaggg gtcgggcaag agccagcaac tttgctgaga aagccagcag   46560
acccagaaca tgtgtgccgg cgtccccagg ggccgtcttg cctggggtct gatacttgct   46620
tcttttatgg tgcagagacg ggaggtgagg gggtaaaggg gggaggctga caagttgctg   46680
cgggtgcttc ctggctccgg ccagactccg gagcggatgt gttcatttcc tccctcctgc   46740
agccgctcac gggcaggcct ggccaggctg cttcccggga gcaaacagag gcctttggcc   46800
tagcgctcag gcacgtgggc agggttcccg gagacgggcc gttatgtgtg ttttaagcta   46860
caggtgaact ccctttagtg aggaacttgc agcaaaggca acagaatacc aaggttaagt   46920
gaaagaaaca aacgcagacg gagtcagact tgtccgtccc tgttccaagg cggcagcgtg   46980
acgttgaagt agagtaacta cctattttca catcgcgcag gaaacaaacg tgctgccctt   47040
gaccgtgacc tgttcgtgag tgtccggtcc tctgtggaca actgcagatc tgtataagca   47100
tgtgtgaaat gcttgctctc ccacactggg caccagcagg gccctggtg tgcctggcgg    47160 gggcgggggt cagcgcaagc acaggagggg acttaccagg tcccggagag acccgcacag   47220
gattagaggg gaaaccccgg gggctcacag tcaagaggag tttctgttct caccagctgg   47280
agcgagaaag aacgaaataa aaccccaca cagaacactg ggggtggttg ctcagtcagc     47340
ccacacgaag cttcagagca aagccaacag gagcaggaag cgtgctaagc agagcaagac   47400
acgagaactg aacctgttta acactgccca agacctataa attctacgta aagtcaacac   47460
tgcctggctc ccgccgccga aggggaggag gcgaggtgct cacgtgcagg aggagagccg   47520
tctgcagaag gcgagccgga agtggcctgg gtgggagctg ggaggcaggc agtggtgcta   47580
aaagacgcac tgagctcgga tccctggagg aaaggctgca catgccgaac agaggccggc   47640
ccctgctccc cgctcccttc ccactccctt gctaggcctc acagacgcag ccctcccacc   47700
```

-continued

```
tcccggtcag cccacctgag ctcacgtcca ggccccccta ctgcctcgcc tgtggccgtt   47760
acctggtccc tcaggtgacc gcccgggggt gggtgctagc agccccggca ccctctgttc   47820
tcagtatctc cctgggagga agtggccact gcacgtggcg cagacctggc ctcactgagg   47880
accctccctt tgcctgttct cattggcaga tgccccacga ggctggcaga aggcctggtc   47940
accctgagag cagccctctt gccgctggga ctctgggcgg tgctgggact ctggacgccc   48000
cctcatggcg ctgcagtggt gtagactgac gggcacagcc ggctcagaag ccggaggtca   48060
caccccaccg cgtctgcctg caaacaccac gacaagaagc tgccttcagt gcacgtctcg   48120
cccacctgaa gggaggccag tctctgcctc tcctgtttgg ctcatcagct ggtctcggtt   48180
tgctcctgtg ctcagaagag cctctacccc atccgacgtt gcagactctc ctagagtttt   48240
catcaagtca cagtttctta tgttttgttt gggaaaaaat ctcagccatc gagtccacaa   48300
atattggatc tgctgcatgc tgtgtctcct gctttgttct gttagcacac gcagggctgc   48360
tccggccgcc cagctgcccc gcgtgcctcc cgttccctgc agcaaacccc tgtgcctgtc   48420
ccacacgagt tcccaagtcc tccacactgc agtctggggg attccccagc ttctcaggga   48480
gtgacggaca cgtgttgttt tgtgtcacaa aaagaagcaa gtggaattac tctgtgagcg   48540
ggccggtgca agcacctgac gcacaggtac aggtctgcac gtgtgcacag accgccggga   48600
gaccgcgtca gagaaaacaa gacgctcccc tccagccctg ctgccggcgt ctctccccac   48660
gaagccaaag cccgcgccgg agagggcaaa ccgtcttaca gcttccgagt cgccccatct   48720
gcgtgggccc cgcgtgctca ggataagtga cagactaagc acgagaagac ggggagccac   48780
aggcggtccc ctcagctcag gtgtgaccca ccggatagcg gcttccaccc tcccgtccca   48840
cgtggccttt caaagtgtgg gcaggttaac tgatggccaa taccacccgc cgaggatgaa   48900
agcgggttcc cgaggcgggt ggggacagga agggggtggg ctgttcttgg ccgtgtgtgt   48960
agcagccctg tcagttccac aggtccctcg agatacagcc tccttagtgc gggctggaga   49020
gtggagtgca gtgacctcag cctggaggtg agcaacctgg aacagggcgg caatcacacg   49080
cccgctggca ggagcaggac cagcagcggt cagggacccg gggcttcccg agggcaccca   49140
caacaggaca gactccagag gagcgcctgc agtggctgcc accggggaag tctcgccttg   49200
ggccgtgtgt gagccccagt gagggctgtg cgctccgggc ctggggccga cttgaccgtg   49260
ggcagagagc aggtgagagt gcctgtgtgg ggcactgggg caacaccagc tgtgaggttt   49320
ccccataaag tttgtctgca gaagctggaa caaaagggaa ggcagggctg atggaggagg   49380
ggtcctgggg gccttttttgt gtgtggctga agggcacagt gtgcagggga gcagggcctc   49440
cctcgccagg ggggcagagc agccggacgt gaagggtgaa cgtgagagaa ggtgacggag   49500
gcgtcggtcg agcaggcttg gccacaggcc ccccgccctg gcaacgaggc gctgcgcagg   49560
atggatgggc agagggcggc ccccgcccgg gggcacaggg tgagagccca gccttgccgg   49620
ccaaggcagc tgctgggggc gctgggcagg ggtgtgcctg aagccgcggg gcctcggcga   49680
cgcggggcgt gcgttatggg ccgtgcctga gaggaggaag cgggtgcccg gtgccagcgg   49740
cagtcccatc actgtcaggg cgatgcgggg gaagacggct ttcaaagtaa gctgagagct   49800
gccggtgtgg acggtgctag ggtggaggct tcggaggagg ctagtgcctc caagggccg    49860 caagcaggct tcgaggggcc tctggggggg gcacacaagc tcagcaggag cagcagagtt   49920
tggggtccac gggtggcggc agccagctgt ccctagagac agacagggct gctttgccgt   49980
ggggtgggga tggaccagct gaccaggcac tgggggctgc tacccgtgcc ctggcgggcc   50040
ccgccgctcc cacccactgc agtgccggtt gaggggcttt gtgctccttc ggctggcgcc   50100
```

-continued

```
ttgggccagg agggtctcca ggagctcccc gatcggtgtg caagagtgga gcctcaccgt   50160
gggcctcaag ggcttgggag acactgaggg gggcccggac acccctgagg gaggcaagcc   50220
cttctgggct gccttgctct tgctctgagt gctaaggcgg agggagatgc cggtcagggg   50280
gcagtgggag ggcagcggca ggtgagcaga ggtcagcacc tgagaacccc tgtgtcggca   50340
gacggaggta ggaaggcgcc tgcaggcggg gccaaggggt tacaaaagag cctggggctc   50400
ttagaccggg aacagatagg cagaggggac tcccatctga attaaacccc ctcttccttt   50460
gccagcaaga ctgggcgtta cagggtgagg caggaggaca gggacccctg tgtagccaag   50520
ccctcgctct gcacagagag gctggggctg ggccgccaac gggaggggcc gcgcctggtc   50580
caggcagtgt gtgcaggcgc tccgtgctca gcagcacgtc acacgaggcc agacatgagg   50640
cgggcgtctt ccaaagactg caccccactc agaggacttc cagctgagct gggcctcctt   50700
taaggaaaga ggaaagagct ctggtccgag ggcagagcag tagggtgctc cctgtcctgc   50760
ccgaccgacc gtcagagctt cctcctgctc agacacgttt cagctgcctc cttgggtcct   50820
gattccccgc agaagctggg ttgtggtctc agttctagtt tggctccgag gagcctgggg   50880
ccaagtttca cagcctgtcg gacaccccag gagagagctc caaccctgcc catgtgctgt   50940
cacccctccc ggctgccccg ttgctggctc agggcctgtg tcagcctgtc cagccccagc   51000
gctgccctcc ctcagtgctg cagggcacac agaccctgcg ggctgctgcg ggctctcgag   51060
acggggctgg agccaggctc cagagcagtg tgttctggga tgtgggttgg ctccccgtgc   51120
tgggaacgtg gggtccagag ctggctcagg aggggaagct tccctcctc ccgaagccag   51180 aggagactgg aagttagatg ttcctctgca cctgcaccct ctctgtgagg gcaccgggct   51240
gggctgtgtt cccatgtttg gccgggaagg gtcaagaggt tgggccagag cccttgacag   51300
gcacagggct ccctcctacg tggtccagag ggaggatgca gggacccgca aaccccccaag   51360 ggttgtagga aaaagcgttt cattggccct gctgcagaga tgagggcctg ggaccacacg   51420
gctgttcttt ggtccgcacg cccagggtcg gtgatgctgg ccaggcttct gaactcacag   51480
cttcactggt gccgggaggc cacccgcccg tgtatgcagg gctcacctgt gaggtgcaag   51540
gctgggagtg gccggagtca ggaaagggcg acagctgggc attgagtcct cccagcagga   51600
gacgcactga gggcgcaagg ccacggcggt gcctgggact gtgcacaggg ctgtgaggac   51660
gcagcctgga gcccacccgg gggaggtgct gggcatcacg gggtggcctc cgggctccgc   51720
aggcttgtgg ctcacttctt gtccgggctg tctcctctct ccacaattcc tgggggtcac   51780
agggtttcta aagctcagag gtggaaggtt ccagaaacac ttacccacct tcaccagggc   51840
tccaggaagt gagaaccccg gggaccagtg ggagaggctg ggaggggggcc gctggccaca   51900 ggctggaccc acgtgggagc gaggaggaat tgttggagga agggctccca tccctcccca   51960
aaacctctcc tcagattcaa gagggggcttc cctggcccgg gcccagcctc agcccccttct   52020 cctgggctct gccctcttct tcacagacac ccagctcccg ccaccaacac agggccgcgc   52080
tgccgggcag ccagcaccgc ggtcactctg gctgggggc tacttcatca ggccacgccc   52140
caggaggaag agcccccctgg gcagggccgt gaggacgggc cacaccgggg cacagggcca   52200
cggagccaga cactgcactg ggaggcccca cagcaagcag ggaaatgccc aggagagctg   52260
cagccccacg gccgctcgtc agggtcctca gctccagggg ccctgccggt caccttgtgg   52320
ctccagaggt gacctgcagg agatgcaagg agcagtcagc tccccccggc cctgcctgga   52380
gtggcctcag tgggaagccc gaggggcagc tgagcaccag tcctggaagg ggtggccgga   52440
```

```
cactcctgcc gtctgcaagt tcacaccatg gggcagacca caggcctgga gcgtcctctg   52500
tccagaccca gcgctgaggg acgggggcc gacccgtcca cactgagcct gcacacacca   52560
tgaaccctgc gctggactcc aggcactctg cccacggtcc acacagggtc agctagacca   52620
gtcctgaccc ctcatccagg agccagggcc cctcccccc caggatgagc tgtgaccact   52680
gcccacttgt catctttgtg taacaagctt gcctctcccg tggagccctg gctcggccgc   52740
cagggccttg tgcagagccc tcccccacgc cccagcctct cgggccgcac agagggtaag   52800
gggtaaaatc ggcaagagcg gctgctgtgg atggtggtga gacggggagg ggacgcgcag   52860
gcgctggtgt ggggtccgcg caagctgctc ctgggaaatt actgccaccg catccctcca   52920
ccctgagcat cttccgtctg ctgttcctga agcagctgtg ccccgcccaa agctccagaa   52980
ggcctgcaca gagggccgt gcctgtggag ccaaagccca gccagggcac tcgcccccagc   53040 agcccggccc ccgtcccgct ccgggagcag agggcagctc acgtctccaa gcgccgggtg   53100
tggctagcag ctcggggtct ccacccacac agctctgggg tgacctgccg actcacagac   53160
ccgggcattg ccgtgcgagc tgctccaggt ggcagaggga cgtggaaacg gccatcatag   53220
gaaacctgcc cccacgcccc caaaaggaga aacgggctga tctgcacgcc aacaaagagc   53280
cgacccgggg aagccggatc ccgtccggcc cctcgaacgc actcagacca ggactagggc   53340
tgtgcagagc gcgccctggc gccagacggg tggcggcccg tgatcctccc agtggaggac   53400
agacccactc tgttagcaaa gtccatccga cagaacccct gtgaacccg ccagacgcca   53460 gggtgcggcc acctctccgc tccacgcttg aggggaccct gaaaagttga cggaatacat   53520
tttgtattta aggccggatg agaaaatcca agcccaacgt ggtccctacc cgaactgggc   53580
cctctctcgt gtgctctgag ccctgcgtta ccggtcagcc acagcttctg caaccggaag   53640
tgcctgctcg gctgtgcagg gccttcttcc cctttgctct gacgctagca agctaatgag   53700
cttctcagga gtgtgggctc tcccagctct gcagggtcct ggtgacctgc ggctggctcc   53760
ggccacggat cctcactcaa cctcgtgcag aacaccaggt ggcatgtcca cgtgcgagcc   53820
tttgtcccaa aaacctgtgt gactgtgcct tcgacttcta ccaggcggag ccatccccgg   53880
agcttctgag actgtctccc gggttataat cctcagtttc gctcaaatct aatcctcttt   53940
ttccttcttc acttgactgt tggttgggtt ttcatcggcc aggtccagtg aacaactggg   54000
aggccccccc cgctctgggc tcagcagccc ccaccctgga gacgtggtgc tgtgctccca   54060
cggacccctc ccggggctcg gcagaggagt cctggtctta cacactagaa gtagtgggcg   54120
ggacgctgac cccaagtcct gtctgtgtgt ctagcacatc tggtgggacg gccctcagag   54180
agcgctcaca gccgtggtgg ccacgcagca aagtcacact tggttggtcc tgggaccagg   54240
aggagcactc gggccagcct ggaggcggac gctcgaggtg ggagggccag gccggagcct   54300
ccaggccgac cacctgaccg gaaaccaccc actccgtgcg ggagcatccg actccaacgt   54360
caccatgtca tctgtgagcc gcaggagaag gctggcgacc ccctgcaccc aaagggaggg   54420
cccttcccaa ggtcagctgc tgggctgggt tactggtcag tccctacct gcagccccaa   54480 agatgcaggg gtgtcccgag tgcccccagc aggcccagca gacacaggag accgcgtggc   54540
tgcggggccg cgtcccccaca cccacatctg gctcccacag ccccgcctca ggcctgagga   54600
ccccgcaatc cgccacaggc tcctggcacg tcggactcac gcccaggacc cttgcagctc   54660
gactgcaggc agagggccca gagctccctg acagccgctc cccgaccact cccaggggac   54720
cctcagtggg cagcccaccg tggacaggca ccacctgccc tttgccctct gaatccctga   54780
cccacgtgtg cccgtcccca aaaatggcct cgctgggtcc cagcctggga ggccccggct   54840
```

-continued

```
gcccccaccg aaaggcagag gcacagagtc tttggaagca gagtccggga gccgttccca   54900
ctggaagctt gggcattcag gccctctcca tcccagtaac tactctcgta aacacggaca   54960
cgggaggacc ggctcctgcg caggtgcccc cggcctgaga ccctgctgct gggacgcatt   55020
catcccgact cagggcacca cacacccagg gacgtgtcct cgtcctagtg accactttcc   55080
gcacaagtgc tgccgggtca gcctcgccag cctcggcgcc tttaagcccc ctcagctcct   55140
ggcctccaga gacactgcgc tcgcagtggg cacggagtcc tgactccacc cccgcatcca   55200
tcctgggccc tcagcgcatc cacggggtca cccttcctgg tccgtccgcg gagccctgag   55260
cccaccccgc ctgcttctgc ggggcccgcc cgccacctct gtgcacacgg gagagactcg   55320
gctctcccct gctgtccaca gcgacggtgt gaagccagtt tccaccactt taatggtcca   55380
ggccctggac agtgaaggca gagcctggcc tttgagaccc ctcacaggcc aggccctcag   55440
gccaagccca gctgcaccag ggctccaagg tcctcgctca cccagggatc cgacctcctc   55500
tggccggcgg ggccctgggc agggtcgtga gctccccgag gaggagggcc ctctcacgcg   55560
aggacaggga caccccgacc acgcccaggg tgagccaccc gtgaccagtg ctgtgaaggg   55620
gacacaggga ggcccccact ggcccacagg tggggatggg cccagccatt cgcacccagt   55680
cagcgtccca ggcccagctg actgacgtaa gtcacaggcg agaacccaaa ccactgtcgg   55740
cgtcttccag gagtcgtgag atgcgggcag gggagccaga ccctggctgc tcacgccggg   55800
gacatggaaa ctctgagggg gcccagtcag cagactggac acaaccagaa gcccctgca   55860 ccgggcagac ggaccaccac acggacctcg gtggacacca gggctgcctg tgctggaaag   55920
gtgggtgcct cgtcccccat gaagggttgg gtcagagtca cccccactca cccgagcaca   55980
cagccgaaac ccactggaaa cgcaggatct ccacctcaga gccggcccgg gccagcaagg   56040
gtgggcaccg acacaccaca cagacggacg gaggattttg agagggtgtg tgtcactgtg   56100
acatactata gtggtagtta ctactacacc cacagtgaca cagcccctgc ccaaaagcgc   56160
cacccgacat gcccgcagga agtggagctg ggcgtgtgca gaacacccag ctcctggcca   56220
ggaagtctcc ccctggggca gaggcggggt gatgcacagg agcagctccc cgatgagaag   56280
gaagaggcgc actgagacac aggccccttc aaacgagacg gatgcccggc ggggcaaggc   56340
actttgtgcg ggtgtctgga atccccgagc ccctgacctg ggcccaccag gagggagccg   56400
gggggctgga cgcgagaaca cagacttgtg cacttgatca ccttcagtgt ttaccctgtg   56460
cacacaccgc acctggaagg ggacttcgga gtctgatgga agggtatctt aagaacatac   56520
tgcctaaggt tgctggaaac cgcacgaagg cctggaccac ggattttgtc ccctggggag   56580
ttgtggcctg gggcatggta cccccacctg ggaacatgga ccaagggccc agagcagtgc   56640
ccacccactg agacttcaca gcaaaggcat cactgggggcc tccaagtggg gacgccaagg   56700
cgcagagcct ccaggaaaga tggggggccg gtggggcagg ggccccaaca aagggccagc   56760
ccttcacctc cagaatctca gggggaactt gaccaaaatg gacgaggcca gccacagcct   56820 gggcacccc aacagactgt gctgggccac accgccgtcc ccgtggttct gggatggacc   56880
agaaacggag cacggggcgt ccccgaggga gcacactgaa ccagcctgtg agctggcctt   56940
gagacaagtt gaggccgtgg gacccaaggc cacgaccaca gagcacgttt gcagcacgca   57000
gcaaacaatc gctccatgca cgcatcgatt gtgtaagatt tatgagcaaa gaaacccaga   57060
ccgcgcacgt gctgacagga aacaggtaaa agcaggacag gtgcgtcgca ggtgcgcacc   57120
tcctgtggca gtaaactgtt gttaaccccc tggtgtctcc ggctgcagcc tgtctggcgg   57180
```

-continued

```
tgtggcaact cctcgtgcat tttttcgttc gggtcgctca gctcctagaa ccccacgtcg   57240
gcctccctcg gctggcacag ccagagcctt taggcctgac catgatccgt gacccacagt   57300
gaccaccaag tagatgccca gaggccatga ggggccacag agggtcaggc tgggccgtgc   57360
tccgggcctg gagccgtgag ggctcaggaa gagggcgccc tgcactgcca cagccaacgt   57420
catcctcgca ggggctccgg acgctcagga agccacccca gagtgggagc agtggggctg   57480
tggggccggg gaggagaggc agccggaccc cctcggctgc gcaggcgcca cgtcctgctg   57540
aggctgcgca gggctgcgtc ccggggtgga aagtgcagct cggacctgga agcccagggt   57600
ggcagcagga tagacccctg cctgctcctg gcctccctgg atggggcacc agcaggcccc   57660
tggaggacag aaggcccccca ggcgacccat acacagtttg ggggcaattt gtcaacccag   57720
gaggccgtca tcgtgggacg aggctccaaa atgggcacag acaccaggtc actgggcttg   57780
gccttgcctc tgggcctcgg cacacggccg ggcatggtcc ccgtgcccct gccaggagag   57840
gcctcccagg tgctcccagc aggacatctg cagccccgag cacgacccgc agcctcccag   57900
ggctctgtgt ccatcactgg tcagcctgta catcccaggt ctcccgcccg gcagaggggg   57960
ttagggcgtg gccctgtgtc actgtggtat tactactgct caggctatgg gtgttatgac   58020
cacagcatca cagcgcccag caaaaacccc acccctggga gtcagagaca cggctctgcc   58080
cctaggattt tgagtgacgc catgtaaccc tgggtaggac ggtcaccaca ggggtgcaga   58140
tcggcaccca gaccacctgg ggcagcgaga ccagggaggc accccagca caccacccccc  58200 caacatgccg ggcgggccag tcaccaacat cactcctgtc caagcccatc agaccataaa   58260
gccgcccaca tctcagccag actcgctcca cggggctcac ccctgttgac ctccccaaca   58320
ccaggagggt cccaaggccc ctgtccaccg gcatccggcc agtggcctgg gacactccct   58380
ccctggggca cctggggggcc gtggctggag gcacagagac cccactctgc aaggaccctg   58440
tgagcctcca tctctgggca ggggcgtcac acaggaaagg ctggaccggt gagctggcac   58500
tgcccccgct ttgcggagac tggacctccc ggccacacca cccatcgaac agcaccccca   58560 cccccccatgt gctatcatac tggttggggg ccctgccctg caggtacaat atgggagagt   58620
ctgtcacctc caggggccgc tgatggtatt tggtttggga aacgctcttc cgagaggaag   58680
ggaggaccca tgtgtccaca tcctggcgct ggcctcactg gactgtcccg cagagcccag   58740
ccgtcctcgc caggggggccc acccaggacc ctcactgcac gtgtgcactg gcacataagg   58800
agacctccag aagtggttgc ccccagacac ccgcctccac ctgtcctcag tcagatccag   58860
gcacggaccc cccagcctgt gtgagacccc cacaggagac gggccagccc cccagggcag   58920
cccctcagcc cggtccccct ggacccctga gaggacttgg gccctcccgt ttccctgtgc   58980 ccacccccttc agcggggggc acgcccgccc tccctgggga gacggtggga ccagtcccga   59040
ccacacttgc agggcaggtg ctgggcacct gtgcagacag ccccactgga cgcctgcacc   59100
tgggcctcca gcagggaagg actcggccag aaacagggct ttttgccaag gtctctccta   59160
ctgtgttact atagcgacta tgaccacagt gacaggcccg gcagcaaaaa cctgctggtc   59220
aggaggccag gcctcagggc cacagagccc agacctttgg cctccagggc tgctcctgct   59280
ggcttggccc acaagcttgt gtccaggcac agtagctgag ggcttcacag ggctctcagg   59340
tgaccacccg accccccaca gccacacacc cagagcccag caagagggca gaaaccaccc   59400
tggctctcga cacccccacc caaaggaatc aggaaggatg gagcccacac caggcaagcc   59460
agcagaggtc aagctcccaa gggcaggccc cagacaccct ccccgtctgc ctggaagccg   59520
gacaagcgca caggcctgga cactggagct gggcctgtat tcggctgcat aggagctcgc   59580
```

-continued

```
tcgctgaggg aagtgggcag ggttcatgga gggtgggagc atctcccagc ccagtgccag   59640
tcgaggagca gggttgtgct ggctctcccg agggcatggc cggagctgcc ctgtgctaga   59700
agccttccca gagtgagcag cctccggagc aaggcccggc ccaccctcgt ctccttccaa   59760
gagcaacagc atggccatcc acccaccccg tctcagccct gccagggcgc tggggctggg   59820
ctggcctccc gacccgccag gtccctggtg aaggatgtcg cccaggggca cccctgcctg   59880
accctctgct gggctactta gggtccggcc catcctctgc aggctctggc ggtccccac    59940 atccagcctg cctaagcgcc tgccagccca gctccctccc ggggcccatc atgagccact   60000
caagcaccct gatcactacc tcatccctcc cagcccaccc caggggcctg cagactgcag   60060
accccagtgc caaccccagc tactgggcac atgcccggcc ccaaggcagc tccagctcct   60120
ctgcagatgc ctggaccctc cctgtcccgg ggaaggtcct cccactgacc cagcctccgg   60180
gacccaggcc ctgctattgt cacgggctgt cagtcagggg ccatatgact tcagcaccca   60240
tggcgatgct gcccacaggg cgagctgggc actgccccat catcaaccac accctccggg   60300
cctcggtctc tgacctcaga cctggcagct cacccctttg ggtctggggt cctcgaggcc   60360
gctgacctct ggcctctggc ctctggcctc tggctctgga gggataggcc tgctcaagca   60420
ggaggcctga gctctggagg ggaactgcag ggctgagtca cacaggctgt tgtggacacg   60480
cagtgtccat catggtctga ggggcagtgc tggggtcagg gtcagatgaa acgagggtgc   60540
aacctgggcc cccacaggca aagcctgagg ggccacagtc ctggggccag cacttgtggg   60600
acagcacaga gccaaggtcc agcacccaag ggattcagct cagtgggtgg cccagctgtc   60660
agggcagatg gagcccaggt ccagtggcca cccacatccc aggggaccat gagtgcagag   60720
ccccaggctg gactccacag acctgtcaca agtacacccc tcttcctccc atcagccccc   60780
ccatagggac tccatcggca cccctccaca gcagggaaac tgaggcacag gccaggccca   60840
cccagccagt gaaggggagg ctgggagccc tgggaggcag cacagaaccc tacctgcacc   60900
aggccacagg agccaccccc agagacaccc tgcccccacc ctgagcctgc aggtagggca   60960
ggccagtaag ggggctgtgg ccctggccgg gataggggtga gcagctgtgg gctgtgtgtc   61020
cggccccagg ccctagtcct ggcctcctct tcctcccctc ggacctccag gatccctcc    61080 gtgggaagag gaagtcacag aggatttagc aggaggattc atcacagtga gactacgggt   61140
tggggtacca ctgtggctgg ttacatagca aataccagcc ggcacctcac ctccagggc    61200 agaggctgga gtggggtgct gctcagggcc tgaacccgtc caccaagctg accctgccag   61260
agctccgtga aaccagccca cctccccacc aaccccgggt gttgtcctct ctctcaactc   61320
caatctccca tcacccagca cctagcaggg caggtgtgga cagagtggcc aggtgcaggg   61380
agtggcgagg gcagctgcag ggtccagggg atttcagctc aagatgcccc caaccccgct   61440
gccccaggcc caccctggc tcagaggagc gtgctggagg ggagacactc tcatgctacg   61500
agcaactgga cccagaagcc cctgtgtgag ccctctgcct ctctgtccag tgggactccc   61560
tcccacagtg gcatagtgac tgaccagctg ggcagcaggc ccttggcatc caggacggac   61620
cccacatgca gaggaggcct ggagccagag ggagctccga gagccggccc agcaggacgc   61680
caggccacca gacctgggct cagactgcca ctagggccca ggacagccaa gctttgcccc   61740
tgaaggggac attttctatg gccacagtgc aggctgggca cagggacctc tgcctcatag   61800
cccacccccc atgcggctca tcctgacccct ggaccaagct gaaagcaccc aaggagtacc   61860
gcacagggag tccccgccct ccttcaggca agaccaacgg gttgctgaac cccaacaggc   61920
```

-continued

```
caggaggttt ctgatcctgt ctgtgtcatg gtggtacggt agtagctggt accacagtga    61980
cacacccagc gccagaaacc gccagcccaa gtggcctcta ccagggagcc cgactggatc    62040
tgaggtcccg gccagcagac ggccccacac cccaacccca cattctcggg ggacacaagg    62100
gtcctgggcc aggaggtggg ctgcccccc ccagcagctt tccgcccag gtgccctgac    62160 ggattctgtg ccggcctgcg gaggcgtggt ccaccctggg gctggggttc agttgcctgg    62220
ggacactcag gagacctgcc tggagcctag agcccaggca ggctcagact caaagggcaa    62280
gctgctggcc ctgtcctgcc accaggaaac cctcacccag cagcccactc ctcagcacgg    62340
aggcccccag gccagcagtg tgaccgggca ttctgagcag ccccgagtca cagtggaact    62400
ggtggcacct acaccgtaag aaaggctgtg gcttaaaccc gcccccaggt ctccgggggt    62460
ccaggccccg gctagagggc agagagtggc tctccagcca ggcactgtcc tcagacccctt    62520 gggtgacccc tacagatgcc cctcggtgcc ccatttcctg gtgagactag ggagctgggc    62580
tggtcagtgg gggctgggcc ctgtccccac agccccgctg tggctcccag accccctggcc    62640 agtgctatct cgagtgtccc aagctggagt gtcccttcct aacaccactg gcccctcgtg    62700
cattgtccag ggacacagac acactcagaa ggcctaggct gggctggccc catgcgtcca    62760
ccaggaccca gacctcccgt gctctgcccc tcgcccgggg caggctgggg tgccagctca    62820
gcgggagaga caccgctgtg ggccgggacc caaccaggtg tcaggcccct ttgctgaaag    62880
ccctgccagg cagccagcac agaaggtggt ggtcagttgt caggccacca ggcacagggc    62940
tcctagctga ggagggccca ggaagaccac cctggagagc cttcaccctg ctcccacctg    63000
cagctcaacc cactgccctc ccctcgcggg agcctctgtc tcagctcggt ggacttgccc    63060
acggcagaca gcggggctac cccagcccac agcaggaccc cagaagcctg aggccccgt    63120 ggggcaggc aggtgggct ctgcatcaca gaaggggcca ccaacctgca cctgcccacc    63180
tgtcacctcc aagccttctc caggagggtc tggagccccg acttggggcg ggggctcagg    63240
gcggcactca ccgagctccc tccttgaaga ggtgaagccc aggagccggg cacacacagg    63300
ccagcgctgg tcaccggtgg ggccacagcc tgaggacagc ccagccccag gcagcctgct    63360
ccctgctggg agacgccccc ccacccaccc agccacccca cacacaggaa gcagacaggc    63420
tccaggccag cccgggcctc tcaccgcaga gccgcttcct gactcccctt cctgccctgc    63480 cccacccca acacacacag gcctgggagg ttgtcagtga gttttaacgt acagcctgga    63540
tggccctgcg cagccttcct gtgatttgtt ttccttcatt cttcactcag tccttcatcc    63600
atttatcacc cagggcatct gagcagggca gggctgtggc cgcagctgga cactggccac    63660
actgctgtcg gtggacttga tcacaagtgt agcttgagtc cgtgaaggga ggcacagggc    63720
acgacacgga gggtgggtct ccctgcccaa tctggtctgg tgtcagtcag ggtgacttcc    63780
tggaggaggt ggcactttta gctacagttg gagacaagga gcaactaggg cttggtgaca    63840
ggactggggg gtgagcaagg acaccccaag gttctgcctc cacaggcatg ggggacacag    63900
ggactcagct ggagaagcca gaggcttcag gccccaggag gactgcccac ggagccagag    63960
gcagggctgg gccaccagga gtcccagctg agagggccac agaggggtg cggcatgcgc    64020 agggacctg tgcagacgag cacatccgct gggccgggcc cccaccaggc cctggagacc    64080
atgcttggcc aggagagccc ccagcagggc cgtggctcct tggacctgaa caagccagcg    64140
cccctgcccc tgggcggggg aaagggtccg agggaggact gggatggcag ggggggcacca    64200 aaggccctcc cacccggctc cgggtccctc agattgtaac cgagcaggat cctattgtca    64260
tcagtgacca cttggcattt gtaactgctt aactgtgcag caatttaaag catgtttttgc    64320
```

```
tgagcagcct tgggctggag aggaggcagg actcgggccc aacccctacc gacacctcgg   64380
agaagctgtc aggtgtcctg tgcaccttat ggctcgtaac tcaccccact gcacatgtct   64440
gcattgttta tagccccgcg gggtttcttt gggttctgtt gtcccagcct gggcagactc   64500
tgcagggaga ggtcccaggc ctcagcccaa aatgccagag gcatctatca acctgactat   64560
aaatggcaca cgttttttctc tggagcactt ttccctggag cccccttccta agcaccctcg   64620 ttccaggtac aagaatatta agagagtccc aaagctggag gaggacttca cacccagcag   64680
agggaagggg gccctgcatc tgcaaaacca ggacaacttt gccacaagct gctacctgag   64740
cggggttgta acagaagaga acaaatctga ctccacatta gatctgttcc tttggcttta   64800
accctgtgcc ctgtttctcta ggcttggtct tgccagctct gcgccttttg tagaacaatg   64860
ttgccttcag cctgaaatac acaggagagc cagttctcaa ggatattaac tttcgtgctt   64920
atataaagat aacaagttgc agaataaaaa ataactcttg ttctgttaga ggttttatgg   64980
gggaaccgtg acttgacccc cgtggacagc tacaagaaca aagaagtttg caacacccaa   65040 ccacacccc ttccctttt agtataaaag gagcctgaat tctgactgga gcaggatggc     65100
tctccaacac attagcctgc catcctctcg ctccgccatc ttcccgaatg aagtcgctac   65160
tccttgcccc agcacctcgt ctcccggttt attggcctgt cgtgcagtga gcagagcgcg   65220
tttggactcg gtaacagggt ctctatggaa accagctgcc ccttgaactt ttactataaa   65280
accccgcccc cctccccagc aggctcgcag cccggaagca tcagcccgcc gtgacctcct   65340
ttgccgggag aaggagtaca gctgcccctt ctgcttcatc acaacctctg tcctcaagtc   65400
tcgattcggt gagtggagcg cggaggctgc gctttgacag caagaccatc tccatcaacc   65460
tttatgcaca agggcccccc agaatctcac ggagacgcag attcagatgc ccaggcaacc   65520
ctgagccact ggtgcacatg aaggggaccc cagagagccc tggaagcgcc tggactagcg   65580
cactgctcag acagcaagtt gctgggaagg aggctgctga gggcgccttc ccccacccatc   65640 cctagccacc cgggggtccc cccctcagaa agcccggccc ctcacacccc accgcaaggc   65700
ctcaaaagcc ccctccctga ccacacagcc gtctgcctgg agctgagcgc tgacctcccg   65760
aggtccctgc agtgacccca ctccgaggag ccagggtgca gggcccccct tccctcccct   65820
ccatggaagc cccagcctca gagtgacatg cacactcaca cgctcaggca cacgcacgca   65880
cgcacactca cacacccca tcgccctccc tctccagtcc ctgtctgccc cccgcccat     65940 gtgcagcccc gtccctgcca ttatgcgggc tgtcctcctc tcccccagc cgcctgtccc     66000 aggcccgcct ctggactccc cagcgcccac cgctctgcct ccagagtcac agtttgcagt   66060
gtccgcccaa cgcccgccct ctctcctctt tccagctacc tccctactgc acctacgacc   66120
ctccccactg cacctccgcc ctctccacct acttgtgtcc cctccacgcc cctcccctcc   66180
ctgtggccag tcctggtgtc tcctcgcccca acaagggcaa tgcaatcctt cacccccccgg   66240 cccggcccac tcagggggact gtgacccagg catcactctg actggtagcc acacaccaag   66300
gtgtgcagct cccactccat cactctctgg ggcagacacc ctggtgctcc attgcccctg   66360
cccccatcct tcccgacaca gtcctctgca gcccagggca gccacatgac ccttgcctgg   66420
acagtgagaa gagacggcgg ccggcaagcc atcgggcttc cggaaggcgg ttcgctgtct   66480
gcccatccta ggatgcagac gcagtggtgt ccaggttctt gtcccgtcac agaaagaatt   66540
cagacatgag agccgggggt taagaagtaa agtggggact tactgaggga gggacaggac   66600
tgtctcatgg ggagcgcggg cagctcaggt gagcagctgc cttgtttctt tggcaagttg   66660
```

-continued

```
gttacacagg gtgtagaagt gaacgggcgg aatattcact ggggagggca ggtttagggt   66720
cgtgttcccg gatcatcatc ccagctcccc cttcccgtgg gcaggaggga tttttatttc   66780
ctttcttagt ctggatcgga agtgtcacgg tggcggtgcg tgatggggac ttctgatccg   66840
caaggctgat tttattgaaa tgagggcata aagagcaaag gtcaccttca gacactggag   66900
attcctgcct ttctcacctt tctttgttct tctccaggcc acttgtcacc ccaaaaagcg   66960
tgatccctta tcagcccaga ggttcctgct tttcctttgc tgcccaggga cccctgctgc   67020
ccacgtgatg tgtgcttccc tgcgtttggc ctgtgcccct ccttcctgcc cagttcctgc   67080
caactggccc gcgtccccct ttccctgctc atacccagct gtctgcctgc tctaacagct   67140
ggaggtgagc agcctctctg cccaccaact aaaggcagca gacagatggg acttcagtca   67200
ccgctggtgt ttgcggctcc tctgctgtca catgggaggt ccaccagatc gaagggcttc   67260
cgccacatcc agcctgactg agtcccacgg aggggcgtcc gacaaccttc cccactgcgt   67320
cctgtccaga ctccctggtc ccaggcagcc ctgtctgccc acctgactca tgtcctcttc   67380
taattcgcca gaataataga aaagacagaa aatagaaaca gaaataatag aaaagagccc   67440
tcccacctgc tcgccggcca acccgcttgc acgtgcgcgg ggccctgggg ggccccagcc   67500
acaccagaca gaggtggcgg cgtgctgtgc aaggggcagt acgtgggcgc acgcacccgc   67560
tgttaccata acacgaaaag agcagtgtct atttcaactt acagattttg tggtatgagt   67620
ttcttttttg ttaaatgaat gttatcactt aattgaaaca gcagaaatag tgccaattag   67680
cagtaagtaa cagcaggact aattaaacaa atggtatgta tttacaaatc taacaagaca   67740
gagggtacag ctcagtggtg gagtgtgtgc tcagcgtgca cgaggtcctg ggttcagtcc   67800
ccagcacctc tgcttgaaga agtaaataac cctaaatcgc ctcccctgc agaacaaaca   67860 aacaaacaaa tccaacggtg tgtctataat gtctctctca ctctcggacc tgccagttta   67920
ctgtaacatt tttttaacac tctagagctt tatttacact tctcaggctg tgttatggta   67980
tgttcttcag atacataaaa gcaagacttt tccagtgggg gcgtaaacac agcagggcca   68040
gtacagacat tcaatagcag taacagtcac gcctctgtcc catgctcacg tctcaccctc   68100
agtattccca gcagctgggg gatgccctgc gcctctgccc tgaaggcagg cagccgtcag   68160
cctcagggcc acccgacccct cgactggcgc ccagcctggc cgcgccgatg ccggcggcat   68220
ccaccgtgca gacctcgagc ctccaggcca aagcgtctga gcgcacagcc ctgggctcac   68280
gcagtccttg gggctgcagg cgcggttccc agctctccaa gcgcgcactc tgtgaccgag   68340
gctggcgccg gtggcgcctg cccctccgcg aggccctttg gttcacaagc gcttcctgtg   68400
ggctccctgc gtctgaacat gcatcgggca tcctcctgag ttagacctga gagtgtctca   68460
gagcaaatgg gcttaaagca gccatttgag cctgtgagat ccaagctgga atccaagcaa   68520
gtcgtggtcc cggcagaaga ctctacgacg cgagcctcag gcccaggcct gccctccccc   68580
gcgtgctctg gcctccaggc cgtctgcgct cctgtcccct cctccctggc cgtgtaacag   68640
ggaggagcaa gcctggcccc acgttgcatc tgttccttcg ggtctcaccc tctgctctgt   68700
accctgtgct cagtcaggct ggttctgcgc cttttgtaaa ggaatgctgc cagagcctga   68760
aatagacagg acagcccgct ctcaaggctc tgacctctaa gggtagaaca ctttcccatt   68820
cacatagaca aaaactgcag aacagagagc aacgtttgtc ttgttggagg tttgcaggca   68880
caccaggacc tgacccacgt ggacagctgc aagaacaaag ggttctgaaa ccaagaagtt   68940
tgcaacaacc aaccacaccc cccccccttt tttagtataa aaagagcctg gattctgact   69000
tggggaagat ggttctctgg gacatgagtc ccccatcctc tctatgtgcc atcttctctg   69060
```

-continued

```
aataaagttg ttactttttg ccccagcacc ttgtctctgg attattggcc tgtcgtgtgg   69120
cgagcagaac gagcttggac ttggtagcag caggcatcct ccatcctcct ctgctccctc   69180
tctcgtcccc gctgctgacc aggccatgcc tagcacagca cgtgccctcc aggcgtccct   69240
agaccagctc atctggtcct ctggttcaaa tgccatttac aggctgatga gtccccagag   69300
aagggtctag ccccggccca gtgggctgag ccacacaccc acccgcctgt gcactgacgc   69360
caggccagag cacaccactt cacgccacgc tgccgggcac ccttcagcct gcctcaggaa   69420
gccctccatg ctcacagaca ctcggggcac acgccttcat gctgtccttg aagttccttt   69480
gctctccccc gtgtccaatc tgtccaaagc tccatggccc tacacagccc cctgcaaaaa   69540
gcctaagtgg ggcccctcac ctacctgtca gccccacgcc gcccctggtc tccgctcctc   69600
aaagctgcac agcgggcctc ccaaatccct gccgggagcc ctccggcggc ccccgcgttc   69660
tcagatggag tcccacagtc cctctaaggc catcgcgtgt cctgcccacc ctccccacac   69720
cactccccca cttcccagaa aagatctgcc caggacggtg gcactggtca catcacctgc   69780
cactggcagg gggaggcagc caagagtcca gaaccagtgt tctgagacac ttaaagcaaa   69840
gttctggaaa gttcttaaag ttcccagaaa aaatggccag agcagtcata aataaacatg   69900
ttttgttaga gatacttgac ttcaagagaa acaaagcaga cacccgtgca cgaggggacg   69960
atctagcctg attcctacaa aaactgagtt taccaatgcc tgcaaaaccc tgctaaagaa   70020
aacacggccc aagaatttta tgtccccaaa actagcaact agcgttcaaa cagattccac   70080
acgtgcacaa agtcgggatt ctctccttga gtccttcctt actgaataaa ctatatatgt   70140
acatatttat ctatttatta taagaaaaac aatttatctt caatagcgta tattgtgcat   70200
actgaataca catgaacacg tgcgtatata cacacacata ctcaacgtga ttgcatagtc   70260
tactgaaaat caaaattaat tatttgaaca aagacaaata tccaaccaag acaaaagagg   70320
aaagactccg acacaaaaga gacagccatt taaagtaaca cttaaaagcc gcaccgcagc   70380
acatgcggct cccggaagcg ggggagcacc ggccccgctg cgcggaggcc ctgtcgggct   70440
gagcccgttc tcggctcggc tcaccagcag gaaggcgggg ggggggcgcc agggcaaagc   70500
caggcggagg gggagagagg ctcaggtgtt gggggagtct gacaagggcc cttgacggtg   70560
gtgcagacag agccagggaa ccagtgctgt ccccaggcca tcgcagctga gcctgaagac   70620
gcagcggggc gtcctgggct gggctcgggg aacagcgcac agaagtgctg cgggaggctc   70680
acggcagcgg gctgcccagg ccagccaccc gagggccaca cagccagcag ccatgggatg   70740
cagaccgccc cacccagcga cgagcgatga gcggggaagg gcggaaggga gcctccgatg   70800
cggaggcaga aacgtcctgc gttcaggcac acctccccac acagcagttt ccccgatctt   70860
cccagaatct gtgcagaagc aaagtgtaga ccttttttaat gggaacttgc gctgtgttat   70920
ggaactggaa aacctgacct aagccccaga atccaaaacg tgtatgaagg ggccagtatc   70980
accccagccc tgccagaacg gccgagtcag ccggacagag agaaaagcac cacctgacat   71040
cactcgcagg tggggtcttc aaaaatgccg cagacgagct tatttacaaa ggagaaaccg   71100
cctcgcaggc atggaacaca cagtcatggt taccggggga gggggtgggg agggatagac   71160
tgggagttcg agatttgcag atcctgacta ctaggcataa aacagataag caagtttctt   71220
ctgtagagct cagggagctt ttagtatctt ctagtaactt gtactgaaaa agaatatgac   71280
aaggaatgca cgtacgtacg tgtacgtgtg actgaagcac gatgccggca ccagaaataa   71340
ttggcacgac actgtaaact gactacacct caattaaaga caattaattt tttagaaaga   71400
```

```
acagctgtta tgaaaaagac cacaaggacg tgttggcgag gacgtggaga aaggggagcc   71460
ctcgtgcact gctggtggga atgcagattg gtgcagccgc tgtggaaaac agtatggagg   71520
ttcctcaaaa tactgaacac agagctgcca cgtgacccag ccccccatt cccgggtatt    71580 cacccgaaga aaacaaaaac attactgtga aaacatgcac gcaccccgtg ttcacagcag   71640
cactacttac aacagccaag acagggaagc aacgcaagcg tccaacaaga tggctggata   71700
gagacggcgt ggcgtgtacg caaatggaat actcgtcagc cacagagcag gaacgctcac   71760
ctgctgtgac gcacggatgg ccctgggcgt tacgctgagc gaagcgagtc aggcagagag   71820
agaccagcac cacacggtct cactcatacg tggaatctga aaaaaaagaa aacaaaaatg   71880
aacaaacgaa ataaaacaga aacagactcc gatacagaga acaaacagga ggtcgccaga   71940
ggtggggagg ggccggacag gtgaagggga attagggaca cacctccagc cgcacgacga   72000
gtaggccacg gggatgtgaa gcgcagcacg aggagcccgg gcaggcacgt tgcagccact   72060
ttgccccagg gcggatggct ctgcgtctac cgcggtgatc atttcttaat gtgcgtaaac   72120
gtcgaattct tgtgcagcac agcttccgcg cgccatctgt cagcgctgct tcaacagtaa   72180
gtaaatgcgc aaataagcca gcggcaggtg acggcaggct gagcgggagg aagtgacgga   72240
cgccgcaggc gcaacggcga ggcccagcag cagcactgca ggaaacacgc tgtctgaaaa   72300
ggaggatgtc tccttggagt tctggagttt agcccttgtt ttccaggacc agccgggagc   72360
cagaatgaag gcagtcgctc gggaagccct tccgtgttga ggcggttcag agacgcaggc   72420
ggcacggggc caggtaggga cgcagacgca ccgcactgcc gctggacgca ctctgtcttt   72480
gcggcggggc gaatccaaaa gccttcgggg tcacaacgct cccgaggctg ccctcctccc   72540
gtcccaagga atcgcctaca aacagcaagt cccgagggtt ttgttcgtga aacagtgagt   72600
cataagcctg aaccagagca gaactgatca agaaaaacca gcagcagatg caccgcaggt   72660
gaacacccac cagaaacaca ctagcgaagg atgaggagag cgtcgcctgc acgggttgag   72720
aagatcacga taacgataac gaagcaactg gattcacaaa ggaaagcaca gctcccaagc   72780
gcaagggcgt gtagaagaga ccggccgctg ccaggaggag gcggagggcg gcctggccga   72840
actgcccacc gctagctcgg agcccccaga ccagctggaa ccacaaggct ggcgatgccc   72900
gaagcgtcac ctggatgcca accaacccga gaaccgtgca ccagcgggtc agacgcgccg   72960
cagcaccccc cgcccccaag gccttcaaca ccccttccct gaaggccctc ggggagttcg   73020
ggcttggagc acgagcggcc cgctctccta gccaggcgcc tgcctttcct ccaccgccac   73080
cggcatcagc agattgcctt tactgcacgc ggacgcgcag actcgagttt ggttcagtaa   73140
cacgcggggt cacgtggggt caaagtccct gggagacaag gaagtccccg gcgtccagac   73200
ttggtgtggg aatcattcca taatgtgtgc aaatgtcagt tcaccgtgca acacagctga   73260
agatgctgcc agtgggcgca gccggagttc caggcccttg tcccgtccca gaaagagttc   73320
agagacaaga cacagtggtt aaaagagtaa agtgaggatt gattaaaggg gggatggtac   73380
attctccagg ccagagcggg caggctcagg ggagcggctg ccctgagttt ctttggcaag   73440
ttagctacat agggtgtaaa aatgaatggg cggaatattc actggggagg gaagggtttg   73500
gggtcgtatt ccctgctcat catcccaact ccccccttccc aaaggggagga gggatttttg   73560 tccccactta gtctggagca gaagtgtcac gtctgtgctt gatggctact tctgatccgc   73620
aaggctgatt ttattgaaat gaggacatag tgagcaaaag gtcacattca gacactggag   73680
attcctgcct ttctcacctt tctttgttct tctccaggcc acttgtcacc ccaaaaagcg   73740
tgatccctta tcagcccaga ggttcctgct tttcctttgc tgcccaggga cccctgctgc   73800
```

```
ccacgtgatg tgtgcttccc tgcgtttggc ctgtgcccct cctttccacc cagttcctgc    73860
cgtttggtct gtgtccccct tctctgctca catctagctg tctgcctgct ccaacaaaac    73920
taacagaatc ctgtgcagca actttatttc agtaaagaaa taaatgggcc aaaagcagct    73980
gacactgggc agaggccaca cgggaggaag tgacagatga tctggaacag tgggtcccgg    74040
gtgtcatgtt ctgggtggat tttctctggc tcccgtgttc cctgtcagga tgtggataca    74100
actgaccaag tgcacccctt gaaaaaccaa gtacccaggc agctgtcttc tgcagagaga    74160
aaggctttat tgccgggcag ccaagaaagg agacggggga caatgctcag aagtaggagc    74220
agggccgggg gaggggttg tgctgggaat cgattggtgg aaagttaagg tacgtttcaa    74280
gagttctgtg cacagatacg gctgctcgtg ccctgcatgg gccgtgtgtg cagtctgggg    74340
gagttctgtg tgttgcacac agcggatttt cagcctctga cgtccaaagt tcatcatcaa    74400
tcatcctagt ccctcagggt gctgtgagga aggggctgat ctgtccacat gttgtttcca    74460
gacctgaggt gttcggcaaa gcaaacctgg ggtctctgtt aatcaccttg tttccccta    74520 agggacttga gtgtgcaagt tgcagggtgt ggtttcacac ccactccccc taaactgagt    74580
tcctctgcca agcttgtgac taatctctct ctccaaaact ttattcccctt tcttgtccga    74640 cacctgttac cactaagact gagggtatca aaggaaacag aggatttaaa ccaagcagga    74700
ccctgtgggg cctctgggta caaaagcctt tccatgtccc ccgcttctca attgcaggaa    74760
aaaggcttca gactcctaga ccttccctga gttcctagcc agggaagtga ggggatgcag    74820
aaatgaagga ggagtcaagg aacagcagag cagcaactga gcagggcccc ggtctctcct    74880
caggggagac acaggacgct gtgcctttga gctcttctgc aggaactcag ccccaccgcc    74940
caaggtggag gatggtaact tcgcaccgag caccagctct ggaccccagg ctggctggaa    75000
ccagaagcct gatgagtgag acccctggaa gaccaccctg gcacccccag cacccggtca    75060
ggggaagggc acacaccctg caggccagcc ctccatcttc ccataaaact ctccgctgaa    75120
gcccatcggg gagtttggac tttccaaagg cacccgtcct cctcactcgg ccctgcagta    75180
acccttcctc tgctccagac tccgacattt cagtttgtct ggactcactg tgcgtggggc    75240
acacaaactt gggtttgacg acagattcat ggagagtatt gccttatttc aagatggagt    75300
ttttgaattc cactttaaaa tatttttct cgtccattac ttttggtagc tgattttgga    75360
aagaattaat ttaggcagca ttcaaaagta caagtcatca acaaggtgga agtcaggctg    75420
gcctttgact tcttaccagc tacatttaac accagtggac agtgaccagt gcccacagga    75480
ccttccaggg aagacatgag gccctggga gctgccatgc accagtctgt cctccgaaa    75540 taaaggccac tggaccaggg gatgcaaact aagtgtccat cggcgggtga atggatgcag    75600
aatgcgtggt atctatatgc agtggaatat tactcagcca tgagaaagga agaaatcctg    75660
ccattggtga caacacgggt ggaccctgaa ggcactatgc caactgagat gagtcaggca    75720
gagaaaaaca gatgtggggt catctcacaa atgcatggaa tctaaaaatc tgaatttgca    75780
gaaacagaat agaaaggtgg ttgggaggtg ggcaaaatgg ggagatgcta tttaaggtac    75840
acacctgtac cttaaattct ggaaatctca gacacagcac agagattata ggcaacagtg    75900
atgtgtgtat tatagacttg agttatgcta ggtcttaatt gttcccatca taaaaaaaaa    75960
gcaatgatga ttatgtgagg tgatagacgt gtcagctaaa accacagtgg tcatcattct    76020
gcaacatata aatgcaccag actaggggag ggtgtagctc agtggtagag catgtgctta    76080
acatgcagaa gatcctggat tcaataccct gtacctccat taaaataagt aaacctagtt    76140
```

-continued

```
acctccctcc acaaaaacat acaaataaat aaataaaaat aaatgtacca aatcaacaag    76200
tgtgctcctt aaactttaca taatattgta aagtcaatta tatctcaata aaaacaaagt    76260
gttttactgc tgtgagaatg tagtttggtg cagccattat ggaaaacact atggagattc    76320
ctcaaaaatc ttaaaacaga cttaccctgt gatccagcga tcccactcct gggcacatat    76380
ccagagggaa ctaatttgaa aagatacatg caccccaatg ttcatagcag cactgtttac    76440
aacagctaag acatggaagc cacctaaatg tccatggtgt atatagacaa tggaatacta    76500
ctcagccata aaaaagaata aaataatgcc atttgcagca acatggatgc tcctagagaa    76560
tgtcattcta agtgaagtaa gccagaaaga gaaagaaaaa taccatatga gatggctcat    76620
atgtgaaatc ttaaaaaaaa aagaaaaaaa gagaacactg tgaactcatc tacaaagcag    76680
aaacagacgc acagacatta tcaatcttat ggttaccagg gttgggaggg gataaatttg    76740
ggagtttgag atttgcaaat gttagccact atatacaaaa atagatttaa aaaacaagta    76800
tcttctgtag agcgcaggga actatattga atatcttgta ataaccttta atgaaaaaga    76860
atatatgtat gtatgtatgc atgtatatgt gtgactggga cgttgtgctg tacaccagaa    76920
attgacacac tgtaactgac tgtacttcaa taaaaaataa taataataaa ttttttagaa    76980
aagcaaagtg ttttataaaa agtcataaag gctaccgaaa acagtttgaa caagcaagaa    77040
tacaggaaat atgtttccat aacgcccagc atggtgcacc tgctagtgga aagcttcagc    77100
taccaacgtg ccagggaggc ggggccaagg ttccagggag gctggggcct actgccaggg    77160
aggcggggcc aaggttccag ggaggctggg gcctactgcc agggaggcgg ggccaaggtt    77220
ccagggaggc tggggcctac tgccagggag gcggggccaa cgtgccaggg aggcggggcc    77280
aacatgccag ggaggctggg gccaaagggc agccgtggat gttcagcgca cttaactccc    77340
tacagagcag aagcttcata actgcccaaa gctggggga gggcagcaaa cgtgggagtc    77400
agagcactgt gaactgctgc ctcctgctag cagctgggtg tccgaggacg tcagtaaggc    77460
caagccaagg actgggagct cagcgagcga gaccgcacag caaacacgaa gaacttgact    77520
ccagaggcca gagtctacag tgggagggaa ggaggacagg ggaagagggg ggccccacct    77580
gcttcacgcg tgtttcggag agggccatgc gtgtgggtga agaggcagca cagaggatgt    77640
cagggacacc ctcgtggtaa aggcgaccac tgcacacaca gcagcaaaga aagacacctt    77700
gaaatgaaaa cctgcttctg caagtttaaa aaataggaaa atgcggcata aaactgtaaa    77760
ccaggattga tgccaaatat atccacctgt cttaccaata agtgtgagca gtctttacat    77820
gcctgctaaa aggaacagcc tttcagactg gatcacaaaa caacagccaa ctctcccagc    77880
acgtgagagc ttcacgcatc acacatcaca cgagaagcgc tggcagacct gactcgagga    77940
atgccaggag atccagccgc ttcctctgcg atacaatgtg aagctctgtg tccccggcag    78000
acgcctctct tagatcggcc tcctgtcccc ttggggaagg aaggctgtta gcaggtgcca    78060
agtgcctttc gcaccaggtc cttcacttcc tttatctctt aattctgcga gactgtggca    78120
agcaagatgc tgttacccac attttttacag atgagggaat ttgatgctca gagcatttaa    78180
gtggcttttc aacgtaacac tgacatcaac gtggagcaga ctcacctagg gagccccgat    78240
ccttccctgc tccaaggcgg gtgggtgggg tccacctact gcaggggccg ctgggagctg    78300
gcgtggctca gagcagacac agcaccgcca gcagaaaagc gattcaccac aggggggctca   78360 ttgcagtggg ccaaggactg tggggcagcg cgtctggatg ggaaggccag cgcatgtcaa    78420
gtcttcagag ggggttctt cacgttctgg aagctggggg aaccgtattt cccgcttctg    78480
tccatcccaa ggcttcaccc atggaacatc tacgaagtcc agcgctgtgt gggtggccag    78540
```

-continued

```
acaggacagt ggtcaccggg agccttccaa ggactctgag ggcacttggt gcttctgcct   78600 tcccttcac cacaggctgg aaactcatga catggagaaa agctagcaag ctgcctcaaa   78660
atgcagaggg cttggtgata caaacaaatg agtgaaaata aattgtgcaa ataaatgtgc   78720
acaaataaat gtgtgtaaat aaatgtgtgc aaatgtatgt gtgcagcaat gatggggccg   78780
tctgtccggt cctgtatgat gtgggtgaat gcccagcgct cttgccccgc ctacggctgt   78840
ggctcccctc cctggggact gtcaaccaag cattgacctt ggcctgattt actgtaaccc   78900
tagggcaaag gaggggtgaa ggagatgtca tggtctcctg atcactgagg ttctgttgaa   78960
catccaggtc attatcctga aggtgtcgtg aggaagaaca agatgggccc cacattagat   79020
ctgctgtttt ggctctcacc ctctgctctg cttcctgtgc tcagtcaggc tggttctgca   79080
cctcttgtga aagaatattg cctggagcct gaagtagacc ggacagccca ttctcaaggc   79140
tctgacttct aagagtataa cccttttccat tcatataaag acagcaagct gaagaagaga   79200
aagtaacatt tgttctgttg gaggtttgca gcgacaccgt gacctgaccc acgtggacag   79260
ctgcaagaac aaagggttca gacaccaaga aatttgcaac aaccaaccac agccctccc   79320 ttttttagta taaaaggagc ctgaattctg actcaaggaa gatggttctc tgggacatga   79380
gtcgcccatc ttctcgctct gccagctttc cacataaagt cgctcttcct tgccccaaca   79440
cctcgcctct tgatttattg gcctgttgcg cagcgagcag aacgagtctg gactgggtaa   79500 caagggggaca ggcatgtccc actgtcaagg ggatgcctcc ctcaggatct gaaccccaag   79560
agttcctgct tccatcactg aaaaccccac tgaggctgct caccccgtc cctgcagcac   79620 tgcccaggag ccgccagtct aaaatgaggt gctcgtacag cagctcagcc tccctcggtc   79680
tccgagagga aggtgctccc ggggccgagg acagcacag ccaggggagg cctgagatgg   79740
acacagcatc gttctggacg tggagacgtg gaatcagcag gcgcttccct tcttccatga   79800
agagccagac tacagtgaga ttgcgtttgc tcctgcccct cctttctgct tccggccaca   79860
gcagctactc tgccatcatg aaggaatggc caagacatcc ccagagatgc agccaccact   79920
ccctgcccca taacctcgtc cctgagcaaa tccccgcccc acctcctcac cccgcgggga   79980
ggccagccgg ccttggtggc cccgttgaag atcagacctt ctgtcgcctg gagctggagg   80040
ttctccttcg cacgggccct gacaacaccc cagtcagtgt ccttctccgg ggacatgggg   80100
cacttaggag actcccgaga gcttacaccc gctccacccc tgcagagggc gggggggcagg   80160 caccaggatc ttttgttctt ttttcgaccg ttgtcttttg aaatgtatgg tgtgagttgg   80220
tgccactttt taaaaatttg cttgtgcgct gtcatcttcc tttctggctt tcccattttt   80280
gctcatgcca ctgggtatga agggtgggca ccccgctcct ctccccttcg gtaacctctc   80340
acagccgctg ctccacgact gaagcagcca cgtgaccttg cattgcttct gccctgaaac   80400
aagacgcgct ttttcctctt gcgtttgtgc ccacaaggac cttccttctg gagtcaagtg   80460
cccagagacc aggtccccgt cggtggaggc cagcagaagc cgagtctcgg gcacaaagcg   80520 ctctcccta gaacacgagg atggttctca ctacttgctg aagcacacct gtgttctggc   80580
catctggtct accactgccc cagctctggg gcaacgggac cctggagtgg gattcacttg   80640
ccaagtcgtg gtggcactgc aggttggagg ccgtggagc ccccaggccc actagcagcc   80700
cctgcccttc gtcaaggcct ctgaccccca ggcagatgtt gggcgtcacc tctgactcgt   80760
ccatctcctg gacgttgtga cccaggagtt caaggagcag agtgaatgct gctgccaccc   80820
gcctcccacc gtggcagacc tgagggcctt tccctctggc tgctcagtcg cagctcactg   80880
```

-continued

```
gctattttca gcagcagctg cacggtgtgt gccgactctc acaaggcagc tgagtggcca   80940
gggcaccctc cctccctgcc tttagaagct cagtcctcag ctcaaatcca agctctgctc   81000
agggaagcca agccaagaga caccttcccg gtcacctgct ccagaggcgg tggggggtgg   81060
gggctgtgag accacagcaa aagccgggag accaactcca catggccgcg gggcccagtt   81120
ctggccaccc catacacaga tccagatgcc acgccggcac tcactgggca cacaccagta   81180
acatgcatgc ccttcccctg gcatgtgctg tggtgggtgg aggcaggagc gagatcccag   81240
aactgggccg tgggatgctg agacagcggg agggggctgc cttgagggag ccctgcctac   81300
aaactgtgag ccgcccacac agccccagag ggtcaggcag aggaaccgca ctcccccagg   81360
gagcaggacc tcagcccacg aggcgagggc aggctcagga ggccataccc cagtggtccc   81420
accccaggtc ttgccagctc tcaggccaca gtcgctgctt cagagcaaca gacccctgct   81480
ccttctccac ccctccccat ctcacctctc ctcttctccc ccaatggcct cctccgtggg   81540
ctcttctggg cactcagtcc acagtgcagc cctcatagct caacgctggg gtctcctctc   81600
accaccccgg acccagacgt gtccacccat tgcccgtggt cctggtgtat ctggggggcct   81660 cccagcacgc ccgccggcct gcctgaggct gctgcgtctg gcatctcccc gcctctccta   81720
gacccaggcc ggagctgtcc caaatcctga ggcagctgcc tcgcagtcac caccgctctt   81780
ccagccctct gtcccccatt ccccccttcct gcccactccc ctgtgggagc ctccctgtac   81840
ctgcaggctc acaaccctct cccagcaccc aggcttccgc ctctgatgcc ccaggccagc   81900
ctgaatctgt cctccggcct gccccagaca gaagccgccc ttcctcagcc tctttgctgg   81960
gcacacagcc ccctttacat ctagtcacat cagaccacct accattctcc tccaggccta   82020
ggacccagcc tctagatctc agcctcagct ggaatcacac acacacacac acacacacac   82080
acacacactt cccctccccc gggaccccca aggtctgggc gggtctgggc agggctccct   82140
tagaccacca tgctcccccc tcgtaaccgc cccccagccc agggcatcaa aagctgagat   82200
ccttcccaaa ggacctgcag cccagggaca gggcagggac ctgggactgt gggcacacag   82260
tggcccgaca ctcggtggac actcggtgca ccctcagccc ctgggagccc gacttccctg   82320
gaggactgtg aacacggaga agtaacaagg ggctgctgcc ggcaccacag ctgcgaccaa   82380
agagagtccc ggacagaccc cacgggggcc aggccggggc agagcccgcc cccctgggg   82440 tcagcactgg cctgggcccc tgcccgctgc cctgcggggg acacgacgcc agtgcaggtg   82500
gcctccagac agccgggagg cacagtctgg aatttgctcc tatttctgaa agaaaaaggc   82560
agccgtgcag gcagccttca acgctttgag gattgttagc agatgacttg tagctggccc   82620
aggaatgcct gtgagggcgg gcagggagag gtctcccctg ggctctgtgg cccacctgcc   82680
agcccttggg gttttggctg agctgggaac cgcagtgcta actggagcca cagtgactga   82740
caactctaca aaaacttctg gccagagccg cccccagggca gccaggtccc cgccccaagg   82800
gctcacggcc aggtgcacaa gggggtcagg tttccggtgg acaagagatg gttcacatcc   82860
caggcaaggg actaggtccc cggggctggg ggaaggggcc agtgcagcag cctgggcccc   82920
aggtcgtggg gagcccagct gggatcaggg ctgtggggtg agtggcgccg agccttggag   82980
cagcagggcg gcagggaaag cgtggtctcg ggggaccaaa gcaagtcagg tgtcaggacg   83040
tccgaatcct tggccaggaa tgatgtagga gggagccagc ggggcctctc ctcaagcaga   83100
gagcaggctt ctggttccgg gggctcccgg gccccagctc cctgcacctg tgcttccccc   83160
attgctgggc cacctgggca cctgggcacc gtgtcctcag gtgagcccag cgtccagtct   83220
ccagcctggg ggactgtggg actggagtgg gctgagccaa gcagtctgct gtcccagact   83280
```

-continued

```
tgggacagga ggtcagggga tggcaggagg tggggggaca ggagaagcag cggggcagag   83340
gccatgctgc tggaacctcg atcactgggg ccagggcacc tggccactgt gtcctcaggt   83400
gagccttccc tgcggctgct ctgcgtgggc gtccggccag gtccctgggc agctccccga   83460
gcctgcctgc ccgaggcctg gatgaggctg cggccccagg ggacaggcag gcttctggcc   83520
ccgttagggg cagtccctcg gggctcacag agctcctggt ggtgagcgag ctcgtgagag   83580
ctgggctgag ggaagcctgg gggacaggtg ccggctggga aggagaagtt gtgggcagag   83640
cccagccagg gcccagctgg gggtttgtgc actgggggcc aggcaagcag accagtgtgg   83700
ctacaggtat ctcgaagttt ggggccaggg caccctggtc actgtctcct caggtaagta   83760
catcctttcc ttcctccctc atcgccctgg gatctgtgtg gccatggaca gtgaggtctg   83820
gcccatccaa ggggcccacg caggtttatg tctgggggag agcagggact atgtccctgt   83880
gcaatgcttt ggacgcatgg ggccagggga ccctggtcac tgtctcctca ggtaagacag   83940
ctctctgccc tcggtcctgg gctgggaagg acatttccag agattcctgg gtctttgcgg   84000
gggccccagg ggctgcttct gaggccctat ggctgttggt cctgggagat ggcgtctctc   84060
cagtggagcg cgggctgggc agagtgggcc cgtgtctgag ccacagagac cgggggccag   84120
ggctttgtgc ggccaggtcg ctgggcaggc ggctcgggtt tttgcacagc acctaacggg   84180
gcccgtggcg ctgtgatgag tatgactact ggggccaggg acccaggtc accgtctcct   84240 caggtgagtc ttctcaagcc tctctccttg gtctctccga gggttttgc tgcgttttag   84300 gggggaaatt agggtgtatg ggtcttggct ctagagggcc tggagtctta ggaagagggc   84360
ctgggggccc caggctcaca ccaacaagga gagtccaggc gccctccctt cctgggctct   84420
gcagccaggg ccttctctgc tggtctcagc cacacttggc ctctgggagc ccgaggtccc   84480
cagccctgta ggccccgcta ggtgtcatat gaggtggtcc caagagctca gccggccacc   84540
agcatttgcc tggggtcttg acacagttgt cacaatgtga cccccagttt gaatactggg   84600
gccagggcac cctggtcact gtctcaggta agattgctct ctgccctcag ttctgggctg   84660
agaaagaaat ttccagagat tccttggttt tgtgggagac gcggggaggc tgtttctgag   84720
gccgtttgtc tgtcggtcct gaggagatga gtctctgccg gtggagcgcg ggctgggcag   84780
agtgggctct gtaattgagc cacagagacc gagggccagg gctttgtgcg accaggtcac   84840
tgggaggggg ctcgggtttt tgcacaccac ctaacggggc ccgtggcgtt gtgctgactt   84900
tggttcctgg ggccagggga cccaggtcac cgtctcctcg ggtgagtcct catccctcc   84960 ccacttccac tgcaactggg gagagctggg gtgtgggggt ctcggtgtta gaggcacagg   85020
ggcattttgg ggctcaggaa ggggagtcgg ggagaggctc ctcgtgaaca ggggctggag   85080
gtgggcctct ctgccccagg gacgccctgg tgtgggggcc gggcggagcc cttggctgct   85140
ctggccattt aattcgagcg ttgccagggg ctcccgtcag cttttggcgg ggtggccgct   85200
tgagcttggc tggatttccg aggtggagtt aggagtctgt gttttgtggt cagatggccc   85260
aggcaggcag tggccgggct tctggggggc cagactgcaa catgggtct ccagggcggt   85320 caggagggag cggcgccaac agagggttct ggggccctct gggtttgtga ctcagagggt   85380
cacttgcatg tggtgccgga gacagtgtgg gtccccaggc agccgcgggg ccgtgccagg   85440
cctccgaggt ttttgtgggg tgaggctgga gcttccgcca ttgtgattac tacggcatgg   85500
actactgggc aaagggacc ctggtcaccg tctcctcagg taagagtggc ccctccaggg   85560
cctttgtgtt cttctcctgt ctgtgggtt ttctgagcat cgatgtctgg tccttaggag   85620
```

-continued

```
ggtccgtgtc ccccaggtgg cctgggcagg gctgaccagg agaggatggg gaccaggttt   85680
cctggggatt tcagagtctc tggattttct gacgcctttc aaaaatcgga atagtgccag   85740
cattcaagag gggtctcagg caggaagggc caccgagagt gagccccagg accccttgg    85800 tggccaggcg gtttggtctg tggcgggaga gcttctgctg ttgcggtcac agagtcggct   85860
gagaggtgtg cccgacgcca gtgtttgcac acacagggca gagtggaatg ctctctgggc   85920
taggagctgc gctctgggct agactgtact gaaaattcct cgttgcttgg aagagaaca    85980 gcctgggtga ggaaggacag gcagagtctt gatcttggtg acagcagggt gcctccctga   86040
agcagagaac ttgggaggct acagccgctg ggctctgtga aacagtttc taagagaaag    86100 ggaggtgttc catcaacagg agtacttcca aaatattaaa aggcaggata gctatgaagt   86160
ggctcctgag acagatgatt aagaaaattg tgactttaaa atgtgagaag ttttcaagca   86220
gatgactttt tttaatgttt aagtatttta aattcttatc attcaattaa caaccatgaa   86280
ccatgtctct cgggagccat tagttctgag ttaggcccag agcagttgtg cggtgctgtt   86340
ggcccctgat ccagggctga gctttgaggt taataaattg agattattat tctttaatta   86400
attgatggtg ttgagttagt caagatggcc gcaggcagag ctggccacct gcagcaggtg   86460
gcaggaagcg gcttcggccg agtctatttt aggaagtgag aaagcccgaa tggtaaattt   86520
acagcttgcg gttgccaggg tggtttgccc agcctcacag cactgaaagt gctccacaga   86580 gcaaacaac  acctggataa tttgcatttc taaaataggg caaacatgct gacagaaaca   86640
gaaggttcct gtttttaacta cttgaactga actctcagac ttagcttatc aactgctcac   86700
ttatactcat tttccaagta agacctttaa gaaattgcat ggcgaggtgc agcttggcaa   86760
tgcgttccta tcacttttaa agcgtcagtc cttcacggtt gctcatcgcg agccgtcccc   86820
cagggtcccc aaagcgctgt tttcacaagg actgtgttca gaggtcttgg ctggtcgatc   86880
ttctcttcgt gacgaagaaa cgctctgctg ttcagctgca gttgctttcg tctccgtgtt   86940
ggtcaaggcc gctgctcagg tgtccacctg aggacgggct ttgggggaaa cgtgtgtgtc   87000
cgtcgtgagc tgtttcggtc agacgtggga gctggtgcat tgagaggacg cccggtgagg   87060
ttctgaatca gaagggcagg acaccctaga aggacagtct gttctggaag gtcgacccag   87120
cgtctgagtt gaaggcgctc cggtggaggg ccccagagcg ggggccccgg cctcgccaca   87180
gccggggctc tcctgggagc ccccggagcg gggagcggca ggtgcagttt gtgccgccgg   87240
gcccctcggc tgtccgtgaa tcagtcttct taatggacct ggaggaatcc ttccatgcca   87300 gggacccac  ggagcttgcc aggggccagg caccgagacg gtaagagagg cagccccact   87360
gccagatttc ctgctcggga cagcgcgtag gcggcgtttc tgctccactc gggggagggc   87420
ggtcttcaac gcccgctcgg tgagacgag actcgggtga atccctcgag gggccgccgt    87480
ccggctgggc cacgtctgac tttccctaaa gaacaggcca aggacagcgt ggcggggggct  87540 gctccacagc cccttaacta ctgccggcgt ggctcccgct gcttccacag acccaaggca   87600
ccccttacca cgtcctcgct taaatggacg cagtttaaac gcagctttgg gtttaaggtc   87660
tttgccgtgt gtgtgaaggt ggccctgcc  ttctgcagag tttatgataa agagcagaat   87720
tgtgagtggc aacctcaggt acaatgcgtt tcctggtcat tttcaatgag ggattttcct   87780
agagggaatt tagtcaagtc gggactcact ttagactcag gagggaggaa ctcgcgccaa   87840
gggtaggtgc gcaggaaggc gaaggcagcc gggagacaat ccccgggggct ctcctctccg   87900 cgaagaagcc atgctgccag ttccagggag ggacctttcc ttctgacagt ggccagtgca   87960
gctcctgaac aagatgtgct aaggagctga aagcctccgg gcagcatttc attcagacag   88020
```

```
cggaagggggg gtagcgactg gtgccgctca ggagccatgg ccgctgggcc tgggcaggga    88080
tggaggagct ggggtacccg gagtgagggg gactccgagg aggagaagga ggaagggcca    88140
ccaggaagga gttgaccctg caccgagccc agctgtgcag gactcctgga tgagatggcc    88200
ttagctgagc caggcgggtc tggcggcccc accctttctg gccagtacca tgagctatca    88260
ggacagaacc gggccgagcc tgagctgaga tgaactaaac tggattaaac tgggcttcct    88320
gagccgggct ggattaagcc aggctgagcc aaactgagcc gagctgagtc gggctgatcc    88380
aggctgagct ggctgagcca agttgagctg ggctgagctg agctgagctg ggctgagctg    88440
ggctgagctg agctgagctg ggctgagctg ggctgagctg ggctgaactg ggctgagctg    88500
agctaggctg agcagggctg agctgagctg ggctgagctg agctgggcta agctgggctg    88560
aactgggttg agctgagctg ggctgagctg ggctgagctg ggttgagctg agctgagctg    88620
ggctgagctg agctgggcta agctggggtg agctgagctg ggctaagttg ggctgagctg    88680
ggctgaactg gtttgagctg agctgggctg agctgggttg atctgggctg agctgggctg    88740
agctgggttg atctgggctg agctgggctg agctgagatg ggctagctgg gctgaactgg    88800
gttgagctga gctgagctgg gctgagctgg gctgagctgg gctgaactgg gctgggctga    88860
gcagggctga gccgtgctgg ctcagctggg ctgaactggg ccgagctgag cttagctggg    88920
ctgagctgag ctgggctaag ctacgctgag ctgagctgag ctgagatgag ctgggctgag    88980
ctgggctggg ctgagctgag ctgagctggg ctgggctgaa ctgagctgag ctgagctgag    89040
ctgggctcag ctgaatagag ttgggatgag ctgggctgaa ctgggctgag ctcagctggg    89100
ctgggctgag ctgagctgag ttgggctgag ctgagcttgg ctaacctggg ctgagctggg    89160
ttgagctgag ctgggctgag ctgggctgag ctgggttgag ctgagctggg ctgagctggg    89220
ctgagctggt ttgagctgag ctgggctgag ctgggttgat ctgggctgag ctgggctgag    89280
ctgagatggg ctagctgggc tgaactgggt tgagctgggc tcagctgggc tgagctgagc    89340
tgagctgggt tgagctgagc tgagctgagc tgggctgagc tgggctgagc tgggctgagc    89400
tgagctgggc tgagctgggc tgaactgggc tgggctgagc agggctgagc tatgctggga    89460
tgaactgggc tgagctgggc tgagctgagc tgggctgagc tgggctaaac ttggctgggc    89520
tgagcagggc tgagccgtgc tgggctgaac tgggctgaac tgggccgagc tgagcttagc    89580
tgggctgagc tgagctgggc taagctacgc tgagctgagc tgagctgaga tgagctgggc    89640
tgagctgggc tgaacttggc tgggctgagc agggctgagc catgctgggc tgaactggga    89700
tgagctgggc tgaactggga tgtactgggc tgaactgggc cgagctgagc ttagctgggc    89760
ttagcttggc tgagcttgtc tgagctgggc tgagctgggc tgagctgaac tgagctgagc    89820
tgggctgaac tgggctgagc tgaactgaat tgggatgagc tgggctgaac tgggttgagc    89880
tgagctgagc tgaactgtgt tgagctgagc tgggctaagc tgggctgagc tgggctaagc    89940
tgaactgaga tgagctgagc tgagctgagc tgggctaagc tgggctgagc tgggctgagt    90000
tgggctgaac tgggttgagc tgagctgagc tgagctgggt tgagctgagc tgagctgggc    90060
tgaactgggt tgagctgggc tgagctgagc tgtgctgagc tgagctgaac tgggctgggc    90120
tgagcagggc tgagccatgc tgggctgaac tgggttcagc tgagcttagc tggcccgagc    90180
tgagctgagc tgggctgaac tgggttgcgt tgagctgggc tgagttggct gagccaggtt    90240
ggattgagct gagctgagct gtgctgagtt gggctgagtt gggctgaact gggttgggct    90300
gagttggtct gaactgggtt gagctgagct gagctgggct gagctgggct gaactgggtt    90360
```

-continued

```
gagctgggct gagctgagct gagttgggct gagctgggct gagctgagca gggctgagct    90420
gtgctgggct gaactgggct gagctgggct gagctgagct cggctgggtt gagctgagct    90480
gagctgggct gagctgggct gagctgagct gggctgaact gggctgaact ggtccgagct    90540
gagcttagct gggctgagcc gggctgagct gggctctact gcgctgaact gggctgagct    90600
ggactgaact gggctgagcc gggctgagcc aggctgggct gaactgggct aagcagggct    90660
gatttggtga ctgggctgga ggtgggttga actgggctga actgaactgg aatgagccgg    90720
gttgacctga ctgggttga  ctgagctgg  gttgagctga gccaggctga gcttggctga    90780
gctgtgctgg gttgagctgg gctgaactgg gccgagctga gcttagctgg gctgagctga    90840
gctgggctaa gctacgctga gctgagctga gctgagatga gctgggctga gctgggctga    90900
acttggctgg gctgagcagg gctgagccat gctgggctga actgggatga gctgggctga    90960
actgggatgt actgggctga actgggccga gctgagctta gctgggctga gcttggctga    91020
gcttgtctga gctgggctga gctgggctgg cggagctggg ctgagctgag ctgaactgtg    91080
ttgtagaact gggttgagct gagctgggct gagccaggct gagttggttt gagctgagct    91140
gagcttggct gagctgggct tggctgagct gggctgggct aggctgggct gagctggcta    91200
agctgagctt tctgagttgg gctgagctga gctggcggag ctgggctgag ctgagctgaa    91260
ctgtgttgta gaactgggtt gagctgagct gggctgagct gggcttagct cggctgagcc    91320
gagctgggct gaacttggtt gagctgaact gagctgagct tggctgagcc gctgggctgg    91380
gctgcaatga gccgagctgg gttgggctgg attgagctga gctgggatga gccggactgg    91440
gctgaactgg gctgagccgg gctgagctgg gctgagctgg gctgaacttg gctgggctga    91500
gccgggctga gccaggctgg gctgaactgg gctaagcagg gctgagccgg gctgagctgg    91560
gttgagctgg gctgaactga actgcagtga gctgggttga ggtgagccag gctgagctgg    91620
gttgagctga gcttggctga gctgtgctgg gttgagctgg gttgaactgg gctaagctga    91680
gctcagctgg cctgacctgg ttaagctggc tgagccgagc tgggctgggc tgcaatgagc    91740
cgagctgggt tgggctggat tgagctgagc tgggatgagc cggactgggc tgaactgggc    91800
tgagccgggc tgagctgggt tgagctgggc tgaactgaac tgcagtgagc tgggttgagg    91860
tgagccaggc tgagctgggt tgagctgagc tgggctgagc caggctgagt tggtttgagc    91920
tgggctgagc tgggctgagc tgggctgagc tgggctgaac tgtgttgtag aactgggttg    91980
agctgagctg ggctgagctg ggcttagctc ggctgagccg agctgggctg aacttggttg    92040
agctgaactg agctgagctt ggctgagccg agctgggctg ggctgcaatg agccgagctg    92100
ggttgggctg gattgagctg agctgggatg agccggactg ggctgaactg ggctgagccg    92160
ggctgagctg ggttgagctg ggctgaactg aactgcagtg agctgggttg aggtgagcca    92220
ggctgagctg ggttgagctg agctgggctg agccaggctg agtttggttt gagctgagct    92280
gagctgggct gagctgggct gagttaaccg tggtgaatga gatggatcca gtagaagtgg    92340
gctggctgag tccgcttgac ctaaacaata tgacgcgctg cttcgggatg gttaaccgtg    92400
gctgaaccag gtgggtctag ctgggctgag ctggccaggc tacaccgtcc tggctgacac    92460
tgggctgacc tcagtgacct gggcatgctg aggacaggcc gagctgagtc cgcgtcagtc    92520
tcgctgatgg cacgcacacc tttcctccaa gcccaggcac ccagggcccg actgcagtgt    92580
ggctgagcca ggggcggaag ggctgggctg gcggggccga gagtgctggc atccgctgca    92640
tggcctcgga gggaaggcag ggcgtgcata ccgttcgtat aatgtatgct atacgaacgg    92700
tagcaggggt gggagtaagc cagcccacct gacgctctgt cttccctgc agtgatttta    92760
```

-continued

```
gatctgcccc ccagcgtgac actcttcatg cccccccgag acggcttctc tggcacttcc   92820
aaacgcacgt ccaagctcat ctgtcaggcc acagacttca gccccaggga gatctccgtg   92880
tcctggtttc gtgagggcaa gcggctggtg tctggcttca ttacggaaga tgtggaagcc   92940
tcaaagtcca atccagggac cttcagtgtc atcagcatgc tgaccatcac cgacggcgac   93000
tggttcagcc aggctgtgta cacctgccag gtggagcaca gagggatggt catcgagaag   93060
aacgtgtctt cccagtgcaa ccccagtgag tggtctggcc cgagcacagc cccgggacag   93120
gggggcccac acacgcagtc tgcagacatc accccagacc tgaccagcag ctccctgagc   93180
cttggcttcc cagagcggcc aagggcaggg aggggggctgt gcaggcagc tcggggagtg   93240 tttcagacat gcccagtgtc ctcccccagc agggcccgga gttcacgagg cactcggcaa   93300
agtcagcccc tgctctttgg gcagccctgt accttggcct gatttcatgc taaccaactg   93360
tctcctatct ccaggtcctt cccccggcat cgaggtcttc gccattcccc cctccttctc   93420
cgacatcttc ctcaacaagt cagccaagct cacctgcctg gtcacaggcc tggtcaccta   93480
cgacagcctg agaatttcct ggacccgcca gggtgaaaag gctgtggatt cccagatcat   93540
tgactccacg atcctcccca acggcacctt cagcgccacg tgtgtggcgt cagtctgcgt   93600
ggaggactgg gagtcaggag acaggttcac gtgcacggtg acccacctgg atctgccctc   93660
acccctgaag cggagcatct tcaagcccac aggtaggccc tgcactgccc ctcccctgc   93720 cccgggactc tccccaggct gcctgggcct gcaggccccc gtgcccatg tcgtccggga   93780 tggcccgcgg cccgccccag ctcaccgctg tctgtcctcc cgcagaagtg cacaagcaca   93840
tgccttccgt ctacgtgctg ccgccggccc gggagcagct gagcctgcgg gagtcagcct   93900
ccatcacctg cctggtgaag ggcttctccc ctccggacgt gtttgtgcag tggctgaaga   93960 aggggggagca ggagcccctg tccctgaca actacgtgac cagtgcccca gtgcccgagc   94020
ccaacagccc gggctactac tttgtccaca gcgtcctgac ggtgagcgag aaggactgga   94080
gtgccggggc gacctacacc tgcgtcgtgg gccatgaggc cctgcccac ttggtgaccg   94140 agaggaccgt ggacaagtcc accggtaaac ccaccctgta caacgtgtcc ctggtcatgt   94200
ccgacacggc cagcacctgc tactgaccgc ctggccgccc acttgggcct gggccagagg   94260
ccctgggtgg ccgtcgctgt gtgtgtgcac gcgggcagac taaccatgtc aatgattggg   94320
atgttgcatt ttataaaaat tagaaataaa aaaagaccat tcaaaagatg ctggttgtga   94380
gtgagcgatg ctctccctgc tggggccatg gctgtgctgc ccccacccg cagaccgccc   94440 tccaccaccc tccccccgc ctctcaccca cagctccgac ccacctctgg aagccctgc   94500 accacttgcc agatgcccac agcaggccaa gcccacactt gctgctcctc tggcggcttc   94560
catggcaaca gaggcacacc agtgtgccac acacacacac acacacacac acactcgtaa   94620
gcacacacac acctgcacac gtgcagggac acgcaggcat gtgggcacac acacacccag   94680
agacacacgg acatgcgcac tcacgcgggt acacacggtc ccaggcactc acacagacac   94740
acatgcacat acatgcacac acgtgcacgt gcacgtgccc ggacaagacg tgggcacacc   94800
gacagtgacg catgcacacg cgtgagcaca cgggcacacg cacagggaca cacagggatg   94860
ctgatgccag cgcttgcact cccacagtca cctagtgccc gctggcggtg tccctctgca   94920
ccacgctggc tgtggggctt cacacccaag ctctgcctgg cctgcctccg cttggaggtg   94980
tgtccgtggg ccgcccagc tgggacccct gccgcagcca ccatccccag gctcaggcg   95040 aagaactcgg agggtcaccc tgggcctggc cagctgcagc tgctcaggaa cgccccagcc   95100
```

-continued

```
cgtgtccagg aggggtgccc ctcccagccc aggctctagt tgaaggtggc agtgcccccc   95160 accccagcc ccacctgcga acagacgcag tcagggcatg tcctgacaga gcaggcagaa    95220
cccagcatca gcctgggagg cagggaggct gtctctggag gcacctcctt ggagcaggac   95280
actcccgtgt gaaccaggtc tgcccctgca gscacccagc cyggaaatgt cgggccctga    95340
ggtccccgga gcagggagtg aggggcatag agcccagcgg gcaggagggg agcaggggcc    95400 agcgggtct cctcttccga caagggcacc cccccagctg cctcctaggc cctccaggag      95460
ccagagctcc agatgccccc aaggacccat cagtgtgcgg tctgcagacc ctactggacg     95520
tcctcagcct gttcatccca acatcactct ctctgggacc ttaggtgtct gtctgattcc     95580
ttggtcccag agccatgggt cctggtgggg ccgacaggcc agccagggcc cctcccggcc     95640
tctcacacgt gttgtagctc caagacggag agagagaaag tgagggccct cgggcacagg     95700
tgtccgcctg ccccagggct ggtcctcaga ggccaagggc cccaccaagc tgcaggggac     95760
aagaggaccc actccctgcc tctcagcccc cagtggccct ggttgtgccc ctacatcctc      95820
caggagagtc tggggtgctg ggggccattc cgctggggct cccgcctccg tggctggcag     95880
agacccttcc tgaccaagcc cgggagctcc tggccccacc gcacacatac cttcctcctg      95940
cttgtttctg ctgcccccac ccccagccct gccggggggg cagcacagcc aagggcccga     96000
gggcgggctc gggtgatggg cagctagggt gggctttgct ggggctgcag ccacactgac      96060
cactctgcgc catgtctccc acagagggg aggtgagcgc ggatgaggaa ggcttcgaga      96120
acctgaacac catggcctcc accttcatcg tcctcttcct cctgagcctc ttctacagca      96180
ccaccgtcac cctgttcaag gtagaccagc ctggccagcg ggcggggggcc ccatgaccct     96240 tggcaccccc caccactcac gccatccctg tcgcctgcag gtgaagtgac ccaccaagca     96300
aggatgtggg agaccagaga cggacaagac gggtgccgcc cggggggcctg gggtcccctg     96360 cctgcgtggc ccatccacat gtactcagac cttccctgtg tccctctcca gcttcaagcg     96420
ctaagaaact ggcttctccc aacacggcca aatgccgtgg ccaagccggg tgcccgcagc      96480
cgtaggccca gcccggccct gctttgtgat gtcgctcttg tggccttgaa ataaagacgt      96540 cagtttatc ttgtgaaact gcttcttcct gaaggctttt cttccccaca cctcacttcg      96600
gtgtgtcaca catcctgaga gttggcccta attccaaagg gctcgtgggc aagggcaaga     96660
gcctgcgggg ctgtgctggg ccgggcacag ccctgctgga gaggatcccc tgcctgggct      96720
cccagcacgc ctaagctggg ggccgggctc aggcctctgg gcttctgcgt gccatcggcg     96780
gggccctgcc ataagcaccg cgcaatgcgt tgtcactcgg tcaccatccg cagcaagccc      96840
agccacaggg agttctgtcc aacctttggg gcatgtactg tgtgtgccag tgggactcag     96900
gaggtgcgct gggcgtgggt gcagccgcag tgcaccctgc agaatcccgg gggggcggat     96960
agtgactaag gtatagaagc gggttcagaa gtttctagtg aaacagcctg gagaatgcat     97020
ggtggggagg ctgggggaaag gggaggcagt gccaggccca ggatggtggc aggaggtggg    97080
ggagccgggc cgccctctgg cgatcagtgc tccctctgag aacagatcgg cgccaggtga    97140
agtaaggaca cctgggggggc ctcgctcagg ctgtggagaa gttcagctgt ggcagcaagg    97200
gtcagggtgg acacaggtgg gaggagagga gagaaggcag aacctggggc ccagaggagg    97260
ggcccaggtg agggctgctc ttgtgagccg ggctcctggg ggcggcaatt tcaggggact     97320
ggagagtggc tgggagaccc caggactgac tctcctgggg tgtctggggc ctgagcacca     97380
gcctggccct gaagaggtgc ctgcccaaga gagatttgta actggacatg ggtcccaaat     97440
ggaacccatt ccctggcttt gggctcccag ggggtgtcca gaccccggct ttgttcccat     97500
```

-continued

```
taaacggacc cccttacagg cccaacctgg caggctgggg acattcgaca aggggtccca   97560
caaagtgcaa gacacctcgg gcagggatgg gggctcccac gcaggctgtg gggttgactg   97620
ttcggggcca cacctacacg agcgtcccag cagggctggc agtcatgaca gaaccacaga   97680
ccagacttaa acgtcatgaa tttattctcc cccggtctgg aggctggaag gaaagtcaag   97740
gcgtcagcta cgctggtttc ttctagggcc atgttggagg gtccggtcaa tgctgccttc   97800
ctagcttccg ggggcggcca gcacctcgtt atcgattaac agagtattta ttatacacta   97860
tgcatgcatg tgttagaaac atatgtcaca gacgtgtgta tgtgtacagt aacactgaac   97920
agtacataca cataataaaa ccgcaaagct ctcccgcgtc cctgcctgcc tggaggctct   97980
gccaagcccg gtggtgggtg tggactccct ggctgcacca gctcggaata atcaggctct   98040
ccttatcctg ttaaagcatt ttcagcaact taggagacac caggtctcgt gacagtagct   98100
cacagtcgct gttaaaaaac agccccaagt gcatcttggg acctggacac aagcggagac   98160
gaaggtgaag gtggcggagc gggtctgagc aggggcggtg atccccggag gaagcgagca   98220
gagcaggggt ggcgggcggt cctgtggggc ccagcagagc acctgggctg gactccgctc   98280
tgggcaggcc ggaaggggca cagcacgcat gtcgcccacc cagcccttgt aggacacgtg   98340
cccgggaagc cccttcccca cccgcggcac ttctgaagtg ggcactacgt tatctcccag   98400
ggaccctgat gctgcaggca cagaaccgcc caggtgctc acggggctcg gagtgagctg   98460
cggcactcca agacaggaga agccgagggt ccccgtcccc actcttggga cacacacagc   98520
ggtggagggc ctgcatgctc tttctcagcc agagagccat cttccagccc cagagaccac   98580
cgtgaactct gcagcacaga agacagctgc tgctggggaa acagcttccc tctgaccttg   98640
cgtgtcacac cgcccttcgg tcagagatgg gggacaggga tggggccacg gatggaggga   98700
gagaagaggc ttggacccag aggagacagc cgcccaccca agaggccgtg ctggcaggcg   98760
gacaggacaa agctgggtta ggttgcagcc tgtgcccacc gcactcacca gagggggagag   98820 aggtgaccac tggccctggg gaggaccgagg gctcggggggg aggccgggtg ccccaggcaa   98880
cagccagcca agcgggcagc atccctgtgg gaggtacgga acaagtgacc gcagggactc   98940
ccactctgag cccgaggtcc caggacacca ctcgccccac ccccaggcac ccacgtgagg   99000
cgcctctgct gcgtctggac tccccccagg ccatctgaga cagaaaccac ccagagaaaa   99060
gggaacttca ggaagcaggc ggtgccaccg gtttcagtcc cgctcttagt gttcgcaggg   99120
ttgcgggcag tcagctcaca tctccgggaa tccagctacg aaatcctagg ggctgggggct   99180 gcgggcacag aggtcggcct ggaggagcgc aggtgcctgg ggccagagta gggaaggggt   99240
gggggcagca cggagaccca ggctgcaggg gagccacctc catggcctcc gccttcggtg   99300
agtgcagccc aagaggagca gggacagagg gagcgcaggg gggcactgga ggggaggccc   99360
cacctcaggg accccacaag ggtccaggag cagctgagta gaaggctggg agctggtggg   99420
cacaggcagc cgacccacca cctggaaggt ccaggggcca ggggagacct ctggggcacac   99480 tggggacaca aaagagggtg acggtaccca gggacgagga gctctgctgg gagggggcca   99540
gcgtgggact ccaaggagaa agccatccct gctgggaggg ggccagcgtg gggttccagg   99600
gagaaaagac atccctgctg gggtggggggg gccagggtg ggactccagg gagaaagcca   99660
tccctgctgg gaggggggcca gggtggggtt ccagggagaa aaggcatccc tgctggggag   99720 gggggggggcc agggtgggat tccagggagg aaaccagccc tggggttaac acaggagtca   99780
gggagtggag cggaactagg ctgagggctc tgcgttgacc cagagggtca gaggctgcca   99840
```

-continued

```
tgggccagca ccagggacaa aggtcaggga ggctgaatgt aagaggtggc agaacacctg   99900
gaggtcaagg agggcagccc caggcgctct aaaaacacat ggagcttgtg cacatgagca   99960
gaagcctggg agtggacggg ggcaagaagc taacttggag ttcaagagaa gttggagctt  100020
gtgtaagtca gaggccactg aagggcagga gggcagtggg acattccttg aatttccaag  100080
gatgcaagta gagcttttgc aggtgagcag agggctggga gggcagggg cagccccagg  100140 ggctccaagg agcaggttca ccttctccat gggagcagag ggttgcaaga tcaggggcca  100200
gcccaggggg ctccagggag caggtggagc tcttgcgggt cagcagatgg ctgtgagggc  100260
agaggccagc cccatgggtt ccagggagca ggttgagatt gtgaaggtag cagagggctg  100320
gcagggcagg gggcagaccc aggagctcca gggagcaggt tgagcttctg caggggagca  100380
gagagctggg agggcagtgg gcagcccagg ggttccaggc agcatgttga gcttctgccg  100440
gggagcagag gcctgcgagg gcaagggga acccaaggg gctccagggc acaggttgaa  100500
cttctgcatg ggagcagagg gctgggaggg catgggcag ccccagggtt tccagggcac  100560
aggttgagct tgtgcatggg agcagagggc tgggagggca gggggcagcc ccagggtttc  100620
cagggcacag gttgagtttg tgcatgggag cagagggctg ggagggcagg gggcagcccc  100680
agggtttcca gggcacaggt tgagcttgtg catgggagca gagtgctggg aggtcaggga  100740
gcagccccag gtgttccagg gcacaggttc agcttctgca tgggagcaga tggctgggag  100800
gtcagggagc agccccaggg gctccagggc gcaggctgag ctttgcagga gagaaggggg  100860
cacggagggc aggggcagc cccaggggct ccagggcaca ggttgagctt gtgcatggga  100920
gcagagggct gggagggcag ggggcagccc caggggtttcc agggcacagg ttgagcttgt  100980
gcatgggagc agagtgctgg gaggtcaggg agcagcccca ggtgttccag ggagcaggtt  101040
gagcttgtgc aggggagcag agggcaggga gggcagggag cagccccagg ggctccaggg  101100
cgcaggctga gctttgcagg agagcagagg gcacggaggg caggggcag ccccagtggc  101160 tccagtgcac aggttgagct tgtgcagggg agcagagggc tgggagggca gggagcagcc  101220 ccagggggctc cagggcacag gttgagcttc tgcatgggag cagaggtctg ggaggtcagg  101280
gagcagcccc aggggttcca gggagcaggt tgagcttatg caagtgagca gaggcctgcg  101340
agggcagggg gcagcccagg gggactccag ggagcaggtg gagctcttgc gggtcagcag  101400
atggctggga gggcagggg cagccccagg ggctccaggg cacaggttga gcttgtgcat  101460
gggagcagag tgctgggagg tcagggagca gccccaggtg ttccagggag caggttgagc  101520
ttgtgcaggg gagcagaggg cagggagggc agggagcagc cccaggggct ccaggcgca  101580 ggctgagctt tgcagaagag cagagggcac ggagggcagg gggcagcccc aggggctcca  101640
gggcacaggt tgagcttgtg catgggagca gaggctggg aggcagggg gcagccccag  101700 ggtttccagg gcacaggttg agcttgtgca tgggagcaga gtgctgggag gtcagggagc  101760
agccccaggt gttccaggga gcaggttgag cttgtgcagg ggagcagagg gcagggaggg  101820
cagggagcag cccagggggc tccagggcgc aggctgagct ttgcagaaga gcagagggca  101880
cggagggcag gggcagccc caggggctcc agggcacagg ttgagcttgt gcatgggagc  101940
agagggctgg gagggcaggg ggcagcccca gggtttccag gcacaggtt gagcttgtgc  102000 atgggagcag agtgctggga ggtcagggag cagccccagg tgttccaggg agcaggttga  102060
gcttgtgcag gggagcagag ggcagggagg gcagggagca gccccagggg ctccagggca  102120
caggttcagc ttctgcatgg gagcagatgg ctggaggtc aggagcagc cccaggggct  102180 ccagggcgca ggctgagctt tgcaggagag aaggggcac ggagggcagg gggcagcccc  102240
```

-continued

```
aggggctcca gggcacaggt tgagcttgtg catgggagca gagggctggg agggcagggg 102300
gcagccccag ggtttccagg gcacaggttg agcttgtgca tgggagcaga gtgctgggag 102360
gtcagggagc agccccaggt gttccaggga gcaggttgag cttgtgcagg ggagcagagg 102420
gcagggaggc agggagcag ccccagggc tccagggcac aggttcagct tctgcatggg 102480
agcagatggc tgggaggtca gggagcagcc ccaggggttc cagggagcag gatgagctta 102540
tgcaagtgag cagaggcctg cgagggcatg gggcagcccc aaggggctcc agggcacagg 102600
ttgagcttct gcatgggagc agatgcctgg gagggtaggg ggcagcccca gggtttccag 102660
ggagctggtt gggcttatgt aggtgatcag gggtcagaga gggcaaggag cagcatccag 102720
ggatccaggg agcaggttta gctagggcag gtcagcagag ggctaggagg gcaagggaca 102780
gccccaggtg ctccaaggag caggttgagc ttctccatgg gagcagaggg tygcaagatc 102840
aggggcagcc caggggggact ccagggagca ggtggagctc ttgcgggtca gcagatggct 102900
gggagggcag gggcagccc caggggctcc agggcacagg ttgagcttct gcaggggagc 102960
agagggctgg gaggtcaggg agcagcccca ggggttccag ggagcaggtt gagcttctgc 103020
atgggagcag atgcctggga gggtaggggg cagccccagg gtttccaggg agctggttgg 103080
gcttatgtag gtgatcaggg ggcagagagg gcaaggagca gcctccacgg atccagagag 103140
caggtttagc tagggcaggt cagcagaggg ctgggagggc aagggacagc cttaggggct 103200
ccaaggagca tgtagagcac gtgtgggtga acagagggct gggcggtcag ggggaagccc 103260
caggggctcc agggcacagg ttgagcttct gcaggggagc agagggctgg gagggcaggg 103320
ggcagcccca ggggttccaa ggaataagtt gagcttgtac agatgagcgg agggctacga 103380
gggcagaggg cagccctgag gggctccagg gagcagtttg agcttgtgca ggacagcaga 103440
gggctgggag ggcaggggc agccctgagg gactccaggg aggaggttga gcttgtgcag 103500
gatagcagag gcctaggagg gcaggaggaa agccccaggg gctccaggga gcaatcagag 103560
ttatgacctg taggctgcgg gcaggcaggt acaggactgc cctgaggaga tccaaggagc 103620
tggtagagct tgtattgcta aacaggcggc taggagtgca gggggcagcc taactggctc 103680
caggaataaa gtaaagcttg tgcaagtagc agagggctgg gaaggcaggg agcagcccca 103740
ggggctccag ggagcaggtt gagcttctgc aggggagcag aggcctagga gggcaggggg 103800
cagccccaga ggttccaggg agcaatcaga gctatcacct gtaggctggg ggcaggcaga 103860
tacaggactc tgccctgagg aattccaaga agctagtaga gcttgtattg gtgaacaggg 103920
ggatggaagg gcagtaggca gcttaaagta gtcaaggaag ccagttgtaa ttgtgagaat 103980
gagcaaaggg tccgcatgac agcgggactc ccctgtaact agtggattaa tgcccggacc 104040
taaggtacaa ccacatgagg agctgagcca gggtgacggc tgtggggatg ctcacagggg 104100
ccacggatgc tcctgggaca agagtctcag aggctgctag tgagcagggg gctgaggtca 104160
gaggacaggg atctgggaac cacgagctgg ggtggggtca ggggcccggg ttggagggg 104220 aagtgagctg agggtctcca gctggaggac cagaagaggg actggagctc tccgaggcac 104280
agactcggca gcctggctga ggccacaggg atgaaagggg aggggccaag gaggagacct 104340
gcagggatag ggtccaaggg ggccagggtc catagggggcc atgggccagg gcccaggtgc 104400
tctgactgca gagctgaccc agaagacacg ggcccggagg acaaagaaca ggacaggcaa 104460
ggggccacaa gcaggcttct gtgtggtgga ggcccaccaa gccaaggaga ggcctgctca 104520
cctagggcag ggccgggcta gggcagcagg acggtgagct caggggacca gcggatgctg 104580
```

-continued

```
cccgggagca cgcagcactg gtaaggactc agacacaggg ctgagtcagg ccaggcacct 104640
gcaggaggtt agggacctgg ggggctgtca cccaggtgat cacccagctc tgacccacag 104700
ctgcagaggc acaaggcccc aggtggtgag ggccctgccg gccagctggt ttgcagacat 104760
tctggaagca catgggcgct gggctcaggg gtgcccagaa ctgggctcgt gacaccctgc 104820
ccggaccctc ccaggggtga agccctggtg gtcacacggc ctacattctt gcagcctcca 104880
ccaaggcccc atcggtctat cctctgactg cttgatgcgg ggacacgcct ggctccacag 104940
tggccttcgg ctgcctggtc tggggctaca tccctgagcc ggtgaggtga cttggaactc 105000
aggtgccgtg tccaacggca tccacacctt cccatctatt ctcatgtcct tggggctcta 105060
ctccctcagc agcttggtaa ccatgcccgc cagcagctca actggcaaga ccttcatctg 105120
caacatagcc cacctggcca gcagcaccaa ggtggacaag cgtgtggata agtggacagg 105180
cctcagggag ggcgtccact cccagacagg accgaggtca gccttcctcc cggctcgaac 105240
cacatgccag tatggcgacc tctgtccagg gtatcagagg aggagcggtc tcctcgcctg 105300
gaggcctccc aggctatggg aggggacctc tgggtgtttc tatcaggtcc aaggtgggca 105360
caggctgcac aacgctaccg cacatagctg gtgctggacc tgccaaaatc cgtccctgcc 105420
ctatgcccgc cccaacagac ctgccccctc acccagaaac ctcctgtctg ctttctttgc 105480
agaacccaag acaccaaaac cacaaccaca accacaacca caaccacaac ccaatcctac 105540
aacagaatcc aagtgtccca aatgtccagg tgagtcagac aagccaacca ccttttcaag 105600
ggggtggcca cagccctggt atgctgggaa tacatatgcc ctggacaacg ctggcccagg 105660
tgctaactgc ccaccttgtc ttccctgcca gcccctgagc tcctgggagg gccctcagtc 105720
ttcatcttcc ccccgaaacc caaggacgtc ctctccattt ctgggaggcc cgaggtcacg 105780 tgcgttgtg tagacgtggg ccaggaagac cccgaggtca gtttcaactg gtacattgat 105840
ggcgctgagg tgcgaacggc caacacgagg ccaaaagagg aacagttcaa cagcacgtac 105900
cgcgtggtca gcgtcctgcc catccagcac caggactggc tgacggggaa ggaattcaag 105960
tgcaaggtca acaacaaagc tctcccggcc cccatcgaga agaccatctc caaggccaaa 106020
ggtgggacga caacgggcg cgggagggtc ctgtgggtct gcttggagct accatcatgc 106080
tcacagacac acctgtcccc ccagggcaga cccgggagcc gcaggtgtac gccctggccc 106140
cacaccggga agagctggcc aaggacaccg tgagcgtaac ctgcctggtc aaaggcttct 106200
acccacctga tatcaacgtt gagtggcaga ggaacggtca gccggagtca gagggcacct 106260
acgccaccac gccaccccag ctggacaacg acgggaccta cttcctctac agcaagctct 106320
cggtgggaaa gaacacgtgg cagcggggag aaaccttcac ctgtgtggtg atgcacgagg 106380
ccctgcacaa ccactacacc cagaaatcca tcacccagtc ttcgggtaaa tgagcttcac 106440
cccggcaccc cagcgaaccc cccaccccga agctcccagg ctcccgcgtg gaggcctgag 106500 ccccaccct gtgtacatac ctcacaggcc agcatgaaat aaaacaccca gggcctccct 106560
ggggccctgc agcaatgtca tggttctttc cgagcagagc tccggcgccc gccgggcctg 106620
cgggaggcgg gggcagccca ggctctgagg acaaccttgg tgccatcagg ggactgggga 106680
tgaccagagg caaggatgg ggtctgccag aggcagcagc tccctagggt ccagtgtcga 106740
gccagcacct gctcaggctg gagtgtgcag aggacactgg tagagcctcc cagggaccct 106800
cacggaaatg aatacatagt tcttcccacc tctgtccaag cccaactgtg ggacagtggc 106860
aggtccttat cccgcagtt cccgacccg ggcctcaaa ggcccacgtg ctgacaccct 106920
gtcaacatgg gatccacgcc aggccagcaa tggggcaca ggcctcctgc tcgcaggacg 106980
```

-continued

```
cacggggatc aggccccaca ttcccgcagg caaggttctc gggccagaac ggtacactcg 107040
aggggacatt cacctagacc cataggaaac aagccttctc atggagcaca acagcctgca 107100
cacccctcgt cctcctgcat actcacgcac actcatttcc tgtgcaactg cacaaagcgc 107160
tgaaccacaa aagtgcacac aggccagcct tgctcactgg gtcctcaacg gggtacccgc 107220
ccggggccag accggagcct gcagccgggt ctcatgaacc ctctgtggac aacagcttgg 107280
tccccactcc tcaaagcccc agcagcacag accacactct gaccacactg gtcagctcag 107340
acccccaccc ctcctctccc cagaacacct gcaccccctc ctcaacacac agagacccaa 107400
cagcccactg gtccctagca cgccgacccc accccttgg gcacacaagg acaccccaag 107460
gttgcctccg cccttccctg cagtaggacc caccacagcc ctgctctgca gaccctgcct 107520
tctaggcctg gcctccagtg ggagggaagg caggggtcag ggcaccctcc ccgcagagga 107580
ccccatgaaa ggcacagcag aggagaggat aggggccccc actgaccagg ccgagatctg 107640
ggcccaagga gtccggccaa gactgaggcc caagctggag gaatggggga cacgaggtcg 107700
ctgcccaggg actgacctaa gggaaccatt gatccagccc cccaggggga tcctagtgcc 107760
ccacccgccc tgtcacagag ggacccaccc caggcgccac tgaccctgcc ctggcacgtg 107820
acgggcagcc acagagctga acaccccctc cctgtccaga gccactcctg gaggaggaga 107880
gctgtgccga ggcccagagc ggggagctgg acgggctgtg gaccaccatc tccatattca 107940
tcaccctctt cctgctcagc gtgtgctaca gcgccacagt gaccctcttc aaggtgggcg 108000
ggccaggcca gcggtgcctg ctgtccccac acggtgcccg cacagtcccc ctaccctgtc 108060
cactccctgt ccctccatgt ccctccctgt ccccttcctg tccctcaca gtcccgtcac 108120 tgtctcctca ctctccccctc ttgtcctctc tgtccactgt ctgtcctcct ctgtctctcc 108180
agtccattct attctctcac tgtccctcta tgtcctggtc gggacctcgc tgtccgcggc 108240
tgtgcccatg tagtcctcgc gccacccac ctgagcacac ttgcggccgg cagtcccagg 108300
gctgggaggc caggtccttg ggggaagctg gcatgggggc cccggctgtg ctcacacccg 108360
ccgtccctgc aggtgaagtg gatcttctcc tcggtgttgg agctgaagca gacgatcgtc 108420
ccagactaca gaaacatgat cgggcagggg gcctagcgtg tcctctgggg gtgtccacgg 108480
ccaccacagg ccccagaggt accccgttca tcactccgag ctgctcagcc actactccgc 108540
ccgctgccct gccagttctg agctctcggc catgctcacc cgcacctcca tcctccgact 108600
taaaggcaac cactgaccac accctgcaca ttgctcacgt tcaggggcca ggtgggcagc 108660
aggtgctacc accaacctga gcttaggggt ctgcctgtcc tcaccgggag tgcccggggc 108720
accctcaggt tcccttggat gagcaggagg ctggcatccc ggggcagtgg gcagggatag 108780
ctctgtggac accatcagat tggtcatcaa gcagggtccc caaggggagg tgcctgtgtc 108840
agatccttgg tgggaacata tgcagccctg gccaacgtct cgcagcaggg aagcttctgg 108900
atgtgccacc aacggtcagc caagtactca gctctgagaa gggcctgggc ccatggcccc 108960
tacaggagcc aggcctgcca ggaacggcag tgaggtctcc ccactccagc ttcccagaga 109020
cggaactggt gaccgggtcc cccaggggca ggacacagcc tcgctggaca cagcaagagg 109080
gacactggca caacagggca gtggccgcag ccagcctgtc ccttggccag cggcctgagt 109140
caccttcagc aggagctccc ctgcaccggg gggtgggtg agaggcgacc ccgggaggag 109200
ggagcccgac accccggcgt cccggcccga gaccctggg cctctcctgt cttgtccctg 109260
gatgggaggg ggcaggcccc actgccgggt ggtggcgggg gagaggggc gcgctacagc 109320
```

-continued

```
cagaggtcac gccaggcctg gcttggggag ctgtgcatcc tttctaaacg tctggagccc 109380
atgaactttc tgcgctgttt ctctttggtt tgggtttttg ttgcgagact ctggcttctc 109440
atattttcgg ttctctagac aataaagcat cctttaccat tccatagctc cctggcagtc 109500
gctctgtgtt gcggcccctc ccctggggac tccacagcct ggccgcccgc cacaccctcc 109560
cagccccagg cctcagctct cccccacca cacccatccc tggggttccc tgggggcgcg 109620
gagtcagcag caagtcccag gggtcggacg cctggtcagc acggctgctg taacacgcac 109680
cgcagtcggg ttggaaccac agaaatgatt gtctcccgtc ctggagcagc acgtcccagc 109740
tcgaggagcg tgaaggccac tgtgcccacc ggctgccaag gctgcaggga cgcagtcagg 109800
actcggtcct ccggggaggc cagaccctga gctccaggcc ctcctggtgg ctccatctca 109860
aaggaacagt ctcaggtccc gggctgtagg agacacagca ctccccagag ggcagacaca 109920
ggatccacag ctgtctgccc ttcgcaggaa atgctccagg aaacggaggc cagtgcctgg 109980
tcagggctgg ctctgctggg cggtccaggc cagcgctaca ggagagctca gtcatccacg 110040
ggacgcggcc ctgggcggct ggacattgtc caagtgtctg tgtgagcctt tcagtgtgtc 110100
agggaagagg gggcgaaatc aacgtgccga gtctgtgcyt ccacggcccc aggggaggcc 110160
agcaggacag gctcctggag gggagctggg acccagcact gagtggaaag ggccattcca 110220
gcttcctgtg ggcacagaca gacagacagc cagaggaaga cagagaactt catgcaggaa 110280
agggacagct cgctccagtg ggctctgcac cagagacggt gaggccatgg ggcgggcagc 110340
cgggtccagg ggcatcgccg gccctcaggg accctgccag gcgtgaggac actgggcacc 110400
ctctgcctcc agggtgctcc ggaagccatc ctgggggtct cccccactcg ccatttccct 110460
cacacggaac acctaaccaa caagctgaac ctgcctatgg tccctgcagc atgcccagcc 110520
ccaggccctg cccctcacct ccatcccctg gagcccggat ctgcctccag ccacacattc 110580
ccacggggac accaggacgc tcgatgccgg gctggccccg cgggtccttg aggagcacca 110640
gtcccagaac agctgccccc caccaggcct gagggccccg tcctgacccc ggggcaacac 110700
caggccacag cgcgtccccc atgcacagcc cctcctggga ccctggaagc gaagtggccg 110760
acgccttccc ttgagcccct gtgtcagcac cggtgcgagc ctgagctcag ctttctgctg 110820
ctcctgaccc ctaggggcgc tgccccgggc aatagctccg acacactcct gtcagtgtct 110880
cacctatccg acccgcaccc ccatccacat cttacacaca cacacacaca cacacacaca 110940
caccctgggc tgccacccca ctgcgctcct gggcccccac caggtccccc ctcctcccgc 111000
actccaaggg gaacgcctgc cggtctgagc tttgaaaacc tggattgctg tccgtgtgtg 111060
gtgtccgtgg atggacgaat tcctgcagcc cggggggatcc actagttcta gagcggccgt 111120
ttaccgttcg tataatgtat gctatacgaa cggtagaata gtaacttctc catcccaccc 111180
aggagcacag gcagcacctc ggaggccgga tgcacctggg agtgagggct gggtttgaca 111240
gcgaccttga ctgcaagcca tccagagggc agagggacag gcacctgccc gagaaggggc 111300
tctcgtcggg gcccagggct caccctcccc tctgaggcat cctgccagga caccttgctg 111360
ccccgctaga gggcaggacc cagaccagtg cctctccctg cccagcgcag caccagtgag 111420
acagtggtgg acacactggg tcgggcaggg agcaggacac acagcgcagc ctgagctgga 111480
gggtggggtc caggccccag gccaccaaag gagccaggca gagggagatg cccagtgggg 111540
accagagtca gcaaagtggg gcgggctgtg ggggtgggc aggaagcctc cggctccacc 111600
ggggtcaggg atcttgcgtg cagccctgac tgtcgccacg ggcagtcccc cagcagcaga 111660
gatgcccaga cagcagctcc agccccgctg cctcccccga cagcttggca cggccacccg 111720
```

```
ctgagcaaca gtccctccag ccccgcaggg ttccccagag tgtggctgcc cctccgcacc 111780
ccggcccgcc tgggcccag cgggtcttct cctgaagctc cagccccgtt cctggctgcc 111840
caccgggggc cagggccgtt tgtccacaat ccgcgttcac agcacagccc ctcccaatcc 111900
gggcgccatc tgtgctgggc cgcctgccgg ggctcatgcc cctcaggcct gtccgttccc 111960
cggtcgctga agtggactcc tgaccgggcc cacagtctgt ccgaaggagg accacccct 112020 caagggctcc ctgagagccg agtcctcact gacccaaccc ccggcctgcc gtcctccaca 112080
ccccgcagac aggccgcccc aggcacacag ccagctcttc caggtctcag gtccgggagg 112140
gtctggacgg gccgcctccc aggccttggc ccaagactct cccatctctt gcaggggcta 112200
aaggtatatc cacctgccag ggccgcacac tctgaagaca gtgcatagca gaagctgtag 112260
gcggccaggc cagtccccag ggcctccagg agtgagggaa ggaagccctc cacagaaggc 112320
cagagccaca ccacccgccc caggtctgag cccagaggcg tgctcaggaa ggcagctggg 112380
gcttccctgc ctggacccct cctccagaca ggtggagggg tccagaactg ctccctgctt 112440
agggcagcct cgcccccgcc ccacagccag tcctccgtgg cctcagcccc agctggattg 112500
cagcctctgc ttccactggg ccagctgtcc ctgcagtggt gactttgctg ccttgggcag 112560
tcctgtggcc tttcccccgt cctgcatcca caggccaccc cctccctctc cagtctaggg 112620
tcagcccacc actgtcccct gcagaacaag catgccctct acggttgtca tcgtggttaa 112680
acgtccctct ggcctggccg ctcctcagcc cacagcccca cctcatgaga cggccacctc 112740
tgcccaggcc catggacaag ccaggacacc tcacccctcc gtcaccctcg cagctggcag 112800
ccccccgact cctgaatcct cccgcttctc tccgtgggcc ctgcgccatt tctcccctcc 112860
ctgcaggtct cccagccagt gttgcctcct tcactccgtg gccagggtga tctttaaacc 112920
ccatcagggc tctgcctcca cttaggatgc agtcagtagc aagatagtca ctcaggcggc 112980
aagaaaatga caccggcaaa taaactgtag ctgaagagct gagggcttgg agatgtcgca 113040
ctgacctaga ttctcagggg agaagaggca cttggccgct ttgtcctcac cgcaaccgca 113100
ggaggacaga ggcgtggctg tccgtgacag gagggggtgt gagggagtca gccaggatct 113160
cgtgtctgca gagctggcac aaggcgggcg atactgatga gccccagaaa aatcccccc 113220 acccactgac cgccccaccc gggaccgtgg ctgggcgagc agcggctggg agcagagcgg 113280
ggtggcagca agccgtctcc agccttgcac gaagcttaga gcccaaagcc cgaccccacc 113340
cgaaggcgta gtcaggagcc acctctcctg ccacccagcc cgaccgaggc gagtggaaga 113400
cgcgtgtgta catgcggcct caggctcgct gtgtctgtgc acaacgtgca gcatccaatc 113460
aaaacttcaa gatgcaaata agcggaaagc cctcactcgt aatccaaaca caatgtcaga 113520
gtgagagccc ggggacccgg gtgctggagt caaacgcgat ctggtcatgt cactgctccc 113580
tcatctgaaa cgctcctcat ggcttccttg tgccctaaga agaaattcca ggccctgccc 113640
caggggttct gggactgtgc ccgagggact gcccgccgac ctgccctgtc cctctcaaga 113700
ggcgtgaatg gggcatgact tctcccacct acaattcttc tcaatgccgc gtctctcgtc 113760
caaagccttt ccgccttctc agccagctga cttccgcttc tcattcacac gagctcttct 113820
gtgtgtctga gaagacgccc tgcccccag gcctgggtca cggggatcc gtgcacctgg 113880 cctttacctg ggcggagcac gtccgtgggg agctgtccct gtgcttagct gtctgacggg 113940
ccccagaccc ctcaccactg cattccaagt gtctagaaca ggctctttca agttctccat 114000
gccacaggac tgtggccttt ttaattttt ccaattaatc atggaccaat accttcgtag 114060
```

-continued

```
agtacagtgg ggattaatta ctagaaaaat gaaacagaaa caaagacatg ccagtgtttt 114120
cttattagag tcaacagact gctgtaaaaa gttttctgat gcacacatca cttgcatact 114180
taccccccgt gccctgtgac cagtggtccc cagctggcac cacccacgga ccccacctcc 114240
agcagctgtg gtcaaacaca aggtggaccc gcaaaaacca cgcacagaat gaataacctgg 114300 aaaactctat gacgtgtgac aggtcccagg actcagcacc tcccacctgc ccataggcct 114360
tcccgccgga tcgcggcgtg cgctctgggc ctggacgccc gcacgtccct cccaccctgc 114420
cttgccctgc gcccgctcca gtctccatca gaaatgactt cctcttatac aggttggtcc 114480
cgacgtgccc ttgcttaaag cccttggatg gctcctcacc actctcagga caaagtcacc 114540
agcggatcct gggccctgct cagctctggc ctctcctccg cggaacgctg agcaccccgc 114600
tgcaggcgcc cggggctcct gtcactctcc ccagccaggc tctcccgata ccgggcgttc 114660
atgatgccga taccgggcgt ccgtgatgtc gcgccctctg ctctctgcct ggtgggcacc 114720
gtcagctctt tctttcaccc tggccagtga ggctgccgct gcacagccgg ctgggccgcc 114780
cccgtgcgtc cgcgtcttcc ctgcgcgcccg cacagcctgg cagggagaag gcagttctca 114840
gatgctggtc gggggtggca gggcaccccct agcataggcc ctggctgtca gctgcctgcc 114900
gtgtgctggg gcgggcgcag gaccaatctt ctcaccagcg cctgctcctc cccagatctg 114960
gcctcctgga cctcccagag ccacggcgag agtggcagtg gctattctgg cctggaggac 115020
accaaccgac tgtggctaac cttcatggcc ctgctcctcg tgactctggt ctacagcggc 115080
tgcatcgcct tcattaaggt ggggtgagga ccccgcccgc acgggtgggc agctccctcg 115140
cccgccagcc agcacccctg cgtccagggc tgtggggaca ctggagtccg cccgggatc 115200 ctgagggagc gggaggaata cttgggccgt tggtgggcca cctggaccct ctcagctgta 115260
gggctgcacc cttccttcca cccgcagccc ccctagagaa gaacaggcac tccacaccca 115320
ctcgcctggg atgggggccc tgactcggct ggcaggaggg gaccagacat ggaagcttgc 115380
accctgtcct ccaagagaag caaggcccca gctgtgccat gtgctccagg gaccctgctc 115440
tcagtgcccc ctctcccgca gcctgtaccc accagcccct tcttgacact gggctcttgc 115500
catgggcaaa gctgccccag agagcagacg ccggcaccgc ggagggaagc tgccagaggg 115560
cagagggtcc ggcctgcact ctgtcctgtg cacggggccc ttccagcccc gtcttgttca 115620 cacccgcct gccctggctc tcctctgtcc acgcagagcc cagcccacca gagaggaggc 115680 tctcccccg gagtcccccc agtcctgact atagcccct tgacttccca cccacggtcc 115740
tgccccataa acagctttgg ctcatctcac ctgcctcctg tttctctgtc ccagcagtct 115800
ggctcttccc aggtcagagg accaggaggc tgaggacaga catccagggg aatccacaca 115860
cgagcaagat aggttgccag cagggtcgga gaagcagcgg gggcagccat ggtgcagaag 115920
ccagcagagc tgagaggccc tgctccccac atcaaacaca ggcaaacaca ggggcctgtg 115980
cccaagcaca cccatgtgca gtccgtgccc acacacgggc acgcacaccg cacacaacac 116040
acacacgagc acacgggcgc tcacacagaa ggcggcactg agtggtgaga caggagcggc 116100
tgggcacaca gagtcctggg ggggtccagc ccaccccttca ctgtctgcac agctgggcag 116160
cccttgagac cccccctcgc acccactccc tccatcagac agggtgagag ccccccctcag 116220 gtagagtggg gtgagcagtt ggtgaagtgc tgtctgaagg gacctggaga gaccctggca 116280
ctggtcactg gtcagtgcct ggtcacttct ggcctcctgc tgtccccaga gcccccacag 116340 cgggcccttgg tccactgcag tctttcctct ccctgccagg tgaggggcca cccatgcacg 116400
gggaggccag cgaggagggc accgtgcagg tgccagcccc gggcggcctc ccagcctcca 116460
```

-continued

```
ctctgcagac cagtggtcgg tgcccaggct gctcccctcc ggcctgccca cctcgcggac 116520
tccgggtctt actcctagtc tggctccgat gccacaccat cccccatcc cccagtccag 116580 ccttgaccca gcagcacctc ttcatggctt ccacgcccac cccatccctg aatgtggccc 116640
ttactccaca tgttggcctg ggagggtggc cgcacatctc acactcagca cacccgcaac 116700
tgaccatcca gatggcaggc tgaacgtggc cgtgaggctg ctgatctgat ccctggagcc 116760
tgcaagtggc gcccatgcag atgtgctcag cccgggatcc tgacacaaca aggagactct 116820
ggcttcttgg gctggcccag tgtcaccaca aggtcctcgc gggagggagg caggggaacc 116880
ccggcaagga gaagccaggc gggtgacata gaggcaggag gctacacttc tggctgcgaa 116940
gacggaggac cgcccacccg tgcttgaggt cctgcgagac tcgtgtcaga ctcctgcctc 117000
cattcggtga caaggcaagt gcctgcgggg atctgctgca gtggccgcaa caaggaaaac 117060
accattggtc cctccagaag cagcccgtcc cctgcgtcct ccccatccca gcaagagcgc 117120
cccatccctc ccacagctca ggtccagact ctgaatggac tcccatcttt ctctgcacct 117180
cgtcccagtc tagcagcgga cctgccccag ctctgcccac tttcctgggc ctggccgtgt 117240
ctgcagggcc tcagtcacat cctccaggcc tcccatccca actcgcccgc tgcggccttc 117300
tcagccagcc tggcagtgag gtggccctgt cgcgagatcg ccgatgaggg ctcagctcgc 117360
ccgctgcccg aaagggcctc acattttatc cgaaatttgt acatgggtcc acaccctgac 117420
ctcccgtcct tccatcgtca gagcctccgg cctggctgtg ccctggcaga gacctctctc 117480
ccggcctctg gacctgcact cccagtcctt cactgcagcc cgccccgtgg ccctgcccag 117540
aacgacggcg cactgccctc atccccccac ccctgctcca agttctctgc tctgcccctt 117600
ccagcccttc ccaagtttca catgcgcatt gtgctagttg gtcatttctt tctcctcgta 117660
gaaacctaga aagttaactc caagagcgca gggtttttatc tccctgatga gccccaacac 117720
gtggaccaga gcccatgggc agtagtgcca gcaaacactc actgagcgac ggaggtcagg 117780
gccgcgcccg agtcccaggg tcacgggccc tcccgggaca ggcaggccca gtggagtgtg 117840
ccacgccact tcccttctga gagcaactcc tggcccactc tgccccatct cagtaagtga 117900
ccacctccag actccaggct cacccactcc ccagcccaca gccaggggg tcttttaaaa 117960 cctgaatctg tcctgggagt cccagctcaa acccaatgaa gagttcttgt tacaagagtg 118020
aaatcaaaat tttcatgcct ccccactgac ccagccaggc ccagggccca gatgggcccc 118080
accaccctgc ttatgacggt ccatgcttgc tccccacttt ccacagtgtg tcactacctg 118140
tggggccctg ggtactgcct gcctccagtc aggacctgaa gtccctcaag agcagcagct 118200
gaaggaaggt gtgaaggaag aaggggtgg cctgcctcgg gggagaggcc tcagagcctc 118260
caaggagagc atgcacaggg ccctcactgc aggagccccc gagcgatcgt cactgttacc 118320
cagctatccc caagtccaca gccccaaggg tttgcactgt ggagtcctgt ctgcaggccc 118380
caggaggctg ggaggaggc cagagggagg ccagacacca aagcctgcag gttccctgag 118440
catggagggt gcctggtttg gtccaaggag cctgtatttg agtttctttc tgctcaggaa 118500
acattttcac acaaagcacg agagcccctc caaccacagc cagggcctca gcctgttggg 118560
tggacgccgg gcccttcact cagttcttca acaggaaaac ccaggggcc ttccagcaga 118620 ccctctttta tcttcaagaa ccaccagtct atctctgcca gaggcgtgtg acagcccggg 118680
gccctggggc cagccatttc ccctcacaag actgcttgtg gccttcctgg caccgcagcc 118740
actggcctcc gcccagcccc gggccgttgg tcctgcacgc tctgcagctc acccgagtca 118800
```

-continued

```
ccacgatccc acccgcctgg caccctcctc tcggggcaga aacatctgtt tccagctttg 118860
gcgacaaaca ggacgcaccc gcctcctacc cctaagtcaa ggcttgatga gcccagtccc 118920
ctggtgtgga gcccacccc tggccacctg tgtgaggccc gactgaacgc cctccctcag 118980
tgtttggggg aggttccgag ccagccctgc cctctgaggc ttgtggactg aggcttccca 119040
ggacccaggc agaaaccagg ctgtgatctc cagccaagga atgtgttcat tcctggtcca 119100
cagccgggcc cgtgttgact gagttaattc tggaaggcat atggctggga caagacctca 119160
aaagagagtt gggggacagg aagatcaggg acagcgtctc tgccctcacg gtcaggacaa 119220
gagtaaagtc ggaaccagca gcatgcaaat cggtaagcag gccagaggaa gttacgggaa 119280
cctgtctgcg ttccattggg gtgaatgagt gctttctcag aatgacacca aggccaggaa 119340
gtttaaaagt gacattgaga gatttgccta cagaaagaaa aaattttaaa tctatgaaga 119400
taaagtctct acaaacaaaa agttaaatgc tgtgggagag agagtgggca aagtgagtaa 119460
cttcaaaaag agtctgcagt agtcagggtt ctccaagaat agatgtatga gacagaaatg 119520
acagacagac agataaacgt atgtgtgtat actgatatat acatagagag aaagagagat 119580
ttttaaggaa ttgggtcctg tgatcgtgaa ggcttggagc atccaaaatc cgcagggcag 119640
gccagcagtc cagagctcca gggaagagtt gatgttacag tctgagtcca aaggccatct 119700
gcgggcagaa ttccctcttc ctcaggaaac ctcactcttt tttctcttaa ggtcttcaac 119760
tgaatagatg aggcctaccc atgtagaaca atctgcttta cccaatgtct actgctttaa 119820
atatcaacac attttttcaaa taccttcact ctttggatta gtgtttgacc aaatatctgg 119880
gcactatatc ctagccaagt taatccataa aattaaccat cagaaagccc aactaaatga 119940
gcgttggaaa aaatgcaatg aatgggacaa atctgaccta taagaagttt ttggtggaag 120000
tgggagtgga gggatcattt ccagtagttt gtaaacaaca aatagccaat aaaacatgaa 120060
attgttagcc atcacacata atcaaagcag tgactttaaa caactgacca tcagttcagg 120120
tgacaactgt tcatggcagc ctaccatgcg ccaagcaggc atccaagtgg gagtgtgcag 120180
tgtgactgct ctgtggcacc actgccctga tgggagagga acaacacaac tggacacaga 120240
tcaaatgccc taccaaagac aaggaggcca ggcgaggacc gacacctcac tgccaggtgc 120300
tgtcctggca gatgaagggc ctgcaggcat cggggaggca cgtccaggca gaaggagcag 120360
aaggcagaaa ggtcctgggt cagaaatgtg ctttacaagt tcaaggagca gcaggaaggc 120420
tagtggggct gcatcagaag ctgggagact ggggaggagg aggtggggaa gataaagtga 120480
ggccatacga gcccgttcaa gcttcatgct ttgctctggg gtgatgggat gcccccaaag 120540
gcatttgggt tggggggttt tcaattttgc actggaaagt cagctgcact ggagggaggg 120600
tttaagtcaa gggccctgga gatctgtgca ggagtccttc tggggagtag caggaggcag 120660
agcaggggca gtggcagcag agagaagggc tcagatcatg catgtgcctg aaagtggagc 120720
tgagggtctg cagagagaag tcgcacccac gagatcccct gcatcacagc atgaatgcag 120780
tgccattcac tgatctctgg ggtcaacaac tctcccttca gtgtgccag ttcaagctgc 120840 caattacata cacaggaatg gatgtgggag tggatgctcc tgttggacct gggctctggg 120900
gcttaggaag aagtcactgg aggaggagga gtaaatccag gactgcacat ggtgctgtgg 120960
ctgatactcc caggactagc agggacacca agaaaggtgc gtggaaggga gccaaagtca 121020
atgtgtggca ccaggtggag gggaggactt ggaagccagg gtcagaggca ggagtcagaa 121080
agatacaggg ctagaaggag gacatcatgt gcagggacac tctgcacgtg gtgccaagga 121140
aggacttggt ccactgcatg catgctccgg aggcgtgtct ccaggaggct gacagggagc 121200
```

-continued

```
aaggggtcct ctcaagagca gtctcaacag caaggtggcc aagacctggc tagagtggcc 121260
tcaagaagga ggagggaggg gtgagtggat gcaaaagtca gggcacacca gacctaggag 121320
cagagtccac cagcctggtc aagccgacac cagcatcaca gagcacgcac atacatcgaa 121380
cacaaacctg cttgtgaagc ctgatgtcca ctgcaccatc gataaactga aaaaaactaa 121440
agtcatggta tcaagatctc caacagtgca gcaaatgaga gagacaacca tggcgaaggg 121500
gtaaatgggc tcctacacac agctcacggg tcaaatcaga agagaagtcc atagccttaa 121560
atgtctgtga ggcagaaagc actgagttaa tacagagccc aaactgaaaa gttgggaaaa 121620
gaacagcaaa ataaacacaa aaaaacggaa ataatcatat aagccaaaaa aaatcaatta 121680
cttcaaaaac acacctgcac cccagtgttc atagcagcac tatttacaac agccaagaca 121740
gcctaaatgt ccatcaacag atgactggat aaagaagaaa tggtatgttt ttacaatgga 121800
atactactca gccataaaaa aatgacaaca taacgccatt tgcagcaaca tggatgcccc 121860
tggagaatgt cattctaagt gaagtaagcc agaaagagaa agaaaaatac catatgagat 121920
cactcatatg tggaatctaa aaaacatgaa tataaataca aaacagaaac agactcatag 121980
acacagaaca caaacttgtg gttgccaaag gggtgggggg tgggaaggga cagactgggt 122040
ggtcaaaatg tagaataaac aaggctatac tgtatagcat aggcaaatat atgcaagatc 122100
ttatagtagc ttacagcgaa aaaatgtgac aatgaatgta tatatgttca tgtataactg 122160
aaaaattgtg ctctaccctg gaatttgatg taacattgta aaatgacaat aactcagtaa 122220
aaaatatttt ttaaaaacta gttattgatg aaaaagtaat aagaggaaat aataaataaa 122280
tttattccac tagtatatag taaaaatttt aaatcccagg acagtatctt atcaaaaatg 122340
actcaggaat agaaaagctc aatagtacca tatttattaa acttctttgt tttatttatt 122400
acataaatta aagcagtaga tttaaatctt ttcaaataaa aataccaggg ccatgtttcc 122460
tgaagctctt aaaaaaatgt attattcaaa ttttatttaa aaaactatca aaaagtgaag 122520
aagaaggaat aacacccaac tcattctata aagccaatat aacactgatt gggaatcaga 122580
aaaggaaagc atggaaaaga aaagctatgg gacagtctta ctcatgaaac agataaaaat 122640
actccagaga aaatattaac aaataatttt gaacctcatg aaaaaacaga taattcacta 122700
tgtccaagtc aggtttatcc caaaaatata aggatagttt aacctaatga aatctattat 122760
tgtcattcaa agcatgttca taataaagaa gaagaatttt aagatcatct taaaggcaga 122820
gagaaaatgt tgaaagaatg tatactcttt caagatataa aacttttgc taactaaaac 122880 acaatggaat tctttgatct gacaaagttt atcaaccaaa attctttgaa tttttttct 122940 tagaggaaaa ttggaagcaa ctgtgtacta gaagtcttga tgtattccat aagaccaaaa 123000
atatattaaa acatgataac tttctaagta gaaaaaatcc agaaaaatat ataaaaataa 123060
taacaattaa aaataacagg taacttgcta caataccaat atacagaaat caagtttttt 123120
gctattaacc agtagcaaac agaaagtcat ttttgtaaag atgccagatg tctgcttctg 123180
ttaagggcat acaggtaatg tggcccaacc ttcccattga ggaatactag aaaaagctgg 123240
aaaagtactt ttagaatctt cctgaaggta gtgacaagtt aacaaagtca tgaataatca 123300
cgggattgag agccagagga gactgaaatt cagagattca aacctggcag ccacttttc 123360 cccaaagcct tttactgatt ctagaataaa gttgagacac tgagcagcaa ttttgacaat 123420
cccatagggg gagggagaag aaatttggaa ttttagaact aatgtgtaca actgcatgaa 123480
ttaaggactc aacagacaga tttagaagca gagttaacac agctggagaa ttagtaaacc 123540
```

-continued

```
agaagctgaa acaaaagaaa ggagctataa tgtagaccag aaaacaaagg catgagttga 123600
aagaagagtg ggtacactga caaagtccaa cgtgtaagtg cttaaagccc tagagaaaga 123660
gagagagaag agaagacaca gtcataaaga ggtaattgca gaaatctttc caaacttaag 123720
gagaggtacc acccttggt tcaaacagaa taaaacacac acacgcagaa agtcacaccc 123780
atccataaca taaaactact gaatactaaa ggagaaaatc ttgaaggcag ctgaaggaat 123840
ggggaacctt acattatctt caaaggagca acaataagat ggacagctga tgtcacaaca 123900
gaaggagaag caaggagagt gatgctctgt ccatagtgct gaataaaacc accgataagc 123960
caggaaaacc atccttcaga aatgaagatg accctgcttt tcccttctcc ttagctatag 124020
tttcctggga ctgtgataac aaagtaccac taactgggtg gcttaaaacc actctctcac 124080
agttctggaa gctagagatc tgaaaccagt atgccctcag ggctgtgctc cctctgaagt 124140
ctctagggga ggagatttcc tcgcttcttc tagcctttga tggttgccag caatccttgg 124200
catccattgg cttgcagatg caccctccaa tctctgcctc taccttcaca tggagttttc 124260
cctgtctctg ggtctctggg tctaaatttt cctcttctta tgaggatact agtcatatca 124320
gatttagggc ccaccttact caagtacaac cacatcagaa cttggtgata gctgcaaaga 124380
cgctgttcca aatatggtca cagtcacagg ttccagatgg acatgaattt gggatgcac 124440 tgcaaggccc agtatacttt cctttcctgt gcaatttagg tgaagctctt aggtgagcag 124500
atcaatgtga acgtgtgcac ggtggggttg ggagcggcag aggcctggaa taggccctgt 124560
gtgggtgggg agggtggcct gatgcgcgaa gtaagatctg gagcaagatg agagggctcc 124620
acctggctga gggtatagac tagaatgacc agaatctcag aacctgaagt gagagaggaa 124680
agcattatgt ggcacggagg ggaggttggt agctcacaag ggaactgatg aaataagtga 124740
atatactgag aagcacagac aaaagagaag agagttacga agatcaaaag gaagaaaact 124800
agaatggatc atgtgatttg gagctggatt gtatgcatct gtcagaattc acattttcaa 124860
cacatgcaga tacagagaga gagagtaagt agtggccaaa aacttcccaa atttgatgaa 124920
atatatgaat ctgcacatcc aagagagatg ggcaaggatg ggtggctcaa cacccagggg 124980
aagtgagaga ggcaggaagg ctgtaggtgt gctccaaatc ctgggtctac ccagaaccat 125040
gggaatggtg ggcagtgatc atgccctcag cccagtccct ggccactcca ctggaaaagt 125100
cttggcctgc ctcagcccag accccctccc ccaccccttc tcagacagac ttggcagaca 125160
gggagctagc ctgtggccac atggatcttc agcttaatgt caccctaaaa acttattaaa 125220
gacataggaa cacatggatc attaaaatca tactaggaac accaggcctg agagcttact 125280
gtacacatcc aactaaaaag gtgtcacatt ctcacgtgaa cccatgacga ggacaacacc 125340
taacactgta acggcgatgg cgccactaaa ctgtcatctg atcacctggt atatacatca 125400
agagatccag tggcagatta tccacgagtg tcccagagcc ttccttggct tagtaccctc 125460
tgttgacatg gttcattatg ttacatatga ctgcccgttt acttgtctgc ctggactcca 125520
tcctgtccat tgcctgtaag gtctttaggg tcctgaaggt tgcctctgta cttgactcaa 125580
tcttgaggct cagtgcaggt ttgatcttac agcttgactc tacaaagaga ctccactggg 125640
gtctccagca gacttccagt atctattctc ttctgttcta tcctgtagat gcttctgttt 125700
tctgcataaa atttcttgtc atcctgttag ctttctgcat gcttatcagg aatacagaag 125760
actattgtga tagtctagaa ccaactggac tctgggaaat attcagggag gtcatgtgta 125820
gtgagatacc tgcctttctc gactctgaga gccctgtctc cgagcaggga taaactctcc 125880
attctgcatc tccagggcct cgatgagctg actattctag tcctctgcca gatagctgtg 125940
```

-continued

```
tggccttggg tgatgctggc tgacctcagg ctggtctggg ttgtccctgg ctgacacccc 126000
ttgactctgg atgatcctgg gaagaccata cttaatctta attggacttg ttctcattgg 126060
gacagaacat ggcctcacta aggcacgagt gtggatggcc ttgggtgatg ggggttgggg 126120
cctcctcagc ccctggcagg ctcccctggc tcccacccct catccatgtc ccaggcccac 126180
ctggcctggt ccagtgtgat gtgattctca gaacagtagc tctggtttgg ggcacctgtg 126240
ctgagacagg ctcaggatga ctcagctgcc ctcagctgag agctgctttg aatgtttcag 126300
caggtgatag acaacagaga cttcagaaga gagaaaaaca agttgctaat gtgagcatcc 126360
ctgccctacc cccacacctg tactgcaaac attgttgacc ccagatagag atcccaggac 126420
agcaggtgat agacaaagga ggctccagag gagagaaaaa tagtatctat aagcatgact 126480
acctctgccc tgccccacac ctgccctgca aacctccctg acgatgctga ccccacatct 126540
gtagacccca ggccagaggt ccatctccca gggcctggct tttgtctcca ttctgtgcct 126600
ctgagcctgg gcaagtccta tgagcaaagg ggtactgtcc cagttcagcc cagtgtgtga 126660
acagtgttgt ggggattctg gaatcttctg caggaatccc ctgtaggatc atcctaatgt 126720
gaatgaggca tggggctaga gttcaggttt tgaagtcaat gttgaggatc agggcccaat 126780
gactaggtca ggacccatng atcagtacag gagccagtta attagaacca gaactcagta 126840
tctagaactg ggacccaggg tccatgccca gaactcagtg ctgtagacta gggtaaaatg 126900
cccatgacca ggacaaagac ccagtgataa ggatctgggt ccagttatca gaatgtcagt 126960
ctgttatcag accccaggta tattgctaag gatcaggcct tagtgaccga ggattgacac 127020
ttagctatca gagactggat ctggtgacag gaacctagga ctgctgagtt ggttgtaggt 127080
gccgcagtag agagagaagc taacccagga gctaagcctt cattttctgg aggagcggag 127140
ggctttattc tccttggaaa gaagattgac cccagctagc tcacttcagt tactttattc 127200
aaacattata cagagtttct tggagctggg aaaggttcca cccacccaca gacatctcag 127260
tccctttcaa ccatggctag ccatttttaa aagtaagaat tcgcagactc actgttcacc 127320
atgaacccag ctagtcagat tcatatgtga aactcatatc agcctctgca cacacataca 127380
cacacataca cacatattac acccatgcac acacatgtac acatacatac acatgtacac 127440
atacatgtgt acacacacat atagagaagg cattggtggg gaaaacwtgt aggccatkgc 127500
ttcagtacag gattcaggcg ggcaagaatg tggtcaggct gggtcagcat aacaagaaca 127560
cttggacaaa gtgagggtag tgtgtgtgtg tgtgtgtgtg tgtgtgtgtg tgtgtgcacg 127620
ttgaaagtct tcagtagact ggtatcacta gccctgatat gggcaacaca gcaagcctgg 127680
gtcacactca agctgagtat cagggtagcc agggccttct aaccaagggt agatgcagcc 127740
tgtgttccgt ttactgacca gtgagaagcc atgagctgaa ccagaccaga agacccttac 127800
tgttcccacc caacccccac ccagtttagt ctcagcaaga ccctgtactg tgggccacag 127860
ctctccccca caccccacct gtagcacaaa cactatttgc aaacatttct aaaaatgatg 127920
agaacaggaa ccacagagca gaggggggga ctggcgtgga aagccccatt cacccatggg 127980
actgaaactc agggaaccag aaccgtaagg agatttgcat ggtgmtgggg gaggttggcc 128040
ctggatcagt gagcccagag agttactggt ttctcacttc catcatgtca acctcctcaa 128100
cccccaaaaa tggccaggcc taggctatgg atgagtttca atgaccaggc cctaaggacg 128160
agtcacagag gacttcctgg tgggctcagg cagcagacct gctcagatgg attgcagagc 128220
cagagggagc catggccagg aaggccagac gccttagggg tgtgctgtct ctgcatcctt 128280
```

-continued

```
tgccctctct gctcctcaca gtccatctgc catctcacaa tccctgctgt cgctctgggg 128340
cccagacctg gccagtctgg gtacctgtgg aatacaccca aagaagcaat ccccagcctc 128400
aggatccaca actacttccc ctacagacat gagtgatctc agcccacatg tctgggggcc 128460
acagaagccc ctaagaccct actctgctaa taggccctcc tcccaccagc caagacaata 128520
cacaggcaag gtgatgtgga tgagagtcac tccatgggta cctgtgtctg agatacaccc 128580
tgtgggtatc ctggccagaa tctggtgacc aacccaacct gtgtccctag aggagtactc 128640
cgtgcctgca ctcacctacc cacctaactc caagctaatt cctgcggccg tcgaccaatt 128700
ctcatgtttg acagcttatc atcgaatttc tgccatcatc cgcttattat cacttattca 128760
ggcgtagcaa ccaggcgttt aagggcacca ataactgcct taaaaaaatt acgccccgcc 128820
ctgccactca tcgcagtact gttgtaattc attaagcatt ctgccgacat ggaagccatc 128880
acaaacggca tgatgaacct gaatcgccag cggcatcagc accttgtcgc cttgcgtata 128940
atatttgccc atggtgaaaa cggggcgaa gaagttgtcc atattggcca cgtttaaatc 129000
aaaactggtg aaactcaccc agggattggc tgagacgaaa aacatattct caataaaccc 129060
tttagggaaa taggccaggt tttcaccgta cacgccaca tcttgcgaat atatgtgtag 129120
aaactgccgg aaatcgtcgt ggtattcact ccagagcgat gaaaacgttt cagtttgctc 129180
atggaaaacg gtgtaacaag ggtgaacact atcccatatc accagctcac cgtctttcat 129240
tgccatacga aattccggat gagcattcat caggcgggca agaatgtgaa taaaggccgg 129300
ataaaacttg tgcttatttt tctttacggt ctttaaaaag gccgtaatat ccagctgaac 129360
ggtctggtta taggtacatt gagcaactga ctgaaatgcc tcaaaatgtt ctttacgatg 129420
ccattgggat atatcaacgg tggtatatcc agtgatttt ttctccattt tagcttcctt 129480
agctcctgaa aatctcgata actcaaaaaa tacgcccggt agtgatctta tttcattatg 129540
gtgaaagttg gaacctctta cgtgccgatc aacgtctcat tttcgccaaa agttggccca 129600
gggcttcccg gtatcaacag ggacaccagg atttatttat tctgcgaagt gatcttccgt 129660
cacaggtatt tattcgcgat aagctcatgg agcggcgtaa ccgtcgcaca ggaaggacag 129720
agaaagcgcg gatctgggaa gtgacggaca gaacggtcag gacctggatt ggggaggcgg 129780
ttgccgccgc tgctgctgac ggtgtgacgt tctctgttcc ggtcacacca catacgttcc 129840
gccattccta tgcgatgcac atgctgtatg ccggtatacc gctgaaagtt ctgcaaagcc 129900
tgatgggaca taagtccatc agttcaacgg aagtctacac gaaggttttt gcgctggatg 129960
tggctgcccg gcaccgggtg cagtttgcga tgccggagtc tgatgcggtt gcgatgctga 130020
aacaattatc ctgagaataa atgccttggc ctttatatgg aaatgtggaa ctgagtggat 130080
atgctgtttt tgtctgttaa acagagaagc tggctgttat ccactgagaa gcgaacgaaa 130140
cagtcgggaa aatctcccat tatcgtagag atccgcatta ttaatctcag gagcctgtgt 130200
agcgtttata ggaagtagtg ttctgtcatg atgcctgcaa gcggtaacga aaacgatttg 130260
aatatgcctt caggaacaat agaaatcttc gtgcggtgtt acgttgaagt ggagcggatt 130320
atgtcagcaa tggacagaac aacctaatga acacagaacc atgatgtggt ctgtcctttt 130380
acagccagta gtgctcgccg cagtcgagcg acagggcgaa gccctcgagc tggttgccct 130440
cgccgctggg ctggcggccg tctatggccc tgcaaacgcg ccagaaacgc cgtcgaagcc 130500
gtgtgcgaga caccgcggcc ggccgccggc gttgtggata cctcgcggaa aacttggccc 130560
tcactgacag atgagggggcg gacgttgaca cttgaggggc cgactcaccc ggcgcggcgt 130620
tgacagatga ggggcaggct cgatttcggc cggcgacgtg gagctggcca gcctcgcaaa 130680
```

-continued

```
tcggcgaaaa cgcctgattt tacgcgagtt tcccacagat gatgtggaca agcctgggga 130740
taagtgccct gcggtattga cacttgaggg gcgcgactac tgacagatga ggggcgcgat 130800
ccttgacact tgaggggcag agtgctgaca gatgaggggc gcacctattg acatttgagg 130860
ggctgtccac aggcagaaaa tccagcattt gcaagggttt ccgcccgttt ttcggccacc 130920
gctaacctgt cttttaacct gcttttaaac caatatttat aaaccttgtt tttaaccagg 130980
gctgcgccct gtgcgcgtga ccgcgcacgc cgaagggggg tgcccccct tctcgaaccc 131040 tcccggtcga gtgagcgagg aagcaccagg gaacagcact tatatattct gcttacacac 131100
gatgcctgaa aaaacttccc ttggggttat ccacttatcc acgggatat ttttataatt 131160 atttttttta tagtttttag atcttctttt ttagagcgcc ttgtaggcct ttatccatgc 131220
tggttctaga gaaggtgttg tgacaaattg ccctttcagt gtgacaaatc accctcaaat 131280
gacagtcctg tctgtgacaa attgcccta accctgtgac aaattgccct cagaagaagc 131340
tgttttttca caaagttatc cctgcttatt gactcttttt tatttagtgt gacaatctaa 131400
aaacttgtca cacttcacat ggatctgtca tggcggaaac agcggttatc aatcacaaga 131460
aacgtaaaaa tagcccgcga atcgtccagt caaacgacct cactgaggcg gcatatagtc 131520
tctcccggga tcaaaaacgt atgctgtatc tgttcgttga ccagatcaga aaatctgatg 131580
gcaccctaca ggaacatgac ggtatctgcg agatccatgt tgctaaatat gctgaaatat 131640
tcggattgac ctctgcggaa gccagtaagg atatacggca ggcattgaag agtttcgcgg 131700
ggaaggaagt ggttttttat cgccctgaag aggatgccgg cgatgaaaaa ggctatgaat 131760
cttttccttg gtttatcaaa cgtgcgcaca gtccatccag agggctttac agtgtacata 131820
tcaacccata tctcattccc ttctttatcg ggttacagaa ccggtttacg cagtttcggc 131880
ttagtgaaac aaaagaaatc accaatccgt atgccatgcg tttatacgaa tccctgtgtc 131940
agtatcgtaa gccggatggc tcaggcatcg tctctctgaa aatcgactgg atcatagagc 132000
gttaccagct gcctcaaagt taccagcgta tgcctgactt ccgccgccgc ttcctgcagg 132060
tctgtgttaa tgagatcaac agcagaactc caatgcgcct ctcatacatt gagaaaaaga 132120
aaggccgcca gacgactcat atcgtatttt ccttccgcga tatcacttcc atgacgacag 132180
gatagtctga gggttatctg tcacagattt gagggtggtt cgtcacattt gttctgacct 132240
actgagggta atttgtcaca gttttgctgt ttccttcagc ctgcatggat tttctcatac 132300
tttttgaact gtaatttta aggaagccaa atttgagggc agtttgtcac agttgatttc 132360
cttctctttc ccttcgtcat gtgacctgat atcggggggt agttcgtcat cattgatgag 132420
ggttgattat cacagtttat tactctgaat tggctatccg cgtgtgtacc tctacctgga 132480 gttttttccca cggtggatat ttcttcttgc gctgagcgta agagctatct gacagaacag 132540
ttcttctttg cttcctcgcc agttcgctcg ctatgctcgg ttacacggct gcggcgagcg 132600
ctagtgataa taagtgactg aggtatgtgc tcttcttatc tccttttgta gtgttgctct 132660
tattttaaac aactttgcgg tttttttgatg actttgcgat tttgttgttg ctttgcagta 132720
aattgcaaga tttaataaaa aaacgcaaag caatgattaa aggatgttca gaatgaaact 132780
catggaaaca cttaaccagt gcataaacgc tggtcatgaa atgacgaagg ctatcgccat 132840
tgcacagttt aatgatgaca gcccggaagc gaggaaaata acccggcgct ggagaatagg 132900
tgaagcagcg gatttagttg gggtttcttc tcaggctatc agagatgccg agaaagcagg 132960
gcgactaccg cacccggata tggaaattcg aggacgggtt gagcaacgtg ttggttatac 133020
```

-continued

```
aattgaacaa attaatcata tgcgtgatgt gtttggtacg cgattgcgac gtgctgaaga 133080
cgtatttcca ccggtgatcg gggttgctgc ccataaaggt ggcgtttaca aaacctcagt 133140
ttctgttcat cttgctcagg atctggctct gaaggggcta cgtgttttgc tcgtggaagg 133200
taacgacccc cagggaacag cctcaatgta tcacggatgg gtaccagatc ttcatattca 133260
tgcagaagac actctcctgc ctttctatct tggggaaaag gacgatgtca cttatgcaat 133320
aaagcccact tgctggccgg ggcttgacat tattccttcc tgtctggctc tgcaccgtat 133380
tgaaactgag ttaatgggca aatttgatga aggtaaactg cccaccgatc cacacctgat 133440
gctccgactg gccattgaaa ctgttgctca tgactatgat gtcatagtta ttgacagcgc 133500
gcctaacctg ggtatcggca cgattaatgt cgtatgtgct gctgatgtgc tgattgttcc 133560
cacgcctgct gagttgtttg actacacctc cgcactgcag ttttttcgata tgcttcgtga 133620 tctgctcaag aacgttgatc ttaaagggtt cgagcctgat gtacgtattt tgcttaccaa 133680
atacagcaat agcaatggct ctcagtcccc gtggatggag gagcaaattc gggatgcctg 133740
gggaagcatg gttctaaaaa atgttgtacg tgaaacggat gaagttggta aaggtcagat 133800
ccggatgaga actgtttttg aacaggccat tgatcaacgc tcttcaactg gtgcctggag 133860
aaatgctctt tctatttggg aacctgtctg caatgaaatt ttcgatcgtc tgattaaacc 133920
acgctgggag attagataat gaagcgtgcg cctgttattc caaaacatac gctcaatact 133980
caaccggttg aagatacttc gttatcgaca ccagctgccc cgatggtgga ttcgttaatt 134040
gcgcgcgtag gagtaatggc tcgcggtaat gccattactt tgcctgtatg tggtcgggat 134100
gtgaagttta ctcttgaagt gctccggggt gatagtgttg agaagacctc tcgggtatgg 134160
tcaggtaatg aacgtgacca ggagctgctt actgaggacg cactggatga tctcatccct 134220
tcttttctac tgactggtca acagacaccg gcgttcggtc gaagagtatc tggtgtcata 134280
gaaattgccg atgggagtcg ccgtcgtaaa gctgctgcac ttaccgaaag tgattatcgt 134340
gttctggttg gcgagctgga tgatgagcag atggctgcat tatccagatt gggtaacgat 134400
tatcgcccaa caagtgctta tgaacgtggt cagcgttatg caagccgatt gcagaatgaa 134460
tttgctggaa atatttctgc gctggctgat gcggaaaata tttcacgtaa gattattacc 134520
cgctgtatca acaccgccaa attgcctaaa tcagttgttg ctcttttttc tcaccccggt 134580
gaactatctg cccggtcagg tgatgcactt caaaaagcct ttacagataa agaggaatta 134640
cttaagcagc aggcatctaa ccttcatgag cagaaaaaag ctggggtgat atttgaagct 134700
gaagaagtta tcactctttt aacttctgtg cttaaaacgt catctgcatc aagaactagt 134760
ttaagctcac gacatcagtt tgctcctgga gcgacagtat tgtataaggg cgataaaatg 134820
gtgcttaacc tggacaggtc tcgtgttcca actgagtgta tagagaaaat tgaggccatt 134880
cttaaggaac ttgaaaagcc agcaccctga tgcgaccacg ttttagtcta cgtttatctg 134940
tctttactta atgtcctttg ttacaggcca gaaagcataa ctggcctgaa tattctctct 135000
gggcccactg ttccacttgt atcgtcggtc tgataatcag actgggacca cggtcccact 135060
cgtatcgtcg gtctgattat tagtctggga ccacggtccc actcgtatcg tcggtctgat 135120
tattagtctg gaccacggt cccactcgta tcgtcggtct gataatcaga ctgggaccac 135180
ggtcccactc gtatcgtcgg tctgattatt agtctgggac catggtccca ctcgtatcgt 135240
cggtctgatt attagtctgg gaccacggtc ccactcgtat cgtcggtctg attattagtc 135300
tggaaccacg gtcccactcg tatcgtcggt ctgattatta gtctgggacc acggtcccac 135360
tcgtatcgtc ggtctgatta ttagtctggg accacgatcc cactcgtgtt gtcggtctga 135420
```

-continued

```
ttatcggtct gggaccacgg tcccacttgt attgtcgatc agactatcag cgtgagacta 135480
cgattccatc aatgcctgtc aagggcaagt attgacatgt cgtcgtaacc tgtagaacgg 135540
agtaacctcg gtgtgcggtt gtatgcctgc tgtggattgc tgctgtgtcc tgcttatcca 135600
caacattttg cgcacggtta tgtggacaaa atacctggtt acccaggccg tgccggcacg 135660
ttaaccgggc tgcatccgat gcaagtgtgt cgctgtcgac gagctcgcga gctcggacat 135720
gaggttgccc cgtattcagt gtcgctgatt tgtattgtct gaagttgttt ttacgttaag 135780
ttgatgcaga tcaattaata cgatacctgc gtcataattg attatttgac gtggtttgat 135840
ggcctccacg cacgttgtga tatgtagatg ataatcatta tcactttacg ggtcctttcc 135900
ggtgatccga caggttacgg ggcggcgacc tcgcgggttt tcgctattta tgaaaatttt 135960
ccggtttaag gcgtttccgt tcttcttcgt cataacttaa tgtttttatt taaaataccc 136020
tctgaaaaga aaggaaacga caggtgctga aagcgagctt tttggcctct gtcgtttcct 136080
ttctctgttt ttgtccgtgg aatgaacaat ggaagtccga gctcatcgct aatgtttgac 136140
agcttatcat cgataagctt taatgcggta gtttatcaca gttaaattgc taacgcagtc 136200
aggcaccgtg tatgaaatct aacaatgcgc tcatcgtcat cctcggcacc gtcaccctgg 136260
atgctgtagg cataggcttg gttatgccgg tactgccggg cctcttgcgg gatatcgtcc 136320
attccgacag catcgccagt cactatggcg tgctgctagc gctatatgcg ttgatgcaat 136380
ttctatgcgc acccgttctc ggagcactgt ccgaccgctt tggccgccgc ccagtcctgc 136440
tcgcttcgct acttggagcc actatcgact acgcgatcat ggcgaccaca cccgtcctgt 136500
ggatcctcta cgccggacgc atcgtggccg gcatcaccgg cgccacaggt gcggttgctg 136560
gcgcctatat cgccgacatc accgatgggg aagatcgggc tcgccacttc gggctcatga 136620
gcgcttgttt cggcgtgggt atggtggcag gccccgtggc cgggggactg ttgggcgcca 136680
tctccttgca tgcaccattc cttgcggcgg cggtgctcaa cggcctcaac ctactactgg 136740
gctgcttcct aatgcaggag tcgcataagg gagagcgtcg accgatgccc ttgagagcct 136800
tcaacccagt cagctccttc cggtgggcgc ggggcatgac tatcgtcgcc gcacttatga 136860
ctgtcttctt tatcatgcaa ctcgtaggac aggtgccggc agcgctctgg gtcatttttcg 136920 gcgaggaccg ctttcgctgg agcgcgacga tgatcggcct gtcgcttgcg gtattcggaa 136980
tcttgcacgc cctcgctcaa gccttcgtca ctggtcccgc caccaaacgt ttcggcgaga 137040
agcaggccat tatcgccggc atggcggccg acgcgctggg ctacgtcttg ctggcgttcg 137100
cgacgcgagg ctggatggcc ttccccatta tgattcttct cgcttccggc ggcatcggga 137160
tgcccgcgtt gcaggccatg ctgtccaggc aggtagatga cgaccatcag gacagcttc 137220 aaggatcgct cgcggctctt accagcctaa cttcgatcac tggaccgctg atcgtcacg 137280 cgatttatgc cgcctcggcg agcacatgga acgggttggc atggattgta ggcgccgccc 137340
tataccttgt ctgcctcccc gcgttgcgtc gcggtgcatg gagccgggcc acctcgacct 137400
gaatggaagc cggcggcacc tcgctaacgg attcaccact ccaagaattg gagccaatca 137460
attcttgcgg agaactgtga attcgatgcg ccgcaaggg gttcgcgtca gcgggtgttg 137520
gcgggtgtcg gggctggctt aactatgcgg catcagagca gattgtactg agagtgcacc 137580
atatgcggtg tgaaatacca cacagatgcg taaggagaaa ataccgcatc aggcgccatt 137640
cgccattcag ctgcgcaact gttgggaagg cgatcggtg cgggcctctt cgctattacg 137700
ccagctggcg aaagggggat gtgctgcaag gcgattaagt tgggtaacgc cagggttttc 137760
```

-continued

```
ccagtcacga cgttgtaaaa cgacggccag tgaattgtaa tacgactcac tataggggcga  137820 attcgagctc ggtacccggg gatcctctag agtcgacctg caggcatgca              137870

<210> SEQ ID NO 31
<211> LENGTH: 99808
<212> TYPE: DNA
<213> ORGANISM: Lama glama

<400> SEQUENCE: 31
aagcttgcac cctgtcctcc aagagaagca aggccccagc tgtgccatgt gctccaggga   60
ccctgctctc agtgcccct ctcccgcagc ctgtacccac cagcccccttc ttgacactgg   120 gctcttgcca tgggcaaagc tgccccagag agcagacgcc ggcaccgcgg agggaagctg   180
ccagagggca gagggcccgg cctgcactct gtcctgtgca cggggcccctt ccagccccgt   240 cttgttcaca ccccgcctgc cctggctctc ctctgtccac gcagagccca gcccaccaga   300
gaggaggctc tcccccggga gtcccccag tcctgactat agcccccttg acttcccacc   360
cacggtcctg ccccataaac agctttggct catctcacct gcctcctgtt tctctgtccc   420
agcagtctgg ctcttcccag gtcagaggac caggaggctg aggacagaca tccaggggaa   480
tccatacacg agcaagatag gttgccagca gggtcggaga agcagcgggg gcagccatgg   540
tgcggaagcc agcagagctg agaggccctg ctccccacat caaacacagg caaacacagg   600
ggcctgtgcc caagcacacc catgtgcagt ccgtgcccac acacgggcac gcacaccgca   660
cacaacacac acacgagcac acgggcgctc acacagaagg cggcactgag tggtgagaca   720
ggagcggctg ggcacacaga gtcctggggg ggtccagccc gcccctcact gtctgcacag   780
ctgggcagcc cttgagaccc cccctcgcac ccactccctc catcagacag ggtgagagcc   840
cccctcaggt agagtggggt gagcagttgg tgaagtgctg tctgaaggga cctggagaga   900
ccctggcact ggtcactggt cagtgcctgg tcacttctgg cctcctgctg tccccagagc   960
ccccacagcg ggccctggtc cactgcagtc tttcctctcc ctgccaggtg aggggccacc   1020
catgcacggg gaggccagcg aggagggcac cgtgcaggtg ccagccccgg gcggcctccc   1080
agcctccact ctgcagacca gtggtcggtc cccaggctgc tcccctccgg cctgcccacc   1140
tcgcggactc ctggtcttac tcctagtctg gctccgatgc cacaccatcc ccccatcccc   1200
cagtccagcc ttgacccagc agcacctctt catggcttcc acgcccaccc catccctgaa   1260
tgtggccctt actccacatg ttggcctggg agggtggcca cacatctcac actcagcaca   1320
cccgcaactg accatccaga tggcaggctg aacgtggccg tgaggctgct gatctgatcc   1380
ctggagcctg caagtggcgc ccatgcagat gtgcttagcc cgggatcctg acacaacgag   1440
gagactttgg cttcttgggc tggcccagtc tcaccacaag gtcctcgcgg gagggaggca   1500
ggggaacccc ggcaaggaga agccaggcgg gtgacataga ggcaggaggc tacacttctg   1560
gctgcgaaga cggaggaccg cccacccgtg cttgaggtcc tgcgagactc gtgtcagact   1620
cctgcctcca ttcggtgaca aggcaagtgc ctgcggggat ctgctgcagt ggccgcaaca   1680
aggaaaacac cattggtccc tccagaagca gcccgtcccc tgcgtcctcc ccatcccagc   1740
aagagcgccc catccctccc acagctcagg tccagactct gaatggactc ccatctttct   1800
ctgcacctcg tcccagtcta gcagcggacc tgccccagct ctgcccactt tcctgggcct   1860
ggccgtgtct gcagggcctc agtcacatcc tccaggcctc ccatcccaac tcgcccactg   1920
cggccttctc agccagcctg gcagtgaggt ggccctgtcg cgagatcgcc gatgagggct   1980
cagctcgccc gctgcccgaa agggcctcac atttttatccg aaatttgtac atgggtccac   2040
```

-continued

```
accctgacct cccgtccttc catcgtcaga gcctccggcc tggctgtccc ctggcagaga    2100
cctctctccc ggcctctgga cctgcactcc cagtccttca ctgcagcccg ccccgtggcc    2160
ctgcccagaa cgacggcgca ctgccctcat ccccccaccc ctgctccaag ttctctgctc    2220
tgccccttcc agcccttccc aagtttcaca tgcgcattgt gctagttggt catttctttc    2280
tcctcgtaga aacctagaaa gttaactcca agagcgcagg gttttatctc cctgatgagc    2340
cccaacacgt ggaccagagc ccatgggcag tagtgccagc aaacactcac tgagcgacgg    2400
aggtcagggc cgcgcccgag tcccagggtc acgggccctc ccgggacagg caggcccagt    2460
ggagtgtgcc acgccacttc ccttctgaga gcaactcctg ccccactctg ccccatctca    2520
gtaagtgacc acctccagac tccaggctca cccactcccc agcccacagc caggggggtc    2580
ttttaaaacc tgaatctgtc ctgggagtcc cagctcaaac ccaatgaaga gttcttgtta    2640
caagagtgaa atcaaaattt tcatgcctcc ccactgaccc agccaggccc agggcccaga    2700
tgggccccac caccctgctt atgacggtcc atgcttgctc cccactttcc acagtgtgtc    2760
actacctgtg gggccctggg tactgcctgc ctccagtcag gacctgaagt ccctcaagag    2820
cagcagctga aggaaggtgt gaaggaagga aggggtggcc tgcctcgggg gagaggcctc    2880
agagcctcca aggagagcat gcacagggcc ctcactgcag gagcccccga gcgatcgtca    2940
ctgttaccca gctgtcccca agtccacagc cccaagggtt tgcactgtgg agtcctgtct    3000
gcaggcccca ggaggctggg agggaggcca gagggaggcc agacaccaaa gcctgcaggt    3060
tccctgagca tggaggtgc ctggtttggt ccaaggagcc tgtatttgag tttctttctg    3120
ctcaggaaac attttcacac aaagcacgag agcccctcca accacagcca gggcctcagc    3180
ctgttgggtg gacgccgggc ccttcactca gttcttcaac aggaaaaccc aggggggcctt    3240 ccagcagacc ctctttttatc ttcaagaacc accagtctat ctctgccaga ggcgtgtgac    3300
agcccggggc cctggggcca gccatttccc ctcacaagac tgcttgtggc cttcctggca    3360
ccgcagccac tggcctccgc ccagccccgg gccgttggtc ctgcacgctc tgcagctcac    3420
ccgagtcacc acgatcccac ccgcctggca ccctcctctc ggggcagaaa catctgtttc    3480
cagctttggc gacaaacagg acgcacccgc ctcctacccc taagtcaagg cttgatgagc    3540
ccagtcccct ggtgtggagc ccaccccctg gccacctgtg tgaggcccga ctgaacgccc    3600
tccctcagtg tttgggggag gttccgagcc agccctgccc tctgaggctt gtggactgag    3660
gcttcccagg acccattcag aaaccaggct gtgatctcca gccaaggaat gtgttcattc    3720
ctggtccaca gccgggcccg tgttgactga gttaattctg gaaggcatat ggctgggaca    3780
agacctcaaa agagagttgg gggacaggaa gatcagggac agcgtctctg ccctcacggt    3840
caggacaaga gtaaagtcgg aaccagcagc atgcaaatcg gtaagcaggc cagaggaagt    3900
tacgggaacc tgtctgcgtt ccattggggt gaatgagtgc tttctcagaa tgacaccaag    3960
gccaggaagt ttaaaagtga cattgagaga tttgcctaca gaaagaaaaa attttaaatc    4020
tatgaagata aagtctctac aaacaaaaag ttaaatgctg tgggagagag agtgggcaaa    4080
gtgagtaact tcaaaaagag tctgcagtag tcagggttct ccaagaatag atgtatgaga    4140
cagaaatgac agacagacag ataaacgtat gtgtgtatac tgatatatac atagagagaa    4200
agagagattt ttaaggaatt gggtcctgtg atcgtgaagg cttggagcat ccaaaatccg    4260
cagggcaggc cagcagtcca gagctccagg gaagagttga tgttacagtc tgagtccaaa    4320
ggccatctgc gggcagaatt ccctcttcct caggaaacct cactcttttt tctcttaagg    4380
```

-continued

```
tcttcaactg aatagatgag gcctacccat gtagaacaat ctgctttacc caatgtctac     4440
tgctttaaat atcaacacat ttttcaaata ccttcactct ttggattagt gtttgaccaa     4500
atatctgggc actatatcct agccaagtta atccataaaa ttaaccatca gaaagtccaa     4560
ctaaatgagc gttggaaaaa atgcaatgaa tgggacaaat ctgacctata agaagttttt     4620
ggtggaagtg ggagtggagg gatcatttcc agtagtttgt aaacaacaaa tagccaataa     4680
aacatgaaat tgttaggcat cacacataat caaagcagtg actttaaaca actgaccatc     4740
agttcaggtg acaactgttc atggcagcct accatgcgcc aagcaggcat ccaagtggga     4800
gtgtgcagtg tgactgctct gtggcaccac tgccctgatg ggagaggaac aacacaactg     4860
gacacagatc aaatgcccta ccaaagacaa ggaggccagg cgaggaccga cacctcactg     4920
ccaggtgctg tcctggcaga tgaagggcct gcaggcatcg gggaggcacg tccaggcaga     4980
aggagcagaa ggcagaaagg tcctgggtca gaaatgtgct ttacaagttc aaggagcagc     5040
aggaaggcta gtggggctgc atcagaagct gggagactgg ggaggaggag gtggggaaga     5100
taaagtgagg ccatacgagc ccgttcaagc ttcatgcttt gctctggggt gatgggatgc     5160
ccccaaaggc atttgggttg gggggttttc aattttgcac tggaaagtca gctgcactgg     5220
agggagggtt taagtcaagg gccctggaga tctgtgcagg agtccttctg ggggagtagc     5280
aggaggcaga gcaggggcag tggcagcaga gagaagggct cagatcatgc atgtgcctga     5340
aagtggagct gagggtctgc agagagaagt cgcacccacg agatcccctg catcacagca     5400
tgaatgcagt gccattcact gatctctggg gtcaacaact ctcccttcag tgtggccagt     5460
tcaagctgcc aattacatac acaggaatgg atgtgggagt ggatgctcct gttggacctg     5520
ggctctgggg cttaggaaga agtcactgga ggaggaggag taaatccagg actgcacatg     5580
gtgctgtggc tgatactccc aggactagca gggacaccaa gaagggtgcg tggaagggag     5640
ccaaagtcaa tgtgtggcac caggtggagg ggaggacttg gaagccaggg tcagaggcag     5700
gagtcagaaa gatacagggc tagaaggagg acatcatgtg cagggacact ctgcacgtgg     5760
tgccaaggaa ggacttggtc cactgcatgc atgctccgga ggcgtgtctc caggaggctg     5820
acagggagca aggggtcctc tcaagagcag tctcaacagc aaggtggcca agacctggct     5880
agagtggcct caagaaggag gagggagggg tgagtggatg caaaagtcag ggcacaccag     5940
acctaggagc agagtccacc agcctggtca agccgacacc agcatcacag agcacgcaca     6000
tacatcgaac acaaacctgc ttgtgaagcc tgatgtccac tgcaccatcg ataaactgaa     6060
aaaaactaaa gtcatggtat caagatctcc aacagtgcag caaatgagag agacaaccat     6120
ggcgaagggg taaatgggct cctacacaca gctcacgggt caaatcagaa gagaagtcca     6180
tagccttaaa tgtctgtgag gcagaaagca ctgagttaat acagagccca aactgaaaag     6240
ttgggaaaag aacagcaaaa taaacacaaa aaaacggaaa taatcatata agccaaaaaa     6300
aatcaattac ttcaaaaaca cacctgcacc ccagtgttca tagcagcact atttacaaca     6360
gccaagacag cctaaatgtc catcaacaga tgactggata aagaagaaat ggtatgtttt     6420
tacaatggaa tactactcag ccataaaaaa tgacaacata acgccatttg cagcaacatg     6480
gatgcccctg gagaatgtca ttctaagtga agtaagccag aaagagaaag aaaaatacca     6540
tatgagatca ctcatatgtg gaatctaaaa aacatgaata taaatacaaa acagaaacag     6600
actcatagac acagaacaca aacttgtggt tgccaagggg gtggggggtg ggaagggaca     6660
gactgggtgg tcaaaatgta gaataaacaa gactatactg tatagcatag gcaaatatat     6720
gcaagatctt atagtagctt acagcgaaaa aatgtgacaa tgaatgtata tatgttcatg     6780
```

-continued

```
tataactgaa aaattgtgct ctaccctgga atttgatgta acattgtaaa atgacaataa    6840
ctcagtaaaa aatatttttt aaaaactagt tattgatgaa aaagtaataa gaggaaataa    6900
taaataaatt tattccacta gtatatagta aaaattttaa atcccaggac agtatcttat    6960
caaaaatgac tcaggaatag aaaagctcaa tagtaccata tttattaaac ttctttgttt    7020
tatttattac ataaattaaa gcagtagatt taaatctttt caaataaaaa taccagggcc    7080
atgtttcctg aagctcttaa aaaaatgtat tattcaaatt ttatttaaaa aactatcaaa    7140
aagtgaagaa gaaggaataa cacccaactc attctataaa gccaatataa cactgattgg    7200
gaatcagaaa aggaaagcat ggaaaagaaa agctatggga cagtcttact catgaaacag    7260
ataaaaatac tccagagaaa atattaacaa ataattttga acctcatgaa aaaacagata    7320
attcactatg tccaagtcag gtttatccca aaaatataag gatagtttaa cctaatgaaa    7380
tctattattg tcattcaaag catgttcata ataaagaaga agaattttaa gatcatctta    7440
aaggcagaga gaaaatgttg aaagaatgta tactctttca agatataaaa cttttttgcta   7500 actaaaacac aatggaattc tttgatctga caaagtttat caaccaaaat tctttgaatt    7560 tttttttctta gaggaaaatt ggaagcaact gtgtactaga agtcttgatg tattccataa   7620
gaccaaaaat atattaaaac atgataactt tctaagtaga aaaaatccag aaaaatatat    7680
aaaaataata acaattaaaa ataacaggta acttgctaca ataccaatat acagaaatca    7740 agttttttgct attaaccagt agcaaacaga aagtcatttt tgtaaagatg ccagatgtct    7800
gcttctgtta agggcataca ggtaatgtgg cccaaccttc ccattgagga atactagaaa    7860
aagctggaaa agtactttta gaatcttcct gaaggtagtg acaagttaac aaagtcatga    7920
ataatcacgg gattgagagc cagaggagac tgaaattcag agattcaaac ctggcagcca    7980 cttttttcccc aaagcctttt actgattcta gaataaagtt gagacactga gcagcaattt   8040
tgacaatccc atagggggag ggagaagaaa tttggaattt tagaactaat gtgtacaact   8100
gcatgaatta aggactcaac agacagattt agaagcagag ttaacacagc tggagaatta    8160
gtaaaccaga agctgaaaca aaagaaagga gatataatgt agaccagaaa acaaaggcat    8220
gagttgaaag aagagtgggt acactgacaa agtccaacgt gtaagtgctt aaagccctag    8280
agaaagagag agagaagaga agacacagtc ataaagaggt aattgcagaa atctttccaa    8340
acttaaggag aggtaccacc ccttggttca aacagaataa aacacacaca cgcagaaagt    8400
cacacccatc cataacataa aactactgaa tactaaagga gaaaatcttg aaggcagctg    8460
aaggaatggg gaaccttaca ttatcttcaa aggagcaaca ataagatgga cagctgatgt    8520
cacaacagaa ggagaagcaa ggagagtgat gctctgtcca tagtgctgaa taaaaccacc    8580
gataagccag ggaaaccatc cttcagaaat gaagatgacc ctgctttttcc cttctcctta   8640 gctatagttt cctgggactg tgataacaaa gtaccactaa ctgggtggct taaaaccact    8700
ctctcacagt tctggaagct agagatctga aaccagtatg ccctcagggc tgtgctccct    8760
ctgaagtctc taggggagga gatttcctcg cttcttctag cctttgatgg ttgccagcaa    8820
tccttggcat ccattggctt gcagatgcac cctccaatct ctgcctctac cttcacatgg    8880
agttttccct gtctctgggt ctctgggtct aaattttcct cttcttatga ggatactagt    8940
catatcagat ttagggccca ccttactcaa gtacaaccac atcagaactt ggtgatagct    9000
gcaaagacgc tgttccaaat atggtcacag tcacaggttc cagatggaca tgaatttggg    9060
atgacactgc aaggcccagt atactttcct ttcctgtgca atttaggtga cgctcttagg    9120
```

-continued

```
tgagcagatc aatgtgaacg tgtgcacggt ggggttggga gcggcagagg cctggaatag    9180
gccctgtgtg ggtgggggagg gtggcctgat gcgcgaagta agatctggag caagatgaga    9240
gggctccacc tggctgaggg tatagactag aatgaccaga atctcagaac ctgaagtgag    9300
agaggaaagc attatgtggc acggaggggga ggttggtagc tcacaaggga actgatgaaa    9360
taagtgaata tactgagaag cacagacaaa agagaagaga gttacgaaga tcaaaaggaa    9420
gaaaactaga atggatcatg tgatttgggg ctggattgta tgcatctgtc agaattcaca    9480
ttttcaacac atgcagatac agagagagag agtaagtagt ggccaaaaac ttcccaaatt    9540
tgatgaaata tatgaatctg cacatccaag aagcttagcg aactccggta aagtaagctc    9600
aaatatgact caaaatcaaa tggactaaaa tgctcaaagt tttttggggg gggggctgaa    9660
atatatgtat ataatatttt atatatgtta tatataatat aaatgtaata taaaatatta    9720
agctgattaa gctaacccaa tagtgtttac aaaagagaaa tacaaaacac aaggccacag    9780
aaagtttgaa agtataggat gataaaagac atactatgca aacattagtc aaaggaaagc    9840
tgctgtcact gtagtaatct cagacaaaac agactgtaag gcaaaaagca ttaatggaga    9900
ttaagtggga tgatgcaatt ctaaatgttt atgcacctaa aacagagctt taaaatgtaa    9960
aatttaaaaa ttgtcagagc tagaggaaga attatgtaaa ttcagttacg gtgtaatgtg   10020
ttaacattta cctttttagta acttatagta caagcagaca aaatactaat aatgatgcac   10080
ttgatttgaa caaaatactc tacaaatttg acctgctgcg catatgcaga ccttggaaag   10140
aacagctaca gaaggcacac ttgttctgag cctgtgaaac attcacacat tatactatat   10200
catggccata aaggaagata caacacattt tcagagccaa aaatatttag ttatggtgta   10260
acaatagtac aattaagcct ttaatgattt tcatcatctt tttttgtgtt tccctcgacc   10320
ctagccagca cttctgcagg acagtgctct ccacctgcca gaacagccta aacctccatt   10380
tccatttttt gcatggcctc agaccccagg caaaagtact catccaggtc ttagggccct   10440 atttttttcac tatcgtgccc ttttcttagt ggaagaagct ttggagcttt tgagttcaac   10500
cttctttgta atcctactac tctaacaatt aagtattggg cctaattttc agtactgttt   10560
gccctctggc tgcaggagat ggttactatt taaacactat catggagaat ttctgatttc   10620
cacactgttc cctgagttta caaggaaggt gggagattgg gggctgaccc gaggctgaca   10680 ttttcttcttct ttactgtttc aatttcactc aacactaacc aagataccc actattctat   10740 agttatcaca ttttccacca gctttataat tatgactgct ctcatgcctc tcaaaagcta   10800
tattgcaaaa ggtgcaccct accttgctac ctatgtccca taatgataat tcaagaacgg   10860
tttctttaca aagggactgt ttacaaaagt gcatttaatg aaaatgaaaa gaccagtttc   10920
aacctgggaa aatatatttg caacacctat aagtgacaaa ggaatgttat caataacatg   10980
taagcaacta ctacaaatca agagaaaatg acaaataacc caatagaaaa cactggccaa   11040
aagacatcaa tagacatttc agaagtaaga atcaaattag gccaataatc atataaaaag   11100
atgtcaactt cattaacaat cagaaggaat tcaaatcaag agcagaataa attatcatct   11160
tagtaaaatg atactggcag aaactaagaa gtctgaccat accaggtgtt aggatgtaga   11220
ttcacagact ctttcaaaca ttgctgctgg aaagtcacat tgaaaaagtc agtttggaaa   11280
aaagtttacc taccattgct ttcaaatgtt gcataattc atatttcact cacagataaa   11340
taatagagtg aatcccttgt gtgtatacac aagaaaatac atatagtgaa tcttttggtt   11400
cagttagggc tcttttggaa gtgcagggtc accaggagtg atacgaata gatgatatga   11460 ggaattagat tctgcacaac tgtgggatca gttgggcaag taaagtcctg agggatccac   11520
```

-continued

```
tctagaatta gaaagaagtc actgaccaaa gaccctgaag gggggccaat gaggtctatg   11580
gacggctctt gcctctgaat ctgtcagatg gtctgaaggt gctgtgcttc atcaagacag   11640
gcagttgtga aggaaatctg gctgaaaagt agggaagaga gagaagtcta agaagatagg   11700
agagtaggaa gcacctagac agctgcactg gcacaatcta tgtcatgtaa acatttggaa   11760
ctctgaagtc cattgaaggc ttgcaagtta cagataaagt cttgcatagt acatggtagt   11820 taattttttgg tcaattttgt ctcttagcac agaagaagct aaccaacccc tagccccatt   11880
cctatggcag aaagcagtgc acatattccc agggcaactt gcacgcagct ctgaagaaac   11940
caggagtggc aaaaaggatg cagtcctcca aatatcagag atctgtgctc cactcactaa   12000
ttgctacttc tgatcacaga ggtgccaata aagaggaggg cttccacagc tgttgtacct   12060
acctcattgc tataagacaa ctctctggct gaagtgactt ccaggggatt taaagggctg   12120
aaactgcctt catcttcctc ttttctcatc tttatttttc tctttttttcc cttttgggaa   12180 ccaaaagtca aaaactaaga tattcaaagg caactatact tatagggaaa actagaaagt   12240
ggctgcgtat gctgagagaa agtcagcaag gtagcaggtt acaagattaa cgttcaaaag   12300
tcagttgcat ttctttatac taacgatgaa tcaacagaaa aagaaagtaa agaaacaatc   12360
ccctttaaaa tagtatccaa aataataaaa tacctaggaa taaatctaac caaagaagtg   12420
aaagaattat acacagaaaa ctatatgcca ttgatgaagg aaattaaaga agactttaaa   12480
aaatggaaag atatcccatg ctcctggatt ggaagaatca atattgttaa aatggtcaca   12540
ctgcccaagg cagtctacag atttaatgca atccctatca aattacccag gacatatttc   12600
acagaactag aacaagtcat aataaaattt atatggaacc atcaaaggcc tagaattgcc   12660
aaagcattac tgaagaaaaa gaaaggggct ggaggaataa ctcttccaga cttcagacaa   12720
tactatagag ctgcagtcat gaagacagca tggtattggt acaaaaacag atgtatagac   12780
caatggaaca gaatagagag cccagaaatg aagccacaag cttttggtca actaatctcc   12840
tcaaaggagg aaagaatata caatggaata aagacagtct cttcagcaaa tgatgttggg   12900
aaaactggac agcagcacgt aaatcaatga agctagaaca cttccttaca ccatacacaa   12960
aaataaactc aaaatggatc aaagacttga acataagaca aggtacaata aatctcctag   13020
aagaaaatat aggcaaaaca ttatctcaca tacatctcaa aaatgttctc ctatgacagt   13080
ctactcaagc aatagaaata aaagcaagaa ttaaccaatg ggacctaatg aaacttgcaa   13140
gctcctgcac agcaaaggaa accataagta aaacaaaaag acaacctacg gaatgggaga   13200
aaatttttgc aaacgaaact gacataggct tgatctctgg aatatataag cagctcatat   13260
gacttaataa gaaaaaaaca aacagcctaa tccaaaaatt ggcagaagac ctaaagaagc   13320
aattcttcaa ggaagaaaca caaatgatca acaggcacat gaaaaaatgc tcaatatcac   13380
taattatcaa agaaatgtaa atcaaaacta aacgaggta tcacctcaca ccagtcagaa   13440
tggccatcat tcaaaaatcc acaaatgaca aatgctggag aggctatgga gaaagggaa   13500 ccctcctaca ctactggtgg gaatgcagtt tggtgcagcc actatggaaa acagtgtggg   13560
gattcctcaa aagactagga atagacttac catatgaccc aggaatccca ctcctgggct   13620
tgtatccaga aggaatccta cttcaggatg acacctgcac cccgacgttc atagcagcac   13680
tatttacaat agccaaaaca tggaaacagc ctaaatgtcc atcaacagga gactggataa   13740
agaagaagtg atatatttat acaatggaat actactcagc cataaaaatc gacaacataa   13800
cgccatttgc agcaacatgg atgctcctgg agaatgtcat tctaagtgaa gtaagccaga   13860
```

```
aagagaaaga aaaataccat atgagatcac tcatatgtgg aatctaaaaa acaaaaacaa   13920
acaaacaaac aaacaaacaa aacaaagtgt aaatacagga cagaaataga cttatagaca   13980
tagaatacag acttgtggct gccagggagg cagagggtgg gaagggatag actgggattt   14040
caaaattgta gaatagatag acgaaattat actgtatagc acagggaaat atacacaaaa   14100
tgttatggta gctcacagag aaaaaaatgt gacaatgagt atgtatatgt ccatgcgtga   14160
ctgaaaaatt gtgctgaaca ctggaatttg acacaacatt gtaaaatgat tataaatcaa   14220
taaaaatgtt attaaaagaa gataataaaa ctagatataa aattatctct gttcacagat   14280
ggtataaatt tatatgcaga aaaccctaaa gatgctgtat tttttaaaaac tgttagaact   14340 aatgaatgaa tttagcaaag tgttaggata caaagtcaac acaaaaaatc agttgcattt   14400
ctatacacaa acaatgaaca gtcggaaaag aaaattacca aaaaatccat ttataaatagc   14460 atcaaaaaga ataaaatact tagaaattaa cataaccaaa aaggtgaaag acttgtacaa   14520
taaaaactac aaaatattgc tggaataatt tgaacagaac ataaaataaat ggaagcacat   14580 ctcatgttcc tgaagactag ctgttgtagg atacctgtac tacccaaagt gacctacaga   14640
atcaatgcaa cctgaccaaa ttcccagtga tattttttgca taaatagttt taaaaactga   14700
tcccaaaatc ttcaaaaatt caacactaac aaaaaaaact aacctgatgc aaaagtgggc   14760
aagatatttg aataaatatt tctccaaaga aaacatacaa aaagtcaaca agcacatgga   14820
aagttgctta acatcactaa tcattagaga aatgcaaatc caaaaaatga gataccacct   14880
caagcatgca catttgaatg gctaatattt ttaaataaga tcgggtgcat tcagggtggt   14940
atggccatag tacaatggct actattttta aaaaacagaa gataacaaat gttggtgagg   15000 ataggggagaa attggaaccc ttttgcactg ttggagagaa tgtaaaatgg catagccaat   15060
gaggaaaaca gtttggaatt tcctcaaaaa atatttttaa aaaactacca tacttccacc   15120
aatttcagtt ctgggtatat accaaaaaaa atgcaaagct gtgtcttgaa gagacacctg   15180
aatactcatg ttcacaacaa tattattcac aatacctgaa atgagcaagc aacttaaaca   15240
tccatcaaca gatgaatgga tgaggaaaat gtggtctata tgtacaatgg aaaattactc   15300
cctctttaaa acaagtaaat tatgatatat gtaacaacat ggatgaaact tgaagacatt   15360
ctactaagta aaataagcca gttgcaagaa gataaatact gtacgattcc gcttatatga   15420
ggtacttaga gtcacttaat ccaaggacac agaaaataga ataatggttg caccagggtg   15480
agaaaagggg attattgttt aagggtatag agtttcaatt ttacaagatg aaaagagtta   15540
tggaaacata ggtggtcatg atttcacttt atgaatgtat ttaatatcct tgaactgaac   15600
acttagaaag atttaattaa accttggtaa ttttgttatg tgcaacttat ggcaataaaa   15660
aaatttttaa gcaggagaaa gtaagagaaa actgacccat aaagaaaact gaaacccttc   15720
agaaagatct agagcctgtg tctctccctg tggaagaaac tggtgacatc aggatggagc   15780
tgcacacccg cctggaccag gactggacca cctgaggggg cagcaggagc tggaggagca   15840
gcttctccac actgacagca caactatgca ggtcagtgac aacattcaca gcctgtagca   15900
ggacctgagg ctctgtacca gccttccaag catatggact gtcccttcgg tttgctctcc   15960
aaaaactgaa gacttctctt gtgatcagcc ctaatctagg gagatacaca aaaaggctaa   16020
gaaatctggt taaagcttag ctaacttggc atagaaaaaa aaacaccaca atccactcct   16080
tgtcagccac tttggaccac ttgtatcttc caattctctt taaacagcaa tattgtttgt   16140
tttccaccta ctacagtgaa attattccac ctaaaattta aaacatgcca attcctcctc   16200
caaaaaagaa gattgaagtc taatatatca catgaaatat ctttggctga tgttcacttc   16260
```

-continued

```
ttctgttgat gaataacact caactttgga tatcctacag cttatagctg agatatgaaa   16320
tatcaccact aatacatctt atgtcagatg ataagggaat gaggatgagg ggaaataaaa   16380
gaaaagtatg caggaggaga tggagatggt ggggtagcag gacatggagc ccaccaccca   16440
caaggaacac attcaaatta catctatgtg tggagcacct ttcactgaaa ataaactgga   16500
gattagcaga aagacaggcc aagaatctaa agacaggtcc acaataagtc atttagaaag   16560
ggaagtggag tagtcaggtt ggaacctcat ctgtaggagc ggacacagga cagggagaga   16620
tatcatgggc ttgaaggccc tccctgagga atgggcagct tgaaagcatt agtaatatga   16680
atgctaacta aattggggaa aaaaatagat gaacacagtg atggttttta caaggaacta   16740
gaaaatataa aaagataatc actcacctga agaatacaat aactgaaatt taaaacactg   16800
gaaggaaata acagcagatt aggtgatact gaagatccca taagtgatct ggaaggtaga   16860
ataatggaaa ttacccagtc agaactacaa aaagaaaaaa aattttttaa atgacagcag   16920
tttaagggat ctatggaact acatcaactg tactaacatg ggcatggtag gggtcccaga   16980
aggagaagag agatagaaaa cacgtgatgt gtacttcata aatttatggc agaaaacttt   17040
ccaaacatga agaaacaatg agatttacag gtagaggaag cataaagagt cccaaacaat   17100
gagaacccaa agagacccac accaagacat aacacaatta aactggcaaa agttaaagat   17160
aaagagagaa ttttgaaaac aaaaagagaa cattaaagag tcacatacaa ggaaccaaca   17220
caaagttatc agttgatttt tctgtaaaca ccctgcagtc tggacaagag agtcatgcta   17280
catttcaaat gctgcacgga aaaagtctac aaagtaggag acactaccca aaaaaattta   17340
ccatttagaa ttgaaggaga gataaatgta acaaaagaga aacagaacac agatagactg   17400
ataatattag tggttaccag tgcacagagg ggaggggggaa ggggcaacat aaggacagag   17460
aaataagcaa cacaactaca atgtataaaa aaaaagccta cccagatgta ttgtacagca   17520
cagggagtat agtcagtgct tctaataact tcaagtggaa tgtactctct aaaagtattc   17580
aatcaccatt ttgtatgttg tccacccgaa actaatataa ctttctcagt gaagtgtatt   17640
taacttaaat ctatgtatat acacaaattc atatcaaaat aaggaaccat cttcaaattc   17700
cacccaccac acttgggatc aatcatgctt ctctgtgggg cgtgactcca agacattggg   17760
ccaagaagag tactcaggtt acgaagatgg acatggctcc tgccccgaga cacacgaggt   17820
cttgggacgc tggtccagac tgcgttcttc ctctgaaact accttgcgtt ccacagggcc   17880
catttgctgt ccatgaggcc ttttccacgt caggcaatgg ctgagccatg tgtgtaccca   17940
aggccttcca ggccgctgtc cgtggtcctg acgcagacta gcaggctgtt tcagctactg   18000
tccacggtcc tgcttctgct gctctgcacg gagtaatgat attttttagat taaacagact   18060 ttgcccttt agggtagttt caggctaaca gaaagtccac agagctccgt aaattccagt   18120
gccccacaca tacacccagt ttcacctgtt gtgaatatct tactccagtg tgctacattt   18180
gtcagaagtg atgaaccaag ttaatacatt atgattaact gaagtccata ggcaacacca   18240
tggctcacta ttatctgcac aattctatga gttttgacaa atgcatggtg tcatttgcat   18300
ccagaggccc cgaggctgct gtccatggaa ctgccttgat caggtacact gttcaggctg   18360
ctgcccatcg gtccaccatt tcagcaacac acactacaat ttcactgcct tgaagacccc   18420
ctgtacctca ccgcctcatt cccccacccct cccacacaaa ctcctggcag ccactcgcct   18480
tctcattgtc tccataggtg agctccttca aataccgtgt agtaggaatc tcacagcgag   18540
cataaccttc tccggttggc ccctttcact tagcaatgcg cattttcatt tccccatgtc   18600
```

-continued

```
cttttgtgcc tcaatggctc atttcttctt cgtttttaat ggtcgtttct tactttgggg   18660
gactatggga gggtaattag ttttccttca tggagatact ggggattgaa ccaaggacct   18720
catgcatgct aagcacacgc tctatcattg atcaataccc tcccccatt gcttctccta    18780 ctaacttctt ttttcaacag ctttgttgag atacaattga tacacaaaat aaatgcatat   18840
attcgaggta catctgagtt tgcacatatg cagacacctg tgaaaccatc gtcactgtca   18900
gggtagtcga tatatccatt cctctaaaag tttccttgtg ctttgggttt attgggatgg   18960
gggagcagca catgtatgtg aagagccctt atcacgaaat ctactctctt aacaagtatc   19020
tgggtgcaca atgcagtgtt gtaaaccgtc agcacaatgt tacacacgga gcctcggaat   19080
agatctcatt ctgcataact gaaaatttat acctattgaa tcacggcaga atcaaagagt   19140
atcaccacaa aaaatcaatg aagcacaaaa gaaagaagca agaaggaata gaggaacaag   19200
ttcactacaa gacaggcaga gaactattaa aaacaacagt gataataggc ctttccctgc   19260
cacaattacc ttaaatgtaa atggattaca ttatcagagc aaaagatata cagtggctga   19320
gtggataaca agcaaggccc agatctgtgc caacacaagg cactcacttt aggcttaagg   19380
acacatgtag gctggtcacg aagggatgga aaaacgtact ccatggaaaa ggcaaacaaa   19440
aggaagcaag gatgcgtaca cttggacaaa atagacttga aggtaaaaac agtcataaga   19500
gacccagaag gatgctatac aatgatgaaa aaaatcagtt cttcacagac ggcttcgtcc   19560
tttttattct gcaatcctgt tcctctgcct ggatgcatcc actcacctac tgagggacat   19620
cctgtgcgca tccaagtttg aattaagcta cgaatgaagc atctgtagac atttataaac   19680
catacacatc gctgcacaga tttggggtgg acatgagttt tcagcccatt tgaacaggtg   19740
agtatctagg aatgcagttg ccgggttgta tggcaagatt aggtttagat tctggagaaa   19800
ctgccgagct ctcctgcaga cgggctcttc ccgtttgcac ccacccgcag cggaggaggc   19860
ctcctgctgc cccacaccct caccagcgtc gggaggtgcc gggtttcggt gttgcttctg   19920
gacgtccacc gttctaacag ctgcgtggtg gtcttccttg ttttcgctta cagcctccaa   19980
cgacgtcgga tgtggaggaa acttgtgctt ccttctctgc atctgtgagt cttcttaggt   20040
gagaggtctg tccagggctt ttagtcactt ttgactgggt cgtttgtttc cttgttgtgg   20100
acttttaaca cttctccgca tattgcggac acgagtcctt catcagatac gaggtttgca   20160
aatgtgtgat tctcccagtc catggcctgc ctttcattct ctcgacagtg tcttccacag   20220
gcaggcattt ccacttcagt taagttcagc tagtgacttc ttttccgtgg aatgcgcttt   20280
tggtgttgta cctactgact cttcgccgaa gtcaaggtca cctagattcc catagttccc   20340 tttttttgcat tgaggtcaat gacccactgt gagttaactt catgaccagt gtgagcatgc   20400
gcctcagctc gtttcctgct gggatgcagg tgctccacca ccacttggtg aaaagagccc   20460
cttctccatc aagttacctt cactccagtc gagccctcag aggtgggcat gggcagggag   20520
aggtcactcc cttgtctgag ctcctttggt gcttctagaa tgttctgtca ctgagggggga   20580 catgcaatca aatggcctta aaccatctgc agaaaaatta tttctaacag aatttacacc   20640
caaaccaagg ataaagtgta aaggtaggat aaaggcatcc tctgacatgc aagatctcaa   20700
acaacgtccc tccaggcatc ctctctcagg aagacagcag acggcctttg gacctgaact   20760
ctccacgtca gcggcctggg ccccggcaga tcatggactc cagccaccat catggtgcca   20820
gtcacttctt tacgacaagt ctctttctag atacggacca tatacacaga gataggggta   20880
catcctacgg attctgttcc cctggagact aacacaccct ggggcacaac gcagtcttct   20940
tccaacccac aggaaccgac tgactccaga ggggatgggg gggcaggtcc aaggcactca   21000
```

-continued

```
gcagcgttcc tgaagagggg gtctaaactg cactggaaag ccagctcaag agcccagcat   21060
cgatgcttaa ttaagtctaa agcacgtgct tccatacgta caacgtggga atgttcagct   21120
acacgcactg ggtctgttca caacacagcg tgtttcttcc taaacggtac atcgagcgat   21180
tgagcctcgt agagggaaca gcatcctgga tttgaacggc agcaagtgtc acaaacctgc   21240
tggaaagcag agtggatccc tcccgcgggc ggccccactc ggcttgctca ctgggtgccc   21300
agcactcgag ctgctcagga aggcacctcc gtgtggtcct gctgtgagga gcatgagccg   21360
ttctccacct tgggagacaa aacgctggct tcctgtaaga aaaaatacgg tgctgcccag   21420
ggtccttgcg cttcacctgg ccgtgaaggt gagtttcccc cgtcaggatc tgtggcacct   21480
agttcaccac acgcagcaga gggaggcggc ccaggccagc caacgcgttc cagacccaca   21540
tcccggccct ctccgaccct ctccacgccc tcttctctgg ctgctgcacg tctcagtgag   21600
gggctggggg aacgcacacc tgactgcagc ttgtcagctg agctggagcc tcaaccaagt   21660
gacagccttg gagcaggtgg gccatggaag aagcccccgt gatacaggaa actgggggctc   21720 aagacgctgg cggtgtccca agtcccaggt gagtccccgg gatgcacccc atcaagggag   21780
ggtccttggc ttcacacggg gcagaattca agagcaagcc ataggtgagt aaaagtaggt   21840
tgtttagaca gatgcacact ccgtagacag agcacgggcg tcccgctcag cagggagagc   21900
ggccacgcgg agtgggggtg ctggttccca tgggctcagt agcgtcacat gctaactagt   21960
gggaggatcg ttccagccac cttggggaag gggcaggggt tcccaggtct tgggccacca   22020
cccacttgtt agccttatgg ccagcctcag aactgtcctg gcccctgtgg gaacgccatt   22080
taccaggcta gtatattaca atgagcctat agtgaagctc aaggccaact ggaagtcaac   22140
gcttccacca tcttgggcct caagatctac tgggagttga gtctcccacc gtcttggtgc   22200
taatcgtcgt gtcattcctt caatggcggt gccctgcccc cttccctcct gtcccacccg   22260
gacagcagac ctcagcggca ggcaaatctg tgagcccccg ggagtggttt aacacaaatt   22320
ctctcccggg gccgcagcct tccattgctc cctcactcct ctggacccct ctcgctcccc   22380
acaccttcct ccaaggggag ctgcgggctc ccgtgcccat cagccgccaa ccactgtgat   22440
aacagcgtca gcacccaggg aacggaggga gcaaggccca gccagcgccc tggcccgtcg   22500
ttggctaact ccgtctgtgg ctcttgccca ggggccgtcc tgcgtttcct ccttctgtaa   22560
acgcacagcc tccccacact gctcaacagc tccatcctcc aaccatagac tcagctcctc   22620
tccctgctcc actccagcac agggcgcacc caccatgctg ccatcaccac ccaccgagca   22680
gcctgcctgc cgtcctggtg ggtctcagcc cagggtggtc tctgccgtgg gaggtagggt   22740
gcagcaggag tcaagaaacc agtccctact ctgcctccgt cacactcagt gtgatgggcc   22800
tggggggcag gcttgggtgt cactgatgcg ccccagtcat aaactctgct tggacggggc   22860 acgggaggg gctttgtggt taaaagctgc aggctcgggg agctgagagg tcaggggtgt   22920
ggcccagcag gagccccagg agctgccctc ccacctgcac ggttcagacg gatgcctcca   22980
aggagaccgc tggagaaggc agtgatgggg gagccgcttg cggacccagg tatgagctga   23040
gcgtggggcc ccgagccctg cacacctccc cgtggtccgt ctaagccaca cagcatggac   23100
gcaaggattg tttcgagccg caggcaatca gaaaagcagg cacaaggcaa actctccgcc   23160
tcctgcctcc tacgaggcaa agcagggcga cacctgggga cacagcagac ccttatcagc   23220
acctgccagg gcctgccctg caagccggcc tcactgcctc tcccgtcagc ccgtgtaccc   23280
accttccccg ctacgctggc cagagacaca gagtccctct ccttcgtctt caccccttggc   23340
```

-continued

```
tacgactcaa gtccttttgt ccgggtctgt ccaccccgtg tcgaccccct gccccgtgct   23400
catccggggc accctctgtt cctatattcc aatccccccg ggagacgctt gtttcagaaa   23460
cctgaggtgg aaggggggaac tggcccccctc tcctacaaga gcaagcctct cccggacctg   23520
gcaaggggca agcaaagtct gagagccctg gcaaagagga gggagcgtgc acagggaggt   23580
gtccatcagc cctgcaggaa gacagccagg cagcttccac ctctagctac ctccatctga   23640
tccctgtcca gccagtactg ggagtgccag gaggcactag agatctgagt tgaggcagga   23700
gagcagagtg aaatgtggat ctgagctggg aggacctggg tgcactgcag atctgtgctg   23760
gaggaccagg gtgcacagaa gatctgagct ggcaggacca ggatgcacgg gagacctgtg   23820
ctgggaggat gagggtgcac agaagatctg agctggcagg accaggatgc acgggagatc   23880
tgagctggga ggatgagggt gcacagaaga tctgagctgg caggaccagg atgcacggga   23940
gacctgtgct gggaggatga gggtgcacag aagatctgag ctggcaggac caggatgcac   24000
gggagacctg tgctgggagg atgagggtgc acagaagatc tgagctggca ggaccaggat   24060
gcacgggaga cctgtgctgg gaggatgagg gtgcacagaa gatctgagct ggcaggacca   24120
ggatgcacag gagatctgag ctgggaggac cgagatgcac gggagaccat ctacagcaac   24180
cagcccagga agccgcctgc tccccacacg gcagacctgc aggaagtgag acctctacct   24240
ccagtgaaag tccaagaagc cgagcaacct gtaacagcac ccccatgccc ggcaggggtg   24300
cgaccagtaa ccgacagcgt ccatcatttt gtccctgcgt ccaccttagg acccacggga   24360
gaaagccgga cgtgccccca gccatcacag gggcgcctgc gtccagcctc cccaggggcg   24420
tccagcttcc ccagcccacc gccccatcat gcaccccaga gctcgcccctt tttctataaa   24480 gaacctccct atacacagag actattttaa tcgattaaca gagtatttat tatacactat   24540
gcatgcatgt gttagaaaca tatgtcacag acgtgtgtat gtgtacagta acactgaaca   24600
gtacatacac ataataaaac cgcaaagctc tcccgcgtcc ctgcctgcct ggaggctctg   24660
ccaagcccgg tggtgggtgt ggactccctg gctgcaccag ctcggaataa tcaggctctc   24720
cttatcctgt taaagcattt tcagcaactt aggagacacc aggtctcgtg acagtagctc   24780
acagtcgctg ttaaaaaaca gccccaagtg catcttggga cctggacaca agcggagacg   24840
aaggtgaagg tggcggagcg ggtctgagca ggggcggtga tccccggagg aagcgagcag   24900
agcaggggtg gcgggcggtc ctgtggggcc cagcagagca cctgggctgg actccgctct   24960
gggcaggccg gaaggggcac agcacgcatg tcgcccaccc agcccttgta ggacacgtgc   25020
ccgggaagcc ccttccccac ccgcggcact tctgaagtgg gcactacgtt atctcccagg   25080
gaccctgatg ctgcaggcac agaaccgccc agggtgctca cggggctcgg agtgagctgc   25140
ggcactccaa gacaggagaa gccgagggtc cccgtcccca ctcttgggac acacacagcg   25200
gtggagggcc tgcatgctct ttctcagcca gagagccatc ttccagcccc agagaccacc   25260
gtgaactctg cagcacagaa gacagctgct gctggggaaa cagcttccct ctgaccttgc   25320
gtgtcacacc gcccttcggt cagagatggg ggacagggat ggggccacgg atggaggag   25380 agaagaggct tggacccaga ggagacagcc gcccacccaa gaggccgtgc tggcaggcgg   25440
acaggacaaa gctgggttag gttgcagcct gtgcccaccg cactcaccag aggggagaga   25500
ggtgaccact ggccctggga ggaccgaggg ctcggggggga ggccgggtgc cccaggcaac   25560
agccagccaa gcgggcagca tccctgtggg aggtacggaa caagtgaccg cagggactcc   25620
cactctgagc ccgaggtccc aggacaccac tcgccccacc cccaggcacc cacgtgaggc   25680
gcctctgctg cgtctggact ccccccaggc catctgagac agaaaccacc cagagaaaag   25740
```

```
ggaacttcag gaagcaggcg gtgccaccgg tttcagtccc gctcttagtg ttcgcagggt   25800
tgcgggcagt cagctcacat ctccgggaat ccagctacga aatcctaggg gctggggctg   25860
cgggcacaga ggtcggcctg gaggagcgca ggtgcctggg gccagagtag ggaaggggtg   25920
ggggcagcac ggagacccag gctgcagggg agccacctcc atggcctccg ccttcggtga   25980
gtgcagccca agaggagcag ggacagaggg agcgcagggg ggcactggag gggaggcccc   26040
acctcaggga ccccacaagg gtccaggagc agctgagtag aaggctggga gctggtgggc   26100
acaggcagcc gacccaccac ctggaaggtc caggggccag gggagacctc tggggacact   26160
ggggacacaa aagagggtga cggtacccag ggacgaggag ctctgctggg aggggggccag   26220 cgtgggactc caaggagaaa gccatccctg ctgggagggg gccagcgtgg ggttccaggg   26280
agaaaagaca tccctgctgg ggtggggggg gccaggtggg gactccaggg agaaagccat   26340
ccctgctggg aggggggccag ggtggggttc cagggagaaa aggcatccct gctggggagg   26400
gggggggcca gggtgggatt ccagggagga aaccagccct ggggttaaca caggagtcag   26460
ggagtggagc ggaactaggc tgagggctct gcgttgaccc agagggtcag aggctgccat   26520
gggccagcac cagggacaaa ggtcagggag gctgaatgta agaggtggca gaacacctgg   26580
aggtcaagga gggcagcccc aggcgctcta aaaacacatg gagcttgtgc acatgagcag   26640
aagcctggga gtggacgggg gcaagaagct aacttggagt tcaagagaag ttggagcttg   26700
tgtaagtcag aggccactga agggcaggag ggcagtggga cattccttga atttccaagg   26760
atgcaagtag agcttttgca ggtgagcaga gggctgggag ggcaggggggc agccccaggg   26820 gctccaagga gcaggttcac cttctccatg ggagcagagg gttgcaagat caggggccag   26880 cccaggggggc tccagggagc aggtggagct cttgcgggtc agcagatggc tgtgagggca   26940
gaggccagcc ccatgggttc cagggagcag gttgagattg tgaaggtagc agagggctgg   27000
cagggcaggg ggcagaccca ggagctccag ggagcaggtt gagcttctgc aggggagcag   27060
agagctggga gggcagtggg cagcccaggg gttccaggca gcatgttgag cttctgccgg   27120
ggagcagagg cctgcgaggg caaggggggag acccaagggg ctccagggca caggttgaac   27180
ttctgcatgg gagcagaggg ctgggagggc atggggcagc cccagggttt ccaggcacaca   27240 ggttgagctt gtgcatggga gcagagggct gggagggcag ggggcagccc cagggtttcc   27300
agggcacagg ttgagtttgt gcatgggagc agagggctgg gagggcaggg ggcagcccca   27360
gggtttccag ggcacaggtt gagcttgtgc atgggagcag agtgctggga ggtcagggag   27420
cagccccagg tgttccaggg cacaggttca gcttctgcat gggagcagat ggctgggagg   27480
tcagggagca gccccagggg ctccagggcg caggctgagc tttgcaggag agaaggggggc   27540 acggagggca gggggcagcc ccaggggctc caggggcacag gttgagcttg tgcatgggag   27600
cagagggctg ggagggcagg gggcagcccc agggtttcca gggcacaggt tgagcttgtg   27660
catgggagca gagtgctggg aggtcaggga gcagcccag gtgttccagg gagcaggttg   27720
agcttgtgca ggggagcaga gggcagggag ggcagggagc agccccaggg gctccagggc   27780
gcaggctgag ctttgcagga gagcagaggg cacggagggc aggggggcagc cccagtggct   27840 ccagtgcaca ggttgagctt gtgcagggga gcagagggct gggagggcag ggagcagccc   27900
caggggctcc agggcacagg ttgagcttct gcatgggagc agaggtctgg gaggtcaggg   27960
agcagcccca ggggttccag ggagcaggtt gagcttatgc aagtgagcag aggcctgcga   28020 gggcagggggg cagcccaggg ggactccagg gagcaggtgg agctcttgcg ggtcagcaga   28080
```

-continued

```
tggctgggag ggcagggggc agccccaggg gctccagggc acaggttgag cttgtgcatg   28140
ggagcagagt gctgggaggt cagggagcag ccccaggtgt tccagggagc aggttgagct   28200
tgtgcagggg agcagagggc agggagggca gggagcagcc ccagggggctc cagggcgcag   28260 gctgagcttt gcagaagagc agagggcacg gagggcaggg ggcagcccca ggggctccag   28320
ggcacaggtt gagcttgtgc atgggagcag agggctggga gggcagggggg cagccccagg   28380 gtttccaggg cacaggttga gcttgtgcat gggagcagag tgctgggagg tcagggagca   28440
gccccaggtg ttccagggag caggttgagc ttgtgcaggg gagcagaggg cagggagggc   28500
agggagcagc cccaggggct ccagggcgca ggctgagctt tgcagaagag cagagggcac   28560
ggagggcagg gggcagcccc aggggctcca gggcacaggt tgagcttgtg catgggagca   28620
gagggctggg agggcagggg gcagccccag ggtttccagg gcacaggttg agcttgtgca   28680
tgggagcaga gtgctgggag gtcagggagc agccccaggt gttccaggga gcaggttgag   28740
cttgtgcagg ggagcagagg gcagggaggg cagggagcag ccccagggggc tccagggcac   28800 aggttcagct tctgcatggg agcagatggc tgggaggtca gggagcagcc ccaggggctc   28860
cagggcgcag gctgagcttt gcaggagaga aggggggcacg gagggcaggg ggcagcccca   28920
ggggctccag ggcacaggtt gagcttgtgc atgggagcag agggctggga gggcagggggg   28980 cagccccagg gtttccaggg cacaggttga gcttgtgcat gggagcagag tgctgggagg   29040
tcagggagca gccccaggtg ttccagggag caggttgagc ttgtgcaggg gagcagaggg   29100
cagggagggc agggagcagc cccaggggct ccagggcaca ggttcagctt ctgcatggga   29160
gcagatggct gggaggtcag ggagcagccc caggggttcc agggagcagg atgagcttat   29220
gcaagtgagc agaggcctgc gagggcatgg ggcagcccca aggggctcca gggcacaggt   29280
tgagcttctg catgggagca gatgcctggg agggtagggg gcagccccag ggtttccagg   29340
gagctggttg ggcttatgta ggtgatcagg ggtcagagag ggcaaggagc agcatccagg   29400
gatccaggga gcaggtttag ctagggcagg tcagcagagg gctaggaggg caagggacag   29460
ccccaggtgc tccaaggagc aggttgagct tctccatggg agcagagggt gcaagatca   29520 ggggcagccc aggggggactc cagggagcag gtggagctct tgcgggtcag cagatggctg   29580
ggagggcagg gggcagcccc aggggctcca gggcacaggt tgagcttctg caggggagca   29640
gagggctggg aggtcaggga gcagccccag gggttccagg gagcaggttg agcttctgca   29700
tgggagcaga tgcctgggag ggtaggggggc agccccaggg tttccaggga gctggttggg   29760
cttatgtagg tgatcagggg gcagagaggg caaggagcag cctccacgga tccagagagc   29820
aggtttagct agggcaggtc agcagagggc tgggagggca agggacagcc ttaggggctc   29880
caaggagcat gtagagcacg tgtgggtgaa cagagggctg ggcggtcagg gggaagcccc   29940
aggggctcca gggcacaggt tgagcttctg caggggagca gagggctggg agggcagggg   30000
gcagccccag gggttccaag gaataagttg agcttgtaca gatgagcgga gggctacgag   30060
ggcagagggc agccctgagg ggctccaggg agcagtttga gcttgtgcag gacagcagag   30120
ggctgggagg gcaggggggca gccctgaggg gactccaggga ggaggttgag cttgtgcagg   30180
atagcagagg cctaggaggg caggaggaaa gccccagggg ctccaggagg caatcagagt   30240
tatgacctgt aggctgcggg caggcaggta caggactgcc ctgaggagat ccaaggagct   30300
ggtagagctt gtattgctaa acaggcggct aggagtgcag ggggcagcct aactggctcc   30360
aggaataaag taaagcttgt gcaagtagca gagggctggg aaggcaggga gcagccccag   30420
gggctccagg gagcaggttg agcttctgca ggggagcaga ggcctaggag ggcagggggc   30480
```

```
agccccagag gttccaggga gcaatcagag ctatcacctg taggctgggg gcaggcagat   30540
acaggactct gccctgagga attccaagaa gctagtagag cttgtattgg tgaacagggg   30600
gatggaaggg cagtaggcag cttaaagtag tcaaggaagc cagttgtaat tgtgagaatg   30660
agcaaagggt ccgcatgaca gcgggactcc cctgtaacta gtggattaat gcccggacct   30720
aaggtacaac cacatgagga gctgagccag ggtgacggct gtggggatgc tcacaggggc   30780 cacgatgct cctgggacaa gagtctcaga ggctgctagt gagcagggg ctgaggtcag    30840 aggacaggga tctgggaacc acgagctggg gtggggtcag gggcccggt tggagggga    30900 agtgagctga gggtctccag ctggaggacc agaagaggga ctggagctct ccgaggcaca   30960
gactcggcag cctggctgag gccacaggga tgaaaggga ggggccaagg aggagacctg    31020
cagggatagg gtccaagggg gccagggtcc ataggggcca tgggccaggg cccaggtgct   31080
ctgactgcag agctgacccca gaagacacgg gcccggagga caaagaacag gacaggcaag   31140
gggccacaag caggcttctg tgtggtggag gcccaccaag ccaaggagag gcctgctcac   31200
ctagggcagg gccgggctag ggcagcagga cggtgagctc aggggaccag cggatgctgc   31260
ccgggagcac gcagcactgg taaggactca gacacagggc tgagtcaggc caggcacctg   31320
caggaggtta gggacctggg gggctgtcac ccaggtgatc acccagctct gacccacagc   31380
tgcagaggca caaggcccca ggtggtgagg gccctgccgg ccagctggtt tgcagacatt   31440
ctggaagcac atgggcgctg ggctcagggg tgcccagaac tgggctcgtg acaccctgcc   31500
cggaccctcc caggggtgaa gccctggtgg tcacacggcc tacattcttg cagcctccac   31560
caaggcccca tcggtctatc ctctgactgc ttgatgcggg gacacgcctg gctccacagt   31620
ggccttcggc tgcctggtct ggggctacat ccctgagccg gtgaggtgac ttggaactca   31680
ggtgccgtgt ccaacggcat ccacaccttc ccatctattc tcatgtcctt ggggctctac   31740
tccctcagca gcttggtaac catgcccgcc agcagctcaa ctggcaagac cttcatctgc   31800
aacatagccc acctggccag cagcaccaag gtggacaagc gtgtggataa gtggacaggc   31860
ctcagggagg gcgtccactc ccagacagga ccgaggtcag ccttcctccc ggctcgaacc   31920
acatgccagt atggcgacct ctgtccaggg tatcagagga ggagcggtct cctcgcctgg   31980
aggcctccca ggctatggga gggggacctct gggtgtttct atcaggtcca aggtgggcac   32040
aggctgcaca acgctaccgc acatagctgg tgctggacct gccaaaatcc gtccctgccc   32100
tatgcccgcc ccaacagacc tgcccctca cccagaaacc tcctgtctgc tttctttgca   32160
gaacccaaga caccaaaacc acaaccacaa ccacaaccac aaccacaacc caatcctaca   32220
acagaatcca agtgtcccaa atgtccaggt gagtcagaca agccaaccac cttttcaagg   32280
gggtggccac agccctggta tgctgggaat acatatgccc tggacaacgc tggcccaggt   32340
gctaactgcc caccttgtct tccctgccag ccctgagct cctgggaggg ccctcagtct    32400
tcatcttccc cccgaaaccc aaggacgtcc tctccatttc tggaggccc gaggtcacgt    32460 gcgttgtggt agacgtgggc caggaagacc ccgaggtcag tttcaactgg tacattgatg   32520
gcgctgaggt gcgaacggcc aacacgaggc caaaagagga acagttcaac agcacgtacc   32580
gcgtggtcag cgtcctgccc atccagcacc aggactggct gacggggaag gaattcaagt   32640
gcaaggtcaa caacaaagct ctcccggccc ccatcgagaa gaccatctcc aaggccaaag   32700
gtgggacgga caacgggcgc gggagggtcc tgtgggtctg cttggagcta ccatcatgct   32760
cacagacaca cctgtccccc cagggcagac ccgggagccg caggtgtacg ccctggcccc   32820
```

-continued

```
acaccgggaa gagctggcca aggacaccgt gagcgtaacc tgcctggtca aaggcttcta   32880
cccacctgat atcaacgttg agtggcagag gaacggtcag ccggagtcag agggcaccta   32940
cgccaccacg ccaccccagc tggacaacga cgggacctac ttcctctaca gcaagctctc   33000
ggtgggaaag aacacgtggc agcggggaga aaccttcacc tgtgtggtga tgcacgaggc   33060
cctgcacaac cactacaccc agaaatccat cacccagtct tcgggtaaat gagcttcacc   33120
ccggcacccc agcgaacccc ccaccccgaa gctcccaggc tcccgcgtgg aggcctgagc   33180
cccacccctg tgtacatacc tcacaggcca gcatgaaata aaacacccag ggcctccctg   33240
gggccctgca gcaatgtcat ggttctttcc gagcagagct ccggcgcccg ccgggcctgc   33300
gggaggcggg ggcagcccag gctctgagga caaccttggt gccatcaggg gactggggat   33360
gaccagaggc aagggatggg gtctgccaga ggcagcagct ccctagggtc cagtgtcgag   33420
ccagcacctg ctcaggctgg agtgtgcaga ggacactggt agagcctccc agggaccctc   33480
acggaaatga atacatagtt cttcccacct ctgtccaagc ccaactgtgg gacagtggca   33540
ggtccttatc cccgcagttc ccgaccccgg ggcctcaaag gcccacgtgc tgacaccctg   33600
tcaacatggg atccacgcca ggccagcaat gggggcacag gcctcctgct cgcaggacgc   33660
acggggatca ggccccacat tcccgcaggc aaggttctcg ggccagaacg gtacactcga   33720
ggggacattc acctagaccc ataggaaaca agccttctca tggagcacaa cagcctgcac   33780
acccctcgtc ctcctgcata ctcacgcaca ctcatttcct gtgcaactgc acaaagcgct   33840
gaaccacaaa agtgcacaca ggccagcctt gctcactggg tcctcaacgg ggtacccgcc   33900
cggggccaga ccggagcctg cagccgggtc tcatgaaccc tctgtggaca acagcttggt   33960
ccccactcct caaagcccca gcagcacaga ccacactctg accacactgg tcagctcaga   34020
cccccacccc tcctctcccc agaacacctg caccccctcc tcaacacaca gagacccaac   34080
agcccactgg tccctagcac gccgacccca ccccttggg cacacaagga cacccaagg   34140 ttgcctccgc ccttccctgc agtaggaccc accacagccc tgctctgcag accctgcctt   34200
ctaggcctgg cctccagtgg gagggaaggc aggggtcagg gcaccctccc cgcagaggac   34260
cccatgaaag gcacagcaga ggagaggata gggcccccca ctgaccaggc cgagatctgg   34320
gcccaaggag tccggccaag actgaggccc aagctggagg aatgggggac acgaggtcgc   34380
tgcccaggga ctgacctaag ggaaccattg atccagcccc ccaggggat cctagtgccc   34440 cacccgccct gtcacagagg gacccacccc aggcgccact gaccctgccc tggcacgtga   34500
cgggcagcca cagagctgaa caccccctcc ctgtccagag ccactcctgg aggaggagag   34560
ctgtgccgag gcccagagcg gggagctgga cgggctgtgg accaccatct ccatattcat   34620
caccctcttc ctgctcagcg tgtgctacag cgccacagtg accctcttca aggtgggcgg   34680
gccaggccag cggtgcctgc tgtccccaca cggtgcccgc acagtccccc taccctgtcc   34740
actccctgtc cctccatgtc cctccctgtc cccttcctgt cccctcacag tcccgtcact   34800
gtctcctcac tctcccctct tgtcctctct gtccactgtc tgtcctcctc tgtctctcca   34860
gtccattcta ttctctcact gtccctctat gtcctggtcg ggacctcgct gtccgcggct   34920
gtgcccatgt agtcctcgcg ccacccacc tgagcacact tgcggccggc agtcccaggg   34980
ctgggaggcc aggtccttgg gggaagctgg catgggggcc ccggctgtgc tcacacccgc   35040
cgtccctgca ggtgaagtgg atcttctcct cggtgttgga gctgaagcag acgatcgtcc   35100
cagactacag aaacatgatc gggcaggggg cctagcgtgt cctctggggg tgtccacggc   35160
caccacaggc cccagaggta ccccgttcat cactccgagc tgctcagcca ctactccgcc   35220
```

-continued

```
cgctgccctg ccagttctga gctctcggcc atgctcaccc gcacctccat cctccgactt   35280
aaaggcaacc actgaccaca ccctgcacat tgctcacgtt caggggccag gtgggcagca   35340
ggtgctacca ccaacctgag cttaggggtc tgcctgtcct caccgggagt gcccggggca   35400
ccctcaggtt cccttggatg agcaggaggc tggcatcccg gggcagtggg cagggatagc   35460
tctgtggaca ccatcagatt ggtcatcaag cagggtcccc aaggggaggt gcctgtgtca   35520
gatccttggt gggaacatat gcagccctgg ccaacgtctc gcagcaggga agcttctgga   35580
tgtgccacca acggtcagcc aagtactcag ctctgagaag ggcctgggcc catggcccct   35640
acaggagcca ggcctgccag gaacggcagt gaggtctccc cactccagct tcccagagac   35700
ggaactggtg accgggtccc ccaggggcag gacacagcct cgctggacac agcaagaggg   35760
acactggcac aacagggcag tggccgcagc cagcctgtcc cttggccagc ggcctgagtc   35820
accttcagca ggagctcccc tgcaccgggg ggtggggtga gaggcgaccc cgggaggagg   35880
gagcccgaca ccccggcgtc ccggcccgag acccctgggc ctctcctgtc ttgtccctgg   35940
atggggaggg gcaggcccca ctgccgggtg gtggcggggg agaggggcg cgctacagcc   36000 agaggtcacg ccaggcctgg cttggggagc tgtgcatcct ttctaaacgt ctggagccca   36060
tgaactttct gcgctgtttc tctttggttt gggtttttgt tgcgagactc tggcttctca   36120
tattttcggt tctctagaca ataaagcatc ctttaccatt ccatagctcc ctggcagtcg   36180
ctctgtgttg cggcccctcc cctggggact ccacagcctg gccgcccgcc acaccctccc   36240
agccccaggc ctcagctctc cccccaccac acccatccct ggggttccct gggggcgcgg   36300
agtcagcagc aagtcccagg ggtcggacgc ctggtcagca cggctgctgt aacacgcacc   36360
gcagtcgggt tggaaccaca gaaatgattg tctcccgtcc tggagcagca cgtcccagct   36420
cgaggagcgt gaaggccact gtgcccaccg gctgccaagg ctgcagggac gcagtcagga   36480
ctcggtcctc cggggaggcc agaccctgag ctccaggccc tcctggtggc tccatctcaa   36540
aggaacagtc tcaggtcccg ggctgtagga gacacagcac tccccagagg gcagacacag   36600
gatccacagc tgtctgccct tcgcaggaaa tgctccagga aacggaggcc agtgcctggt   36660
cagggctggc tctgctgggc ggtccaggcc agcgctacag gagagctcag tcatccacgg   36720
gacgcggccc tgggcggctg gacattgtcc aagtgtctgt gtgagccttt cagtgtgtca   36780
gggaagaggg ggcgaaatca acgtgccgag tctgtgcctc cacggcccca ggggaggcca   36840
gcaggacagg ctcctggagg ggagctggga ccagcactga gtggaaaggg ccattccagc   36900
ttcctgtggg cacagacaga cagacagcca gaggaagaca gagaacttca tgcaggaaag   36960
ggacagctcg ctccagtggg ctctgcacca gagacggtga ggccatgggg cgggcagccg   37020
ggtccagggg catcgccggc cctcaggac cctgccaggc gtgaggacac tgggcaccct   37080
ctgcctccag ggtgctccgg aagccatcct ggggtctcc cccactcgcc atttccctca   37140
cacggaacac ctaaccaaca agctgaacct gcctatggtc cctgcagcat gcccagcccc   37200
aggccctgcc cctcacctcc atccctgga gcccggatct gcctccagcc acacattccc   37260
acggggacac caggacgctc gatgccgggc tggccccgcg ggtccttgag gagcaccagt   37320
cccagaacag ctgccccca ccaggcctga gggccccgtc ctgaccccgg ggcaacacca   37380
ggccacagcg cgtcccccat gcacagcccc tcctgggacc ctggaagcga gtggccgac   37440 gccttccctt gagccctgt gtcagcaccg gtgcgagcct gagctcagct ttctgctgct   37500
cctgacccct aggggcgctg ccccgggcaa tagctccgac acactcctgt cagtgtctca   37560
```

-continued

```
cctatccgac ccgcacccc atccacatct tacacacaca cacacacaca cacacacaca  37620
ccctgggctg ccaccccact gcgctcctgg gcccccacca ggtcccccct cctcccgcac  37680
tccaagggga acgcctgccg gtctgagctt tgaaaacctg gattgctgtc cgtgtgtggt  37740
gtccgtggat gtggagaaaa gaaacccttg tgcgctgctg gtgagaacat aagatggcat  37800
taccgttgtg caaaacggtt tggaagcccc tcaaagacat ttcagaaaca actaccacac  37860
ttgcagcaat ctcactgctg acaataaacc cgagcgaaca tacaacaggt cttaaagagg  37920
cacttgaaca cccacttcac agcaactccg ttgacaagac ctaccacgag gcacgaactc  37980
gagtgtcctt ccggggatgg acagatgagc acgatgtggg ctgagcgtac aatggaacag  38040
tactgccccg agaaagaaga acactctgac gtgtgtgaca gcacgggggc acctggagga  38100
catcggaacg cgtaccgtga gccgcgggca agacggtgaa tcgtgtgcga ttccactcgg  38160
gtgagcgatt aggagtggcc gcattcacag aaggagaaaa cacagaagtg gttgcagccg  38220
ggggagaacg gggggttgtt gtttacgggc atagggtttc acacgtaaag atgggaagag  38280
ttatggagac acggcggtc gtgactgcac tttatgaatg catttgctgt ccccaaaacc  38340
cggagaaagg cttaacatgg tacactttct tggggcaaa tcctattctt ttaaacggga  38400
gaaatctaac ccgttaaata aaatctgaaa gccttcagga agacctggag cccgtgtctc  38460
tccctgtgga agaaaccggt ggcagcagga gaaatctaac ccgttaaata aaatctgaaa  38520
gccttcagga agacctgggg cccgtgtctc tccctgtgga agaaaccggt ggcagcagga  38580
tggagctgca cacctgcctg gcccagggct ggacccctgc ggaggccggc gggcgccgga  38640
ggagcagctt ctccacactg acggcgtgag ggtgccggtc agtgacaacg tgcacggctg  38700
tagcagagcc ccccagccaa gggactgctc cttcagtttg ctctccaaca ggtgtaaact  38760
tctcttctgg acaaccctaa cctagagaca cacgaaggga agggaacgct aagaaagctg  38820
ctcacggctt agctaacctg acgtagaaca agaacagcac aacccactgc ttgtcggcca  38880
ccgtgcacca cgttaagctt cccgattaaa aggcagcaat acactttgtg tttccaccta  38940
atgcagggga attacctcag atgtaatata aaaatgccaa ccctcctcca agaaaggctt  39000
caactcccat tgcccacctt acgtaccttc ggctgatgtt cacgtctcgt gttgatgaat  39060
aacctccgcc ttgggtgtcc tgcagcttat acgctgaggt atgtagcatc acctctaaca  39120
cgtcctttgt cacacggtgg gggggggtg gacggaacag gttggttatg agaggaggag  39180
acggagacgg tggagtagaa ggacacagag cacattcaca ttacatgtac atgtggacca  39240
cgtctcactg gagaaaaatg gagactggca gagagactcc tgtacagcca aggcgctgaa  39300
gaaaggtcca cgaggagtca cgtagggagg gaagagaggt actcggtttg gaacgcagcc  39360
tcggggaggg gacccgggac aggggacac gtcatgggca cgcaggtctt ccctgggag  39420 tgggcagctt gagagcgtta gtaatatgaa tgctaaccaa gttagggaaa aggacacatg  39480
aaaacagttt gaacctttac agggacctgg aaaatataaa aagagaacca ctcaccagag  39540
gggtacgatg gctaaaactt aaaacactgg aaggggcgaa cagggcacta ggtggcaccg  39600
gagaccccac gcgacctgga agacagaacc atgggaatta cccagtcaga actacaaaag  39660
gaaaaacaac ttttttaaca ctgagagcag ttgacggaat ctatggaacg acatcaactg  39720
tcctaacttc ggcatgatcg gggtcccaga agcagaaggg agagagagag aagttgaaaa  39780
tgtacttagt gaaattatgg caaaaactca ccaaccatga agaaagagag acatttccag  39840
gcgtaggaat cacacagtcc caaacaaaca caacccagag agacccacac caagacacgt  39900
cacaattaag ttggcaaaag ttaaggataa agagaggatt ctgaagacag aaagagaaca  39960
```

-continued

```
ttaaagagtc acatacaagg aaccaacaca aagttatcag ttgatttttc tgtaaacacc   40020
ctgcagtctg gacaagagag tcatcctaca tttcaaatgc tgcacggaaa aagtctacaa   40080
agtaggagac actacccaaa aaaatttacc atttagaatt gaaggagaga taaatgtaac   40140
aaaagagaaa cagaacacag atagactgat aatattagtg gttaccagtg cacagagggg   40200 aggggaagg ggcaacataa ggacagagaa ataagcaaca caactacaat gtataaaaaa   40260
aagcctaccc agatgtattg tacagcacag ggagtatagt cagtgcttct aataacttca   40320
agtggaatgt actctctaaa agtattcaat caccattttg tatgttgtcc acccgaaact   40380
aatataactt tctcagtgaa gtgtatttaa cttaaatcta tgtatataca caaattcata   40440
tcaaaataag gaaccatctt caaattccac ccaccacact tgggatcaat catgcttctc   40500
tgtggggcgt gactccaaga cattgggcca agaagagtac tcaggttacg aagatggaca   40560
tggctcctgc cccgagacac acgaggtctt gggacgctgg tccagactgc gttcttcctc   40620
tgaaactacc ttgcgttcca cagggcccat ttgctgtcca tgaggccttt tccacgtcag   40680
gcaatggctg agccatgtgt gtacccaagg ccttccaggc cgctgtccgt ggtcctgacg   40740
cggactagca ggctgtttca gctactgtcc atggtcctgc ttctgctgct ctgcacggag   40800
taatgatatt tttagattaa acagactttg cccttttagg gtagtttcag gctaacagaa   40860
agtccacaga gctccataaa ttccagtgcc ccacacatac acccagtttc acctgttgtg   40920
aatatcttgc tccagtgtgc tacatttgtc agaagtgatg aaccaagtta atacattatg   40980
attaactgaa gtccataggc aacaccatgg ctcactatta tctgcacaat tctatgagtt   41040
ttgacaaatg catggtgtca tttgcatcca gaggccccga ggctgctgtc catggaactg   41100
ccttgatcag gttcactgtt caggctgctg cccatcggtc caccatttca gcaacacaca   41160
ctacaatttc actgccttga agaccccctg tacctcaccg cctcattccc cacccctccc   41220
acacaaactc ctggcagcca ctcgccttct cattgtctcc ataggtgagc tccttcaaat   41280
accgtgtagt aggaatctca cagcgagcat aaccttctcc ggttggcccc tttcacttag   41340
caatgcgcat tttcatttcc ccatgtcctt ttgtgcctca atggctcatt tcttcttcgt   41400
ttttaatggt cgtttcttac tttgggggac tatgggaggg taattagttt tccttcatgg   41460
agatactggg gattgaacca aggacctcat gcatgctaag cacacgctct atcattgatc   41520
aataccctcc ccccattgct tctcctacta acttcttttt tcaacagctt tgttgagata   41580
caattgatac acaaaataaa tgcatatatt cgaggtacat ctgagtttgc acatatgcag   41640
acacctgtga aaccatcgtt actgtcaggg tagtcgatat atccattcct ctaaaagttt   41700
ccttgtgctt tgggtttatt gggatggggg agcagcacat gtatgtgaag agcccttatc   41760
acgaaatcta ctctcttaac aagtatctgg gtgcacaatg cagtgttgta aaccgtcagc   41820
acaatgttac acacggagcc tcggaataga tctcattctg cataactgaa aatttatacc   41880
tattgaatca cggcagaatc aaagagtatc accacaaaaa atcaatgaag cacaaaagaa   41940
agaagcaaga aggaatagag gaacaagttc actacaagac aggcagagaa ctattaaaaa   42000
caacagtgat aataggcctt tccctgccac aattaccttt aatgtaaatg gattacatta   42060
tcagagcaaa agatatacag tggctgagtg gataacaagc aaggcccaga tctgtgccaa   42120
cacaaggcac tcactttagg cttaaggaca catgtaggct ggtcacgaag ggatggaaaa   42180
acgtactcca tggaaaaggc aaacaaaagg aagcaaggat gcgtacactt ggacaaaata   42240
gacttgaagg taaaaacagt cataagagac ccagaaggat gctatacaat gatgaaaaaa   42300
```

-continued

```
atcagttctt cacagacggc ttcgtccttt ttattctgca atcctgttcc tctgcctgga    42360
tgcatccact cacctactga gggacatcct gtgcgcatcc aagtttgaat taagctacga    42420
atgaagcatc tgtagacatt tataaaccat acacatcgct gcacagattt ggggtggaca    42480
tgagttttca gcccatttga acaggtgagt atctaggaat gcagttgccg ggttgtatgg    42540
caagattagg tttagattct ggagaaactg ccgagctctc ctgcagacgg gctcttcccg    42600
tttgcaccca cccgcagcgg aggaggcctc ctgctgcccc acaccctcac cagcgtcggg    42660
aggtgccggg tttcggtgtt gcttctggac gtccaccgtt ctaacagctg cgtggtggtc    42720
ttccttgttt tcgcttacag cctccaacga cgtcggatgt ggaggaaact tgtgcttcct    42780
tctctgcatc tgtgagtctt cttaggtgag aggtctgtcc agggctttta gtcacttttg    42840
actgggtcgt ttgtttcctt gttgtggact tttaacactt ctccgcatat tgcggacacg    42900
agtccttcat cagatacgag gtttgcaaat gtgtgattct cccagtccat ggcctgcctt    42960
tcattctctc gacagtgtct tccacaggca ggcatttcca cttcagttaa gttcagctag    43020
tgacttcttt tccgtggaat gcgcttttgg tgttgtacct actgactctt cgccgaagtc    43080
aaggtcacct agattcccat agttcccttt tttgcattga ggtcaatgac ccactgtgag    43140
ttaacttcat gaccagtgtg agcatgcgcc tcagctcgtt tcctgctggg atgcaggtgc    43200
tccaccacca cttggtgaaa agagcccctt ctccatcaag ttaccttcac tccagtcgag    43260
ccctcagagg tgggcatggg cagggagagg tcactccctt gtctgagctc ctttggtgct    43320
tctagaatgt tctgtcactg aggggacat gcaatcaaat ggccttaaac catctgcaga    43380
aaaattattt ctaacagaat ttacacccaa accaaggata aagtgtaaag gtaggataaa    43440
ggcatcctct gacatgcaag atctcaaaca acgtccctcc aggcatcctc tctcaggaag    43500
acagcagacg gcctttggac ctgaactctc cacgtcagcg gcctgggccc cggcagatca    43560
tggactccag ccaccatcat ggtgccagtc acttctttac gacaagtctc tttctagata    43620
cggaccatat acacagagat aggggtacat cctacggatt ctgttcccct ggagactaac    43680
acaccctggg gcacaacgca gtcttcttcc aacccacagg aaccgactga ctccagaggg    43740
gatggggggg caggtccaag gcactcagca gcgttcctga agaggggtc taaactgcac    43800 tggaaagcca gctcaagagc ccagcatcga tgcttaatta agtctaaagc acgtgcttcc    43860
atacgtacaa agtgggaatg ttcagctaca cgcactgggt ctgttcacaa cacagcgtgt    43920
ttcttcctaa acggtacatc gagcgattga gcctcgtaga gggaacagca tcctggattt    43980
gaacggcagc aagtgtcaca aacctgctgg aaagcagagt ggatccctcc cgcgggcggc    44040
cccactcggc ttgctcactg ggtgcccagc actcgagctg ctcaggaagg cacctccgtg    44100
tggtcctgct gtgaggagca tgagccgttc tccaccttgg gagacaaaac gctggcttcc    44160
tgtaagaaaa aatacggtgc tgcccagggt ccttgcgctt cacctggccg tgaaggtgag    44220
tttcccccgt caggatctgt ggcacctagt tcaccacacg cagcagaggg aggcggccca    44280
ggccagccaa cgcgttccag acccacatcc cggccctctc cgaccctctc cacgccctct    44340
tctctggctg ctgcacgtct cagtgagggg ctgggggaac gcacacctga ctgcagcttg    44400
tcagctgagc tggagcctca accaagtgac agccttggag caggtgggcc atggaagaag    44460
cccccgtgat acaggaaact ggggctcaag acgctggcgg tgtcccaagt cccaggtgag    44520
tccccgggat gcaccccatc aagggagggt ccttggcttc acacggggca gaattcaaga    44580
gcaagccata ggtgagtaaa agtaggttgt ttagacagat gcacactccg tagacagagc    44640
acgggcgtcc cgctcagcag ggagagcggc cacgcggagt gggggtgctg gttcccatgg    44700
```

-continued

```
gctcagtagc gtcacatgct aactagtggg aggatcgttc cagccacctt ggggaagggg   44760
caggggttcc caggtcttgg gccaccaccc acttgttagc cttatggcca gcctcagaac   44820
tgtcctggcc cctgtgggaa cgccatttac caggctagta tattacaatg agcctatagt   44880
gaagctcaag gccaactgga agtcaacgct tccaccatct tgggcctcaa gatctactgg   44940
gagttgagtc tcccaccgtc ttggtgctaa tcgtcgtgtc attccttcaa tggcggtgcc   45000
ctgccccctt ccctcctgtc ccacccggac agcagacctc agcggcaggc aaatctgtga   45060
gcccccggga gtggtttaac acaaattctc tcccgggggcc gcagccttcc attgctccct   45120
cactcctctg gaccccctctc gctccccaca ccttcctcca aggggagctg cgggctcccg   45180
tgcccatcag ccgccaacca ctgtgataac agcgtcagca cccagggaac ggagggagca   45240
aggcccagcc agcgccctgg cccgtcgttg gctaactccg tctgtggctc ttgcccaggg   45300
gccgtcctgc gtttcctcct tctgtaaacg cacagcctcc ccacactgct caacagctcc   45360
atcctccaac catagactca gctcctctcc ctgctccact ccagcacagg gcgcacccac   45420
catgctgcca tcaccaccca ccgagcagcc tgcctgccgt cctggtgggt ctcagcccag   45480
ggtggtctct gccgtgggag gtagggtgca gcaggagtca agaaaccagt ccctactctg   45540
cctccgtcac actcagtgtg atgggcctgg ggggcaggct tgggtgtcac tgatggcgcc   45600
ccagtcataa aactctgctt ggacggggca cggggagggg ctttgtggtt aaaagctgca   45660
ggctcgggga gctgagaggt caggggtgtg gcccagcagg agccccagga gctgccctcc   45720
cacctgcacg gttcagacgg atgcctccaa ggagaccgct ggagaaggca gtgatggggg   45780
agccgcttgc ggacccaggt atgagctgag cgtggggccc cgagccctgc acacctcccc   45840
gtggtccgtc taagccacac agcatggacg caaggattgt ttcgagccgc aggcaatcag   45900
aaaagcaggc acaaggcaaa ctctccgcct cctgcctcct acgaggcaaa gcagggcgac   45960
acctggggac acagcagacc cttatcagca cctgccaggg cctgccctgc aagccggcct   46020
cactgcctct cccgtcagcc cgtgtaccca ccttccccgc tacgctggcc agagacacag   46080
agtccctctc cttcgtcttc acccttggct acgactcaag tccttttgtc cgggtctgtc   46140
caccccgtgt cgacccctg ccccgtgctc atccggggca ccctctgttc ctatattcca   46200 atcccccgg gagacgcttg tttcagaaac ctgaggtgga aggggggaact ggcccctct   46260 cctacaagag caagcctctc ccggacctgg caaggggcaa gcaaagtctg agagccctgg   46320
caaagaggag ggagcgtgca cagggaggtg tccatcagcc ctgcaggaag acagccaggc   46380
agcttccacc tctagctacc tccatctgat ccctgtccag ccagtactgg gagtgccagg   46440
aggcactaga gatctgagtt gaggcaggag agcagagtga aatgtggatc tgagctggga   46500
ggacctgggt gcactgcaga tctgtgctgg aggaccaggt tgcacagaag atctgagctg   46560
gcaggaccag gatgcacggg agacctgtgc tgggaggatg agggtgcaca gaagatctga   46620
gctggcagga ccaggatgca cgggagatct gagctgggag gatgagggtg cacagaagat   46680
ctgagctggc aggaccagga tgcacgggag acctgtgctg gaggatgag ggtgcacaga   46740 agatctgagc tggcaggacc aggatgcacg ggagacctgt gctgggagga tgagggtgca   46800
cagaagatct gagctggcag gaccaggatg cacgggagat ctgagctggg aggatgaggg   46860
tgcacagaag atctgagctg gcaggaccag gatgcacggg agacctgtgc tgggaggatg   46920
agggtgcaca gaagatctga gctggcagga ccaggatgca cgggagatct gtgctgggag   46980
gatgagggtg cacagaagat ctgagctggc aggaccgaga tgcacgggag accatctaca   47040
```

```
gcaaccagcc caggaagccg cctgctcccc acacggcaga cctgcaggaa gtgagacctc   47100
tacctccagt gaaagtccaa gaagccgagc aacctgtaac agcacccca tgcccggcag    47160 gggtgcgacc agtaaccgac agcgtccatc attttgtccc tgcgtccacc ttaggaccca    47220
cgggagaaag ccggacgtgc ccccagccat cacaggggcg cctgcgtcca gcctccccag    47280
gggcgtccag cttccccagc ccaccgcccc atcatgcacc ccagagctcg ccctttttct    47340
ataaagaacc tccctataca cagagactat tttaatcgat taacagagta tttattatac    47400
actatgcatg catgtgttag aaacatatgt cacagacgtg tgtatgtgta cagtaacact    47460
gaacagtaca tacacataat aaaaccgcaa agctctcccg cgtccctgcc tgcctggagg    47520
ctctgccaag cccggtggtg ggtgtggact ccctggctgc accagctcgg aataatcagg    47580
ctctccttat cctgttaaag cattttcagc aacttaggag acaccaggtc tcgtgacagt    47640
agctcacagt cgctgttaaa aaacagcccc aagtgcatct tgggacctgg acacaagcgg    47700
agacgaaggt gaaggtggcg gagcgggtct gagcagggc ggtgatcccc ggaggaagcg    47760
agcagagcag gggtggcggg cggtcctgtg gggcccagca gagcacctgg gctggactcc    47820
gctctgggca ggccggaagg ggcacagcac gcatgtcgcc cacccagccc ttgtaggaca    47880
cgtgcccggg aagcccttc cccacccgcg gcacttctga agtgggcact acgttatctc    47940
ccagggaccc tgatgctgca ggcacagaac cgcccagggt gctcacgggg ctcggagtga    48000
gctgcggcac tccaagacag gagaagccga gggtccccgt ccccactctt gggacacaca    48060
cagcggtgga gggcctgcat gctctttctc agccagagag ccatcttcca gccccagaga    48120
ccaccgtgaa ctctgcagca cagaagacag ctgctgctgg ggaaacagct tccctctgac    48180
cttgcgtgtc acaccgccct tcggtcagag atgggggaca gggatggggc cacggatgga    48240
gggagagaag aggcttggac ccagaggaag acagccgccc acccaagagg ccgtgctggc    48300
aggcggacag gacaaagctg ggttaggttg cagcctgtgc ccaccgcact caccagaggg    48360
gagagaggtg accactggcc ctgggaggac cgagggctcg gggggaggcc gggtgcccca    48420
ggcaacagcc agccaagcgg gcagcatccc tgtgggaggt acggaacaag tgaccgcaga    48480
gactcccact ctgagcccga ggtcccagga caccactcgc cccaccccca ggcacccacg    48540
tgaggcgcct ctgctgcgtc tggactcccc ccaggccatc tgagacagaa accacccaga    48600
gaaaagggaa cttcaggaag caggcggtgc caccggtttc agtcccgctc ttagtgttcg    48660
cagggttgcg ggcagtcagc tcacatctcc gggaatccag ctacgaaatc ctaggggctg    48720
gggctgcggg cacagaggtc ggcctggagg agcgcaggtg cctggggcca gagtagggaa    48780
ggggtggggg cagcacggag acccaggctg caggggagcc acctccatgg cctccgcctt    48840
cggtgagtgc agcccaagag gagcaggac agagggagcg cagggggca ctggagggga    48900 ggccccacct cagggacccc acaagggtcc aggagcagct gagtagaagg ctgggagctg    48960
gtgggcacag gcagccgacc caccacctgg aaggtccagg ggccagggga gacctctggg    49020
gacactgggg acacaaaaga gggtgacggt acccagggac gaggagctct gctgggaggg    49080
ggccagcgtg ggactccaag agaaaagcca tccctgctgg gaggggggcca gcgtggggtt    49140 ccagggagaa aagacatccc tgctggggtg gggggggcca gggtgggact ccagggagaa    49200
agccatccct gctgggaggg ggccagggtg gggttccagg agaaaaggc atccctgctg    49260 gggagggggg gggccagggt gggattccag ggaggaaacc agccctgggg ttaacacagg    49320
agtcagggag tggagcggaa ctaggctgag ggctctgcgt tgacccagag ggtcagaggc    49380
tgccatgggc cagcaccagg gacaaaggtc agggaggctg aatgtaagag gtggcagaac    49440
```

```
acctggaggt caaggagggc agccccaggc gctctaaaaa cacatggagc ttgtgcacat   49500
gagcagaagc ctgggagtgg acggggggcaa gaagctaact tggagttcaa gagaagttgg   49560
agcttgtgta agtcagaggc cactgaaggg caggagggca gtgggacatt ccttgaattt   49620
ccaaggatgc aagtagagct tttgcaggtg agcagagggc tgggagggca gggggcagcc   49680 ccagggctc caaggagcag gttcaccttc tccatgggag cagagggttg caagatcagg   49740
gggcagccca gggggctcca gggagcaggt ggagctcttg cgggtcagca gatggctggg   49800
agggcagggg gcagccccag gggctccaag gcacaggttg agcttgtgca tgggagcata   49860
ggcctgggag gtcagggagc agccccaggg gttccacgga gcaggatgag cttatgcaag   49920
tgagcagagg cctgcgaggg caggggggcag ccccaagggg ctccagggca caggttgagc   49980
ttctgcatgg gagcagatgc ctgggagggt aggggggcagc cccagggttt ccagggagct   50040
ggttgggctt atgtaggtga tcaggggggca gagagggcaa ggagcagcat ccagggatcc   50100
agggagcagg tttagctagg gcaggtcagc agagggctag gagggcaagg gacagcccca   50160
ggggctccaa ggagcaggtt gagcttctcc atgggagcag agggttgcaa gatcaggggg   50220
ccagcccagg aggactccag ggagcaggtg gagctcttcc gggtcagcag atggctggga   50280
gggcaggggt caggaccagg ggctccaggg cacaggttga gcttctgcag gggagcagag   50340
ggctgggagg gcaggggggta gccccagggg ctccagggca caggttgagc ttctgcatgg   50400
gagcagaggc ctgggagggt aggggggcagc cccagggttt ccagggagca ggttgagctt   50460
ctgcaaggga gcataggact gggaggtcag ggagcagccc caggggttcc agggagcagg   50520
ttgagcttat gcaagtgagc agatgcctgg gagggtaggg ggcagcccca gggtttccag   50580
ggagctggtt gggcttatgt aggtgatcag gggtcagaga gggcaaggag cagcctccac   50640
ggatccagag agcaggttta gctagggcag gtcagcagag ggctaggagg gcaagggaca   50700
gccttagggg ctccaaaaag catgtagagc acgtgtgggt gaacagaggg ctgggcggtc   50760 aggggggaagc cccaggggct ccagggcaca ggtttagctt ctgcagggaa gcagagggct   50820
gggagggcag ggggcagccc cagggggctcc agggagcagg ttgagcttat gcaagtgagc   50880
agaggcctgc gagggcaggg ggcagcccac ggggactcca gggagcagtt ggagcttctg   50940
catgggagca gagggctggg agagcagggg gcaccccag gggctccagg gcacaggttg   51000
agcttctgca tgggagcaaa gggctgggag ggcagggggc agccttaggg gctccaggga   51060
gcaggttgag attctgcatg ggagcagagg tctgggaggg caagggggcag ccccagggac   51120 tccagggagc aggttgggct tccacagggg agcagagggc tgggagggca ggggggcagcc   51180 ccaggagctc cagggagcag gttgagcttc tgcataggag cagagggctg ggagggcagg   51240 gtgataccc aggggcacca gggcacaggt tgaacttctg caggggagca gagggctggg   51300
aagtcagggg gcagccccag ggactccagg gagcaggttg agattctgca tgggagcaga   51360
gggctgggag ggcaaggggc atccccaggg actccaggga gcaggttggg cttccacagg   51420
ggagcagagg gctgggaggg cagggggcag ccccaggagc tccaggggagc aggttgagct   51480 tctgcataga agcagagggc tgtgaagtca gggggcagcc ccagggggctc cagggcgcag   51540 gttgagcttc tgcaggggag cagaggactg ggagggtagg gggcagcccc agggtttcca   51600
gggagctggt tgggcttatg taggtgatca gggggggagag ggcaagaagc agcatccagg   51660
gatccaggga gcaggtttag ctagggcagg tcagcagagg gctaggaggg caaggacag   51720 ccccagggggc tccagggcac aggttgagct tctgcatggg agcagagggc tgggagggca   51780
```

-continued

```
gggggaagcc ccaggggctc cagggcacag gttgagcttc tgcatgggag cagagggctg   51840
ggagggcagg ggtcaggacc aggggctcca gggcacaggt tgagcttctg catgggagca   51900
gaggcctggg agggtagggg gcagccccag ggtttccagg gagcaggttg agcttctgca   51960
agggagcaga gggctgggag gtcagggagc agccccaggg gttccaggga gcaggttgag   52020
cttatgcaag tgagcagagg cctgcgaggg caggggggcag ccccaagggg ctccagggca   52080
caggttgagc ttctgcatgg gagcagatgc ctgggagggt aggggcagc cccagggttt   52140 ccagggagct ggttgggctt atgtaggtga tcagggggca gagagggcaa ggagcagcct   52200
ccacggatcc agagagcagg tttagctagg gcaggtcagc agagggctgg gagggcaagg   52260
gacagcctta ggggctccaa ggagcatgta gagcacgtgt gggtgaacag agggctgggc   52320
ggtcaggggg aagccccagg ggctccaggg cacaggttga gcttctgcag gggagcagag   52380
ggctgggagg gcagggggca gccccagggg ttccagggca caggttgagc ttatgcaagt   52440
gagcagaggc ctgcgagggc aggggggcagc ccaggggggac tccagggagc aggtggagct   52500
tctgcatggg agcagagggc tgggagagca ggggggcagcc ccagggggctc cagggcacag   52560 gttgagcttc tgcaagggag cagagggctg ggaggtcagg gagcagtccc aggggttcca   52620
gggagcaggt tgagcttatg caagtgagca gaggcctgcg aaggcagggg gcagccccaa   52680
ggggctccag ggcacaggtt gagcttctgc atgggagcag atgcctggga gggtaggggg   52740
cagccccagg gtttccaggg agctggttgg gcttatgtag gtgatcaggg ggcagagagg   52800
gcaaggagca gcctccacgg atccagagag caggtttagc tagggcaggt cagcagaggg   52860
ctgggagggc aagggacagc cttaggggct ccaaggagca tgtagagcac gtgtgggtga   52920
acacagcgct gggcggtcag ggggaagccc caggggctcc agggcacagg ttgagcttct   52980
gcaggggaac agagggctgg gaagttaggg cgcagcccct ggggattcat tgtgcaatca   53040
gtgctgtcac ctgtaggctg ggggcagcca ggtacaggac taccctgaag agctccaagg   53100
agctagtaga acttgaattg gtgaacaggg ggatgggagg gcagaaggca gcctaaagtg   53160
gtccaggaag ccagttgtaa ttgagagaat gagcaagggc tccgcatgac tgcagggctc   53220
ccctgtagct agcggattaa agcccggacc taaggtacag ccaaacgtgg agctgagcca   53280
gggtgacggc tgtggggatg gccagacggg ccacggctgc tcttgaacag tgtctcctgg   53340
gacaagggtc tcagaggctt ccagtgagca gggggctaag gtcagaggac agggacctgg   53400
gagcaacgag ctggggtggc gtcaggggcc ccggttggag gggttagtga gctgaggggc   53460
tccagctgga ggaccagaag agggaccgga gctccccgag gcacagactc gtcagcctgg   53520
ctgaggccac agggatgaaa ggggaggggc caaggaggtg acctgcaggg ccagggtcca   53580 aggggggccat tgttcagggg ggccagggcc caggcccag gtgctctgca tgcaaagctg   53640
acccagaaca catgggcccg gagggcaaag aacaggccag gcatgggggcc acaagcaggc   53700 ttctgggtgg tggaggacca ccacgtcaag gagaggcccg ctcacctagg gcagggccag   53760
gctaggacag caggacggtg agctcagggg accagcggat gctggccgtg agtacgcagc   53820
actagtcagg actcagacac agggctcagt caggccaggc acttgcagga ggttacggac   53880 aagggggggct atcagccagg tgatcaccca gctctgaccc acagatgcag aggcacaagg   53940
ccccaggtgg tgagggccct gccggccagc tggtttgcag acattctgga agcacgtggg   54000
cacgggctca agggtgccca gacctgagct cgtgagaccc tgcccggacc ctcccagggg   54060
tgaagccctg gtggtcacat ggcctacttt cttgcagcct ccaccaaggc cccatcggtc   54120
tatcctctga ctgctagatg cggggacacg cctggctcca cagtggcctt cggctgcctg   54180
```

-continued

```
gtctggggct acatccctga gccggtgacg gtgacgtgga actcggacgc cctgtccagc   54240
ggcgtccaca ccttcccatc agtcttcatg tcctcggggc tctacaccct cagcagcttg   54300
gtgacactgc ccgccagcag ctcgaccggc aagaccttca tctgcaacgt agcccacccg   54360
gccagcagca ccaaggtgga caagcgtgtg ggtaagtgca caggcctcag ggaggacatc   54420
cactcccaca caggaccgag gtcagccctc ctcccggctc gaaccacatg ccagtatggc   54480
gacctctgtc cagggtatca gaggaggagc ggtctcctcg cctggaggcc tcccaggcta   54540
tgggagggga cctctgggtg tttctatcag gtccaaggtg ggcacaggct gcacaacgct   54600
accgcacata gctggtgctg gacctgccaa aatctgtccc tgccctatgc ccgccccaac   54660
agacctgccc cctcacccag aaacctcctg tctgctttct ttgcagaact caagacaccc   54720
caacctcaat cccaaccaga atgccggtgt cccaaatgtc caggtgagtc agacaagcca   54780
ctccctcttt aacaaagagg tgaccacagc cctggcatgc tgggaatacg tgtgccctgg   54840
agaacactgg cccaggtgct aacagcccac cctgtcttcc ctgccagccc ctgagctcct   54900
gggagggccc tcagtcttca tcttccccc gaaacccaag gacgtcctct ccatttctgg   54960
gaggcccgag gtcacgtgcg ttgtggtaga cgtgggccag gaagaccccg aggtcagttt   55020
caactggtac attgctggcg ctgaggtgcg aacggccaac acgaggccaa aagaggaaca   55080
gttcaacagc acgtaccgcg tggtcagcgt cctgcccatc cagcaccagg actggctgac   55140
ggggaaggaa ttcaagtgca aggtcaacaa taaagctctc ccagccccca tcgagaggac   55200
catctccaag gccaaaggtg ggacggacaa cgggcgcggg agggtcctgt ggggctgctt   55260
ggagcgacca tcgtgctcac agacacacct gtccccacag ggcagacccg ggagccgcag   55320
gtgtacaccc tggcccccaca ccgggaagag ctagccaagg acaccgtgag tgtaacatgc   55380
ctggtcaaag acttctaccc agttgacatc aacattgagt ggcagaggaa cgggcagcca   55440
gagtcagagg gcacctacgc caccacgccg ccacagctgg acaacgacgg gacctacttc   55500
ctctacagca agctctcggt gggaaagaac acgtggcagc ggggagaaac cttcacctgt   55560
gtggtgatgc acgaggccct gcccaaccac tacacccaga aatctatcac ccagtcttcg   55620
ggtaaatgag cctcaccccg gcaccccagc gaaccccct ccccgaggct cccaggctcc   55680
cgcgtggagg cctgagcccc accctgtgt acatacctcc cgggccagca tgaaataaaa   55740
cacccagggc ctccctgggg ccctgcagca atgtcatggt tctttccgag cagagctccg   55800
gcgcccgccg ggcctgcggg aggcgggggt aggccaggct ctaaggacaa acttggtgcc   55860
atcatgggac tgaggatgac ccaaggcaag ggatgggatc tgccagaggc agcagatccc   55920
tagggtccag cgtccggcca gcacctcctc aggttggagt gtgcagaggg gactggtaga   55980
gcctcccagg gaccctcacg gaaatgagtg cacggttctt cccacctctg tcaaagccca   56040
actgtgggac agtggcaggt ccttgtcccc gcagttcccg tccccggggc ctcgaggacc   56100
aacatgctga caccctgtca acatgggatc cacgccaggc cagcaatggg ggcacaggcc   56160
tcctgctcgc aggacgcacg gggatcaggc cccacattcc cgcaggcaag gttctcgggc   56220
cagaacggta cactcgaggg gacattcacc tagacccata ggaaacaagc cttctcatgg   56280
agcacaacag cctgcacacc cctcgtcctc ctgcatactc acgcacactc atttcctgtg   56340
caactgcaca aagcgctgaa ccacaaaagt gcacacaggc cagccttgct cactgggtcc   56400 tcaacgggt accgccgg ggccagaccg gagcctgcag ccgggtctca tgaaccctct   56460
gtggacaaca gcttggtccc cactcctcaa agccccagca gcacagacca cactctgacc   56520
```

-continued

```
acactggtca gctcagaccc ccacccctcc tctccccaga acacctgcac cccctcctca   56580
acacacagag acccaacagc ccactggtcc ctagcacgcc gacccccaccc ccttgggcac   56640 acaaggacac cccaaggttg cctccgccct tccctgcagt aggacccacc acagccctgc   56700
tctgcagacc ctgccttcta ggcctggcct ccagtgggag ggaaggcagg ggtcagggca   56760 ccctcccgc agaggacccc atgaaaggca cagcagagga gaggataggg gcccccactg   56820
accaggccga gatctgggcc caaggagtcc ggccaagact gaggcccaag ctggaggaat   56880
gggggacacg aggtcgctgc ccagggactg acctaaggga accattgatc cagcccccca   56940 ggggatcct agtgccccac ccgccctgtc acagagggac ccaccccagg cgccactgac   57000
cctgccctgg cacgtgacgg gcagccacag agctgaacac cccctccctg tccagagcca   57060
ctcctggagg aggagagctg tgccgaggcc cagagcgggg agctggacgg gctgtggacc   57120
accatctcca tattcatcac cctcttcctg ctcagcgtgt gctacagcgc cacagtgacc   57180
ctcttcaagg tgggcgggcc aggccagcgg tgcctgctgt ccccacacgg tgcccgcaca   57240 gtcccctac cctgtccact ccctgtccct ccatgtccct ccctgtcccc ttcctgtccc   57300
ctcacagtcc cgtcactgtc tcctcactct cccctcttgt cctctctgtc cactgtctgt   57360
cctcctctgt ctctccagtc cattctattc tctcactgtc cctctatgtc ctggtcggga   57420
cctcgctgtc cgcggctgtg cccatgtagt cctcgcgcca ccccacctga gcacacttgc   57480
ggccggcagt cccagggctg ggaggccagg tccttggggg aagctggcat ggggggccccg   57540 gctgtgctca cacccgccgt ccctgcaggt gaagtggatc ttctcctcgg tgttggagct   57600
gaagcagacg atcgtcccag actacagaaa catgatcggg caggggggcct agcgtgtcct   57660 ctgggggtgt ccacggccac cacaggcccc agaggtaccc cgttcatcac tccgagctgc   57720
tcagccacta ctccgcccgc tgccctgcca gttctgagct ctcggccatg ctcacccgca   57780
cctccatcct ccgacttaaa ggcaaccact gaccaaaccc tgcacattgc tcacgttcag   57840 gggcaggtg ggcagcaggt gctaccacca acctgagctt aggggtctgc ctgtcctcac   57900
cgggagtgcc cggggcaccc tcaggttccc ttggatgagc aggaggctgg catcccgggg   57960
cagtgggcag ggatagctct gtggacacca tcagattggt catcaagcag ggtccccaag   58020
gggaggtgcc tgtgtcagat ccttggtggg aacatatgca gccctggcca acgtctcgca   58080
gcagggaagc ttctggatgt gccaccaacg gtcagccaag tactcagctc tgagaagggc   58140
ctgggcccat ggcccctaca ggagccaggc ctgccaggaa cggcagtgag gtctccccac   58200
tccagcttcc cagagacgga actggtgacc gggtcccca ggggcaggac acagcctcgc   58260
tggacacagc aagagggaca ctggcacaac agggcagtgg ccgcagccag cctgtccctt   58320
ggccagcggc ctgagtcacc ttcagcagga gctcccctgc accggggggt ggggtgagag   58380
gcgaccccgg gaggagggag cccgacaccc cggcgtcccg gcccgagacc cctgggcctc   58440
tcctgtcttg tccctggatg gggagggggca ggccccactg ccgggtggtg gcgggggaga   58500
gggggcgcgc tacagccaga ggtcacgcca ggcctggctt ggggagctgt gcatcctttc   58560
taaacgtctg gagcccatga actttctgcg ctgtttctct ttggtttggg tttttgttgc   58620
gagactctgg cttctcatat tttcggttct ctagacaata aagcatcctt taccattcca   58680
tagctccctg gcagtcgctc tgtgttgcgg ccccctcccct ggggactcca cagcctggcc   58740
gcccgccaca ccctcccagc cccaggcctc agctctcccc ccaccacacc catccctggg   58800
gttccctggg ggcgcggagt cagcagcaag tcccagggggt cggacgcctg gtcagcacgg   58860
ctgctgtaac acgcaccgca gtcgggttgg aaccacagaa atgattgtct cccgtcctgg   58920
```

-continued

```
agcagcacgt cccagctcga ggagcgtgaa ggccactgtg cccaccggct gccaaggctg   58980
cagggacgca gtcaggactc ggtcctccgg ggaggccaga ccctgagctc caggccctcc   59040
tggtggctcc atctcaaagg aacagtctca ggtcctgggc tgtaggagac acagcactcc   59100
ccagagggca gacacaggat ccacagctgt ctgcccttcg caggaaatgc tccaggaaac   59160
ggaggccagt gcctggtcag ggctggctct gctgggcggt ccaggccagc gctacaggag   59220
agctcagtca tccacgggac gcggccctgg gcggctggac attgtccaag tgtctgtgtg   59280
agcctttcag tgtgtcaggg aagagggggc gaaatcaacg tgccgagtct gtgcctccac   59340
ggccccaggg gaggccagca ggacaggctc ctggagggga gctgggacca gcactgagtg   59400
gaaagggcca ttccagcttc ctgtgggcac agacagacag acagccagag gaagacagag   59460
aacttcatgc aggaaaggga cagctcgctc cagtgggctc tgcaccagag acggtgaggc   59520
catggggcgg gcagccgggt ccaggggcat cgccggccct cagggaccct gccaggcgtg   59580
aggacactgg gcaccctctg cctccagggt gctccggaag ccatcctggg ggtctccccc   59640
actcgccatt tccctcacac ggaacaccta accaacaagc tgaacctgcc tatggtccct   59700
gcagcatgcc cagccccagg ccctgcccct cacctccatc ccctggagcc cggatctgcc   59760
tccagccaca cattcccacg gggacaccag gacgctcgat gccgggctgg ccccgcgggt   59820
ccttgaggag caccagtccc agaacagctg ccccccacca ggcctgaggg cccgtcctg    59880 accccggggc aacaccaggc cacagcgcgt cccccatgca cagcccctcc tgggaccctg   59940
gaagcgaagt ggccgacgcc ttcccttgag cccctgtgtc agcaccggtg cgagcctgag   60000
ctcagctttc tgctgctcct gaccctagg ggcgctgccc cgggcaatag ctccgacaca    60060
ctcctgtcag tgtctcacct atccgacccg cacccccatc cacatcttac acacacacac   60120
acacacacac acacaccctg ggctgccacc ccactgcgct cctgggcccc caccaggtcc   60180
cccctcctcc cgcactccaa ggggaacgcc tgccggtctg agctttgaaa acctggattg   60240
ctgtccgtgt gtggtgtccg tggatgtgga gaaaagaaac ccttgtgcgc tgctggtgag   60300
aacataagat ggcattaccg ttgtgcaaaa cggtttggaa gcccctcaaa gacatttcag   60360
aaacaactac cacacttgca gcaatctcac tgctgacaat aaacccgagc gaacatacaa   60420
caggtcttaa agaggcactt gaacacccac ttcacagcaa ctccgttgac aagacctacc   60480
acgaggcacg aactcgagtg tccttccggg gatggacaga tgagcacgat gtgggctgag   60540
cgtacaatgg aacagtactg ccccgagaaa gaagaacact ctgacgtgtg tgacagcaac   60600
gggggcacct ggaggacatc ggaacgcgta ccgtgagccg cgggcaagac ggtgaatcgt   60660
gtgcgattcc actcgggtga gcgattagga gtggccgcat tcacagaagg agaaaacaca   60720
gaagtggttg cagccggggg agaacggggg gttgttgttt acgggcatag ggtttcacac   60780
gtaaagatgg gaagagttat ggagacacgg gcggtcgtga ctgcacttta tgaatgcatt   60840
tgctgtcccc aaaacccgga gaaaggctta acatggtaca cttcttgggg ggcaagtcct   60900 attctttaa acgggagaaa tctaacccgt taaataaaat ctgaaagcct tcaggaagac    60960
ctggagcccg tgtctctccc tgtggaagaa accggtggca gcaggagaaa tctaacccgt   61020
taaataaaat ctgaaagcct tcaggaagac ctggggcccg tgtctctccc tgtggaagaa   61080
accggtggca gcaggatgga gctgcacacc tgcctggccc agggctggac ccctgcggag   61140
gccggcgggc gccggaggag cagcttctcc acactgacgg cgtgagggtg ccggtcagtg   61200
acaacgtgca cggctgtagc agagccccca gccaagggac tgctccttca gtttgctctc   61260
```

-continued

```
caacaggtgt aaacttctct tctggacaac cctaacctag agacacacga agggaaggga    61320
acgctaagaa agctgctcac ggcttagcta acctgacgta gaacaagaac agcacaaccc    61380
actgcttgtc ggccaccgtg caccacgtta agcttcccga ttaaaaggca gcaatacact    61440
ttgtgtttcc acctaatgca ggggaattac ctcagatgta atataaaaat gccaaccctc    61500
ctccaagaaa ggcttcaact cccattgccc accttacgta ccttcggctg atgttcacgt    61560
ctcgtgttga tgaataacct ccgccttggg tgtcctgcag cttatacgct gaggtatgta    61620
gcatcacctc taacacgtcc tttgtcacac ggtggggggg ggggtggacg gaacaggttg    61680
gttatgagag gaggagacgg agacggtgga gtagaaggac acagagcaca ttcacattac    61740
atctacatgt ggaccacgtc tcactggaga aaaatggaga ctggcagaga gactcctgta    61800
cagccaaggc gctgaagaaa ggtccacgag gagtcacgta gggagggaag agaggtactc    61860
ggtttggaac gcagcctcgg ggaggggacc cgggacaggg ggacacgtca tgggcacgca    61920
ggtcttccct ggggagtggg cagcttgaga gcgttagtaa tatgaatgct aaccaagtta    61980
gggaaaagga cacatgaaaa cagtttgaac ctttacaggg acctgaaaaa tataaaaaga    62040
gaaccactca ccagaggggt acgatggcta aaacttaaaa cactggaagg ggcgaacagg    62100
gcactaggtg gcaccggaga ccccacgcga cctggaagac agaaccatgg gaattaccca    62160
gtcagaacta caaaaggaaa aacaactttt ttaacactga gagcagttga cggaatctat    62220
ggaacgacat caactgtcct aacttcggca tgatcggggt cccagaagca gaagggagag    62280
agagagaagt tgaaaatgta cttagtgaaa ttatggcaaa aactcaccaa ccatgaagaa    62340
agagagacat ttccaggcgt aggaatcaca cagtcccaaa caaacacaac ccagagagac    62400
ccacaccaag acacgtcaca attaagttgg caaaagttaa ggataaagag aggattctga    62460
agacagaaag agaacattaa agagtcacat acaaggaacc aacacaaagt tatcagttga    62520 ttttttctgta aaaaccctgc agtctggaca agagagtcat cctacatttc aaatgctgca    62580
cggaaaaagt ctacaaagta ggagacacta cccaaaaaaa tttaccattt agaattgaag    62640
gagagataaa tgtaacaaaa gagaaacaga acacagatag actgataata ttagtggtta    62700
ccagtgcaca gaggggaggg ggaaggggca acataaggac agagaaataa gcaacacaac    62760
tacaatgtat aaaaaaaagc ctacccagat gtattgtaca gcacagggag tatagtcagt    62820
gcttctaata acttcaagtg gaatgtactc tctaaaagta ttcaatcacc attttgtatg    62880
ttgtccaccc gaaactaata taactttctc agtgaagtgt atttaactta aatctatgta    62940
tatacacaaa ttcatatcaa aataaggaac catcttcaaa ttccacccac cacacttggg    63000
atcaatcatg cttctctgtg gggcgtgact ccaagacatt gggccaagaa gagtactcag    63060
gttacgaaga tggacatggc tcctgccccg agacacacga ggtcttggga cgctggtcca    63120
ggctgcgttc ttcctctgaa actaccttgc gttccacagg gcccatttgc tgtccatgag    63180
gcctttccca cgtcaggcaa tggctgagcc atgtgtgtac ccaaggcctt ccaggccgct    63240
gtccgtggtc ctgacgcgga ctagcaggct gtttcagcta ctgtccacgg tcctgcttct    63300
gctgctctgc acggagtaat gatattttta gattaaacag actttgccct tttagggtag    63360
tttcaggcta acagaaagtc cacaaattcc agtgccccac acatacaccc agtttcacct    63420
gttgtgaata tcttgctcca gtgtgctaca tttgtcagaa gtgatgaacc aagttaatac    63480
attatgatta actgaagtcc ataggcaaca ccatggctca ctattatctg cacaattcta    63540
tgagttttga caaatgcatg gtgtcatttg catccagagg ccccgaggct gctgtccatg    63600
gaactgcctt gatcaggttc actgttcagg ctgctgccca tcggtccacc atttcagcaa    63660
```

-continued

```
cacacagtac aatttcactg ccttgaagac cccctgtacc tcaccgcctc attccccacc   63720
cctcccacac aaactcctgg cagccactcg ccttctcatt gtctccatag gtgagctcct   63780
tcaaataccg tgtagtagga atctcacagc gagcataacc ttctccggtt ggctcctttc   63840
acttagcaat gcgcattttc atttccccat gtccttttgt gcctcaatgg ctcatttctt   63900
cttcgttttt aatggtcgtt tcttactttg ggggactatg ggagggtaat tagttttcct   63960
taatggagat actggggatt gaaccaagga cctcatgcat gctaagcaca cgctctatca   64020
ttgatcaata ccctcccccc attgcttctc ctactaactt cttttttcaa cagctttgtt   64080
gagatacaat tgatacacaa aataaatgca tatattcgag gtacatctga gtttgcacat   64140
atgcagacac ctgtgaaacc atcgtcactg tcagggtagt cgatatatcc attcctctaa   64200
aagtttcctt gtgctttggg tttattggga tggaggagca gcacatgtat gtgaagagcc   64260
cttatcacga aatctactct cttaacaagt atctgggtgc acaatgcagt gttgtaaacc   64320
gtcagcacaa tgttacacac ggagcctccg aatagaactc attctgcata actgaaaatt   64380
tatacctatt gaatcacggc agaatcaaag agtatcacca caaaaaatca atgaagcaca   64440
aaagaaagaa gcaagaagga atagaggaac aagttcacta caagacaggc agagaactat   64500
taaaaacaac agtgataata ggcctttccc tgccacaatt accttaaatg taaatggatt   64560
acattatcag agcaaaagat atacagtggc tgagtggata acaagcaagg cccagatctg   64620
tgccaacaca aggcactcac tttaggctta aggacacatg taggctggtc acgaagggat   64680
ggaaaaacgt actccatgga aaaggcaaac aaaaggaagc aaggatgcgt acacttggac   64740
aaaatagact tgaaggtaaa aacagtcata agagacccag aaggatgcta tacaatgatg   64800
aaaaaaatca gttcttcaca gacggcttcg tcctttttat tctgcaatcc tgttcctctg   64860
cctggatgca tccactcacc tactgaggga catcctgtgc gcatccaagt ttgaattaag   64920
ctacgaatga agcatctgta gacatttata aaccatacac atcgctgcac agatttgggg   64980
tggacatgag ttttcagccc atttgaacag gtgagtatct aggaatgcag ttgccgggtt   65040
gtatggcaag attaggttta gattctggag aaactgccga gctctcctgc agacgggctc   65100
ttcccgtttg cacccacccg cagcggagga ggcctcctgc tgccccacac cctcaccagc   65160
gtcgggaggt gccgggtttc ggtgttgctt ctggacgtcc accgttctaa cagctgcgtg   65220
gtggtcttcc ttgtttttcgc ttacagcctc caacgacgtc ggatgtggag gaaacttgtg   65280
cttccttctc tgcatctgtg agtcttctta ggtgagaggt ctgtccaggg cttttagtca   65340
cttttgactg ggtcgtttgt ttccttgttg tggacttttta acacttctcc gcatattgcg   65400
gacacgagtc cttcatcaga tacgaggttt gcaaatgtgt gattctccca gtccatggcc   65460
tgcctttcat tctctcgaca gtgtcttcca caggcaggca tttccacttc agttaagttc   65520
agctagtgac ttcttttccg tggaatgcgc ttttggtgtt gtacctactg actcttcgcc   65580
gaagtcaagg tcacctagat tcccatagtt cccttttttg cattgaggtc aatgacccac   65640
tgtgagttaa cttcatgacc agtgtgagca tgcgcctcag ctcgtttcct gctgggatgc   65700
aggtgctcca ccaccacttg gtgaaaagag ccccttctcc atcaagttac cttcactcca   65760
gtcgagccct cagaggtggg catgggcagg gagaggtcac tcccttgtct gagctccttt   65820
ggtgcttcta gaatgttctg tcactgaggg ggacatgcaa tcaaatggcc ttaaaccatc   65880
tgcagaaaaa ttatttctaa cagaatttac acccaaacca aggataaagt gtaaaggtag   65940
gataaaggca tcctctgaca tgcaagatct caaacaacgt ccctccaggc atcctctctc   66000
```

```
aggaagacag cagacggcct ttggacctga actctccacg tcagcggcct gggccccggc  66060
agatcatgga ctccagccac catcatggtg ccagtcactt ctttacgaca agtctctttc  66120
tagatacgga ccatatacac agagataggg gtacatccta cggattctgt tccctggag  66180 actaacacac cctggggcac aacgcagtct tcttccaacc cacaggaacc gactgactcc  66240
agaggggatg gggggcagg tccaaggcac tcagcagcgt tcctgaagag ggggtctaaa  66300
ctgcactgga aagccagctc aagagcccag catcgatgct taattaagtc taaagcacgt  66360
gcttccatac gtacaacgtg ggaatgttca gctacacgca ctgggtctgt tcacaacaca  66420
gcgtgtttct tcctaaacgg tacatcgagc gattgagcct cgtagaggga acagcatcct  66480
ggatttgaac ggcagcaagt gtcacaaacc tgctggaaag cagagtggat ccctcccgcg  66540
ggcggcccca ctcggcttgc tcactgggtg cccagcactc gagctgctca ggaaggcacc  66600
tccgtgtggt cctgctgtga ggagcatgag ccgttctcca ccttgggaga caaaacgctg  66660
gcttcctgta agaaaaaata cggtgctgcc cagggtcctt gcgcttcacc tggccgtgaa  66720
ggtgagtttc ccccgtcagg atctgtggca cctagttcac cacacgcagc agagggaggc  66780
ggcccaggcc agccaacgcg ttccagaccc acatcccggc cctctccgac cctctccacg  66840
ccctcttctc tggctgctgc acgtctcagt gaggggctgg gggaacgcac acctgactgc  66900
agcttgtcag ctgagctgga gcctcaacca agtgacagcc ttggagcagg tgggccatgg  66960
aagaagcccc cgtgatacag gaaactgggg ctcaagacgc tggcggtgtc ccaagtccca  67020
ggtgagtccc cgggatgcac cccatcaagg gagggtcctt ggcttcacac ggggcagaat  67080
tcaagagcaa gccataggtg agtaaaagta ggttgtttag acagatgcac actccgtaga  67140
cagagcacgg gcgtcccgct cagcaggag agcggccacg cggagtgggg gtgctggttc  67200
ccatgggctc agtagcgtca catgctaact agtgggagga tcgttccagc caccttgggg  67260
aaggggcagg ggttcccagg tcttgggcca ccacccactt gttagcctta tggccagcct  67320
cagaactgtc ctggccctg tgggaacgcc atttaccagg ctagtatatt acaatgagcc  67380
tatagtgaag ctcaaggcca actggaagtc aacgcttcca ccatcttggg cctcaagatc  67440
tactgggagt tgagtctccc accgtcttgg tgctaatcgt cgtgtcattc cttcaatggc  67500
ggtgccctgc ccccttccct cctgtcccac ccggacagca gacctcagcg gcaggcaaat  67560
ctgtgagccc ccgggagtgg tttaacacaa attctctccc ggggccgcag ccttccattg  67620
ctccctcact cctctggacc cctctcgctc cccacacctt cctccaaggg gagctgcggg  67680
ctcccgtgcc catcagccgc caaccactgt gataacagcg tcagcaccca gggaacggag  67740
ggagcaaggc ccagccagcg ccctggcccg tcgttggcta actccgtctg tggctcttgc  67800 ccagggccg tcctgcgttt cctccttctg taaacgcaca gcctccccac actgctcaac  67860
agctccatcc tccaaccata gactcagctc ctctccctgc tccactccag cacagggcgc  67920
acccaccatg ctgccatcac cacccaccga gcagcctgcc tgccgtcctg gtgggtctca  67980
gcccagggtg gtctctgccg tgggaggtag ggtgcagcag gagtcaagaa accagtccct  68040
actctgcctc cgtcacactc agtgtgatgg gcctggggg caggcttggg tgtcactgat  68100
ggcgccccag tcataaaact ctgcttggac ggggcacggg gaggggcttt gtggttaaaa  68160
gctgcaggct cggggagctg agaggtcagg ggtgtggccc agcaggagcc ccaggagctg  68220
ccctcccacc tgcacggttc agacggatgc ctccaaggag accgctggag aaggcagtga  68280 tggggggagcc gcttgcggac ccaggtatga gctgagcgtg gggccccgag ccctgcacac  68340
ctccccgtgg tccgtctaag ccacacagca tggacgcaag gattgtttcg agccgcaggc  68400
```

-continued

```
aatcagaaaa gcaggcacaa ggcaaactct ccgcctcctg cctcctacga ggcaaagcag   68460
ggcgacacct ggggacacag cagaccctta tcagcacctg ccagggcctg ccctgcaagc   68520
cggcctcact gcctctcccg tcagcccgtg tacccacctt ccccgctacg ctggccagag   68580
acacagagtc cctctccttc gtcttcaccc ttggctacga ctcaagtcct tttgtccggg   68640
tctgtccacc ccgtgtcgac cccctgcccc gtgctcatcc ggggcaccct ctgttcctat   68700
attccaatcc ccccgggaga cgcttgtttc agaaacctga ggtggaaggg ggaactggcc   68760
ccctctccta caagagcaag cctctcccgg acctggcaag gggcaagcaa agtctgagag   68820
ccctggcaaa gaggagggag cgtgcacagg gaggtgtcca tcagccctgc aggaagacag   68880
ccaggcagct tccacctcta gctacctcca tctgatccct gtccagccag tactgggagt   68940
gccaggaggc actagagatc tgagttgagg caggagagca gagtgaaatg tggatctgag   69000
ctgggaggac ctggggtgca ctgcagatct gtgctggaag gaccagggtg cacagaagat   69060
ctgagctggc aggaccagga tgcacgggag acctgtgctg ggaggatgag ggtgcacaga   69120
agatctgagc tggcaggacc aggatgcacg ggagatctga gctgggagga tgagggtgca   69180
cagaagatct gagctggcag gaccaggatg cacgggagac ctgtgctggg aggatgaggg   69240
tgcacagaag atctgagctg gcaggaccag gatgcacggg agacctgtgc tgggaggatg   69300
agggtgcaca agatctgag ctggcagga ccaggatgca cgggagatct gagctgggag   69360
gatgagggtg cacagaagat ctgagctggc aggaccagga tgcacgggag acctgtgctg   69420
ggaggatgag ggtgcacaga agatctgagc tggcaggacc aggatgcacg ggagatctgt   69480
gctgggagga tgagggtgca cagaagatct gagctggcag gaccgagatg cacgggagac   69540
catctacagc aaccagccca ggaagccgcc tgctccccac acggcagacc tgcaggaagt   69600
gagacctcta cctccagtga aagtccaaga agccgagcaa cctgtaacag caccccatg   69660 cccggcaggg gtgcgaccag taaccgacag cgtccatcat tttgtccctg cgtccacctt   69720
aggacccacg ggagaaagcc ggacgtgccc ccagccatca caggggcgcc tgcgtccagc   69780
ctccccaggg gcgtccagct tccccagccc accgccccat catgcacccc agagctcgcc   69840 cttttctat aaagaacctc cctatacaca gagactattt taatcgatta acagagtatt   69900
tattatacac tatgcatgca tgtgttagaa acatatgtca cagacgtgtg tatgtgtaca   69960
gtaacactga acagtacata cacataataa aaccgcaaag ctctcccgcg tccctgcctg   70020
cctggaggct ctgccaagcc cggtggtggg tgtggactcc ctggctgcac cagctcggaa   70080
taatcaggct ctccttatcc tgttaaagca ttttcagcaa cttaggagac accaggtctc   70140
gtgacagtag ctcacagtcg ctgttaaaaa acagccccaa gtgcatcttg ggacctggac   70200
acaagcggag acgaaggtga aggtggcgga gcgggtctga gcaggggcgg tgatccccgg   70260
aggaagcgag cagagcaggg gtggcgggcg gtcctgtggg gcccagcaga gcacctgggc   70320
tggactccgc tctgggcagg ccggaagggg cacagcacgc atgtcgccca cccagccctt   70380
gtaggacacg tgcccgggaa gcccttccc cacccgcggc acttctgaag tgggcactac   70440
gttatctccc agggaccctg atgctgcagg cacagaaccg cccagggtgc tcacggggct   70500
cggagtgagc tgcggcactc caagacagga gaagccgagg gtccccgtcc ccactcttgg   70560
gacacacaca gcggtggagg gcctgcatgc tctttctcag ccagagagcc atcttccagc   70620
cccagagacc accgtgaact ctgcagcaca gaagacagct gctgctgggg aaacagcttc   70680
cctctgacct tgcgtgtcac accgcccttc ggtcagagat gggggacagg gatggggcca   70740
```

-continued

```
cggatggagg gagagaagag gcttggaccc agaggaagac agccgcccac ccaagaggcc   70800
gtgctggcag gcggacagga caaagctggg ttaggttgca gcctgtgccc accgcactca   70860
ccagagggga gagaggtgac cactggccct gggaggaccg agggctcggg gggaggccgg   70920
gtgccccagg caacagccag ccaagcgggc agcatccctg tgggaggtac ggaacaagtg   70980
accgcaggga ctcccactct gagcccgagg tcccaggaca ccactcgccc cacccccagg   71040
cacccacgtg aggcgcctct gctgcgtctg gactccccc aggccatctg agacagaaac   71100
cacccagaga aaagggaact tcaggaagca ggcggtgcca ccggtttcag tcccgctctt   71160
agtgttcgca gggttgcggg cagtcagctc acatctccgg gaatccagct acgaaatcct   71220
aggggctggg gctgcgggca cagaggtcgg cctggaggag cgcaggtgcc tggggccaga   71280
gtagggaagg ggtgggggca gcacggagac ccaggctgca ggggagccac ctccatggcc   71340
tccgccttcg gtgagtgcag cccaagagga gcagggacag agggagcgca ggggggcact   71400
ggaggggagg ccccacctca gggaccccac aagggtccag gagcagctga gtagaaggct   71460
gggagctggt gggcacaggc agccgaccca ccacctggaa ggtccagggg ccaggggaga   71520
cctctgggga cactggggac acaaaagagg gtgacggtac ccagggacga ggagctctgc   71580 tgggagggggg ccagcgtggg actccaagga gaaagccatc cctgctggga ggggggccagc   71640 gtggggttcc aggagaaaaa gacatccctg ctggggtggg ggggccagg gtgggactcc   71700 agggagaaag ccatccctgc tgggaggggg ccagggtggg gttccaggga gaaaaggcat   71760
ccctgctggg gaggggggg gccagggtgg gattccaggg aggaaaccag ccctggggtt   71820
aacacaggag tcaggagtg gagcggaact aggctgaggg ctctgcgttg acccagaggg   71880
tcagaggctg ccatgggcca gcaccaggga caaaggtcag ggaggctgaa tgtaagaggt   71940
ggcagaacac ctggaggtca aggagggcag ccccaggcgc tctaaaaaca catggagctt   72000
gtgcacatga gcagaagcct gggagtggac ggggggcaaga agctaacttg gagttcaaga   72060
gaagttggag cttgtgtaag tcagaggcca ctgaagggca ggagggcagt gggacattcc   72120
ttgaatttcc aaggatgcaa gtagagcttt tgcaggtgag cagagggctg ggagggcagg   72180
gggcagcccc aggggctcca aggagcaggt tcaccttctc catgggagca gagggttgca   72240
agatcagggg gcagcccagg gggctccagg gagcaggtgg agctcttgcg ggtcagcaga   72300
tggctgtgag ggcagaggcc agccccatgg gttccaggga gcaggttgag attgtgaagg   72360
tagcagaggg ctggcagggc aggggggcaga cccaggagct ccagggagca ggttgagctt   72420
ctgcagggga gcagagagct gggagggcag tgggcagccc aggggttcca ggcagcatgt   72480
tgagcttctg ccggggagca gaggcctgcg agggcaaggg ggagaccaa ggggctccag   72540 ggcacaggtt gaacttctgc atgggagcag agggctggga gggcatgggg cagccccagg   72600
gtttccaggg cacaggttga gcttgtgcat gggagcagag ggctgggagg gcagggggca   72660
gccccagggt ttccagggca caggttgagc ttgtgcatgg gagcagagtg ctgggaggtc   72720
agggagcagc cccaggtgtt ccaggcaca ggttcagctt ctgcatggga gcagatggct   72780
gggaggtcag ggagcagccc caggggctcc agggcgcagg ctgagcattg caggagagaa   72840
gggggcacgg agggcagggg gcagcccag gggctccagg gcacaggttg agcttgtgca   72900
tgggagcaga gggctgggag ggcaggggggc agccccaggg tttccagggc acaggttgag   72960
cttgtgcatg ggagcagagt gctgggaggt cagggagcag ccccaggtgt tccagggagc   73020
aggttgagct tgtgcagggg agcagagggc agggagggca gggagcagcc ccagggggctc   73080 cagggcgcag gctgagcttt gcaggagagc agagggcacg gagagcaggg ggcagcccca   73140
```

-continued

```
ggggctccag ggcacaggtt gagctctgtg catgggagca gagtgctggg aggtcaggga   73200
gcagccccag gtgttccagg gagcaggttg agcttgtgca ggggagcaga gggcagggag   73260
ggcagggagc agccccaggg gctccagggc gcaggctgag ctttgcagga gagcagaggg   73320
cacggagggc agggggcagc cccaggggct ccagtgcaca ggttgagctt gtgcagggga   73380
gcagagggct gggagggcag ggagcagccc caggggctcc agggcacagg ttgagcttct   73440
gcatgggagc agaggtctgg gaggtcaggg agcagcccca ggggttccag ggagcaggtt   73500
gagcttatgc aagtgagcag aggcctgcga gggcagggggg cagcccaggg ggactccagg   73560
gagcaggtgg agctcttgcg ggtcagcaga tggctgggag ggcagggggc agccccaggg   73620
gctccagggc acaggttgaa cttctgcagg ggagcacagg gctgggaggg caggggggcag   73680 ccccagggtt tccagggcac aggttgagct tgtgcatggg agcagagggc tgggagggcg   73740
gaggggtgcg gtcaggggca gcccaatggg ctccaggag caggttgagc ttctgaagag   73800
gagcagaggg ctgggagttc aggggggcagc cccaggggct ccaggagca atcagagcta   73860 tcacctgtag gctgcgggcc ggcaggtaca ggactgccct gaggagctcc tagaagctac   73920
tagagcttgt attggtgaac aggggggatgg gagggcagaa ggaagcctaa agtggtccag   73980
gaggccagtt gttattgtga gaatgagcaa gggctcagca tgacagcggg gctccctgt   74040 agctagcgga ttaaagcccg gaactaaggc acagccaaac gaggagctca gccagggtac   74100
ggctgctctt gatcagtgtc tcctgcgaca aggatctcag aggctgccag tgagcagggg   74160
gctgaggtca gaggatagtg acctgggagc cacgagctgg ggtggcgtca ggggccccgg   74220
ttggaggggg tagttagctg aggggctcaa gctggaggac cagaagaggg accagagctc   74280
cccgaggcaa agactcagca acctggctga ggccacaggg atgaaaggag aggggccaag   74340
gaggagacct gcagggccag ggtccaaggg agcctgggtc caggggggcc aggtcccagg   74400
gcacaggtgc tctgcatgca gagctgaccc acgagacaca ggcccaaagg gcaaagagca   74460
ggccaggcaa gggggctacga gcaggcttct aggtggtgga ggcccaccac gccaaggaga   74520
ggcccgctca cccagggcag ggccgggcta gggcaacagg acggtgagct caggggacca   74580
gcggatgctg cccgggtagc acgcagcact ggtgaggact cagacacagg gctcagtcag   74640
gccaggcact tgcaggaggt tagggacttg ggggggctgtc acccaggtga tcacccagct   74700
ctgacccaca gatgcagagg cacgaggccc cgggtggtga gggccctgcc gaccagctgg   74760
tttacagaca ttctggaagc acgtgggcac tgggctcagg ggtgcccaga cctgggctcg   74820
ttacaccctg cccggaccct cccagggggtg aagccctggt agtcacacgg cctactatct   74880
tgcagcctcc accaaggccc catcggtcta tcctctgact gctagatgcg gggacacgcc   74940
tggctccaca gtggccttcg gctgcctggt ctggggctac atccctgagc cggtgacggt   75000
gacttggaac tcaggcgccc tgtccagcgg cgtccacacc ttcccatcag tcttcatgtc   75060
ctcggggctc tactccctca gcagcttggt gacactgccc acaagcagct caaccggcaa   75120
gaccttcatc tgcaacgtag cccacccggc cagcagcacc aaggtggaca gcgtgtggg   75180 taagtgcaca ggcctcaggg agggtgtcca ctcccacaca ggaccgaggt cagccctcct   75240
cccggctcga accacatgcc agtatggcga cctctgtcca gggtatcaga ggaggagcgg   75300
tctcctcgcc tggaggcctc ccaggctatg ttaggggtcc tctggatttt ccaccaggtt   75360
caaggtgggc acaggctgca caacgctacc gcacatagct ggtgctggac ctgccaaaat   75420
ctgtccctgc cctatgcccg ccccaacagg cctgcctcct caccaagaaa cctcctgtct   75480
```

-continued

```
gctttctttg cagaaccaca tggaggatgc acgtgtcccc aatgtccagg tgagtcagac    75540
aagccactcc ctctttaaca aggaggtggc cacagccctg gtatgctggg aatgcatgtg    75600
ccctggacaa ggctggccca ggtgctaact gcccaccctg tcttccttgc cagcccctga    75660
gctcccagga gggccctctg tctttgtctt cccccccgaaa cccaaggacg tcctctccat    75720
ttctgggagg cccgaggtca cgtgcgttgt agtggacgtc ggaaaggaag accccgaggt    75780
caatttcaac tggtatattg atggcgttga ggtgcgaacg gccaatacga agccaaaaga    75840
ggaacagttc aacagcacgt accgcgtggt cagcgtcctg cccatccagc accaggactg    75900
gctgacgggg aaggaattca agtgcaaggt caacaacaaa gctctcccgg cccccatcga    75960
gaggaccatc tccaaggcca aaggtgggat ggacaacggg cgcgggagag tcctgtgggg    76020
ctgctcggag tgaccatcgt gctcacagac acacctgtcc ccacagggca gacccgggag    76080
ccgcaggtgt acaccctggc cccacaccgg gaagagctgg ccaaggacac cgtgagcgta    76140
acatgcctgg tcaaaggctt ctacccagct gacatcaacg ttgagtggca gaggaacggt    76200
cagccggagt cagagggcac ctacgccaac acgccgccac agctggacaa cgacgggacc    76260
tacttcctct acagcaagct ctcggtggga aagaacacgt ggcagcgggg agaaacctta    76320
acctgtgtgg tgatgcatga ggccctgcac aaccactaca cccagaaatc catctcccag    76380
tctccgggta aatgagcctc accccggcac cccagcgaac cccctcccc gaggctccca    76440 gggtcccgag tggacgcctg agccccaccc ctgtgtacat acctcccagg ccagcatgaa    76500
ataaaacacc cagggcctcc ctggggccct gcagcactgt cacggttctt tccgagcaga    76560
gctccggcgc ccgccgggcc tgcgggaggc ggggggcagcc caggctctga ggacaaccttt    76620 ggtgccatca ggggactggg gatgaccaga ggcaagggat ggggtctgcc agaggcagca    76680
gctccctagg gtccagtgtc gagccagcac ctgctcaggc tggagtgtgc agaggacact    76740
ggtagagcct cccagggacc ctcacggaaa tgaatacata gttcttccca cctctgtcca    76800
agcccaactg tgggacagtg gcaggtcctt atccccgcag ttcccgaccc cggggcctca    76860
aaggcccacg tgctgacacc ctgtcaacat gggatccacg ccaggccagc aatgggggca    76920
caggcctcct gctcgcagga cgcacgggga tcaggcccca cattcccgca ggcaaggttc    76980
tcgggccaga acggtacact cgagggggaca ttcacctaga cccataggaa acaagccttc    77040
tcatggagca caacagcctg cacacccctc gtcctcctgc atactcacgc acactcattt    77100
cctgtgcaac tgcacaaagc gctgaaccac aaaagtgcac acaggccagc cttgctcact    77160
gggtcctcaa cggggtaccc gcccggggcc agaccggagc ctgcagccgg gtctcatgaa    77220
ccctctgtgg acaacagctt ggtccccact cctcaaagcc ccagcagcac agaccacact    77280
ctgaccacac tggtcagctc agacccccac ccctcctctc cccagaacac ctgcacccccc    77340 tcctcaacac acagagaccc aacagcccac tggtccctag cacgccgacc ccaccccctt    77400
gggcacacaa ggacaccca aggttgcctc cgcccttccc tgcagtagga cccaccacag    77460
ccctgctctg cagaccctgc cttctaggcc tggcctccag tgggagggaa ggcagggggtc    77520 agggcaccct ccccgcagag gaccccatga aaggcacagc agaggagagg atagggccc    77580 ccactgacca ggccgagatc tgggcccaag gagtccggcc aagactgagg cccaagctgg    77640
aggaatgggg gacacgaggt cgctgcccag ggactgacct aagggaacca ttgatccagc    77700
cccccagggg gatcctagtg ccccacccgt cctgtcacag agggacccac cccaggcgcc    77760
actgaccctg ccctggcacg tgacgggcag ccacagagct gaacacccc tccctgtcca    77820 gagccactcc tggaggagga gagctgtgcc gaggcccaga gcggggagct ggacgggctg    77880
```

```
tggaccacca tctccatatt catcaccctc ttcctgctca gcgtgtgcta cagcgccaca   77940
gtgaccctct tcaaggtggg cgggccaggc cagcggtgcc tgctgtcccc acacggtgcc   78000
cgcacagtcc gccttccctg tccccttcct gtcccctcac agtcccgtca ctgtctcctc   78060
actctcccct cttgtcctct ctgtccactg tctgtcctcc tctgtctctc cagtccattc   78120
tattctctca ctgtccctct atgtcctggt cgggacctcg ctgtccgcgg ctgtgcccat   78180
gtagtcctcg cgccacccca cctgagcaca cttgcggccg gcagtcccag ggctgggagg   78240
ccaggtcctt gggggaagct ggcatggggg ccccggctgt gctcacaccc gccgtccctg   78300
caggtgaagt ggatcttctc ctcggtgttg gagctgaagc agacgatcgt cccagactac   78360
agaaacatga tcgggcaggg ggcctagcgt gtcctctggg ggtgtccacg gccaccacag   78420
gccccagagg taccccgttc atcactccga gctgctcagc cactactccg cccgctgccc   78480
tgccagttct gagctctcgg ccatgctcac ccgcacctcc atcctccgac ttaaagcaac   78540
cactgaccac accctgcaca ttgctcacgt tcaggggcca ggtgggcagc aggtgctacc   78600
accaacctga gcttaggggt ctgcctgtcc tcaccgggag tgcccggggc accctcaggt   78660
tcccttggat gagcaggagg ctggcatccc ggggcagtgg gcaggatag  ctctgtggac   78720 accatcagat tggtcatcaa gcagggtccc caaggggagg tgcctgtgtc agatccttgg   78780
tgggaacata tgcagccctg gccaacgtct cgcagcaggg aagcttctgg atgtgccacc   78840
aacggtcagc caagtactca gctctgagaa gggcctgggc ccatggcccc tacaggagcc   78900
aggcctgcca ggaacggcag tgaggtctcc ccactccagc ttcccagaga cggaactggt   78960
gaccgggtcc cccaggggca ggacacagcc tcgctggaca cagcaagagg gacactggca   79020
caacagggca gtggccgcag ccagcctgtc ccttggccag cggcctgagt caccttcagc   79080
aggagctccc ctgcaccggg gggtggggtg agaggcgacc ccgggaggag ggagcccgac   79140 accccgcgt cccggcccga  accccctggg cctctcctgt cttgtccctg gatggggagg   79200
ggcaggcccc actgccgggt ggtggcgggg gagaggggggc gcgctacagc cagaggtcac   79260
gccaggcctg gcttggggag ctgtgcatcc tttctaaacg tctggagccc atgaactttc   79320
tgcgctgttt ctctttggtt tgggtttttg ttgcgagact ctggcttctc atattttcgg   79380
ttctctagac aataaagcat cctttaccat tccatagctc cctggcagtc gctctgtgtt   79440
gcggcccctc ccctggggac tccacagcct ggccgcccgc cacaccctcc cagccccagg   79500
cctcagctct ccccccacca cacccatccc tggggttccc tgggggcgcg gagtcagcag   79560
caagtcccag gggtcggacg cctggtcagc acggctgctg taacacgcac cgcagtcggg   79620
ttggaaccac agaaatgatt gtctcccgtc ctggagcagc acgtcccagc tcgaggagcg   79680
tgaaggccac tgtgcccacc ggctgccaag gctgcaggga cgcagtcagg actcggtcct   79740
ccggggaggc cagaccctga gctccaggcc ctcctggtgg ctccatctca aaggaacagt   79800
ctcaggtccc gggctgtagg agacacagca ctccccagag ggcagacaca ggatccacag   79860
ctgtctgccc ttcgcaggaa atgctccagg aaacggaggc cagtgcctgg tcagggctgg   79920
ctctgctggg cggtccaggc cagcgctaca ggagagctca gtcatccacg ggacgcggcc   79980
ctgggcggct ggacattgtc caagtgtctg tgtgagcctt tcagtgtgtc agggaagagg   80040
gggcgaaatc aacgtgccga gtctgtgcct ccacggcccc aggggaggcc agcaggacag   80100
gctcctggag gggagctggg accagcactg agtggaaagg gccattccag cttcctgtgg   80160
gcacagacag acagacagcc agaggaagac agagaacttc atgcaggaaa gggacagctc   80220
```

-continued

```
gctccagtgg gctctgcacc agagacggtg aggccatggg gcgggcagcc gggtccaggg    80280
gcatcgccgg ccctcaggga ccctgccagg cgtgaggaca ctgggcaccc tctgcctcca    80340
gggtgctccg gaagccatcc tggggggtctc ccccactcgc catttccctc acacggaaca    80400
cctaaccaac aagctgaacc tgcctatggt ccctgcagca tgcccagccc caggccctgc    80460
ccctcacctc catcccctgg agcccggatc tgcctccagc cacacattcc cacgggggaca   80520 ccaggacgct cgatgccggg ctggccccgc gggtccttga ggagcaccag tcccagaaca    80580
gctgcccccc accaggcctg agggccccgt cctgacccccg gggcaacacc aggccacagc    80640
gcgtccccca tgcacagccc ctcctgggac cctggaagcg aagtggccga cgccttccct    80700
tgagcccctg tgtcagcacc ggtgcgagcc tgagctcagc tttctgctgc tcctgacccc    80760 tagggggcgct gcccccgggca atagctccga cacactcctg tcagtgtctc acctatccga    80820
cccgcacccc catccacatc ttacacacac acacacacac acacacacac cctgggctgc    80880 cacccccactg cgctcctggg cccccaccag gtcccccctc ctcccgcact ccaaggggaa    80940
cgcctgccgg tctgagcttt gaaaacctgg attgctgtcc gtgtgtggtg tccgtggatg    81000
tggagaaaag aaacccttgt gcgctgctgg tgagaacata agatggcatt accgttgtgc    81060
aaaacggttt ggaagccccct caaagacatt tcagaaacaa ctaccacact tgcagcaatc    81120
tcactgctga caataaaccc gagcgaacat acaacaggtc ttaaagaggc acttgaacac    81180
ccacttcaca gcaactccgt tgacaagacc taccacgagg cacgaactcg agtgtccttc    81240
cggggatgga cagatgagca cgatgtgggc tgagcgtaca atggaacagt actgccccga    81300
gaaagaagaa cactctgacg tgtgtgacag cacggggggca cctggaggac atcggaacgc    81360
gtaccgtgag ccgcgggcaa gacggtgaat cgtgtgcgat tccactcggg tgagcgatta    81420
ggagtggccg cattcacaga aggagaaaac acagaagtgg ttgcagccgg gggagaacgg    81480
ggggttgttg tttacgggca tagggtttca cacgtaaaga tgggaagagt tatggagaca    81540
cgggcggtcg tgactgcact ttatgaatgc atttgctgtc cccaaaaccc ggagaaaggc    81600
ttaacatggt acactttctt gggggcaaat cctattcttt taaacgggag aaatctaacc    81660
cgttaaataa aatctgaaag ccttcaggaa gacctggagc ccgtgtctct ccctgtggaa    81720
gaaaccggtg gcagcaggag aaatctaacc cgttaaataa aatctgaaag ccttcaggaa    81780
gacctggagc ccgtgtctct ccctgtggaa gaaaccggtg gcagcaggag aaatctaacc    81840
cgttaaataa aatctgaaag ccttcaggaa gacctggggc ccgtgtctct ccctgtggaa    81900
gaaaccggtg gcagcaggat ggagctgcac acctgcctgg cccagggctg gacccctgcg    81960
gaggccggcg ggcgccggag gagcagcttc tccacactga cggcgtgagg gtgccggtca    82020
gtgacaacgt gcacggctgt agcagagccc cccagccaag ggactgctcc ttcagtttgc    82080
tctccaacag gtgtaaactt ctcttctgga caaccctaac ctagagacac acgaagggaa    82140
gggaacgcta agaaagctgc tcacggctta gctaacctga cgtagaacaa gaacagcaca    82200
acccactgct tgtcggccac cgtgcaccac gttaagcttc ccgattaaaa ggcagcaata    82260
cactttgtgt ttccacctaa tgcaggggaa ttacctcaga tgtaatataa aaatgccaac    82320
cctcctccaa gaaaggcttc aactcccatt gcccacctta cgtaccttcg gctgatgttc    82380
acgtctcgtg ttgatgaata acctccgcct tgggtgtcct gcagcttata cgctgaggta    82440
tgtagcatca cctctaacac gtcctttgtc acacggtggg ggggggggtgg acggaacagg    82500 ttggttatga gaggaggaga cggagacggt ggagtagaag gacacagagc acattcacat    82560
tacatgtaca tgtggaccac gtctcactgg agaaaaatgg agactggcag agagactcct    82620
```

-continued

```
gtacagccaa ggcgctgaag aaaggtccac gaggagtcac gtagggaggg aagagaggta   82680
ctcggtttgg aacgcagcct cggggagggg acccgggaca gggggacacg tcatgggcac   82740
gcaggtcttc cctggggagt gggcagcttg agagcgttag taatatgaat gctaaccaag   82800
ttagggaaaa ggacacatga aaacagtttg aacctttaca gggacctgga aaatataaaa   82860
agagaaccac tcaccagagg ggtacgatgg ctaaaactta aaacactgga aggggcgaac   82920
agggcactag gtggcaccgg agaccccacg cgacctggaa gacagaacca tgggaattac   82980
ccagtcagaa ctacaaaagg aaaaacaact tttttaacac tgagagcagt tgacggaatc   83040
tatggaacga catcaactgt cctaacttcg gcatgatcgg ggtcccagaa gcagaaggga   83100
gagagagaga agttgaaaat gtacttagtg aaattatggc aaaaactcac caaccatgaa   83160
gaaagagaga catttccagg cgtaggaatc acacagtccc aaacaaacac aacccagaga   83220
gacccacacc aagacacgtc acaattaagt tggcaaaagt taaggataaa gagaggattc   83280
tgaagacaga aagagaacat taaagagtca catacaagga accaacacaa agttatcagt   83340
tgatttttct gtaaaaaccc tgcagtctgg acaagagagt catcctacat ttcaaatgct   83400
gcacggaaaa agtctacaaa gtaggagaca ctacccaaaa aaatttacca tttagaattg   83460
aaggagagat aaatgtaaca aaagagaaac agaacacaga tagactgata atattagtgg   83520
ttaccagtgc acagagggga gggggaaggg gcaacataag gacagagaaa taagcaacac   83580
aactacaatg tataaaaaaa aagcctaccc agatgtattg tacagcacag ggagtatagt   83640
cagtgcttct aataacttca agtggaatgt actctctaaa agtattcaat caccattttg   83700
tatgttgtcc acccgaaact aatataactt tctcagtgaa gtgtatttaa cttaaatcta   83760
tgtatataca caaattcata tcaaaataag gaaccatctt caaattccac ccaccacact   83820
tgggatcaat catgcttctc tgtggggcgt gactccaaga cattgggcca agaagagtac   83880
tcaggttacg aagatggaca tggctcctgc cccgagacac acgaggtctt gggacgctgg   83940
tccaggctgc gttcttcctc tgaaactacc ttgcgttcca cagggcccat ttgctgtcca   84000
tgaggccttt tccacgtcag gcaatggctg agccatgtgt gtacccaagg ccttccaggc   84060
cgctgtccgt ggtcctgacg cggactagca ggctgtttca gctactgtcc atggtcctgc   84120
ttctgctgct ctgcacggag taatgatatt tttagattaa acagactttg ccctttttagg   84180 gtagtttcag gctaacagaa agtccacaga gctccataaa ttccagtgcc ccacacatac   84240
acccagtttc acctgttgtg aatatcttgc tccagtgtgc tacatttgtc agaagtgatg   84300
aaccaagtta atacattatg attaactgaa gtccataggc aacaccatgg ctcactatta   84360
tctgcacaat tctatgagtt ttgacaaatg catggtgtca tttgcatcca gaggccccga   84420
ggctgctgtc catggaactg ccttgatcag gttcactgtt caggctgctg cccatcggtc   84480
caccatttca gcaacacaca gtacaatttc actgccttga agaccccctg tacctcaccg   84540
cctcattccc caccccctccc acacaaactc ctggcagcca ctcgccttct cattgtctcc   84600
ataggtgagc tccttcaaat accgtgtagt aggaatctca cagcgagcat aaccttctcc   84660
ggttggctcc tttcacttag caatgcgcat tttcatttcc ccatgtcctt ttgtgcctca   84720
atggctcatt tcttcttcgt ttttaatggt cgtttcttac tttgggggac tatgggaggg   84780
taattagttt tccttaatgg agatactggg gattgaacca aggacctcat gcatgctaag   84840
cacacgctct atcattgatc aataccctcc ccccattgct tctcctacta acttcttttt   84900
tcaacagctt tgttgagata caattgatac acaaaataaa tgcatatatt cgaggtacat   84960
```

-continued

```
ctgagtttgc acatatgcag acacctgtga aaccatcgtc actgtcaggg tagtcgatat   85020
atccattcct ctaaaagttt ccttgtgctt tgggtttatt gggatggagg agcagcacat   85080
gtatgtgaag agcccttatc acgaaatcta ctctcttaac aagtatctgg gtgcacaatg   85140
cagtgttgta aaccgtcagc acaatgttac acacggagcc tccgaataga actcattctg   85200
cataactgaa aatttatacc tattgaatca cggcagaatc aaagagtatc accacaaaaa   85260
atcaatgaag cacaaaagaa agaagcaaga aggaatagag gaacaagttc actacaagac   85320
aggcagagaa ctattaaaaa caacagtgat aataggcctt tccctgccac aattacctta   85380
aatgtaaatg gattacatta tcagagcaaa agatatacag tggctgagtg gataacaagc   85440
aaggcccaga tctgtgccaa cacaaggcac tcactttagg cttaaggaca catgtaggct   85500
ggtcacgaag ggatggaaaa acgtactcca tggaaaaggc aaacaaaagg aagcaaggat   85560
gcgtacactt ggacaaaata gacttgaagg taaaaacagt cataagagac ccagaaggat   85620
gctatacaat gatgaaaaaa atcagttctt cacagacggc ttcgtccttt ttattctgca   85680
atcctgttcc tctgcctgga tgcatccact cacctactga gggacatcct gtgcgcatcc   85740
aagtttgaat taagctacga atgaagcatc tgtagacatt tataaaccat acacatcgct   85800
gcacagattt ggggtggaca tgagtttttca gcccatttga acaggtgagt atctaggaat   85860
gcagttgccg ggttgtatgg caagattagg tttagattct ggagaaactg ccgagctctc   85920
ctgcagacgg gctcttcccg tttgcaccca cccgcagcgg aggaggcctc ctgctgcccc   85980
acaccctcac cagcgtcggg aggtgccggg tttcggtgtt gcttctggac gtccaccgtt   86040
ctaacagctg cgtggtggtc ttccttgttt tcgcttacag cctccaacga cgtcggatgt   86100
ggaggaaact tgtgcttcct tctctgcatc tgtgagtctt cttaggtgag aggtctgtcc   86160
agggctttta gtcacttttg actgggtcgt ttgtttcctt gttgtggact tttaacactt   86220
ctccgcatat tgcggacacg agtccttcat cagatacgag gtttgcaaat gtgtgattct   86280
cccagtccat ggcctgcctt tcattctctc gacagtgtct tccacaggca ggcatttcca   86340
cttcagttaa gttcagctag tgacttcttt tccgtggaat gcgcttttgg tgttgtacct   86400
actgactctt cgccgaagtc aaggtcacct agattcccat agttcccttt tttgcattga   86460
ggtcaatgac ccactgtgag ttaacttcat gaccagtgtg agcatgcgcc tcagctcgtt   86520
tcctgctggg atgcaggtgc tccaccacca cttggtgaaa agagcccctt ctccatcaag   86580
ttaccttcac tccagtcgag ccctcagagg tgggcatggg cagggagagg tcactccctt   86640
gtctgagctc ctttggtgct tctagaatgt tctgtcactg aggggacat gcaatcaaat   86700 ggccttaaac catctgcaga aaaattattt ctaacagaat ttacacccaa accaaggata   86760
aagtgtaaag gtaggataaa ggcatcctct gacatgcaag atctcaaaca cgtccctcc   86820 aggcatcctc tctcaggaag acagcagacg gcctttggac ctgaactctc cacgtcagcg   86880
gcctgggccc cggcagatca tggactccag ccaccatcat ggtgccagtc acttctttac   86940
gacaagtctc tttctagata cggaccatat acacagagat aggggtacat cctacggatt   87000
ctgttcccct ggagactaac acaccctggg gcacaacgca gtcttcttcc aacccacagg   87060
aaccgactga ctccagaggg gatggggggg caggtccaag gcactcagca gcgttcctga   87120 agaggggggtc taaactgcac tggaaagcca gctcaagagc ccagcatcga tgcttaatta   87180
agtctaaagc acgtgcttcc atacgtacaa cgtgggaatg ttcagctaca cgcactgggt   87240
ctgttcacaa cacagcgtgt ttcttcctaa acgtacatc gagcgattga gcctcgtaga   87300
gggaacagca tcctggattt gaacggcagc aagtgtcaca aacctgctgg aaagcagagt   87360
```

-continued

```
ggatccctcc cgcgggcggc cccactcggc ttgctcactg ggtgcccagc actcgagctg   87420
ctcaggaagg cacctccgtg tggtcctgct gtgaggagca tgagccgttc tccaccttgg   87480
gagacaaaac gctggcttcc tgtaagaaaa aatacggtgc tgcccagggt ccttgcgctt   87540
cacctggccg tgaaggtgag tttcccccgt caggatctgt ggcacctagt tcaccacacg   87600
cagcagaggg aggcggccca ggccagccaa cgcgttccag acccacatcc cggccctctc   87660
cgaccctctc cacgccctct tctctggctg ctgcacgtct cagtgagggg ctgggggaac   87720
gcacacctga ctgcagcttg tcagctgagc tggagcctca accaagtgac agccttggag   87780
caggtgggcc atggaagaag cccccgtgat acaggaaact ggggctcaag acgctggcgg   87840
tgtcccaagt cccaggtgag tccccgggat gcaccccatc aagggagggt ccttggcttc   87900
acacggggca gaattcaaga gcaagccata ggtgagtaaa agtaggttgt ttagacagat   87960
gcacactccg tagacagagc acgggcgtcc cgctcagcag ggagagcggc cacgcggagt   88020
gggggtgctg gttcccatgg gctcagtagc gtcacatgct aactagtggg aggatcgttc   88080
cagccacctt ggggaagggg caggggttcc caggtcttgg gccaccaccc acttgttagc   88140
cttatggcca gcctcagaac tgtcctggcc cctgtgggaa cgccatttac caggctagta   88200
tattacaatg agcctatagt gaagctcaag gccaactgga agtcaacgct tccaccatct   88260
tgggcctcaa gatctactgg gagttgagtc tcccaccgtc ttggtgctaa tcgtcgtgtc   88320
attccttcaa tggcggtgcc ctgccccctt ccctcctgtc ccacccggac agcagacctc   88380
agcggcaggc aaatctgtga gcccccggga gtggtttaac acaaattctc tcccggggcc   88440
gcagccttcc attgctccct cactcctctg gaccctctc gctccccaca ccttcctcca   88500
aggggagctg cgggctcccg tgcccatcag ccgccaacca ctgtgataac agcgtcagca   88560
cccagggaac ggagggagca aggcccagcc agcgccctgg cccgtcgttg gctaactccg   88620
tctgtggctc ttgcccaggg gccgtcctgc gtttcctcct tctgtaaacg cacagcctcc   88680
ccacactgct caacagctcc atcctccaac catagactca gctcctctcc ctgctccact   88740
ccagcacagg gcgcacccac catgctgcca tcaccaccca ccgagcagcc tgcctgccgt   88800
cctggtgggt ctcagcccag ggtggtctct gccgtgggag gtagggtgca gcaggagtca   88860
agaaaccagt ccctactctg cctccgtcac actcagtgtg atgggcctgg ggggcaggct   88920
tgggtgtcac tgatggcgcc ccagtcataa aactctgctt ggacggggca cggggagggg   88980
ctttgtggtt aaaagctgca ggctcgggga gctgagaggt caggggtgtg gcccagcagg   89040
agccccagga gctgccctcc cacctgcacg gttcagacgg atgcctccaa ggagaccgct   89100
ggagaaggca gtgatggggg agccgcttgc ggacccaggt atgagctgag cgtggggccc   89160
cgagccctgc acacctcccc gtggtccgtc taagccacac agcatggacg caaggattgt   89220
ttcgagccgc aggcaatcag aaaagcaggc acaaggcaaa ctctccgcct cctgcctcct   89280
acgaggcaaa gcagggcgac acctggggac acagcagacc cttatcagca cctgccaggg   89340
cctgccctgc aagccggcct cactgcctct cccgtcagcc cgtgtaccca ccttccccgc   89400
tacgctggcc agagacacag agtccctctc cttcgtcttc acccttggct acgactcaag   89460
tccttttgtc cgggtctgtc cacccgtgt cgacccctg ccccgtgctc atccggggca   89520
ccctctgttc ctatattcca atcccccgg gagacgcttg tttcagaaac ctgaggtgga   89580 aggggggaact ggcccctct cctacaagag caagcctctc ccggacctgg caaggggcaa   89640
gcaaagtctg agagccctgg caaagaggag ggagcgtgca cagggaggtg tccatcagcc   89700
```

-continued

```
ctgcaggaag acagccaggc agcttccacc tctagctacc tccatctgat ccctgtccag   89760
ccagtactgg gagtgccagg aggcactaga gatctgagtt gaggcaggag agcagagtga   89820
aatgtggatc tgagctggga ggacctgggt gcactgcaga tctgtgctgg aggaccaggg   89880
tgcacagaag atctgagctg gcaggaccag gatgcacggg agacctgtgc tgggaggatg   89940
agggtgcaca gaagatctga gctggcagga ccaggatgca cgggagatct gagctgggag   90000
gatgagggtg cacagaagat ctgagctggc aggaccagga tgcacgggag acctgtgctg   90060
ggaggatgag ggtgcacaga gatctgagc tggcaggacc aggatgcacg ggagacctgt   90120
gctgggagga tgagggtgca cagaagatct gagctggcag gaccaggatg cacgggagat   90180
ctgagctggg aggatgaggg tgcacagaag atctgagctg gcaggaccag gatgcacggg   90240
agacctgtgc tgggaggatg agggtgcaca gaagatctga gctggcagga ccaggatgca   90300
cgggagatct gtgctgggag gatgagggtg cacagaagat ctgagctggc aggaccgaga   90360
tgcacgggag accatctaca gcaaccagcc caggaagccg cctgctcccc acacggcaga   90420
cctgcaggaa gtgagacctc tacctccagt gaaagtccaa gaagccgagc aacctgtaac   90480
agcaccccca tgcccggcag gggtgcgacc agtaaccgac agcgtccatc attttgtccc   90540
tgcgtccacc ttaggaccca cgggagaaag ccggacgtgc ccccagccat cacaggggcg   90600
cctgcgtcca gcctccccag gggcgtccag cttccccagc ccaccgcccc atcatgcacc   90660
ccagagctcg ccctttttct ataaagaacc tccctataca cagagactat tttaatcgat   90720
taacagagta tttattatac actatgcatg catgtgttag aaacatatgt cacagacgtg   90780
tgtatgtgta cagtaacact gaacagtaca tacacataat aaaaccgcaa agctctcccg   90840
cgtccctgcc tgcctggagg ctctgccaag cccggtggtg ggtgtggact ccctggctgc   90900
accagctcgg aataatcagg ctctccttat cctgttaaag cattttcagc aacttaggag   90960
acaccaggtc tcgtgacagt agctcacagt cgctgttaaa aaacagcccc aagtgcatct   91020
tgggacctgg acacaagcgg agacgaaggt gaaggtggcg gagcgggtct gagcaggggc   91080
ggtgatcccc ggaggaagcg agcagagcag gggtggcggg cggtcctgtg gggcccagca   91140
gagcacctgg gctggactcc gctctgggca ggccggaagg ggcacagcac gcatgtcgcc   91200
cacccagccc ttgtaggaca cgtgcccggg aagccccttc cccacccgcg gcacttctga   91260
agtgggcact acgttatctc ccagggaccc tgatgctgca ggcacagaac cgcccagggt   91320
gctcacgggg ctcggagtga gctgcggcac tccaagacag gagaagccga gggtcccccgt   91380 ccccactctt gggacacaca cagcggtgga gggcctgcat gctctttctc agccagagag   91440
ccatcttcca gccccagaga ccaccgtgaa ctctgcagca cagaagacag ctgctgctgg   91500
ggaaacagct tccctctgac cttgcgtgtc acaccgccct tcggtcagag atgggggaca   91560
gggatggggc cacggatgga gggagagaag aggcttggac ccagaggaag acagccgccc   91620
acccaagagg ccgtgctggc aggcggacag gacaaagctg ggttaggttg cagcctgtgc   91680
ccaccgcact caccagaggg gagagaggtg accactggcc ctgggaggac cgaggctcg   91740 gggggaggcc gggtgcccca ggcaacagcc agccaagcgg gcagcatccc tgtgggaggt   91800
acggaacaag tgaccgcaga gactcccact ctgagcccga ggtccaggga caccactcgc   91860 cccacccca ggcacccacg tgaggcgcct ctgctgcgtc tggactcccc ccaggccatc   91920
tgagacagaa accacccaga gaaaagggaa cttcaggaag caggcggtgc caccggtttc   91980
agtcccgctc ttagtgttcg cagggttgcg ggcagtcagc tcacatctcc gggaatccag   92040
ctacgaaatc ctaggggctg gggctgcggg cacagaggtc ggcctggagg agcgcaggtg   92100
```

-continued

```
cctggggcca gagtagggaa ggggtggggg cagcacggag acccaggctg caggggagcc   92160
acctccatgg cctccgcctt cggtgagtgc agcccaagag gagcagggac agagggagcg   92220
caggggggca ctggagggga ggccccacct cagggacccc acaagggtcc aggagcagct   92280
gagtagaagg ctgggagctg gtgggcacag gcagccgacc caccacctgg aaggtccagg   92340
ggccagggga gacctctggg gacactgggg acacaaaaga gggtgacggt acccagggac   92400
gaggagctct gctgggaggg ggccagcgtg ggactccaag gagaaagcca tccctgctgg   92460
gagggggcca gcgtggggtt ccagggagaa aagacatccc tgctggggtg gggggggcca   92520
gggtgggact ccagggagaa agccatccct gctgggaggg ggccagggtg gggttccagg   92580
gagaaaaggc atccctgctg gggaggggggg gggccagggt gggattccag ggaggaaacc   92640
agccctgggg ttaacacagg agtcaggag tggagcggaa ctaggctgag ggctctgcgt   92700
tgacccagag ggtcagaggc tgccatgggc cagcaccagg acaaaggtc agggaggctg   92760 aatgtaagag gtggcagaac acctggaggt caaggagggc agccccaggc gctctaaaaa   92820
cacatggagc ttgtgcacat gagcagaagc ctgggagtgg acgggggcaa gaagctaact   92880
tggagttcaa gagaagttgg agcttgtgta agtcagaggc cactgaaggg caggagggca   92940
gtgggacatt ccttgaattt ccaaggatgc aagtagagct tttgcaggtg agcagagggc   93000
tgggagggca ggggggcagcc ccaggggctc caaggagcag gttcaccttc tccatgggag   93060
cagagggttg caagatcagg gggcagccca gggggctcca gggagcaggt ggagctcttg   93120
cgggtcagca gatggctgtg agggcagagg ccagccccat gggttccagg gagcaggttg   93180
agattgtgaa ggtagcagag ggctggcagg gcaggggca gacccaggag ctccagggag   93240
caggttgagc ttctgcaggg gagcagagag ctgggagggc agtgggcagc ccaggggttc   93300
caggcagcat gttgagcttc tgccggggag cagaggcctg cgagggcaag ggggagaccc   93360
aaggggctcc agggcacagg ttgaacttct gcatgggagc agagggctgg gagggcatgg   93420
ggcagcccca gggtttccag ggcacaggtt gagcttgtgc atgggagcag agggctggga   93480 gggcagggggg cagccccagg gtttccaggg cacaggttga gtttgtgcat gggagcagag   93540
ggctgggagg gcaggggggca gccccagggt ttccagggca caggttgagc ttgtgcatgg   93600
gagcagagtg ctgggaggtc agggagcagc cccaggtgtt ccagggcaca ggttcagctt   93660
ctgcatggga gcagatggct gggaggtcag ggagcagccc caggggctcc agggcgcagg   93720
ctgagcattg caggagagaa gggggcacgg agggcagggg gcagcccag gggctccagg   93780 gcacaggttg agcttgtgca tgggagcaga gggctgggag ggcagggggc agccccaggg   93840
tttccagggc acaggttgag cttgtgcatg gagcagagt gctgggaggt cagggagcag   93900
ccccaggtgt tccagggagc aggttgagct tgtgcagggg agcagagggc agggagggca   93960
gggagcagcc ccagggggctc cagggcgcag gctgagcttt gcaggagagc agagggcacg   94020
gagagcaggg ggcagcccca ggggctccag ggcacaggtt gagcttgtgc atgggagcag   94080
agtgctggga ggtcagggag cagccccagg tgttccaggg agcaggttga gcttgtgcag   94140
gggagcagag ggcagggagg gcagggagca gccccagggg ctccagggcg caggctgagc   94200
tttgcaggag agcagagggc acggagggca ggggcagcc ccaggggctc cagtgcacag   94260
gttgagcttg tgcagggggag cagagggctg ggagggcagg gagcagcccc aggggctcca   94320
gggcacaggt tgagcttctg catgggagca gaggtctggg aggtcaggga gcagcccag   94380 gggttccagg gagcaggttg agcttatgca agtgagcaga ggcctgcgag ggcaggggggc   94440
```

-continued

```
agcccagggg gactccaggg agcaggtgga gctcttgcgg gtcagcagat ggctgggagg    94500 gcaggggca gccccagggg ctccagggca caggttgaac ttctgcaggg gagcacaggg    94560
ctgggagggc aggggcagc cccagggttt ccagggcaca ggttgagctt gtgcatggga    94620
gcagagggct gggagggcgg aggggtgcgg tcagggcag cccaatgggc tccagggagc    94680
aggttgagct tctgaagagg agcagagggc tgggagttca gggggcagcc ccaggggctc    94740
cagggagcaa tcagagctat cacctgtagg ctgcgggccg gcaggtacag gactgccctg    94800
aggagctcct agaagctact agagcttgta ttggtgaaca gggggatggg agggcagaag    94860
gaagcctaaa gtggtccagg aggccagttg ttattgtgag aatgagcaag ggctcagcat    94920
gacagcgggg ctcccctgta gctagcggat taaagcccgg aactaaggca cagccaaacg    94980
aggagctcag ccagggtacg gctgctcttg atcagtgtct cctgcgacaa ggatctcaga    95040
ggctgccagt gagcaggggg ctgaggtcag aggatagtga cctgggagcc acgagctggg    95100
gtggcgtcag gggccccggt tggaggggt agttagctga ggggctcaag ctggaggacc    95160
agaagaggga ccagagctcc ccgaggcaaa gactcagcaa cctggctgag gccacaggga    95220
tgaaaggaga ggggccaagg aggagacctg cagggccagg gtccaaggga gcctgggtcc    95280
aggggggcca ggtcccaggg cacaggtgct ctgcatgcag agctgaccca cgagacacag    95340
gcccaaaggg caaagagcag gccaggcaag gggctacgag caggcttcta ggtggtggag    95400
gcccaccacg ccaaggagag gcccgctcac ccagggcagg gccgggctag ggcaacagga    95460
cggtgagctc aggggaccag cggatgctgc ccgggtagca cgcagcactg gtgaggactc    95520
agacacaggg ctcagtcagg ccaggcactt gcaggaggtt agggacttgg ggggctgtca    95580
cccaggtgat cacccagctc tgacccacag atgcagaggc acgaggcccc gggtggtgag    95640
ggccctgccg accagctggt ttacagacat tctggaagca cgtgggcact gggctcaggg    95700
gtgcccagac ctgggctcgt tacaccctgc ccggaccctc ccaggggtga agccctggta    95760
gtcacacggc ctactatctt gcagcctcca ccaaggcccc atcggtctat cctctgactg    95820
ctagatgcgg ggacacgcct ggctccacag tggccttcgg ctgcctggtc tggggctaca    95880
tccctgagcc ggtgacggtg acttggaact caggcgccct gtccagcggc gtccacacct    95940
tcccatcagt cttcatgtcc tcggggctct actccctcag cagcttggtg acactgccca    96000
caagcagctc aaccggcaag accttcatct gcaacgtagc ccacccggcc agcagcacca    96060
aggtggacaa gcgtgtgggt aagtgcacag gcctcaggga gggtgtccac tcccacacag    96120
gaccgaggtc agccctcctc ccggctcgaa ccacatgcca gtatggcgac ctctgtccag    96180
ggtatcagag gaggagcggt ctcctcgcct ggaggcctcc caggctatgt tagggtcct    96240 ctggatttc caccaggttc aaggtgggca caggctgcac aacgctaccg cacatagctg    96300
gtgctggacc tgccaaaatc tgtccctgcc ctatgcccgc cccaacaggc ctgcctcctc    96360
accaagaaac ctcctgtctg ctttcttgc agaaccacat ggaggatgca cgtgtcccca    96420
atgtccaggt gagtcagaca agccactccc tctttaacaa ggaggtggcc acagccctgg    96480
tatgctggga atgcatgtgc cctggacaag gctggcccag gtgctaactg cccaccctgt    96540
cttccttgcc agccctgag ctcccaggag ggccctctgt ctttgtcttc cccccgaaac    96600
ccaaggacgt cctctccatt tctgggaggc ccgaggtcac gtgcgttgta gtggacgtcg    96660
gaaaggaaga ccccgaggtc aatttcaact ggtatattga tggcgttgag gtgcgaacgg    96720
ccaatacgaa gccaaaagag gaacagttca acagcacgta ccgcgtggtc agcgtcctgc    96780
ccatccagca ccaggactgg ctgacgggga aggaattcaa gtgcaaggtc aacaacaaag    96840
```

-continued

```
ctctcccggc ccccatcgag aggaccatct ccaaggccaa aggtgggatg gacaacgggc   96900
gcgggagagt cctgtggggc tgctcggagt gaccatcgtg ctcacagaca cacctgtccc   96960
cacagggcag acccgggagc cgcaggtgta caccctggcc ccacaccggg aagagctggc   97020
caaggacacc gtgagcgtaa catgcctggt caaaggcttc tacccagctg acatcaacgt   97080
tgagtggcag aggaacggtc agccggagtc agagggcacc tacgccaaca cgccgccaca   97140
gctggacaac gacgggacct acttcctcta cagcaagctc tcggtgggaa agaacacgtg   97200
gcagcgggga gaaaccttaa cctgtgtggt gatgcatgag gccctgcaca accactacac   97260
ccagaaatcc atctcccagt ctccgggtaa atgagcctca ccccggcacc ccagcgaacc   97320
cccctccccg aggctcccag ggtcccgagt ggacgcctga gccccacccc tgtgtacata   97380
cctcccaggc cagcatgaaa taaaacaccc agggcctccc tggggccctg cagcactgtc   97440
acggttcttt ccgagcagag ctccggcgcc cgccgggcct gcgggaggcg ggggcagccc   97500
aggctctgag gacaaccttg gtgccatcag gggactgggg atgaccagag gcaagggatg   97560
gggtctgcca gaggcagcag ctccctaggg tccagtgtcg agccagcacc tgctcaggct   97620
ggagtgtgca gaggacactg gtagagcctc ccagggaccc tcacggaaat gaatacatag   97680
ttcttcccac ctctgtccaa gcccaactgt gggacagtgg caggtcctta tccccgcagt   97740
tcccgacccc ggggcctcaa aggcccacgt gctgacaccc tgtcaacatg ggatccacgc   97800
caggccagca atggggcac aggcctcctg ctcgcaggac gcacggggat caggccccac   97860
attcccgcag gcaaggttct cgggccagaa cggtacactc gaggggacat tcacctagac   97920
ccataggaaa caagccttct catggagcac aacagcctgc acacccctcg tcctcctgca   97980
tactcacgca cactcatttc ctgtgcaact gcacaaagcg ctgaaccaca aaagtgcaca   98040
caggccagcc ttgctcactg ggtcctcaac ggggtacccg cccgggggcca gaccggagcc   98100 tgcagccggg tctcatgaac cctctgtgga caacagcttg gtccccactc ctcaaagccc   98160
cagcagcaca gaccacactc tgaccacact ggtcagctca gaccccacc cctcctctcc   98220 ccagaacacc tgcaccccct cctcaacaca cagagaccca acagcccact ggtccctagc   98280
acgccgaccc cacccccttg ggcacacaag gacaccccaa ggttgcctcc gcccttccct   98340
gcagtaggac ccaccacagc cctgctctgc agaccctgcc ttctaggcct ggcctccagt   98400
gggagggaag gcaggggtca gggcaccctc cccgcagagg accccatgaa aggcacagca   98460
gaggagagga tagggccccc cactgaccag gccgagatct gggcccaagg agtccggcca   98520
agactgaggc ccaagctgga ggaatggggg acacgaggtc gctgcccagg gactgaccta   98580
agggaaccat tgatccagcc ccccaggggg atcctagtgc cccacccgcc ctgtcacaga   98640
gggacccacc ccaggcgcca ctgaccctgc cctggcacgt gacgggcagc cacagagctg   98700 aacacccct ccctgtccag agccactcct ggaggaggag agctgtgccg aggcccagag   98760
cggggagctg gacgggctgt ggaccaccat ctccatattc atcaccctct tcctgctcag   98820
cgtgtgctac agcgccacag tgaccctctt caaggtgggc gggccaggcc agcggtgcct   98880
gctgtcccca cacggtgccc gcacagtccc cctaccctgt ccactccctg tccctccatg   98940
tccctccctg tccccttcct gtcccctcac agtcccgtca ctgtctcctc actctcccct   99000
cttgtcctct ctgtccactg tctgtcctcc tctgtctctc cagtccattc tattctctca   99060
ctgtccctct atgtcctggt cgggacctcg ctgtccgcgg ctgtgcccat gtagtcctcg   99120
cgccacccca cctgagcaca cttgcggccg gcagtcccag ggctgggagg ccaggtcctt   99180
```

```
gggggaagct ggcatggggg ccccggctgt gctcacaccc gccgtccctg caggtgaagt   99240
ggatcttctc ctcggtgttg gagctgaagc agacgatcgt cccagactac agaaacatga   99300
tcgggcaggg ggcctagcgt gtcctctggg ggtgtccacg gccaccacag gccccagagg   99360
taccccgttc atcactccga gctgctcagc cactactccg cccgctgccc tgccagttct   99420
gagctctcgg ccatgctcac ccgcacctcc atcctccgac ttaaaggcaa ccactgacca   99480
caccctgcac attgctcacg ttcaggggcc aggtgggcag caggtgctac caccaacctg   99540
agcttagggg tctgcctgtc ctcaccggga gtgcccgggg caccctcagg ttcccttgga   99600
tgagcaggag gctggcatcc cggggcagtg ggcagggata gctctgtgga caccatcaga   99660
ttggtcatca agcagggtcc ccaaggggag gtgcctgtgt cagatccttg gtgggaacat   99720
atgcagccct ggccaacgtc tcgcagcagg gaagcttgca tgcctgcagg tcgactctag   99780
aggatccccg ggtaccgagc tcgaattc                                        99808
```

```
<210> SEQ ID NO 32
<211> LENGTH: 121478
<212> TYPE: DNA
<213> ORGANISM: Lama glama

<400> SEQUENCE: 32
aagcttcaat ataaatttta tttaaataaa ggagtacgag tctcattttg gtctttgcag     60
cagccttgga tacctggttc aattctaagt gcagatggca acatggggat ttatgcccca    120
agagtgatga cgttgactgg gtggaaaatg actgtgagga gactacaagg tcaggggat    180 tctgagcagg ctgtctccag gggactcttg atacaggagg tcaggtggt cagatgttcc    240 ctgaagatca taggttaggg gaattggatc aaatattgag ggtgatcaga tttccaaggt    300
aaggaatctc actaacctga ctcagcaggt ttcctgataa aactgggaca tgcagagatg    360
gacacagaat cctgcaggcc cagacctcgg ggagaaaacc atctcaagga gcctgagtga    420
tgaatgttca gagggtcatt gtcgcttcca gagtcaggt tcttatcttc actgacatga    480
ttctctgaga gcagaaggtt taatccgaag ggacacggac tccttctggt cattcctcct    540
cttggtggtt cgtctcagct gtgagcacct cctgggtctg aggaacactg acctctgtgg    600
atggtgctgt gaagtgagtg tgtctctgtg tttccagtcc ccaggtgtcc tgtcatgggt    660
gctggtgtag gagttggtca aagactattg aagactctcc cccgcacctg ctctgtctct    720
gggaccaccc catcacacac agtggttact gtgggatctg tcacacccca gggaaagcac    780
tgggtaactc acctgctttg ggtgtacggt ctatgtctct taaaaggcgc ctccatctcc    840
acagacatag tggagatgag ttttccctgc agcgcagctc tggggtctcc gagggcacag    900
ccatgtgtca ctctcacagg agggagagtg agtgagggga ggccagtgtg gcccacatga    960
aaccagccct gcagggaggg ctcaggccac caggggcac ccagggtcat gaggaaacaa   1020
gagggacagt ttcagagcag gtgcaggaga agccatgggg ggtttcctcc cagagactgt   1080
ggatgctcca ctgggaccatc accttccctg ggagcccacc cataatgatt ccaggcaaac   1140
atcttgtttc tgaacttgag cttttttcat ggagtcagaa ttgtctgtct tcttttcctc   1200
atttgttgta ggaccagaca cagaagaaac atttcttcat gggactttcg tttgaaattt   1260
agtcactacc cacactttta gttgtcaggt ttacagatac ttaatgacac aaatgaaact   1320
tctgtggagc ctcgagtctg ccctccaccc tcaatgtatt tccagtcatt tcatcctcaa   1380
gtgtgtcccc agtcctgttt cctgcagtgc ctttccctag aaaagcacga ggaatgttgt   1440
atatttggga attgatgtct gtgtgacact ggagtcattc tgtcccccag aggacacatg   1500
```

-continued

```
gaagtgtcta gagccaggct gggctgtcac atgtggggtg ggctgcaggc acccagttac    1560
ctagtgggca gagtccttca atgtggccgt gcatcccaca ctgcacacgg cagctcccac    1620
aaaaggaaat tagcctcaga tgtcagtaat gcggaaaaac tctgagagaa agctttgtat    1680
ctcatcaact tcataaaaat gtagacatgc agaaggtaaa tttctctatg tgaatcatca    1740
tcaatgaatg aaaagatgaa caaacaccaa ccctgagtct tcagttcact cacaggcacc    1800
ttacacccta ttcacccctg tgctggttgt gggtcggagg gtcctgagca cagacctgca    1860
agggaagagg acagtggaac agagagcctg cactggggag gggccgtgtc tctgcttcac    1920
ctgagtcccc aaacaagaca gggcaaggct gaacctggtt gtgataatat tcactaaaat    1980
ccaacctata tcagctattt taggtttcta ctttacatta ataattaatc tcaatattaa    2040
ctgatattta acatgcttgt cttatatcta gaatagtttt gaatgtaatt tttcaattct    2100
tgctaatata tccaaacatg ccatttgtgt cacagacaca tggtgacaga aacagcaaga    2160
ccttcaccag catccacaca ccctcccaca ggggctcaca gctagctgc aaatcccctc     2220 acctcctgca agctagacac ggcccettgc tgtctcccac acagggttgc tggtaggaat    2280
gtctgtgaag gtaggaacac atgtgcatcc cagtgacctg ctcagaaaat tgcaagatat    2340
aaaaagtaaa taaataaat aaaataaaaa gtgttacggg aagtaaagat tgttaacata      2400
aataaatgac cacttacttc aaaggcaaaa ctgggtttat ttgggaacaa cagagaatta    2460
cagtttgggg tctgccgtcc tggtgagcca catgcaagtc cccagtgaaa acagagacat    2520
gactctttta cagaatgaaa ggggaggtga gagggctcct gtgaacagga gttcatggat    2580
tttcattggc tgagtcctta ccaggaaaga agaggaggcc ttgcttctcc ctgttgggct    2640
cagacatgaa gttcccagct tacaagatgg aagcctcagt cctcctgcct gagagccact    2700
gtgaaaaggc tgcttagagg ggcttcgcgt aggtgatcag gagtcaagag gtggtcactc    2760
cgtgtgacgc agtcacgagg gacttcattg ctgacgaagg ggagaagcgt agatgtgctg    2820
aggttgagac aacaaagcac agctctgtga ggaccaggga gcaaaagggc agcatgttag    2880
gaagggaggc atctgactga gacatgttga ctgtgatgcg tggacctgaa caaagggtca    2940
gaggccgtga ggaccccaag acagtgggag tctccctgtg ccacagcatc cggctcacgg    3000
ctataaaacc ctagaggtct gcggaggccc ctgtgaattt ggtcaacacc tcaagacagc    3060
cccttgcttt cataccaaac ggagaaaggg gtctggtaat caggttgccc acaaaaggac    3120
gggctcttca aacgctcctt taaggacttg aatctgtgtc ttctggttcc tcccttaaaa    3180
tggagtcggg attgccagtg ttgagaaaac ttcatctagg ttttccttga gagagaagtg    3240
ttgaatccgt ctcagcagta atcagctagc tgtccacagt ccctcacatt tggcaattag    3300
tgttgcattt aggaagcaga aaaacaccat ggatgtacgt agaaccttgt tctgacgtca    3360
gatgccctag acatcaaata tgatgctggg aaactgcaca ttttctgtag ccacatttag    3420
tcccttagag gctaaatgtt tgtaacgagt gaattctgtc ttcctgcaag attgtttgag    3480
aagatgagca aagaggcaaa ttatccacat attgcagccc agcagaaaca ctagaaactt    3540
tgcatcatcc agaccagcct tccagtggct ccagaaatga gaagggctct caatgtccta    3600 gtgagctttta ctcttcccac tgaaggttaa aaggtaacgg cttcctccat cggctggagg    3660
agtaaccagg gcacagtgga caccagttac agtaaaggcc tcacttccag tgggagtgga    3720
tgttagcacc acaggagggt tagggacgac agggtgataa ggattaaagt gcactttact    3780
attgttatta tctttgcaat tattttgctt tttattgaag tgtgtttgat ttacaatgtt    3840
```

-continued

```
agttttggt gcatagcaaa cagattcagt tatgcatata catatatatt tttcagact    3900 ttttcccacg atatgatatt ataagacatg gaacacagtt ccctgcacta tacagcagct    3960
ctttgtttta tatctgtgtt acataaggtc atgtgtatct gtgaatccca aactcttaat    4020
ttatccctcc cctgccctat gcactttggt gaacatagtt tgttttcaac gtccgtgagt    4080
ctacttttgt cttgtgagta aaatcttttt tcatttttta attccacgta tcagtgagat    4140
catgggataa gtgttctgct atttgactta actcacttaa tatgattgtg tttttatcca    4200
tctgtgttgc tgccgatggc attatttaac ccttttaaa ctacacgtgg aacacatacg     4260
tgatgaagta ttgctcagcc atatttcaat gcagtttgct aatctgaggt ctggacacca    4320 ctccccccctt ggcatagggg ttttctctcc aggaaaacaa gagtatcaga aacacctaca    4380
agggccagtg aagccttcag ccttggaatc tgctcttctg ggcttcatgg cctgaagggc    4440 ttcctcccctt gcaggacatt gattaatcct gggatggtgt aaattctgt tttaattttg     4500 aaggaggctg cactctgaag tttgccaaaa tgttttgggg attttgcccg aaaaggggtg    4560
gtaactaact aagtaggaaa aatggtcgct gcttctacaa ttagctgtag tatcatcaga    4620
dacaaaacaa gtaaaagtgt ctcagggcca cttaattaat ttcacacata ctttgatggc    4680
tgctctaaca tgccggaatc atttcccct ttggggggaga cagaaactat agcaggatgc     4740
tccactgtga agtctcattc agtaaacaga taggagttga ataagtaagg agtaaatggt    4800
gtacatcgct caaagggcct aaataaaagg gggaggtcca gaggcagaga cccctggagg    4860
ctcatcacag gtccccactg ggtgagctgc tgtagttccc tgagcctggg ctgccttcag    4920
tagctcgggt gagcagggag agtccggctc cagtgcccaa tatgactggg ggagacacac    4980
ttccaatctg gagaaatgct tgtccaagcc tattgagaga aaagactgac aagagcccag    5040
ctattccctc agagcctgtc actgggatca ggaggatgtg agaaggctgg tctgagggct    5100
gatggtgcct gaagtgcaca cgtttgtgac aatctctgtc ccggtgtcct ggctgttggg    5160
aaacaatagc agaaactaag gggggtttggt ttgtattctg gggtttttatt tgctggaatt   5220 caagtttaag aatttaaaca ttcttccttc aggtgactct cctgtagtgt gagagacatg    5280
gtttgtcagc ttaaggaaac ctggagagga cacggtttcc accctgttcc tctgtgaata    5340
gaatggaaag gccctgaagg agccaggctg aaggctgctc agcacaggcc cagcagaaca    5400
gcccctattc ccacgggctg tgaagaagac cagccaatgc ctctggaaca atctgacatc    5460
aaactcagac tgaatgccaa gtaagacctt gcatacagta cacggtctca cctacgaagg    5520
acaaacctta caatagttct cagacaaagc ctgcagagct tcctactgca cagatgtgga    5580
aggtgggctc caggagaatg atttagactc aaactccagg gtagttgaga aacacagggt    5640
gcagccatgg gcccagtgtg ggtcccacac ctgtttgctc atcagaccca cactcatacg    5700
gggtcttgtc tgattccata agggccttga aactgttgac ctgaaacaaa gagatggcca    5760
gttatttctc cagcaaaaag aagtgttttc atctgggatc aacaacaatt tgcgttcagg    5820
gcctggaatg acagttagcc acctgcagct cctagcatac acggggataa gaactttttt    5880
gcagatggga atggatgttg gaggaggggt tgtagtgaac aaggcaccca gggcttctca    5940
ctggctgata tgtgaccacc cctcactgcc tgagtccttg ccaggaggga acagggcgtc    6000
tttcttcttc acacagctgg actcgtctat cctggtagga catgagagcc caccgtgctg    6060
tcaccaaact ctatttaact gaggtttctc tgtactcaga attattgtta ttttttcccac   6120 tttgggggat tggatcattt ttgtttcaga agccaggata ccctagtcag gcaatgctgg    6180
gtttatgagt tcaacttcat ggtgaaataa aagtgaatca tgtggatgac aaaaaatgac    6240
```

-continued

```
ttcacttatt agagacactc attggtagga aactccagag cagatctgga ttatgcaggt   6300
ttttgtattt aagcctggag atgtagcaca gatcagactg tgtctaaacc cagaaccgag   6360
agagaaattg tgctgttccc agcatattca gatattaaga acaaagagct atatgcacat   6420
gagactgtgt tatcaagacg tctccccatg actgaagaat aagggataaa gaatgtgata   6480
attttctaat ataaagagaa tatagaaaca aaccaaaatt ctgctgatgg cacaaaaata   6540
ttggagcccc caacgtggaa aactgctact ttcttacaag gtttaggacc aactcaccat   6600
gaaaccagcc atttcaatac taggtgtatc tctaggtgaa tttcaagctc acgttcactg   6660
aaaacactgt gtgcaggtgc tcgtggggcc ttcacacatg ctgtaaagtg gaaacaaggg   6720
ctaaacccag agctcagtgc agggccgtgt actgatggcg tctgaggtac taagtcctgc   6780
attgtagccc ttgtcatggg atccaagaaa acagagtcac tcagtcaaca ctggaaaata   6840
caggtcctcc atgtttcctc agatgccagc agtttcctgt cccaggatta tgtcttgtgt   6900
gtgtgtaaga caatactttg acagaggagg gtttggatgc agatatgata caagagtgtg   6960
ggtctctgca tatgtgcatg tgcacctgtg tgtccacgtg tgtgtgcatg tccctgcaga   7020
cagacgggag ccctggttac atgtgtgatg atagctttct ggacttccat catccttctg   7080
aatttggaaa atatcagcta attttcttta tcaaaatcac ccaattctat aaagaaatat   7140
ctaatgggat tatttattaa aatcaatgtc ttccccatca tcaatggaat ctatacccag   7200
gattctgact tccctgcggc tgagggctca gtgccagttt catcacccac ttccccctg    7260 gtcatgcttt cctacttctg gcagctaaga ccctcgcctg tatggatgag tctagaccag   7320
aatccttcag gtgctgcagg tctgtggtca gaggacagca cagctgggtg gggagtgctt   7380
gtggtgcaag aagcagtttg aaataatgag cctgaatcag gatgggaatg accctcagtc   7440
ttcacacctg gcagttcaca ctctgaagtt taacacctgg gattttgcag ttcatccaag   7500
agttccagtt ggacctttc ccagctctca tcccacctgg agcgtcaaa ttcaggtaca    7560 gtgaggcttg gtcacatttc ccacgtcaca tagtgtttct atcccgctat gtgaagattt   7620
caacctgcaa cactgaggtg agatttatac cacattacac agattataac ttacataaaa   7680
ataaaatgac aaagtatata acaagcattt attacagcac aatcacaagt aaagagattt   7740
tcttgaatgc aattatttat agaaagacat taaaatattg acactgttaa aaaaaattct   7800
caagaacact gcttacatac tactggtaaa cacagtaaca ctcaaaatca tcatgatctc   7860
atcaccgaac ggggtctggg aaacctgacc aatcttgtcc aaaactctct tgatgctgac   7920
tctgcatcac ttatgtccaa gaggaggagc acaggtgaaa atgctggaca aactctcacc   7980
taacatgtgt ccctgctcag accacatgcg ctccccatct gggggctgcg tacatcacca   8040
acgtgggagg aactctggca ccaacatcac agaatcggtg tgccattgta aaaaataatt   8100 caggtttttaa gggtttaccc tgaaatctca cacaataaac atgatgtttc caaatgctac   8160
caacaccagc aaaccacaga cactcacagc tgctcagggg cctagccctc tctgaggcca   8220
gcaaggcccc gacttttat atagtgagat gacatgcaaa tagggcctcc ctctgaggat    8280
aaagccaccc agccctggcc ctacagctct gggagaggag gcccagccca ggattcccag   8340
ctgctcccgt tctctgatca ggactgagca cagacgactc accatggagc tggggctgag   8400
ctgggtggtc ctgctgctc tactacaagg taattcatgg agaacaagag ctactgagga   8460
tgtgggtggt tgtgagtgag ggaatcagga cgtgtgacag tctcctgacc aggatgtctt   8520
tgtgtttgca ggtgtccagg ctcaggtgca gctggtagag tctggggggag gattggtgca   8580
```

-continued

```
ggctgggggc tctctgagac tctcctgtgc agcctctgga cgcaccttca gtagctatgc      8640
catgggctgg ttccgccagg ctccagggaa ggagcgtgag tttgtagcag ctattagctg      8700
gagtggtggt agcacatact atgcagactc cgtgaagggc cgattcacca tctccagaga      8760
caacgccaag aacacggtgt atctgcaaat gaacagcctg aaacctgagg acacggccgt      8820
ttattactgt gcagcagaca cagtgagggg aagtcattgt gggcccagac aaaaaccttg      8880
ctccctgggg cacccacaga ccccagggg tgctcacgac ccaccaaggg cagggctgag      8940
ccccagagca gttgcagagg tgtgggagga gattgcagtt agaatccttg gtttcctttt      9000
cccgcccatc aactctacta cagaccctct gctggattct aaattttcat tgttgaggta      9060
tgtgttgctg tctgacaata atatttgtaa tcaggatgta ttttacaac tgaaaaaaag       9120 ctccaaacaa tgataaactg tagtataatt ttaaaggtga ctcagaaatt ttcaaacctg      9180
acgaataccc tgagaaggca caggcaccga taaaacacgt gtaaacagtt acacatcttt      9240
gtctctgctc ccggggcagg aggctgcaca ccctgcatct ttctgccaaa gggcacacag      9300
ggtttgcagt gagcaggatg cacgtcacag acgccagctc cagactgccc aggactgcgt      9360
gtgcagggat catcattgct cacggagtcc gggctctaca gatcacatct gggcaaaatt      9420
tgtttccagc ctcaaaagaa aaatgttgca ttttctgaac tcctggacat ttacaacgtg      9480
ggcagcactt tgaatcccca acactcgaac attcccacct gaggtcggtc ggggtgatgc      9540
tctgccctct tgtttcaagt cccatcacgt aaatgagtct ccttccaggt ccagttagtg      9600
ccatgttttt gacactttct gggatatgta ggaaattttc ctgtttaaat tggcccatgt      9660
gcagtcctga agtgcggtcc agtgtccctg agcacaaagt gctgtgagct gacttaagga      9720
gaaaatatct gttgcagaca agctccattc aggcatgaac tatactgatg ggggctgtga      9780
gcttgatgat actgtttaaa aaataaacat tattttctta aatgtaatag atatctcact     9840
ttgggtattt gtgtcagcct taaaaccttg gctcaattcc aaacacagac ggtaaaatgg      9900
agatttatgg ccaagaagat ggcactgctg accgggtgga aaacctctgt gaggagactt      9960
caaggtcggg ggattctggg cagattgtct ccagaggatt cgtggtgcag gaggcggggg     10020
tggttaaaaa ttccctgggg ggtgataggt gtagtgaatt ggatcacata ttgagggtga     10080
tcagagttcc aggtgaggat tcccactaac acgactcagc aggtttcttg ataagactgg     10140
gacatgcaga gatggacgca gaatcccgca ggcccagaac taactgagga aagcatttca     10200
aggaacttca ctggtgtgtg gtcaaacggt cagtgtcagc ttcagagtca gggttcttat     10260
cttcactgac acgattctct gagagccgaa aactaaatcc gaagaacatg aaacctctgg     10320
gcattcctcc tcctgatggc actgccacct ttcagaagaa gaaatcagat gcacagaagc     10380
atcatggatg cacagacacg ggaggaaagt gcatctgagg ctcagtgagg acggggcccc     10440
tgcgagcaaa ggagaaaggc ctcagaagaa cccgaacctc tgggcacctt gatcttggac     10500
ttccggcctc cagatctgag agaaatgcat ttctgctgtt tgagctgccc agtctgttat     10560
ctgtaacggg acctctaccc aagtgataca caaatgatga gcctttcagg tatacatggg     10620
aaagtaagtg tcgtaccgca gaggaaaaat cacctgttct gcacagatgt cctatgatca     10680
cctccaagag tcacatgaac ttctactgaa aaatggtttt ggcctcacgg gagtgggtag     10740
aatgatcctg aacatattaa tgtccagtat ctatcagttt tggtgtaatt tggaaatcac     10800
gatataaaat gtactcaaat tgagaaccaa ccaaacctca gagcagcaag gaatggacgt     10860
cttaaagtct gttcatgatt tctaggggt ctctgagtaa cacactgtag acacaggatg      10920
tgaggtgaag aattgaggaa cagattaaga aattaacaaa acatgtgctg ttgaactgag     10980
```

-continued

```
ttcactactt tgtaataaat gccaacacgg tggcaggaaa tgtgcaaaaa ctttggtgtg    11040
acgtacagga aagagcacag cttttgtttc acaagcagct gagagtcaga gcagagatgc    11100
agagcaggtg agcagggagc agaggggacc ggggggctgg ggggcacgag aggaggaggg    11160
aaagtaagcc ctgctctgct tacggtcact cccctgccct ccgactctcc ttggactgaa    11220
ctccctgctc tgggaggaga gcagctgtgg tcagtgagca gaagggggt ccaccctgga    11280 tataagccag caccgcctcc caagcccaga gacacggcct cacctggccc tctatgttca    11340
tgcggaaaca cgaccccacg tgcatgcgaa ccacacgcag ggctcagggc catcacagca    11400
cctgtgccac ccgggcccag ggtctcctct tcacttacgt catcctctga gggccaaagg    11460
cttggctgac aaggacataa accccctct gcactgcacc acacacagtg ccgtctggtg    11520
ggtctgggtc catcctcccc cagggagagc ccagcagaac ctggggtgct tgggtctggg    11580
agctggacag catacaccct gcctcccccc aaattccccc ccatctccag agacacactg    11640
aaggccccgt gaccctgtag ctcagctctg gggtccctga ggaaacagcc gtgtgctttt    11700
gtcactggaa ggagagtgag tgaggggaca tcagggtgac ccagacacaa aggtccctgc    11760
agggagggct caggccacca ggggtcaccc agggccgtga ggaaaccaga ggacctggtt    11820
cagagcaggt gcagaagcag ccgtggacga gttccctccc ataaaaagaa gattctacgc    11880
tggctcaccg tgtcccctgg gagcccatcc ataatgtttc cagggaaact ttctgatctg    11940
aacttgggcc tttttcacgg agtcaggctt gtctgtttta ttcctcatct aacttaggaa    12000
cagactcaca gaaatatttc tccatgggac tttacttgat atttattcac taactatact    12060
ttctagtcat caactttaca gatacttaat gacaaaaacg attcttctgt gcatccttga    12120
gtttaccttc caccccttggt gtatttccag gcatttcatc ctcgagaggg tccccaggcc    12180
tttttcctgc agtgcctttc cctagaatag catgaggaat gctgtatact tggaaaatga    12240
tgtctgtgag acactggagt cattttgtcc cccagaggac atgtggaaat gtctggggac    12300
aggttgggct gtcacatgtg gggtgggctg caggcgtcca gttccctagt gggcagagtc    12360
cctcaaagct gctcaacact ccacgatgca cacggcctct cccacagcaa gaaacagcct    12420
caaatgtcaa taatgttgta aagctgtgac agaatgctgt acatccaggc aaattcatac    12480
cactgttgcc acgcagaaga tgaatctgct ttatgtaagt tattctcact aaatgaaaaa    12540
gacagacaga cagacaccag aattagcctt cggttcactc agagtcccca ttacacacta    12600
ttcacacagg tctctaggtc tgtgggcaga agggcccgga gcaggatcct ataagcagac    12660
ggggcagcag agcagggacc cagaactggg gaggggggccc atgcctctgt gtcagtgagt    12720
ccccagaaac aaaacacggc ccaggctgga catcattgtt tcaacattta caacttccta    12780
cctgtaattg tatcaatctt aatgtttgca gaattttacg tctgaacaat aatttattct    12840
aatattaaca gatttttcac atatggaaca tgtcacaaat tattatttat tttacatcta    12900
caataacatt gcttgtaatt gtggaacact atcaatatat acaagacaca tgcgactgta    12960
tccctgcccc gctgtggccc accctgacag aaatcactag accttcccca gcacccacat    13020
cccctccccc tcaggagcta cagctcacct tctcctcccc tcaccccctg caggctgctg    13080
ggggccacct tctctcctct gagcatggat gtgaccagga atgtgtgtgg aggtgggagc    13140
tcacgtccag cccagtgacc tcctcagcaa attacaagaa aattgaaaga aagtaaggga    13200
gataaaagtc aacattctca tgggaagtta gctttttttg atgtaaaaca attagacgag    13260
cagttgtttc aatagcgaaa gtgggcttac tctggaccag taaacagctt cagtatgggg    13320
```

-continued

```
tctgcaaccc tgaagagcca catgtacatc tccagtaaaa ggagaacgcc tccttcatca   13380 agggggaag ggagctgaga gagcctgagg gaaccagaga ccatgcattt ctctcggctg    13440
agtcctgccc aggaaagacg gggaagcctt gcttcccca gctgggctct gaggccatca    13500
aagggcatga gagctccccc cgttcaccca gttttactaa actgagattt tcgttatatt   13560
ttaccttttg ccatttgatc aaggttgaga tctttctcgc aaaacatcac tgatgaagac   13620
ttaggatttc tgggcttttt cacgtttttg tctgtcagtg ccaggaagga actcctctgg   13680
gtgtaatgtc tcatgtcaga tggaaagcgc tcttattgag gtcacattcc agtaacatgc   13740
aggagtaaga gggagagctc gcaggctctc tcaccgtaag tccctgtggt atcaacacca   13800
gaggctgcag atcacctgac acgttatatt ctcatcagag acttggcagg aagttgtcca   13860
ataggtctgg cacagatacc ttgggaagct gtctcagcag atgttgccct caattctgag   13920
acgtctccac agtcgggtca ccagatgagc agcaatgtcc agggcccagc tgccttcata   13980
ggtgtgtcac gtgaacccaa gttctaactc tcgggagact ggtggcacaa gggctgctta   14040
gcagcacctg ctggagccct ttccattgag gttgaggagt tcttctggaa gtatcttttc   14100
ctgtaggtaa gatatccagg ttgcaaggtg tgacgcttgc atctctgtct cctgagaggt   14160
actgtgaaga gacggcttct gaggagaatc ttggagacga ccaggaggcg gaaagtggtc   14220
cgtcagtgtt cagcaatcat gagggacgtc agtggtggag caggggagcc gagaggcttc   14280
agtacaggtt ttgctgttga gcgaatcatg ctgaggtcgg gccatatgaa caaatttgga   14340
tgcaggtctc ggcagtgttc agatagctga gagagtctca catttagccc gtagatcagg   14400
gtgttgataa accgagaccc gatggagccc atccgcgtgg aggtacacct ggatttaagt   14460
ggagccctgg ttctgatgtc aggcgtccta aacattgagt ctgcatttgg gtaaactgca   14520
gttttcctca agaaaacgat tgccactgaa ataataagaa ctgtagcaag tggtagatgt   14580
cttccttcaa ggaggattga gaaggagata aaggaaacaa attacccaca aactagaact   14640
tccagaagat gttgcatcat ccaagccagc ctccaggctt acccagaatt agaggggctc   14700
tcaataaatc cctggaacag taatgacccg gtaagtctaa tgctccccat tgaaggcaaa   14760
aagggactgg ccagctctag caactgggat gataaagaat gcagtacact aatcaattgc   14820
agtaaggaat tcaggaacac ggggtggctg ttagccttgt gtgagtgtta gcgacaacac   14880
agtgctgctg cgtttactgt gcagtttcct gccccgaggg cctgacgcgg ctgcacccgt   14940
ggccccgagg ttgtctcctc aggaaaccga ggaaccacag ggacaagttc aaggaatcat   15000
gacgccttga gccttgcaac cttctctttt gggctctatg gcttgaagga tttcttcact   15060
tgtaggatat tgattaatcc tgggaagatg tttccgagaa tatatttgaa ccttgaagga   15120
aggtgcactg tgaattttgc aaacaccagt gtgaggcttt gtcaacatgg aaggtgacag   15180
ctgattcaat gggagaaaaa atcaattcct ccagaacttg ctttagtacc atcagagaca   15240
gaatgaatga aagtgctttc agttcatttc atttaatgtc ttccatcaag ctctagaatg   15300
acttctcttt gcagatacac taattctccc ataatagttc actgaacagt cttaaccgtg   15360
aaatggacaa agctggagga atgaatgaat gaactgtgtg catctctcaa agggcctaaa   15420
tacgagggga ggctcaggc gcagacctgt cgaggctcgt cacaggtccc cacgtgggaa    15480
ctgctctagt tccctgagcc cgggctgctc tcagccgttc cgctgagcag ggagagagcg   15540
gctccttgac cgttaggacg gaaggaacct catcatcaac cgcgaggaac ttctgttgag   15600
agaagggact ggggagactc cgtgtgttcc ctcagagcca ctgggaccca ggaggacatc   15660
aggggggctg ctcagagggc ggacggtgcc cgagtgcatg cagttacaag agtctctttt   15720
```

-continued

```
tcaaagtcct ggatcttggc aataatagca gaaccaggag gggtttcggt tttttctgca   15780
gccttcattc gctgtaaatg aagtttaaga atcagcatgt gtccttctag gtgtctcacc   15840
tacactgtga cagagatggt ttgccacatt aagaaaataa gaggtggaca cagtttccca   15900
ttccatcctg cacctctgcc ctacaattga aatgtcctgt gtcagcttgt ttgtaaacta   15960
ggtttaaaag tggcccaggt ggaatgaaca tatgaagcaa aactgtaatt ttcttttaaa   16020
atgatttgca gttgattgaa ataaacatga acagattcaa cagattttca tgggaaacct   16080
gaatttttat tccaaatgaa agtgttgaga aagtctcaga aattgcccaa tgaatttgcc   16140
tagttgctgc tagagaattt ttatataaca agttcatgga ctcttctcct ggctcaaatt   16200
ctaaacacct tttaggattc tcccagtaag cggtttacaa aagtgctagg tgtgacttca   16260
acaactgcag gaccaggacg atgtaagtca gagaagccgg gctgaagact ctgaggggcc   16320
acattaaatt actctgtgag gaacgttggt ttggaaaatc tttgactaca gttcagtttt   16380
agtccagaaa aaaagaaatg aggagatggt cctctgggtc ctcatatgga tgaagtttaa   16440
gataacaaga cctgacaagt tggaggaata gaatatgggg agaatttcag aggaagtggg   16500
aagtttgtgg agacactgac tgtggaagac ctgagggtac aggggaggtg caggagtaag   16560
aggggaggga ggcattggtg ctggagggaa gcctgagaca cacagcccag ggaaggggag   16620
cccgggcttc agaggcccag gtttctttcc ttagtccctg tttgcctcgt taatcttatg   16680
atcacgtttg aggacaggta acttaaggtt cctaaacatg tttctaaggc acagaataat   16740
gagggaaata ggttttccat taaattttga agatttgtca tatttcacca acttggtttt   16800
aagaaaagta agtttgaggt tttctaaagt cccccataat gaccattgac atgtacattt   16860
aatggaagca tgaatcgcct ttcgccaggt ctgtccattt cactacaaat ttccttaagg   16920
gaggaccctg ggtttaaaac aaaaactcag ctgtggttcc tactgcagaa gtgacctcaa   16980
agcacttaga taacttggac cccatttctc aaggtgattt ctggagaata aaggaataat   17040
ttccaagcag cctaaagggt caaacagcgc aaatagccag cagggctaac accagtcagg   17100
tctaagggat cagtctggtt gtgaaggagc caggctgaag gctgctcagc acaggctcag   17160
tagatcagcc cctattccca aggagtggga ggaaggccgg ccacttccag ctggaacaac   17220
ctgatttcaa actcagactg aatgccaaat aagtacttgc atacagtaca aggtcttacc   17280
tatgaaggac acaccttaca atagttctca gacaaagcct gcagagcttc ctactgcaca   17340
gatgtggaag ctgggatcca ggagaatgat ttagactcaa actccagggt cggggagaat   17400
cacagggtgc agccatgggc ccagtgtggg tcccacacct gtttgctcag cagcctcaca   17460
gtcatacggg gtcttatctg attccatcag ggccgtgaaa atgttgacct gaaacaaaga   17520
gatggccagt tatttctcca gcgaaaagaa gtgtttttcat ctgggatcaa caacgatttg   17580
cgttcagtgc ctggaatcac agtgagccac ctgcagctcc tagcatccac ggggataaga   17640
ctcttttgca gacgggaatg gatgttggag gaggggctgt agtgaacaag gcacccaggg   17700
cttctcactg cctgagctgt gaccacccct cactgcctga gtccttgcca ggagggatca   17760
gggcatcttt ctgcttctaa aagctggact ctgctctcct ggtaggacat gagagcccac   17820
tgtgctgtca ccaaactcta tttaactgag gtttctgtgt attcagaatt attgtgattt   17880
ttcctgcttt ttgagattgg atcatttttg tttcagaagc caggataccc tagtcaggca   17940
atgctgggtt tatgagttca acttcatggt gaaatacaag tgaatcatgt gtataacaaa   18000
aaatgtcttc acgtattaga gacactcatt ggaaggaaac tccacaccag atctggatta   18060
```

-continued

```
tgcatgtttt tgtatttaag cctggagatg gagcagagat cagacagtgg ctaatctgag    18120
aatccagaga gcaattatgt tgttcccaca tgttcagatg ttctgaacac ggagctacat    18180
gcagatgaga ctgtgttatc aagacccgtc cccataactg aagaataggg ataaggaatg    18240
tgataatttt gtaatataaa gaggatattg gagcaaagca gaattctgct gatgggacta    18300
aaaactggag ccccgactac aaaaaagtga caaacttttac aattttttagc atcaactcac    18360 catgaaacca actattccaa tactacgtat ctgactgggt gaaattaaag ctctcgttca    18420
ctggaaacac agtgtgcagg tgctcgtgga gccttcacac atgctgtaaa gtggaaacaa    18480
gggctaaacc cagagctcag tgcagggccg tgtgctgatg gcgtctgagg tactgttaag    18540
ccctgcattg cagcccttgt cgtgggatcc aagaaaacag agtcgctcat tcattactgg    18600
acaatacggg tcctccatgt ttcctcagat gccagcagtt tcctgtccca ggattatgtc    18660
ttgtgtgtgt gtaagacaat accttggaca gaggagggtt tggatggaga tatgatacaa    18720
gagtgtgggt ccctgaatgt atgtgcatgt gcacctgtgt gtgcatgtgt gtgtgtgcat    18780
gtccctgcac acagacggga gccctggtta cttgtgtgat gatggatatg tggacttcca    18840
tcatccttct gaattggaac aatatcagct aattttcttt atcaaaatca cccaattcta    18900
taaagaaatg tctaatagga ttatttattc aaatcaatgt cttccccatc ttcagtggaa    18960
tctataccca ggattctgac attaatattc tcagaagcgt gtgaacctcg gtgcagccca    19020
gcccttctga ggacagtgct gcaaagtcag gatgaagcct tggattctga acccacatcc    19080
caagtctttc ttggctcctg acagaacttc cctgtggctg agggctcagt gcctgtttca    19140
tcatccacct tccctctagt cgtgcttccc tacttctggc agctaagacc ctcgcctgta    19200
tggatgcgtc tagaccagaa tccttcaggt gctgcaggtc tgcgatgtga ggacagcaca    19260
gctgggtggg gagtggttgt ggtgcaagaa gcagtttgaa atgatgagcc tgaaagggggt    19320 gggaatggcc ctcagtcttc acacctggca gttcacactc tgaagtttaa cacctgggat    19380
attgcagttc atcacgaat tccagttgga ccttctccca gctctcatgc cacctggaga    19440
cgtcaaactc aggtagggtg aggcttggtc acatttctca tatcacataa actttctatt    19500
ccactatgtg tagatttcaa tgtgcaacac tgaggtgaga tttatagcac attgtgtagt    19560
ttgtaacttg cataaaaata aaattacaaa gtatataaaa agtgttcatt acagcccaat    19620
cacaagtaaa gaaattttct tgaatgttat tattgataga aagacatcga tatgttagtg    19680
acttttgaaa acaatcctca tgaactctgc ttacagatta ctggtcaaca cagtaactgt    19740
caaaatcatc atgaactcat caccgaaggg ggtcttgtcc aaaactctct tgatgctgac    19800
tctgcatcac ttatgtccaa gaggaggagc acaggtgaaa atgctggaca aactctcacc    19860
taacatgtgt ccctacacag accacaatgc ggtacccgtc tgggggctgc gtacatcacc    19920
aacgagggac gaactctggc accgacatca cagaatccat gtgcacacgt aaaaaaaatt    19980
caggttctaa gtgtttaccc tgaaaactca cacaataaac atgacatttc caaatgctac    20040
caacaccagc aaaccacaga cactcacagc tgctcagggg cctggccctc tctgaggcca    20100
gcaaggccct gacttgctat gtactgagat gacatgcaaa tagggcctcc ctctgaggat    20160
aaagccaccc agccctggcc ctgcagctgt gggagaggag ccccagtccg ggattcccag    20220
ctgctcccgt tctctgatca ggactgagca cagacgactc accatggagc tggggctgag    20280
ctgggtggtc ctggttgctc ttctacaagg taattcatgg agaacaagag ctactgagga    20340
tgtgggtggt cgtgagtgag ggaatcagag gacgtgtgac agtctcctga ccaggatgtc    20400
tttgtgtttg caggtgtcca ggctgaggtg cagctggtgg agtctggggg aggcttggtg    20460
```

-continued

```
cagcctgggg ggtctctgag actctcctgt gcagcctctg gattcacttt tgatgattat   20520
gccatgagct gggtccgaca ggctccaggg aaggggctgg agtgggtctc agctattagc   20580
tggaatggtg gtagcacata ctatgcagaa tccatgaagg gccgattcac catctccaga   20640
gacaacgcca agaacacgct gtatctgcaa atgaacagtc tgaaatctga ggacacggcc   20700
gtgtattact gtgcaaaaga cacagtgagg gaaagtcggt gtgagcccag acacaaacct   20760
ccctgcaggg tcacagacgg tgtgcagggt cacaggggac acttaagacc ccccagggca   20820
ctcaggactc cccagttgtg cccttcagcc ccaggggcag gtgcaggagg cagctggttt   20880
cacggtttcc tgtcaggctc tggagtttcc tctccacagt gcaggaaccc ctctggatcc   20940
gagaatctgg gcttgcacat ttagtctccc aattagaaag ttttttttcta aaaggaaaaa   21000 caacgtttaa aaaaaatcct ctcctgcaca agaggcagag tttctcttgc atttatgtac   21060
tcatgttggc ccctgtccaa atcgggtcaa cgtggagcac tgtaaaacca tcatggtgga   21120
tttacggaca gttagacaca ctctacccte ccctgtgaac tctcagcccc accctactga   21180
tgggggcacg tgtccctgcc aggtggggggc tccttgctga cgtcctccat gagaagcccg   21240
gtgaggctgg cagccccca ggaccacgag cgggtcacag ggaacgaggc cagtgagagg   21300
gaatgggtgg ggccatggcc acgtgggctc ctcctccagg tccagagaat ccctgcagaa   21360
cagaggctcc tgctccctgt tccctgtgca ggtcacgttg ggtcacgagc tcattgatca   21420
attatcaccg atgaacgcac agataattgg gagggagctg ttacagacag gtgggcactg   21480
acgtgtgaaa tttcagaaac cactgcagac gcgctgcggg acgctttctt caccaggcac   21540
gcccggctcg tccaggatct ccttcagggc ggtcaggtcc cgtgcttaca agcccaggtc   21600
tgggcaggag ggctctggcc ccctgctgtg tgctcccccgg caccctgcac gcacgccagg   21660
ctgcacggtg cagctcacac ctgggaaagc aggtaaagct ggtacccgca tcacacgccg   21720
gctgtgccga ggtaaacaca aacaccgcaa cacacaccaa gtgcggggtc cagggcgttc   21780
cccccagcac gtgccccagt gccatgccga ctgcttggac ttacagtggc ttaaggagca   21840
gccaccacaa gagggaccct cggaccttcc ctctgtctcc cagcgcaaga ctcacggctc   21900
tcctgtgaac ggcgcactcc ctgcgtctgg aggtggaagg accccatca ccccacgtgg   21960 ggatccagcc tggcagctcc tggcagcaga ctctgctcct tctgatgcgc taaccccac   22020 acaagctcct ctcaggttct tcactaagtg agccccaaac cacagatttc ttcaccctgt   22080
cagttcccca ggatattgtg tgtctttgtc caaaggtatg cgagctgccc gctttggtct   22140
cttctcgtcc atttctgtgc cacgtccaag agcatgataa atatttacta cttttctccc   22200
aggaatctaa tcatagaaca gcctatgagt aaacgacccc tgtgccctcc gggactaaga   22260
ggagactacg gtaaagagtt tcagacacga ccttgtcacc agtgcccag aatatcctgt   22320 tgcagttcag aaaccagcct ctatactacc cctctgtctg caatcgcagc cgcaaggcct   22380
gagccagagg gagccacccc aggcctggct ggagtcctct tctgaggtcc ccctttgatc   22440
catttactct gccactggct ggccgttcca tcctcgtatt ttgtcaattc aggctgtaaa   22500
aagaccacac agggacacct agagcttgtc caggccagcg gagcttcagg gactgctgcc   22560
taacgtgaaa ccctaactca ctagcaggac ttgcagccaa acagataaat attaggccca   22620
gtgaggcagt gggcttttttg agaacttcac tgtttttgag gagtaaaaaa aaaagaaaaa   22680
caaaaaaaac tggtactggg gtcacagtct gtggtgccag aagcagaccc atcctatagg   22740
ccataaaacc tgtcaaccga tcatgggagc ctcaaaatca aagccgacag ttctggactg   22800
```

-continued

```
cacgattcaa aatttcaaaa agggtttctc aggagactat gggattaaat tgtccccaga   22860
aaaactgcac aggttgtgca agttagagtg acccaccttc agagtgggat ggccctcagg   22920
agtcacactt gacctgccaa ctatccgggc catgtacaga gtaattgcca ggaccccagg   22980
gcaccccaac caattcccat atattgaccc ctggctaaca gtcgcccaaa ccttgccccc   23040
atgggcctgg ttctgcacaa atgatcaggg aaagtgtagg atcctcgtgg cccagacagt   23100
aaaaataaaa aaggaaggtg caacgaagcc aattcttcag ggggaccctg aagaagaacc   23160
agcgatgccc ccgccatgtg tccttccctc tgtggctcca ccacagccac ctccacctga   23220
tagccctcct ccatccgtgt ccccaccgcc acaaccccag gctccatgcc aggaaccctt   23280
agggaagaga ctgttcagcc caactagcca gccagccagc ggccaccctc cagatgcctc   23340
tcccggaggc ccaagggccc caacatgtta acgacaatgg ctccgtgcag cccagacact   23400
ccgtcctgta ccaccagcct ttcagtacaa cagacctcct gaactggcga caccacactc   23460
ctccgtattc agaaaaaccc caggccatga ttgccctcct agagtccatc ttccagaccc   23520
accggccagc ttgggacgac atccgtcagc tgctcctgac gcttcaatgc tgaagaaaga   23580
aagctggtcc tgacagaaac taaaagttgg ctacaagagc agacccccaga gggaaccatg   23640 gacgcagaag ggtcagccct aaatgcagcc ccagaaagaa ggccaaactg ggactttaac   23700
acccaagatg gatgagaggc tctgcagatg tatcagagag ccctcccgca tgggctgcga   23760
gccggggcaa agaaaccaac caacgtgact tagaccatca cggtgatcca aaagccggac   23820
gggtctccat ggactcctat gagaggctat gcgaagcttt cggatctaca ccccatttga   23880
ccccgaagcc cctgaaaccc agcggatggt cagtgctgct tctgtggccc aatcctacac   23940
cggcatccac caaaaacttc aaaaactgaa aggttttgct ggaatgaatt ccactcaact   24000
gctggaggtg gccaacaaag tcttcataaa tcaaggccac gaagcccgac aagaagcagg   24060
cagatgaaca aaacagaaag cacgcctgct ggcgaaaagg ggggacccgt gtggggcccc   24120
cggaggcaag accaacgtgc atactgtaag aaggttggtc actgggaaaa tgaatgtcat   24180
cgcggagaag caaaaaacct accgaagaga aaacctccag ccagcgaagg aaagtaccgg   24240
cccgagcctc ctctgaggaa cctggtcggg ttggtcaggc tggactcagc ctaggggaga   24300
ctgcgtccct gctcctgggc ccaggggagc ccgcagtcaa gatgttggcg gggggccaac   24360
cgatgacatt tacagcagac acggtggtaa tcaaagctgt ggccccttg accgagaaaa   24420 cggcaattat cacaggagcc accggggacc aggcctctcg cccgttttgc catccacgat   24480
catgccagct cggggggacat ttagtcactc atgagtttct ctacctacca gaatgcccca   24540 tcccctttg ggaagagact ttgtaaactg ggggcccgga taacactctc tcctggaaag   24600
caatcacatc taactctgag ggggaaggaa gccttgctca tgatggtgac cgtgccccga   24660
gaagaagaat ggcgcctata ccaaacagaa agcgcccaga caaaccctga ctctctgtga   24720
ggaagctccc ctccgtctgg gcagaagggg gacccccag actggcccga ttggtaatag   24780
acctgcgact gggtgcaacc ccatccaggc tgcgagagta ccccataccc agagaagccc   24840
gtctgggaat tcagaagcac atccagcgtt tgcgtgatga gggagttctc aaagagggcc   24900
agtctccatg gaacatgccc ctcctgcccg tcagaaaggt gggagtaata gactgaaggc   24960
cagtgcagga tctgcgagta gttaacaatg ccgtgaccac aatacaccca gtggtcctga   25020
atccacacgc tcttctcaga ctcctaccgg cccaggccaa atggttcacc tgcctagacc   25080
tcaaagacgc ttccttctgc ctcaggctgg caccagtcag tcaaccaata tttgccttcg   25140
aatgggagga cccccacacg ggcaggaaaa ctcagttaac ctggcctcgc ttaccacagg   25200
```

-continued

```
gttttaaaaa ctcacccacc ctgtttggag aagcactggc cacggatttg actgccttcc   25260
tgggagaagc tctaaactgt gcctgctgcc gtgcgcagac ggcctgttat caggcagccc   25320
caggcaagag ggctgttggg agggaaccca ggccctgtta gcgctgctgt cggatgctgg   25380
ctataaggtc tcctggaaaa aggcacaaat ttataaaaag acagttgagt atctcaggtt   25440
ctttgtctca gaaggacacc gagctttggg cccagagtga aaacaagcca tttgtgcaat   25500
accacagcca ggcaccaaga gagagatccg agaattcctg ggggcagcag ggttctgccg   25560
aatctggatc cctggtttct cagacataga caagtcccta tgtgaagcca ccgctggatc   25620
tgggaaagaa ccctcagact ggggacccaa gcaggaagaa gcatttaatg aggtcaaaag   25680
actgctaacc agggccccag ccctgggact accagacgtg acaagagaat tcagcttgtt   25740
cgtccatgag aagagtcata cagccctaga ggttctcacc caagcagtgg gggcctggca   25800
gtggcccatg gcctatttgt caaagaatct ggacccagta gcttcagggt ggccaccatg   25860
cttacgagca ccggctgcta cagtaaccct acggtcaagg aagcaggcac gctcaccctt   25920
ggagagactg ccagcgtgaa ggttccacac gcagtcccca ccctgacgca cagccagggg   25980
cgccgatggc tgaccaacac tagaatgaca cgttgcccag ggctcctctg tgaaaaccgc   26040
aggatctgcc tggagacagt gcggaccttg agcccagcca ccttcctgcc cgagggagag   26100
ggcccagccg accacgactg tgaggacata gtagaagtct caagcaggcg tgagctgtct   26160
gatgttccgc tccagaaccc tgaacttgaa cttttacaga cgggagcagc tccatgcagg   26220
acggacaaca tacggcagga aacacggtga ccgcagcaca cgatgtaata aaagccgaat   26280
ctctaccact gggatggtcg gcatagaggg cagaaacata ggtgctcatc caggcgtcac   26340
gagagggaag aggaaagcag gtcaacgtcc acacggactc taagcacgcc tttgctaccc   26400
tgcacacaca tggccctgta cataaagaag ggggtctgtt aacagctgga gaaaaggaga   26460
tcaagaataa aggcgagata gtgcaactgt tagaggcagt ctgggagcct gcggggggtc   26520
agtcatccac tgcgaggggc cccgaaggga gacgaccctg taagcagagg aagccgactg   26580
gcagaccagg ctgtgtgaga agcagcaagt cagtctggcc acgccagaga tcctgggacc   26640
gtggcgaagt ttccaccagc acccgaactg ccaacgcctc tggaacacag ccgagaggaa   26700
agctcatggg ccaggaccga aggaggaacc aaaagaaagg agggatggtg ggcgatgcct   26760
gacaaatgga tatacgtacc tgaacactta gcccatcacg tggtcctcca gcagcaggag   26820
ctcacccacg tggacagacg gcctcagagg ccctgctgga tcgatactac ctgatggctc   26880
aacttccacc cctctgtgcc tcagtctcac agcactgcct tgtgcgtgcc cagaacaatg   26940
cagaacgggg gccgactgga ccaaaaggag gctccttctg aagacacgga agcggatttc   27000
acagaaatag ggcctggcag aggacacagg acgcactggc ttttgtctgc accttttcag   27060
ggtgggtgga cacacaccca gcacggactg agaaggcaag ggaagtaaca aaggccttac   27120
tcagaggcac cgttcccgga ttcgggatgc cactgaccac aggggcagac aacgatctg    27180 catttgtggc agaggcgcta cacagccact ggagtccacg tgcagccgac gggcccccga   27240
gctcagggag agcagagcgc gggacccggg ccctgaagca agttacggcg aagcgcagtc   27300
cggaaactca gctgccttgg gctgacactc tgcccccggc tcttctgcgg gtacgctgtg   27360
ccgctcggtc caagacgggg ctctcccttc tgggggcctg tacgggaggc ccgctccttt   27420
aattagacta ggggaaagta ttacagaagt ggggagcgta gaccttcata agcaaataca   27480
gggcctcaga aaggctatgc gagaaatcca caggtgggga actgacagga tcccagtgtc   27540
```

-continued

```
actgggaaca atgtgatacc catatgacct ggggaccaag tctgggcaag agattggcaa    27600
agggagccac tcagacccgc ctggaagggc ccctacccag ttgtgttagc caccccaaca    27660
gctctaaagt tgcagatatc gcccccccgga ttcatcacgc agagtaaaga gagcagcgcc    27720
accacgagac gaggatgtct ggagcgtcgc ccagatcccc agagagcctc ttaaatcagg    27780
atccagagac gcccgcctcg cctgccagag agcacagagc cttgctctag ccacacccgg    27840
aagccttccg tggcggaagc ctgaggaacc gccgatcaag acagaaaatg aactgctgcc    27900
ccgctttatt ttaggactga gtactgtctc tgtattgcga gttgtaggac tgatggccac    27960
tgcaccccag gattgaaaca tgggccagag actaacacca gctgtgctcc gttcctccac    28020
agtaggaagc ccaacggtca gtcagggtct gctggaggaa ccatacctcc ctgtgagaaa    28080
tggtgagacc ccaagccctt cttctgcttg tgaaaggagt tgctgactta tctctttcca    28140
tgacggaggt tccaatggga cccattcacc aaattgcaga agaaacccg gcccacacgc    28200 tcagggccct tctacagacc tagcaagggt tgggaaaaga aaaatagacc taggtccatg    28260
ccttataacc aggacccca attaagtccc ttatgaagca agtccatcac cttcttcatg    28320
ctactaaccc acaactagca agtgcttgct ggctctgcct gcatcccggc ccctccagca    28380
tgcggccagc ccgatgggcc gctcagatct aaccaagttc aatggctgcc ctgggtggtc    28440
cccagactct gggaaatctg gccactgccc agtgtgccca aacccataac tgcacacctg    28500
tttacagttg tatgcctgcc aagccctggt gcgacactga gcccaggaac ctttttgttt    28560
gcggagcaca ctcctacggt gctgccagcc agttggacag gtacttgcac actggccttc    28620
cttacccctc agatggacat aacacctgat aaccagagcc ttcccgtacc cctgatggcc    28680
catactagat caaaaaaggg ccatccagtt aataccacta ctccttgggc tggaatagcg    28740
actggagtgg gcaaaggaat aggaggaaca gcctcatctt cccactgtta ccagcagtta    28800
tctgctgagg tcactgaagg tttaaaacag gtggctgagt cctgaatgac tctacaaaac    28860
cagttggact ccctagtggc atttgtccta cagaacagga ggggtttaga actgctcact    28920
gccaaaaagg ggggactctg tctcttccta aatgaggaat gctgtttcta cgttaatcaa    28980
tcagcaattg tcagaaatac ggtccaacaa ctacgagatc gagctgaatg cagaaaccag    29040
gaatcagcaa actcctgggc acaggggact aacgcctgga gttgggcctc ctgcctcccc    29100
cccagcaggc cccctcctta tgatccttcc agcgctgctg tttggtccct gcatccttaa    29160
cctcattacc cgtttcatta gctcatggat agagtcactg agacggcagc tactagtcac    29220
tcagtacagg cccctggacc agaagaaccc aatggtgaat aaggggcacc actgtaaggc    29280
tgatgctcgc tgcagatgtt gaagagagca tcaaagtggg gaatgaggcg ggaagcccca    29340
tagaaagacc agcaggaccc ccaagcaggg ccactactct gctgccggca ccatccagtt    29400
ccctggccca gaaacggctt acttatccct aaaaccctat tggttccctg agctcactcc    29460
tgattggtta tttccttcac tcctgattgg tccatttccc taacttctga ttggtccatt    29520
tgtagtgctt catttgcatg gagctcactc ctgactggtt atctctccct cctgatttgt    29580
ccatttctgc aaagcttgtt cctaattagt caactttcat tatacctcat ttgcatgtga    29640
tgttgcaaag tgtacactgg cagcctatga aatcctgtgt aaacctacag acggggtcca    29700
gagcttggag tgctgactcc tctgggcccg ctggcgtagt aaacctgagt tctccagctc    29760
tccgagtgct gcttggtctc ccgcctggac ccaggttgct gacacaactg agctgtaaca    29820
ccgagctgta gcacattttt ccacaacaat gtaatagttc tcatctgagt attttggaaa    29880
atccccatac tgttttccac agtggctgct ccaatttaca tccccaacaa cagtgtacag    29940
```

-continued

```
gggttccctt ttctccacat cctcgacaac atttgtcatt tgtgttcttt ttgatagcag  30000
ccattctgat attttattgt tagtggaaag aaatgcagcc gatttctctg tgctaatcct  30060
gtgttctgct gccttgccga attccttcat cagctccagt cgttttgcgt ggagccttag  30120
ggcttctacg taaagtgcca cgccatctgc atgtggtgac cactttcctg caaatttccc  30180
cagtgacgtt tgtttgcagg gaggtttttg ttgctgattc tggtcacttc tagtgatcat  30240
tctgttcaaa ggatctattt tttcttgatt cagtttggta gactttatgt ttccagaacc  30300
ttgtccgttt cctttagggt gtccaatctg ttgccatata gttgttcata gtgttctcta  30360
gtggtctttt gaatgtctgt ggtattggct gtaatttctc cattttcctt tcttattttg  30420
ttcacttgta tcctctcttt ccttcttggt gaagctggcc agaggtttgt tgattttttt  30480
ttcactcttt aaaaaaaaac agctcttggt ttgattgatt tttttctatt gttttttttt  30540
ttccggtctc tattttattc agttcctccc taatttttat tatttctttc ctgatgctga  30600
cttcaggttt tgctcactct tctttctcta attctttcag gtggcaggtt aggtggttta  30660
tttgaggtca ttcttttttg aggaaggtct gtaccgctgt gctcttccct cttaggatgg  30720
ctttgtctgc gtcctgtaga ttttgtgtgg ttgtgttttc attgtcattt gtctcagggt  30780
attttttaat ttttcctttg atgttttgt cgacacattg gtttttagca gcatgttgtt  30840
tagtctccgt gcagtttgtt ttcttatttt tctttctgtg attgatttct agtttcatga  30900
cattgtggtc aaaactgatg ctcaaaataa attctatcct cttaaatctg ttgaggcttc  30960
tttcgtgccg agtatgtggt ctatccttga gaagtttcca tgcacacttg aaaaggaagt  31020
atatactatt gggggtaat gtaacatctt aaaatatcag ctgagcccaa ctgttccttt  31080
gtgccatttg gtatctcggt tgcctcgtta gtttttctgcc tgggagttct gtccagggcg  31140
ttagtgggtg ttgcagtccc tgctgtcact gtgctcacat cagctttccc ctttcagtct  31200
gtttgtatta gtttcatata ttcagaggct cctatgctgg gtgcatgtat gttaacaaat  31260
gcaatatcct cgtcttgtat ttctactttt attattacat aatgtcattt tttcctgttt  31320
atggcctttg ttttaaagcc tcttttgtct gataggagta ttgctactcc tgctttcttg  31380
ccatttctgt ttgcatggaa tacctttttc caccctctca ctttcaaact atgtgtgtcc  31440
ttcaccctca agtgggtctc ttgcaggcag catattgtag gcttttgttt tattatctgg  31500
tttgctgctc tgtgtctttt gactggagca ttgacatcca tgataattat tgatagacgt  31560
gtgtttattg gcattttaaa ctatgttttc tggttaattt ggcatttctt ctttgttctt  31620 ttcttttgt ttttgtttcc ttttctggtt tgacaacttt cttttgtgtc agcttggttt  31680
ctttttgatg tatgtgactc tactgtatgc ttttgatttg tggttaccct gttttttcaag  31740 tatgttaacc cattactgta tctgtttgct ttagactggt ggtcatgcag gctcaaacac  31800
atcctaagaa gaatgaaaag aaaattgttt tcctgttccc ctctcccaca acttgatttt  31860
tatgtcctct ttcacatttt catgtttatt ctcttagttc tctgatattt tcatgcttca  31920
attatggctt tccataattg aagaaagtag cttcctgctt cttctctatt tacagcagac  31980
cttccaccat ttcctgtagc gtgggtttag tgttgctgaa ctcttctagt ttttgcttgc  32040
ctgtgaagct ctttatctct cctcctatcc taaaggatag ccctgctgga tagagtatcc  32100
taggctgcag cttcttctca ctcaggactg tgaatgtatg ctgccctcc cttctggcct  32160 gcagtgtttg tgcagtggag tcggctgaaa gccttatggg gggacccctg taactcactc  32220 tttttttct cttgcagcct ttagaatctt ttctttatct ttaactttgg ccatcttaat  32280
```

-continued

```
tataatatgt cttggtgtag acctgttaag gttcttcttg tttggggccc tctctgcttc   32340
ctgtacctgg atatctgttt ccttcttgaa gttcgggaag ttttcggtca tgacttcttc   32400
aagtacctgt ttgatccctt tcccctttct tctccttccg ggacccctgt tatgtggagg   32460
ttggcctgct ttatatcacc ccataggtcc ctcatgttgc tttcgttggt ctccgtttgc   32520
tcttctgcct gctgctttga tgtgatcggg tggtttccat tatcccgtca tctaagtcac   32580
ttattcgttc ttctgtatta tttagtctgc tgttgactgc gtttggctca gctttatctc   32640
agcaactgag ttttccgatt ttaattggct cctctttaca gtttctattt ccattttaga   32700
aaaccctgta ttctacattt ctgttgatgg tctttcttat ttccttagtg cttttttgtcg   32760 tctccttttt gaattaggct ctagcagact gtcgggtctg ttttattgtt tgttctttca   32820
gggaacttct ctggtgcctt tactcgggag cagctccccc tcacgttgct tgcacctctc   32880
tggctgtggg tgtagacgtg tcagttacct gctgtgtctg aagggctgtt ttttcaaat    32940 gggtagactg tgcaaatcta acaattttgt cgcaaggaca gtttttagtg tctttcctgc   33000
atgtgtgctg gtttttgtcc ccttgatcag gggtgtggct ggtgttgtga ccagagcctg   33060
ccctggctgt tgaactgggc ctcctctttg ctctgtggtt gtcagagccg ggcctgctcc   33120
cctactgtag gagtcgaaga gtccagaccc gtttctgagc tgcagtgtgt ggcaggcggg   33180
attggagcac ttctgctgga agacgagccc cagaatactc ctccacagga gacgaccgct   33240
ggcaagggcc cttgtgctgt cgcccaccac tagttacttg ggcttccaaa gtgcactctg   33300
cggttgctgc ccttgtcccc cctcagccag gggaatatca gcaacccact ctggtgtccc   33360
caggttctgc cctgcagagc caccagtgca gatccactga catcaggcac tgggacctgg   33420
atccaccatg agccacgggt cagccccgac ctcagcccca tgtccacgtc gggtacgcag   33480
ggccactgtc agcaccaggc ttgccccaca tcaagcacca gaagcccact aggttacctc   33540
agaagtgtgg gtccacaaag gcaccagcta tgcaaatctg ccaccacagc ctggggcttg   33600
aaacaagtct cagtcccacc tgcaaagtca caggaccctg gacatggatt caggtgtcag   33660
ccccacctct gccccggagc ctcgctgcag ggacggtgcc ccccagagaa cgctgagagg   33720
cctgcggttt ctgagcccca cccctcttct agggcaatgt gtgccacaac ggtgctgagc   33780
agtgccctct gggctcatga tgacgactgc tggggctggg ctgctttgca cccctcccca   33840
cgtgccccag cagtggtgct gtcgtggggg ttgacccagc ctgtttttgca cacttctacc   33900 cgcagcctgc accgcactct gcctactgtg gctgcctatg cacactcagc accagccctc   33960
tgcccgggat catccacggg agcctgagct ccagcagccc cacccagccc accctcactg   34020
gctcacacct agagctaggg atggcagaga ccctctgtgc tggtttgtcc cagttctgtc   34080
tgccaagtcg ctatgaattt tccctccaag cttctgaagc tccttttcta tccctgctga   34140
ccttcctgct ggagaggggg cctcctggag tgagcgcact tttcctcctt ctccactccc   34200
tccccagggg gcagctcctg cactgatttt tttttttccc atccggtttt gtgagtattt   34260
ccttgtgttt ccaattgtaa gagatactct gccaaagttc agtaggcagt ctgtgagatt   34320
tgctccattt gcagatgcgg ttttttgtggt attcgggga gagggtgagc acggcctcct   34380
tctacacctc catcttggct gtctcccagt tttgctgttt ttgatatgtc atttttcttc   34440
taaaacctgt tttaagcagt gcactcccct ttcaacaccg tgtaggtctc tgtcctcacc   34500
gctgaggttc gttacggaac ctcactctgt ctggcatctg gtggaggttc tgggaatagt   34560
gagaaggact ccagccccgg aaagcccacg gtctaggaga gatttagtga gaatttgggc   34620
agagggagcc agcaggcagt gctgaggtgg gctttgtgag acaatcaaca gacagcagag   34680
```

-continued

```
ggcagggagg gggtaggtct ctgtccggct ggttctcgat atctgtgcag attgtctatg  34740
tggaaactga gatgcttctt agaacatggc ccctcgaact gctttcagag acctgcccag  34800
aacatggccc agcgctgctg taaagggcac acgtcccttc gcttgttgtc ctgcagtatt  34860
cacgtggaaa cctgagagct gcaccttgta gatgggctgt gtctacaccc cggagactca  34920
gggacaggca cagaaggagg gcacctgtga tcatcagtgc ccaccacagt gacaacgtgt  34980
gaggggggaa cgcgtggcgg gaggacgagc cgcctggggc aagtgtcccg gcgggattct  35040
cacaggcgtg gagtcagtgt gcgcctggaa cacgagagca gctcacaggg tgactgggct  35100
ccgctggtgc ttctcacaga tgatgaaagc cctcaggaag ccctcttgtc aggacagaag  35160
gggagggaca ggagcctgga gaggggacag ccctcctcac tggtggtggc tcatctctaa  35220
acagacagtg tcacttcctt ctctgtcggc tgcgctgaga agatgagaaa ttagggctac  35280
gtggagcaca acacaaaatg tcctggggggg aggctgtaga ggaaatccct gacagagaca  35340
ggaagcccct ttccacccgc ctctgcactt gctcctgggg ctggtctttc tgttctgtga  35400
gtcttgcaca cccccctggtg gacccacaca cttcttagga gggaaggttt gcgtctgggc  35460
tcacaccggc ttcccctcac tgtgcctgtg gcacagtaat acacggccgt gtcctcaggt  35520
ttcaggctgt tcatttgcag atacagcgtg ttcttggcgt tgtctctgga gatggtgaat  35580
cggcccttca cggagtctgc atagtatgtg ttactactgt aactataaat actggacacc  35640
gactccagcc ccttccctgg agcctggcgg acccagctca tgtagtagct actgaaggtg  35700
agtccagagg ctgcacagga gagtctcaga gaaccccccag gctgcaccaa gcctccccca  35760
gactccacca gctgcacctg agcctggaca cctgcaaaca caaagacatc ctggtcagga  35820
gactgtcaca cgtcctctga ttccctcact cacgaccacc cacatcctca gtatctctcc  35880
ttctccatga attaccttgt agaagagcag ccaggaccac ccagctcagc cccagctcca  35940
tggcgagtcg tctgtgctca gtcctgctca gagaatggga gcagctggaa tcctgggctg  36000
ggcctcctct cccagagctg cagatccagg gctgggtggc tttatcccca gagggaggcc  36060
ctatttgcat gtcatctcac tacatagcaa gcctggagtt tgagcaaggg cagtacccca  36120
gagcaggagt gagtgtattg gatttggtgg ttttgataga attctggaaa atacgatttt  36180
ccactatgtg tttttttccag agtaaacacc tgtcacccat gtgtattttg ttttcacata  36240
tggacacaaa ccctgtgatg taagtttcac tgtttcccgc agagtagaga tgtgaactac  36300
agccaaaatg tagtgggctt gttgcgtgtc caaggacacg cctgtgggga gggccagtcc  36360
cagctcctac acctgtgctc atccccacta gacccagctg cccctgcgtc aagtcccgga  36420
aaacaggacc gtgcttgtga ggtttgtgca ccccctccct gaagtgagac gtgaggactt  36480
tgctgccccc tagcgtcgag ggtctgagtt cagaagctgt gttttcagcg gtctccagca  36540
ttgcagcgtc tgtccaccac gtcttccccc gcaggcagcc actctctgtt ggtaacagcc  36600
ttaataagcg tcgcgcatgt agcaagctgc acgtgctgga atgcgctctt tggtacacac  36660
tcacgcaagc atcagcgtaa tcgagagtga gcggagtgct tcccttccat ctattcgctg  36720
gtttctggag ctcctccttc ctctgcctcc tcttttccac gctgttgctt caggttagct  36780
ttcttttccc agaattaccc aggggggcca tattgcgcgc acggccgccc gtacggcttg  36840
tttccctcag cgcagatgcc gtcaatagcg ccattctgct gcgtgtatcg agaatccttg  36900
gttttaacaa catgtgtcat tcccagtaag gatcacagtc tgtctgtctc ttaagctgtt  36960
gtgcggtgtt ggaattattt ctagtttctg ggtgttgcag taaagctggt gcccatctcg  37020
```

-continued

```
gagcggtgag aactaagaag ctgggaaacg actctctttt tcacgttcct acaacaaccg    37080
tacgagtggg caagttgcag attatcaggt tttcattcat atatcagatc actgtggtcg    37140
taaaacaaat gaaactgaaa acttagaagc aaatgctcac agagtaacca agaactagac    37200
tgtaagctta attggggcag aagctgctga ctggaataag aaccgctaca gaatcacact    37260
ggaaacggct ggcttgagga cgcgcgcggt gcagctgtga cagcgtccca gccgtcccct    37320
aactaactcc tctgcgagtg tctacggtgg aagccaggcg acgctgcctc ccttcacgcg    37380
ggtgcctctc tcctaccagg acggctggga gctcctgcct gggaccgcag gccctcccgc    37440
ttcacgggaa ggaaggcctt gggctctggg tgcgacctgg ggctgtttcc cagcacctcc    37500
acctaacagt tcgatgtttg tccagtcatc tcaccaaact gcaccatgta cttcccgcac    37560
acgaggtggg gaagcaggtt ctgtgcggaa gtagataatg aagttctagg tgttgaccga    37620
tgcacaaaaa tactgccaca gctcttgcca gcttcaagtg acaagagcca ctgactttgt    37680
tcaccctctc tgattcggag gggcttgagg aagtccctcc tggccccatg tggggtcact    37740
gtctctgaga tgcacactca cacctacatg aagctgccct tgaacacagg ctgggagctc    37800
agcaggctga gggctgggcc tggtgtccgc cctgtgcaga catcctcttg ggccctgacc    37860
ccaccccagc atggtgactg cggcagccga tgggtccctg ctccagagac cttcctcagg    37920
gcaacatctc acagacctag agtttgatac acgaccccag tactcgcgcc cctaagcact    37980
cacccacccg acttgagact tatgtctcca tcataaacgc acgtgagttc tcgtagcttc    38040
acgtgtaatt gagaaaactg gatgcaacaa aggcattctt cttaaatgaa taaatgagca    38100
atgcatgatg tatccatgca gtggaattcc attcagcaat ttaaatgtta aattatcata    38160
gcatgaaaag gcaaggatga atccaaaatt agcgtattgc tacttttaaa gccagtctga    38220
aactgtatga tttcacctat ttggaattct gggaaaggca agactgtata catagtaagc    38280
aggtcagtat ttactggaat ttggggacaa ggcatttagt gagtgaaaca gagacaatat    38340
ttaagtgtgt tgagattgtt ctctatgaag ctgcagtgtt ggaaacgtgg cactaagaac    38400
ctgtcagaac acatagaact attagcgcaa agagtgaacc ttactgagta gaaatataaa    38460
gggcatttgg aagttcagag gctcaaagat ggaacttgta ggctgtgtag ataatacctc    38520
agatcattat gaatcaactt gactgaagaa ggtgacaaca catttctgac caaagtcact    38580
gtgtgactga gtggagtctg aggacaaggg tccaaggaca ctgcacagaa gctctggagc    38640
ctggctgaca aggatgtttc cagcacgggc caggctagca actccatcac tactgtgcac    38700
gtggggttgc accagcaggt acatggatgg cacgggcggt gccgggtttc tcactggcgg    38760
agtgcaagtg gcaggagcgg gtgggtagac tgaccccgtg gtggtgcact ggggctgggg    38820
acgtaagaat gttctcacat tcaccttaaa gcaggtcaga aggtcagata cagagttagt    38880
tgtagaaatg tgtgtgtgtg catgtgggga aatgcacata gagatgtttc taaggcctgt    38940
tagctgattg gctccagagg caatacccca aataatgaga aagcaccaac atcagtatct    39000
gctccccagc atcttgagta ctgacagtat tctgcggaac aggagccaca ctgcgtctga    39060
ggaatggcta attctagggc tggaatgcag gtgattggcc tgcaggtcct tgtggtgcta    39120
gacagcaagg aaatgttcag ataaatggct ggggcaggt taatggacat aggagccaac    39180
ggattgagct cccagtggcc agcaagctgt aacaactaca ggagctaaag ggataactta    39240
gtattacctt gatacatagt gtgaaaatat acccatgatg tatgctgaca tacggagact    39300
ggatacataa atctaatggg ggaggaaggg caaaagtccc cgaaggatta acaccaggta    39360
atttgttgtg attacccttc ctctaagaag gtgaaactta acacctcatc cctgaatgtg    39420
```

-continued

```
cctggcctca gagtcatggc aggaattgtg ggcgaccttg agtttcacag cgagtgtgta   39480
gacagactac ccgtgacgtg attcatgcaa cttttctgca tctgaattaa aagccatgtt   39540
ctgtgaacaa cagcagctca gcaagaacac tgagggcgca cagacaggcc acgaggcgga   39600
gaacacgctc tcagacgccg tgtctggtga agggcttctg tcacgagcac acgtgaaact   39660
tacagctgag cgacagcaac gaaagcagcc agtcagaact gggcccatgg cccgagaggg   39720
gagacaaaga agagagacaa ggtttgcaac ttggtttttc atgagggaaa caggaaacag   39780
cgtgatgatg agactctgct actgatctgc tacaaaacac tgaaagagta gaacttcggg   39840
catagagtgg accgaaatca cctctcttca gctttctgga aggaatgtgc atagcgacaa   39900
gtctggaagg cccctgacag tctcccgggg gtaagacaga caccatggga tgaggagggg   39960
ccgcccagtg tttatctaaa tactttggat atttatgttc ccaccagtgt ctgcgtggga   40020
aggtttctgt caccttcaca catccgtctt tgacactcct tggatttgct cacagagcag   40080
ggtttcatgg cagcttcgat gtcattagga tgtatgcgtt tctattgttc ctttttaacg   40140
atcacttggc cccactttct agggcagcag ccacctaaat ggctttgtca tcatctcatc   40200
ccagccctgc ctcccagtcc ctcagggttt ctgacacact caggacatga gtggtcacac   40260
tgtgtctctc acacagtaac acacggccgt gtcctcagat ctcagactgc tcagctccac   40320
gtaggctgtg ctggtggacg tgtctgcagt caaggtgact ctgccctgga acttctgtgc   40380
ataatttgtg ccaccgtctt cagggtcaat tcttcccacc cacccaagcc cttgtccagg   40440
ggcctgtcgc acccaagcat gtagtagctg gtgaaggtgt atccagaagc cttgcaggag   40500
accttcagca aagcccagg cttcctcagc tcagccctg gctacaccag ctggacctgc     40560
gagtgggcac ctggcgacaa gagacacaac tggatgagat acccatcgac tggttcccga   40620 tccccctca tcccagagcc tggggagccc ctgacctgca gccactgcca ccaggaagag    40680
ggctccccag ctccagtcca tggtgagggc tgtgcgctgg ggcatctgtg ggggagaggg   40740
aggggctgag tggtgctccc agggctcaga atgtccatgt ttaacaccgg acacctcggc   40800
ttgtttgcat gttcatgagg ctgaaaactt tatgctgatg acctggacca gcttgggagg   40860
gagcaggtgg gggccgaaag ggccctcccg agtaggaggc tgagggtcca caccctcacc   40920
tcgctggagg atgtgtgtgc ctgccacctc cctgagctct gtaaagggag cgcctcccgt   40980
caggagccat tctcacctgg ccgggtcctc gtcgcgaacc caccctcgag cgactcggag   41040
accctgagcc tgctctgggc tttcatagct gagcgacgta ctcctgggat cagacagcct   41100
tccactctgc ctttttgaat taataaagct gtccctgcct cccagatcct ttctactgag   41160
atattaggag cctgaaaatt ctcttttaaa tgtggttccc acggactcac tgagtcgtgt   41220
aaatgcctcc gatacttgaa gacacaccag cagtccttgt cgaattcaca gtatagacgg   41280
aattttgaaa aaagaaccca ggtgctcata ggaaacccct cacacccctt ctgcacctgc   41340
caccgggtct gtgggcgtga gggggctccc gagcgcccct gcagccctac cctcactgtg   41400
cagggcaggg acccatctgg gctcgcagga gacgcgtctc ccagggcctc tggtccagtg   41460
ttcagttcct ctgccatgat gtcagaggac actttcagag acactaagct tttgatctct   41520
tctttcagtt aatgaactgg ccgcaccagg ctggcatgct ctgcaggatg gggccctcct   41580
tccctggagc tgccagatgc actgacgcag tcaacacgca aggcgactcc ggggagaact   41640
ggaggggtgg gggcctctta ctccttcagg ctcgtctgta tgaaggtcac agctgactat   41700
gtctgcgggt ataaacccag gtagcttaga gcccactcca cacgtacctg ttcagcaatg   41760
```

-continued

```
cacccggaca cacacacacg cacacgcaca cacacacgta tgcgcacaca aaccacgcac    41820
acacacatgc acgcacacgc acgcgcacgc acacgcacgc acacgcacat gcgcgcgcac    41880
acctacacac ccacgcacac accccacgca cacacacatg cacgcacacg cacacccaca    41940
cacatgtgca catgcacacg cacacacgtg cacacacgca cacacccac gcgcgcacac     42000 acgcacaccc acatacatgc acacacgcac acacgcgtgc gcacacacac acatgcgcac    42060
acacccatgc acgcacatgc acgcacacac ataggcacac acgtgcacac acacacgcac    42120
acactatggc tggtatttac agctctggcc gcagatttgc cctcctccct gtatgtgact    42180
tgctttctca caaggaagag aagaaatgtg attcaaccag agagctggaa agcgcgctgg    42240
cttacctgtt cccgcagcac caggagcctt gtagatgcct gggtggaagt gtccaggctt    42300
ccttgtgagg gttagacccc ctggcccagc cacgccctgt ccatgcagcc agcactgacc    42360
cccgacgtgg ggagggtccc cctagaccca cagccccagc tggtccccat tgcagaggca    42420
cagccaggag gctggagggc aggaccttga aggacactgg acaggcggt ctcccagcag     42480 aagagcccct catgcaaggg gcacctggcc agctgggggc ttttctgtgg agtcgtcctg    42540
cccctcaggc tctcatgctc cggcccggcc tcacctgctg gggatttatc agagcaccac    42600
caacctgggg aagccaacac ctggcctcac ccccagtcca gccctcctgt ctcaccccag    42660
ggaggggagg cctgagaagc tctcatgggg gtcaaggctc agtacaagga aggccaattg    42720
tggggccaca gacacgtcac ctgccgcata cctgcccgca catcgatggg gtctggttga    42780
caacagggtg tgtgtctgac ttctcactgg gatgggagag ccttccagga gtcttccttc    42840
cccccagact tagggagatg tgactgacag agagccccca tgcgcgtaag gtgtgcaatg    42900
tggtcctttg acaggtgtct gagctgtgac atgtttacca ccatcaggtg agcttgcaca    42960
cccttcacct cgcatgaccc gcgacgtctt gttgctcctc ttgctgtggt gggcgtgata    43020
cagctcagcc ctcagagcga ctccagagca ccaaacacag cacttggaac cctagtctcg    43080 gggctgcgc atctcctgac cgccagcatc tccccactgg ctctgcctca gccctgggcc     43140
cgccctctgc tctgcgctct gctggggacg tggagggcct ttccacgcct ctgctggcca    43200
ttcacgtgtc ttctttgccc aggtgtcggc tcaagcctct gcctgcctgt ccttggggtg    43260
ggctgggcca cttgctggct tgcttctgag gagcaggagc tctccgtcat gctttagatg    43320
ttagcctctc atcagacgtg cctttttgcaa acacatttcc ccgttccgca agggcctttt   43380
tactccgttg gttcctcctt ttctgtgcag aagctttta ggttggtgtg gtcacgctcg     43440
gtgatgttca cttttgttgc ttgtgccttg gggtcatgcc cccaaaaaat caaggcaaga    43500
tattcaggag ttttcatcct aatattctgc atttaagtcc ttaatcaagt ttgcattcgt    43560
tgttgtgaat ggaggaagag ggggtccagc ttaactcttg gacacatgga cattagtttc    43620
ctcaacacca tttattcaaa tgaatactat ttccccattg agcattcttg agattcttgc    43680
caaatgtgcg ctgaccctgc acgtgagt gtgtcctggg ctctctgccc cgttggtctg     43740
tgtctgtgtc tgcaccagcc ccactctgtg cggacatggc tttgcagtga gcttcaaacc    43800
aagagctgtg acgcctccag ggccgttctc actcaaggtt gctctgtttg gggtcttctg    43860
tggtctttgt ggttcggcac aaatgtcaag gatctctttt gttgttgaaa tcccgttggc    43920
ggtttgcagg gacggcgctg caggtccagg tggctggtgt ggagccgacg gcacggcagc    43980
gctgactcgc ctcgtccgtg gcgcgggggct tcgttccgct gactcatgtc ttcttcggct    44040
tctcctcagg gttttacagg tttggggtcc gaagcctgtg cttcttgatc aagtgtgtgt    44100
ctaagggttt actgtttctg atgctgttgt aaaagtaact gtatccttta attccttttt    44160
```

-continued

```
agaaagttta ctgtgtgttc agaaatgcag ctgacttttg tgtgttgagg ttttgtcctg  44220
aagcctcact taggtcatta tctctagtgt ttatctggtg gcgcctgtag ggttctccgt  44280
atacaaggtc gtgtgcgatc agcagacgaa ggcggcttcg cttcttcctt tccgatttgg  44340
agcccttcat ttcttcttct tgcctggttg cctggctgtg gaaccctgag tcccggcacg  44400
acgaggggtg gtgcgcgtgg gtgcccctga cctgatcctg accttagagg caagggtgca  44460
acctctcagg gtcgcagtct cagctccggt tctgtcttgc gtggccttcc tcacgctggc  44520
gtggcttcct tctatttgtc tggagttctt actgtgaaag aaggcgaact tcggtcaaac  44580
gctgtccctg cctctgctga aatggtcaca agactttttg tcttttgttt cattgatctg  44640
gtgtattgcg cttattggct tggagatgct ggcaccctct tcgtccacgg gacaaatcgc  44700
agctgaccct ggcgtgcgct gtgtctagtg tgctgctgag ctcagtgcgc tgctgttttg  44760
ctgagagttg ctgcgtctgt gttcaccagg gtcactgatc agtagttctc ccggcacact  44820
ttcatctggt tgtggtgttg gggtaacgct gcccttgtgc agtgagcctg ggagtgttcg  44880
ctcctcctca gtcttttggg agaggctgag gtgaactggc atcacttctc cttcagcgtt  44940
gggggagttc agtagcgaag cctcctggtc ctgggcttct tgtggagacg gctctgatga  45000
ctgttccagc cccttacgtt tggttggtct actcagactc tccgtttcct cacctttcag  45060
acttggtgct gcagtgcagc tccctgatgc tagtcctttg actgattggt cactcatccg  45120
tcttgaacga acacagtgcc cgctgcgtga agcacgcccg gagaaacgcg cagatgagga  45180
gccgggctgc tgtgccgctg agccccctgc gaggaagccc tcgctaactg accgctcggg  45240
tcggaccctg cttccctctt ccctccagtc ccggccttcc tcctcgcgct catgctttaa  45300
gtttgtgatg aagcatgaaa actagaaacc ctggacaccc cgcccccaga ttctaagtca  45360
ggccgagccc gggccaggcc tgtgcccctc gaccacgacc tcgtgctgtg gccctgggcg  45420
cgcggtgtgc cctgccttgt cctgtcagct cagtgctgct ttcccagttc ccagaaaggc  45480
cggtgctgag gtgcattctg cagtcacgat gagaaccgca gggctggtcc agccacgatg  45540
ctgggtgtgg ggtgggggcg cttggaggcg gggctggcta gctttctctt gggtgagtgc  45600
ctcaggcatc ctagccaagg tctccatcaa tgggcagagc atcttctgtt ctgcctgtag  45660
ttttacaggg gttggaaggc tgacgtttct tccccaggct cataatatgt cacttcctta  45720
atttggtggt cctgtgagat ctcacatctg tggctcctcc tgagaggcgt gcaccagcag  45780
gcatggagac gaccagagac caagcgcaaa tgcagcactg accatcggct tttgctgctg  45840
tccccgtgct ccttggcttc ttggaggagg tccgctgcct acactccacc agcgcccagt  45900
tgcaggcgct gcggcgcgtc ccaggcacat ggcaatggca gcggcttccc ctggtgcaga  45960
cccctctacg cctgcgtttc tcaggtcac cgaataccc ggagcagcca aggtgccgcc  46020
gcaccaggcg tcgccacgga gctttccggg agcaggcggg ccgccaggtc tcgcacaacc  46080
accatctttt gttcctgctg ggggctcctg cagccccaga caccggaccc ccgagatcgg  46140
agactgatgg agggcagcat gagcccccag gcaggtaggc aagtggcgtc agccttctgc  46200
acaggacacc cgctgctgcc cagcctggga gtggatggag tgctcatctc tcctgcgggg  46260
tccgacaggc aaaggcaagt ccctttaggc ccgtatgggg agacccctc atccgatgat  46320 tttggaaaca atgaggaggg agtgaaacag cctatggctg tcccagggtt acaggagag  46380 gctggcaaca cgaggaagaa cccaccagtc atgaagtggc caaggcggag gggaggaaca  46440
aggggcagca ggacccgagg ctctcacagc gtccgcgctc ctgcgcggcc tccggacggc  46500
```

-continued

```
cggccactgg agggacgagg ggtcgggcaa gagccagcaa ctttgctgag aaagccagca    46560
gacccagaac atgtgtgccg gcgtccccag gggccgtctt gcctggggtc tgatacttgc    46620
ttcttttatg gtgcagagac gggaggtgag ggggtaaagg ggggaggctg acaagttgct    46680
gcgggtgctt cctggctccg gccagactcc ggagcggatg tgttcatttc ctccctcctg    46740
cagccgctca cgggcaggcc tggccaggct gcttcccggg agcaaacaga ggcctttggc    46800
ctagcgctca ggcacgtggg cagggttccc ggagacgggc cgttatgtgt gttttaagct    46860
acaggtgaac tccctttagt gaggaacttg cagcaaaggc aacagaatac caaggttaag    46920
tgaaagaaac aaacgcagac ggagtcgagac ttgtccgtcc ctgttccaag gcggcagcgt    46980
gacgttgaag tagagtaact acctattttc acatcgcgca ggaaacaaac gtgctgccct    47040
tgaccgtgac ctgttcgtga gtgtccggtc ctctgtggac aactgcagat ctgtataagc    47100
atgtgtgaaa tgcttgctct cccacactgg gcaccagcag ggccctggt gtgcctggcg      47160 ggggcggggg tcagcgcaag cacaggaggg gacttaccag gtcccggaga gacccgcaca    47220
ggattagagg ggaaaccccg ggggctcaca gtcaagagga gtttctgttc tcaccagctg    47280
gagcgagaaa gaacgaaata aaaccccac acagaacact gggggtggtt gctcagtcag      47340
cccacacgaa gcttcagagc aaagccaaca ggagcaggaa gcgtgctaag cagagcaaga    47400
cacgagaact gaacctgttt aacactgccc aagacctata aattctacgt aaagtcaaca    47460
ctgcctggct cccgccgccg aaggggagga ggcgaggtgc tcacgtgcag gaggagagcc    47520
gtctgcagaa ggcgagccgg aagtggcctg ggtgggagct gggaggcagg cagtggtgct    47580
aaaagacgca ctgagctcgg atccctggag gaaaggctgc acatgccgaa cagaggccgg    47640
cccctgctcc ccgctccctt cccactccct tgctaggcct cacagacgca gccctcccac    47700
ctcccggtca gcccacctga gctcacgtcc aggcccccct actgcctcgc ctgtggccgt    47760
tacctggtcc ctcaggtgac cgccggggg tgggtgctag cagccccggc accctctgtt      47820
ctcagtatct ccctgggagg aagtggccac tgcacgtggc gcagacctgg cctcactgag    47880
gaccctccct ttgcctgttc tcattggcag atgccccacg aggctggcag aaggcctggt    47940
caccctgaga gcagccctct tgccgctggg actctgggcg gtgctgggac tctggacgcc    48000
ccctcatggc gctgcagtgg tgtagactga cgggcacagc cggctcagaa gccggaggtc    48060
acaccccacc gcgtctgcct gcaaacacca cgacaagaag ctgccttcag tgcacgtctc    48120
gcccacctga agggaggcca gtctctgcct ctcctgtttg gctcatcagc tggtctcggt    48180
ttgctcctgt gctcagaaga gcctctaccc catccgacgt tgcagactct cctagagttt    48240
tcatcaagtc acagtttctt atgttttgtt tgggaaaaaa tctcagccat cgagtccaca    48300
aatattggat ctgctgcatg ctgtgtctcc tgctttgttc tgttagcaca cgcagggctg    48360
ctccggccgc ccagctgccc cgcgtgcctc ccgttccctg cagcaaaccc ctgtgcctgt    48420
cccacacgag ttcccaagtc ctccacactg cagtctgggg gattccccag cttctcaggg    48480
agtgacggac acgtgttgtt ttgtgtcaca aaaagaagca agtggaatta ctctgtgagc    48540
gggccggtgc aagcacctga cgcacaggta caggtctgca cgtgtgcaca gaccgccggg    48600
agaccgcgtc agagaaaaca agacgctccc ctccagccct gctgccggcg tctctcccca    48660
cgaagccaaa gcccgcgccg gagagggcaa accgtcttac agcttccgag tcgccccatc    48720
tgcgtgggcc ccgcgtgctc aggataaagtg acagactaag cacgagaaga cggggagcca    48780
caggcggtcc cctcagctca ggtgtgaccc accggatagc ggcttccacc ctcccgtccc    48840
acgtggcctt tcaaagtgtg ggcaggttaa ctgatggcca ataccacccg ccgaggatga    48900
```

-continued

```
aagcgggttc ccgaggcggg tggggacagg aagggggtgg tctgttcttg gccgtgtgtg   48960
tagcagccct gtcagttcca caggtccctc gagatacagc ctccttagtg cgggctggag   49020
agtggagtgc agtgacctca gcctggaggt gagcaacctg gaacagggcg gcaatcacac   49080
gcccgctggc aggagcagga ccagcagcgg tcagggaccc ggggcttccc gagggcaccc   49140
acaacaggac agactccaga ggagcgcctg cagtggctgc caccggggaa gtctcgcctt   49200
gggccgtgtg tgagccccag tgagggctgt gcgctccggg cctggggccg acttgaccgt   49260
gggcagagag caggtgagag tgcctgtgtg gggcactggg gcaacaccag ctgtgaggtt   49320
tccccataaa gtttgtctgc agaagctgga acaaaaggga aggcagggct gatggaggag   49380
gggtcctggg ggcctttttg tgtgtggctg aagggcacag tgtgcagggg agcagggcct   49440
ccctcgccag gggggcagag cagccggacg tgaagggtga acgtgagaga aggtgacgga   49500
ggcgtcggtc gagcaggctt ggccacaggc cccccgcct ggcaacgagg cgctgcgcag   49560
gatggatggg cagagggcgg cccccgcccg ggggcacagg gtgagagccc agccttgccg   49620
gccaaggcag ctgctggggg cgctgggcag gggtgtgcct gaagccgcgg ggcctcggcg   49680
acgcggggcg tgcgttatgg gccgtgcctg agaggaggaa gcgggtgccc ggtgccagcg   49740
gcagtcccat cactgtcagg gcgatgcggg ggaagacggc tttcaaagta agctgagagc   49800
tgccggtgtg gacggtgcta gggtggaggc ttcggaggag gctagtgcct ccaaggggcc   49860
gcaagcaggc ttcgagggc ctctgggggg ggcacacaag ctcagcagga gcagcagagt   49920
ttggggtcca cgggtggcgg cagccagctg tccctagaga cagacagggc tgctttgccg   49980
tggggtgggg atggaccagc tgaccaggca ctggggctg ctacccgtgc cctggcgggc   50040
cccgccgctc ccacccactg cagtgccggt tgaggggctt tgtgctcctt cggctggcgc   50100
cttgggccag gagggtctcc aggagctccc cgatcggtgt gcaagagtgg agcctcaccg   50160
tgggcctcaa gggcttggga gacactgagg ggggcccgga cacccctgag ggaggcaagc   50220
ccttctgggc tgccttgctc ttgctctgag tgctaaggcg gagggagatg ccggtcaggg   50280
ggcagtggga gggcagcggc aggtgagcag aggtcagcac ctgagaaccc ctgtgtcggc   50340
agacggaggt aggaaggcgc ctgcaggcgg ggccaagggg ttacaaaaga gcctggggct   50400
cttagaccgg gaacagatag gcagaggga ctcccatctg aattaaaccc cctcttcctt   50460
tgccagcaag actgggcgtt acagggtgag gcaggaggac agggacccct gtgtagccaa   50520
gccctcgctc tgcacagaga ggctggggct gggccgccaa cgggaggggc cgcgcctggt   50580
ccaggcagtg tgtgcaggcg ctccgtgctc agcagcacgt cacacgaggc cagacatgag   50640
gcgggcgtct tccaaagact gcaccccact cagaggactt ccagctgagc tgggcctcct   50700
ttaaggaaag aggaaagagc tctggtccga gggcagagca gtagggtgct ccctgtcctg   50760
cccgaccgac cgtcagagct tcctcctgct cagacacgtt tcagctgcct ccttgggtcc   50820
tgattccccg cagaagctgg gttgtggtct cagttctagt ttggctccga ggagcctggg   50880
gccaagtttc acagcctgtc ggacacccca ggagagagct ccaaccctgc ccatgtgctg   50940
tcacccctcc cggctgcccc gttgctggca cagggcctgt gtcagcctgt ccagcccag   51000 cgctgccctc cctcagtgct gcagggcaca cagaccctgc gggctgctgc gggctctcga   51060
gacggggctg gagccaggct ccagagcagt gtgttctggg atgtgggttg gctccccgtg   51120
ctgggaacgt ggggtccaga gctggctcag gaggggaagc ttcccctcct cccgaagcca   51180
gaggagactg gaagttagat gttcctctgc acctgcaccc tctctgtgag ggcaccgggc   51240
```

-continued

```
tgggctgtgt tcccatgttt ggccgggaag ggtcaagagg ttgggccaga gcccttgaca    51300
ggcacagggc tccctcctac gtggtccaga gggaggatgc agggacccgc aaacccccaa    51360
gggttgtagg aaaaagcgtt tcattggccc tgctgcagag atgagggcct gggaccacac    51420
ggctgttctt tggtccgcac gcccagggtc ggtgatgctg gccaggcttc tgaactcaca    51480
gcttcactgg tgccgggagg ccacccgccc gtgtatgcag ggctcacctg tgaggtgcaa    51540
ggctgggagt ggccggagtc aggaaagggc gacagctggg cattgagtcc tcccagcagg    51600
agacgcactg agggcgcaag gccacggcgg tgcctgggac tgtgcacagg gctgtgagga    51660
cgcagcctgg agcccacccg ggggaggtgc tgggcatcac ggggtggcct ccgggctccg    51720
caggcttgtg gctcacttct tgtccgggct gtctcctctc tccacaattc ctgggggtca    51780
cagggtttct aaagctcaga ggtggaaggt tccagaaaca cttacccacc ttcaccaggg    51840
ctccaggaag tgagaacccc ggggaccagt gggagaggct gggagggggc cgctggccac    51900
aggctggacc cacgtgggag cgaggaggaa ttgttggagg aagggctccc atccctcccc    51960
aaaacctctc ctcagattca agaggggctt ccctggcccg ggcccagcct cagccccttc    52020
tcctgggctc tgccctcttc ttcacagaca cccagctccc gccaccaaca cagggccgcg    52080
ctgccgggca gccagcaccg cggtcactct gggctggggg ctacttcatc aggccacgcc    52140
ccaggaggaa gagcccctg ggcagggccg tgaggacggg ccacaccggg gcacagggcc    52200
acggagccag acactgcact gggagggccc acagcaagca gggaaatgcc caggagagct    52260
gcagccccac ggccgctcgt cagggtcctc agctccaggg gccctgccgg tcaccttgtg    52320
gctccagagg tgacctgcag gagatgcaag gagcagtcag ctcccccgg ccctgcctgg    52380 agtggcctca gtgggaagcc cgaggggcag ctgagcacca gtcctggaag gggtggccgg    52440
acactcctgc cgtctgcaag ttcacaccat ggggcagacc acaggctgg agcgtcctct    52500 gtccagaccc agcgctgagg acgggggggc cgacccgtcc acactgagcc tgcacacacc    52560
atgaaccctg cgctggactc caggcactct gcccacggtc cacacagggt cagctagacc    52620
agtcctgacc cctcatccag gagccagggc ccctccccc ccaggatgag ctgtgaccac    52680
tgcccacttg tcatctttgt gtaacaagct tgcctctccc gtggagccct ggctcggccg    52740
ccagggcctt gtgcagagcc ctcccccacg ccccagcctc tcgggccgca cagagggtaa    52800
ggggtaaaat cggcaagagc ggctgctgtg gatggtggtg agacggggag gggacgcgca    52860
ggcgctggtg tggggtccgc gcaagctgct cctgggaaat tactgccacc gcatccctcc    52920
accctgagca tcttccgtct gctgttcctg aagcagctgt gccccgccca aagctccaga    52980
aggcctgcac agaggggccg tgcctgtgga gccaaagccc agccagggca ctcgccccag    53040
cagcccggcc cccgtcccgc tccgggagca gagggcagct cacgtctcca agcgccgggt    53100
gtggctagca gctcggggtc tccacccaca cagctctggg gtgacctgcc gactcacaga    53160
cccgggcatt gccgtgcgag ctgctccagg tggcagaggg acgtggaaac ggccatcata    53220
ggaaacctgc ccccacgccc ccaaaaggag aaacgggctg atctgcacgc caacaaagag    53280
ccgacccggg gaagccggat cccgtccggc ccctcgaacg cactcagacc aggactaggg    53340
ctgtgcagag cgcgccctgg cgccagacgg gtggcggccc gtgatcctcc cagtggagga    53400
cagacccact ctgttagcaa agtccatccg acagaacccc tgtgaacccc gccagacgcc    53460
agggtgcggc cacctctccg ctccacgctt gaggggaccc tgaaaagttg acggaataca    53520
ttttgtattt aaggccggat gagaaaatcc aagcccaacg tggtccctac ccgaactggg    53580
ccctctctcg tgtgctctga gccctgcgtt accggtcagc cacagcttct gcaaccggaa    53640
```

-continued

```
gtgcctgctc ggctgtgcag ggccttcttc ccctttgctc tgacgctagc aagctaatga   53700
gcttctcagg agtgtgggct ctcccagctc tgcagggtcc tggtgacctg cggctggctc   53760
cggccacgga tcctcactca acctcgtgca gaacaccagg tggcatgtcc acgtgcgagc   53820
ctttgtccca aaaacctgtg tgactgtgcc ttcgacttct accaggcgga gccatccccg   53880
gagcttctga gactgtctcc cgggttataa tcctcagttt cgctcaaatc taatcctctt   53940
tttccttctt cacttgactg ttggttgggt tttcatcggc caggtccagt gaacaactgg   54000
gaggcccccc ccgctctggg ctcagcagcc cccaccctgg agacgtggtg ctgtgctccc   54060
acggacccct cccggggctc ggcagaggag tcctggtctt acacactaga agtagtgggc   54120
gggacgctga ccccaagtcc tgtctgtgtg tctagcacat ctggtgggac ggccctcaga   54180
gagcgctcac agccgtggtg gccacgcagc aaagtcacac ttggttggtc ctgggaccag   54240
gaggagcact cgggccagcc tggaggcgga cgctcgaggt gggagggcca ggccggagcc   54300
tccaggccga ccacctgacc ggaaaccacc cactccgtgc gggagcatcc gactccaacg   54360
tcaccatgtc atctgtgagc cgcaggagaa ggctggcgac cccctgcacc caaagggagg   54420
gcccttccca aggtcagctg ctgggctggg ttactggtca gtcccctacc tgcagcccca   54480
aagatgcagg ggtgtcccga gtgccccag caggcccagc agacacagga accgcgtgg    54540 ctgcggggcc gcgtccccac acccacatct ggctcccaca gccccgcctc aggcctgagg   54600
accccgcaat ccgccacagg ctcctggcac gtcggactca cgcccaggac ccttgcagct   54660
cgactgcagg cagagggccc agagctccct gacagccgct ccccgaccac tcccagggga   54720
ccctcagtgg gcagcccacc gtggacaggc accacctgcc ctttgccctc tgaatccctg   54780
acccacgtgt gcccgtcccc aaaaatggcc tcgctgggtc ccagcctggg aggccccggc   54840
tgcccccacc gaaaggcaga ggcacagagt ctttggaagc agagtccggg agccgttccc   54900
actggaagct tgggcattca ggccctctcc atcccagtaa ctactctcgt aaacacggac   54960
acgggaggac cggctcctgc gcaggtgccc ccggcctgag accctgctgc tgggacgcat   55020
tcatcccgac tcaggcacc acacacccag ggacgtgtcc tcgtcctagt gaccactttc    55080
cgcacaagtg ctgccgggtc agcctcgcca gcctcggcgc ctttaagccc cctcagctcc   55140
tggcctccag agacactgcg ctcgcagtgg gcacggagtc ctgactccac ccccgcatcc   55200
atcctgggcc ctcagcgcat ccacggggtc acccttcctg gtccgtccgc ggagccctga   55260 gcccacccg cctgcttctg cggggcccgc ccgccacctc tgtgcacacg ggagagactc     55320
ggctctcccc tgctgtccac agcgacggtg tgaagccagt ttccaccact ttaatggtcc   55380
aggccctgga cagtgaaggc agagcctggc ctttgagacc cctcacaggc caggccctca   55440
ggccaagccc agctgcacca gggctccaag gtcctcgctc acccagggat ccgacctcct   55500
ctggccggcg gggccctggg cagggtcgtg agctccccga ggaggagggc cctctcacgc   55560
gaggacaggg acaccccgac cacgcccagg gtgagccacc cgtgaccagt gctgtgaagg   55620
ggacacaggg aggcccccac tggcccacag gtggggatgg gcccagccat cgcacccag    55680 tcagcgtccc aggcccagct gactgacgta agtcacaggc gagaacccaa accactgtcg   55740
gcgtcttcca ggagtcgtga gatgcggca ggggagccag accctggctg ctcacgccgg     55800
ggacatggaa actctgaggg ggcccagtca gcagactgga cacaaccaga agcccctgc     55860 accgggcaga cggaccacca cacggacctc ggtggcacc anggctgcct gtgctggaaa     55920
ggtgggtgcc tcgtccccca tgaagggttg ggtcagagtc accccactc acccgagcac    55980
```

-continued

```
acagccgaaa cccactggaa acgcaggatc tccacctcag agccggcccg ggccagcaag   56040
ggtgggcacc gacacaccac acagacggac ggaggatttt gagagggtgt gtgtcactgt   56100
gacatactat agtggtagtt actactacac ccacagtgac acagccctg cccaaaagcg    56160 ccacccgaca tgcccgcagg aagtggagct gggcgtgtgc agaacaccca gctcctggcc   56220
aggaagtctc cccctggggc agaggcgggg tgatgcacag gagcagctcc ccgatgagaa   56280
ggaagaggcg cactgagaca caggcccctt caaacgagac ggatgcccgg cggggcaagg   56340
cactttgtgc gggtgtctgg aatccccgag cccctgacct gggcccacca ggagggagcc   56400 gggggggctgg acgcgagaac acagacttgt gcacttgatc accttcagtg tttaccctgt  56460
gcacacaccg cacctggaag gggacttcgg agtctgatgg aagggtatct taagaacata   56520
ctgcctaagg gtgctggaaa ccgcacgaag gcctggacca cggattttgt ccctgggga    56580 gttgtggcct ggggcatggt accccacct gggaacatgg accaagggcc cagagcagtg    56640
cccacccact gagacttcac agcaaaggca tcactgggc ctccaagtgg ggacgccaag    56700
gcgcagagcc tccaggaaag atggggggcc ggtggggcag gggccccaac aaagggccag   56760
cccttcacct ccagaatctc aggggggaact tgaccaaaat ggacgaggcc agccacagcc  56820
tgggcacccc caacagactg tgctgggcca caccgccgtc cccgtggttc tgggatggac   56880
cagaaacgga gcacggggcg tccccgaggg agcacactga accagcctgt gagctggcct   56940
tgagacaagt tgaggccgtg ggacccaagg ccacgaccac agagcacgtt tgcagcacgc   57000
agcaaacaat cgctccatgc acgcatcgat tgtgtaagat ttatgagcaa agaaacccag   57060
accgcgcacg tgctgacagg aaacaggtaa aagcaggaca ggtgcgtcgc aggtgcgcac   57120
ctcctgtggc agtaaactgt tgttaacccc ctggtgtctc cggctgcagc ctgtctggcg   57180
gtgtggcaac tcctcgtgca tttttttcgtt cgggtcgctc agctcctaga accccacgtc  57240
ggcctccctc ggctggcaca gccagagcct ttaggcctga ccatgatccg tgacccacag   57300
tgaccaccaa gtagatgccc agaggccatg aggggccaca gagggtcagg ctgggccgtg   57360
ctccgggcct ggagccgtga gggctcagga agagggcgcc ctgcactgcc acagccaacg   57420
tcatcctcgc aggggctccg gacgctcagg aagccacccc agagtgggag cagtggggct   57480
gtggggccgg ggaggagagg cagccggacc ccctcggctg cgcaggcgcc acgtcctgct   57540
gaggctgcgc agggctgcgt cccggggtgg aaagtgcagc tcggacctgg aagcccaggg   57600
tggcagcagg atagacccct gcctgctcct ggcctccctg gatggggcac cagcaggccc   57660
ctggaggaca gaaggccccc aggcgaccca tacacagttt gggggcaatt tgtcaaccca   57720
ggaggccgtc atcgtgggac gaggctccaa aatgggcaca gacaccaggt cactgggctt   57780
ggccttgcct ctgggcctcg gcacacggcc gggcatggtc cccgtgcccc tgccaggaga   57840
ggcctcccag gtgctcccag caggacatct gcagcccga gcacgacccg cagcctccca    57900
gggctctgtg tccatcactg gtcagcctgt acatcccagg tctcccgccc ggcagagggg   57960
gttagggcgt ggccctgtgt cactgtggta ttactactgc tcaggctatg ggtgttatga   58020
ccacagcatc acagcgccca gcaaaaaccc caccctggg agtcagagac acggctctgc    58080
ccctaggatt ttgagtgacg ccatgtaacc ctgggtagga cggtcaccac aggggtgcag   58140
atcggcaccc agaccacctg gggcagcgag accagggagg cacccccagc acaccacccc   58200
ccaacatgcc gggcgggcca gtcaccaaca tcactcctgt ccaagcccat cagaccataa   58260
agccgcccac atctcagcca gactcgctcc acggggctca cccctgttga cctccccaac   58320
accaggaggg tcccaaggcc cctgtccacc ggcatccggc cagtggcctg ggacactccc   58380
```

-continued

```
tccctggggc acctgggggc cgtggctgga ggcacagaga ccccactctg caaggaccct    58440
gtgagcctcc atctctgggc aggggcgtca cacaggaaag gctggaccgg tgagctggca    58500
ctgcccccgc tttgcggaga ctggacctcc cggccacacc acccatcgaa cagcaccccc    58560 acccccatg tgctatcata ctggttgggg gccctgccct gcaggtacaa tatgggagag    58620
tctgtcacct ccaggggccg ctgatggtat ttggtttggg aaacgctctt ccgagaggaa    58680
gggaggaccc atgtgtccac atcctggcgc tggcctcact ggactgtccc gcagagccca    58740
gccgtcctcg ccaggggggcc cacccaggac cctcactgca cgtgtgcact ggcacataag    58800
gagacctcca gaagtggttg cccccagaca cccgcctcca cctgtcctca gtcagatcca    58860
ggcacggacc ccccagcctg tgtgagaccc ccacaggaga cgggccagcc ccccagggca    58920
gcccctcagc ccggtccccc tggacccctg agaggacttg ggccctcccg tttccctgtg    58980 cccaccccctt cagcgggggg cacgcccgcc ctccctgggg agacggtggg accagtcccg    59040
accacacttg cagggcaggt gctgggcacc tgtgcagaca gccccactgg acgcctgcac    59100
ctgggcctcc agcagggaag gactcggcca gaaacagggc tttttgccaa ggtctctcct    59160
actgtgttac tatagcgact atgaccacag tgacaggccc ggcagcaaaa acctgctggt    59220
caggaggcca ggcctcaggg ccacagagcc cagacctttg gcctccaggg ctgctcctgc    59280
tggcttggcc cacaagcttg tgtccaggca cagtagctga gggcttcaca gggctctcag    59340
gtgaccaccc gaccccccac agccacacac ccagagccca gcaagagggc agaaaccacc    59400
ctggctctcg acaccccccac ccaaaggaat caggaaggat ggagcccaca ccaggcaagc    59460
cagcagaggt caagctccca agggcaggcc ccagacaccc tccccgtctg cctggaagcc    59520
ggacaagcgc acaggcctgg acactggagc tgggcctgta ttcggctgca taggagctcg    59580
ctcgctgagg gaagtgggca gggttcatgg agggtgggag catctcccag cccagtgcca    59640
gtcgaggagc agggttgtgc tggctctccc gagggcatgg ccggagctgc cctgtgctag    59700
aagccttccc agagtgagca gcctccggag caaggcccgg cccaccctcg tctccttcca    59760
agagcaacag catggccatc cacccacccc gtctcagccc tgccagggcg ctggggctgg    59820
gctggcctcc cgacccgcca ggtccctggt gaaggatgtc gcccaggggc acccctgcct    59880
gaccctctgc tgggctactt agggtccggc ccatcctctg caggctctgg cggtccccca    59940
catccagcct gcctaagcgc ctgccagccc agctccctcc cggggcccat catgagccac    60000
tcaagcaccc tgatcactac ctcatccctc ccagcccacc ccaggggcct gcagactgca    60060
gaccccagtg ccaaccccag ctactgggca catgcccggc cccaaggcag ctccagctcc    60120
tctgcagatg cctggaccct ccctgtcccg gggaaggtcc tcccactgac ccagcctccg    60180
ggacccaggc cctgctattg tcacgggctg tcagtcaggg gccatatgac ttcagcaccc    60240
atggcgatgc tgcccacagg gcgagctggg cactgcccca tcatcaacca cacccctccgg    60300 gcctcggtct ctgacctcag acctggcagc tcaccccttt gggtctgggg tcctcgaggc    60360
cgctgacctc tggcctctgg cctctggcct ctggctctgg agggataggc ctgctcaagc    60420
aggaggcctg agctctggag gggaactgca gggctgagtc acacaggctg ttgtggacac    60480
gcagtgtcca tcatggtctg aggggcagtg ctggggtcag ggtcagatga aacgagggtg    60540
caacctgggc ccccacaggc aaagcctgag gggccacagt cctggggcca gcacttgtgg    60600
gacagcacag agccaaggtc cagcacccaa gggattcagc tcagtgggtg gcccagctgt    60660
cagggcagat ggagcccagg tccagtggcc acccacatcc caggggacca tgagtgcaga    60720
```

-continued

```
gccccaggct ggactccaca gacctgtcac aagtacaccc ctcttcctcc catcagcccc      60780
cccatagggg ctccatcggc acccctccac agcagggaaa ctgaggcaca ggccaggccc      60840
acccagccag tgaaggggag gctgggagcc ctgggaggca gcacagaacc ctacctgcac      60900
caggccacag gagccacccc cagagacacc ctgcccccac cctgagcctg caggtagggc      60960
aggccagtaa gggggctgtg gccctggccg ggatagggtg agcagctgtg ggctgtgtgt      61020
ccggccccag gccctagtcc tggcctcctc ttcctcccct cggacctcca ggatcccctc      61080
cgtgggaaga ggaagtcaca gaggatttag caggaggatt catcacagtg agactacggg      61140
ttggggtacc actgtggctg gttacatagc aaataccagc cggcacctca cctccagggg      61200
cagaggctgg agtggggtgc tgctcagggc ctgaacccgt ccaccaagct gaccctgcca      61260
gagctccgtg aaaccagccc acctccccac caacccgggg tgttgtcctc tctctcaact      61320
ccaatctccc atcacccagc acctagcagg gcaggtgtgg acagagtggc caggtgcagg      61380
gagtggcgag ggcagctgca gggtccaggg gatttcagct caagatgccc ccaacccgc       61440 tgccccaggc ccacccctgg ctcagaggag cgtgctggag gggagacact ctcatgctac      61500
gagcaactgg acccagaagc ccctgtgtga gccctctgcc tctctgtcca gtgggactcc      61560
ctcccacagt ggcatagtga ctgaccagct gggcagcagg cccttggcat ccaggacgga      61620
ccccacatgc agaggaggcc tggagccaga gggagctccg agagccggcc cagcaggacg      61680
ccaggccacc agacctgggc tcagactgcc actagggccc aggacagcca agctttgccc      61740 ctgaaggggga cattttctat ggccacagtg caggctgggc acagggacct ctgcctcata      61800 gcccacccccc catgcggctc atcctgaccc tggaccaagc tgaaagcacc caaggagtac      61860
cgcacaggga gtccccgccc tccttcaggc aagaccaacg ggttgctgaa ccccaacagg      61920
ccaggaggtt tctgatcctg tctgtgtcat ggtggtacgg tagtagctgg taccacagtg      61980
acacacccag cgccagaaac cgccagccca agtggcctct accagggagc ccgactggat      62040
ctgaggtccc ggccagcaga cggccccaca ccccaacccc acattctcgg gggacacaag      62100
ggtcctgggc caggaggtgg gctgcccccc cccagcagct ttccgcccca ggtgccctga      62160
cggattctgt gccggcctgc ggaggcgtgg tccaccctgg ggctgggtt cagttgcctg      62220 gggacactca ggagacctgc ctggagccta gagcccaggc aggctcagac tcaaagggca      62280
agctgctggc cctgtcctgc caccaggaaa ccctcaccca gcagcccact cctcagcacg      62340 gaggcccccca ggccagcagt gtgaccgggc attctgagca gccccgagtc acagtggaac      62400
tggtggcacc tacaccgtaa gaaaggctgt ggcttaaacc cgcccccagg tctccggggg      62460
tccaggcccc ggctagaggg cagagagtgg ctctccagcc aggcactgtc ctcagaccct      62520
tgggtgaccc ctacagatgc ccctcggtgc cccatttcct ggtgagacta gggagctggg      62580
ctggtcagtg ggggctgggc cctgtcccca cagccccgct gtggctccca gaccctggc       62640 cagtgctatc tcgagtgtcc caagctggag tgtcccttcc taacaccact ggccctcgt       62700 gcattgtcca gggacacaga cacactcaga aggcctaggc tgggctggcc ccatgcgtcc      62760
accaggaccc agacctcccg tgctctgccc ctcgcccggg gcaggctggg gtgccagctc      62820
agcgggagag acaccgctgt gggccgggac ccaaccaggt gtcaggcccc tttgctgaaa      62880
gccctgccag gcagccagca cagaaggtgg tggtcagttg tcaggccacc aggcacaggg      62940
ctcctagctg aggagggccc aggaagacca ccctggagag ccttcaccct gctcccacct      63000
gcagctcaac ccactgccct cccctcgcgg gagcctctgt ctcagctcgg tggacttgcc      63060
cacggcagac agcggggcta ccccagccca cagcaggacc ccagaagcct gaggcccccg      63120
```

-continued

```
tggggcaggg cagggtgggc tctgcatcac agaaggggcc accaacctgc acctgcccac   63180
ctgtcacctc caagccttct ccaggagggt ctggagcccc gacttggggc gggggctcag   63240
ggcggcactc accgagctcc ctccttgaag aggtgaagcc caggagccgg gcacacacag   63300
gccagcgctg gtcaccggtg gggccacagc ctgaggacag cccagcccca ggcagcctgc   63360
tccctgctgg gagacgcccc cccacccacc cagccacccc acacacagga agcagacagg   63420
ctccaggcca gcccgggcct ctcaccgcag agccgcttcc tgactcccct tcctgccctg   63480
ccccaccccc aacacacaca ggcctgggag gttgtcagtg agttttaacg tacagcctgg   63540
atggccctgc gcagccttcc tgtgatttgt tttccttcat tcttcactca gtccttcatc   63600
catttatcac ccagggcatc tgagcagggc agggctgtgg ccgcagctgg acactggcca   63660
cactgctgtc ggtggacttg atcacaagtg tagcttgagt ccgtgaaggg aggcacaggg   63720
cacgacacgg agggtgggtc tccctgccca atctggtctg gtgtcagtca gggtgacttc   63780
ctggaggagg tggcactttt agctacagtt ggagacaagg agcaactagg gcttggtgac   63840
aggactgggg ggtgagcaag gacaccccaa ggttctgcct ccacaggcat gggggacaca   63900
gggactcagc tggagaagcc agaggcttca ggccccagga ggactgccca cggagccaga   63960
ggcagggctg ggccaccagg agtcccagct gagagggcca cagagggggt gcggcatgcg   64020
cagggacctg gtgcagacga gcacatccgc tgggccgggc ccccaccagg ccctggagac   64080
catgcttggc caggagagcc cccagcaggg ccgtggctcc ttggacctga acaagccagc   64140 gccctgccc ctgggcgggg gaaagggtcc gagggaggac tgggatggca ggggggcacc   64200
aaaggccctc ccacccggct ccgggtccct cagattgtaa ccgagcagga tcctattgtc   64260
atcagtgacc acttggcatt tgtaactgct taactgtgca gcaatttaaa gcatgttttg   64320
ctgagcagcc ttgggctgga gaggaggcag gactcgggcc caaccccctac cgacacctcg   64380 gagaagctgt caggtgtcct gtgcacctta tggctcgtaa ctcaccccac tgcacatgtc   64440
tgcattgttt atagccccgc ggggtttctt tgggttctgt tgtcccagcc tgggcagact   64500
ctgcagggag aggtcccagg cctcagccca aaatgccaga ggcatctatc aacctgacta   64560
taaatggcac acgtttttct ctggagcact tttccctgga gcccttcct aagcaccctc   64620 gttccaggta caagaatatt aagagagtcc caaagctgga ggaggacttc acacccagca   64680
gagggaaggg ggccctgcat ctgcaaaacc aggacaactt tgccacaagc tgctacctga   64740
gcggggttgt aacagaagag aacaaatctg actccacatt agatctgttc ctttggcttt   64800
aaccctgtgc cctgttttct aggcttggtc ttgccagctc tgcgcctttt gtagaacaat   64860
gttgccttca gcctgaaata cacaggagag ccagttctca aggatattaa ctttcgtgct   64920
tatataaaga taacaagttg cagaataaaa aataactctt gttctgttag aggttttatg   64980
ggggaaccgt gacttgaccc ccgtggacag ctacaagaac aaagaagttt gcaacaccca   65040
accacacccc cttccctttt tagtataaaa ggagcctgaa ttctgactgg agcaggatgg   65100
ctctccaaca cattagcctg ccatcctctc gctccgccat cttcccgaat gaagtcgcta   65160
ctccttgccc cagcacctcg tctcccggtt tattggcctg tcgtgcagtg agcagagcgc   65220
gtttggactc ggtaacaggg tctctatgga aaccagctgc cccttgaact tttactataa   65280
aaccccgccc ccctccccag caggctcgca gcccggaagc atcagcccgc cgtgacctcc   65340
tttgccggga gaaggagtac agctgcccct tctgcttcat cacaacctct gtcctcaagt   65400
ctcgattcgg tgagtggagc gcggaggctg cgctttgaca gcaagaccat ctccatcaac   65460
```

```
ctttatgcac aagggccccc cagaatctca cggagacgca gattcagatg cccaggcaac    65520
cctgagccac tggtgcacat gaaggggacc ccagagagcc ctggaagcgc ctggactagc    65580
gcactgctca gacagcaagt tgctgggaag gaggctgctg agggcgcctt cccccaccct    65640
ccctagccac ccgggggtcc cccctcaga aagcccggcc cctcacaccc caccgcaagg      65700
cctcaaaagc cccctccctg accacacagc cgtctgcctg gagctgagcg ctgacctccc     65760
gaggtccctg cagtgacccc actccgagga gccagggtgc agggcccccc ttccctcccc     65820
tccatggaag ccccagcctc agagtgacat gcacactcac acgctcaggc acacgcacgc     65880
acgcacactc acacaccccc atcgccctcc ctctccagtc cctgtctgcc ccccgcccca     65940
tgtgcagccc cgtccctgcc attatgcggg ctgtcctcct ctcccccccag ccgcctgtcc    66000 caggcccgcc tctggactcc ccagcgccca ccgctctgcc tccagagtca cagtttgcag     66060
tgtccgccca acgcccgccc tctctcctct ttccagctac ctccctactg cacctacgac     66120
cctccccact gcacctccgc cctctccacc tacttgtgtc ccctccacgc ccctcccctc     66180
cctgtggcca gtcctggtgt ctcctcgccc aacaagggca atgcaatcct tcaccccccg     66240
gcccggccca ctcaggggac tgtgacccag gcatcactct gactggtagc cacacaccaa     66300
ggtgtgcagc tcccactcca tcactctctg gggcagacac cctggtgctc cattgcccct     66360
gcccccatcc ttcccgacac agtcctctgc agcccagggc agccacatga cccttgcctg     66420
gacagtgaga agagacggcg gccggcaagc catcgggctt ccggaaggcg gttcgctgtc     66480
tgcccatcct aggatgcaga cgcagtggtg tccaggttct tgtcccgtca cagaaagaat     66540
tcagacatga gagccggggg ttaagaagta aagtggggac ttactgaggg agggacagga    66600
ctgtctcatg gggagcgcgg gcagctcagg tgagcagctg ccttgtttct ttggcaagtt     66660
ggttacacag ggtgtagaag tgaacgggcg gaatattcac tggggagggc aggtttaggg     66720
tcgtgttccc ggatcatcat cccagctccc ccttcccgtg ggcaggaggg attttattt     66780 cctttcttag tctggatcgg aagtgtcacg gtggcggtgc gtgatgggga cttctgatcc     66840
gcaaggctga ttttattgaa atgagggcat aaagagcaaa ggtcaccttc agacactgga     66900
gattcctgcc tttctcacct ttctttgttc ttctccaggc cacttgtcac cccaaaaagc     66960
gtgatccctt atcagcccag aggttcctgc ttttcctttg ctgcccaggg acccctgctg     67020
cccacgtgat gtgtgcttcc ctgcgtttgg cctgtgcccc tccttcctgc ccagttcctg     67080
ccaactggcc cgcgtccccc tttccctgct catacccagc tgtctgcctg ctctaacagc     67140
tggaggtgag cagcctctct gcccaccaac taaaggcagc agacagatgg gacttcagtc     67200
accgctggtg tttgcggctc ctctgctgtc acatgggagg tccaccagat cgaagggctt     67260
ccgccacatc cagcctgact gagtcccacg gaggggcgtc cgacaacctt ccccactgcg     67320
tcctgtccag actccctggt cccaggcagc cctgtctgcc cacctgactc atgtcctctt     67380
ctaattcgcc agaataatag aaaagacaga aaatagaaac agaaataata gaaaagagcc    67440
ctcccacctg ctcgccggcc aacccgcttg cacgtgcgcg gggccctggg gggccccagc     67500
cacaccagac agaggtggcg gcgtgctgtg caaggggcag tacgtgggcg cacgcacccg     67560
ctgttaccat aacacgaaaa gagcagtgtc tatttcaact tacagatttt gtggtatgag    67620 tttcttttt gttaaatgaa tgttatcact taattgaaac agcagaaata gtgccaatta     67680
gcagtaagta acagcaggac taattaaaca aatggtatgt atttacaaat ctaacaagac     67740
agagggtaca gctcagtggt ggagtgtgtg ctcagcgtgc acgaggtcct gggttcagtc     67800
cccagcacct ctgcttgaag aagtaaataa ccctaaatcg cctcccccctg cagaacaaac    67860
```

-continued

```
aaacaaacaa atccaacggt gtgtctataa tgtctctctc actctcggac ctgccagttt   67920
actgtaacat ttttttaaca ctctagagct ttatttacac ttctcaggct gtgttatggt   67980
atgttcttca gatacataaa agcaagactt ttccagtggg ggcgtaaaca cagcagggcc   68040
agtacagaca ttcaatagca gtaacagtca cgcctctgtc ccatgctcac gtctcaccct   68100
cagtattccc agcagctggg ggatgccctg cgcctctgcc ctgaaggcag gcagccgtca   68160
gcctcagggc cacccgaccc tcgactggcg cccagcctgg ccgcgccgat gccggcggca   68220
tccaccgtgc agacctcgag cctccaggcc aaagcgtctg agcgcacagc cctgggctca   68280
cgcagtcctt ggggctgcag gcgcggttcc cagctctcca agcgcgcact ctgtgaccga   68340
ggctggcgcc ggtggcgcct gcccctccgc gaggcccttt ggttcacaag cgcttcctgt   68400
gggctccctg cgtctgaaca tgcatcgggc atcctcctga gttagacctg agagtgtctc   68460
agagcaaatg ggcttaaagc agccatttga gcctgtgaga tccaagctgg aatccaagca   68520
agtcgtggtc ccggcagaag actctacgac gcgagcctca ggcccaggcc tgccctcccc   68580
cgcgtgctct ggcctccagg ccgtctgcgc tcctgtcccc tcctccctgg ccgtgtaaca   68640
gggaggagca agcctggccc cacgttgcat ctgttccttc gggtctcacc ctctgctctg   68700
taccctgtgc tcagtcaggc tggttctgcg ccttttgtaa aggaatgctg ccagagcctg   68760
aaatagacag gacagcccgc tctcaaggct ctgacctcta agggtagaac actttcccat   68820
tcacatagac aaaaactgca gaacagagag caacgtttgt cttgttggag gtttgcaggc   68880
acaccaggac ctgacccacg tggacagctg caagaacaaa gggttctgaa accaagaagt   68940
ttgcaacaac caaccacacc ccccccctt tttagtata aaaagagcct ggattctgac      69000
ttggggaaga tggttctctg ggacatgagt cccccatcct ctctatgtgc catcttctct   69060
gaataaagtt gttactttt gccccagcac cttgtctctg gattattggc ctgtcgtgtg     69120
gcgagcagaa cgagcttgga cttggtagca gcaggcatcc tccatcctcc tctgctccct   69180
ctctcgtccc cgctgctgac caggccatgc ctagcacagc acgtgccctc caggcgtccc   69240
tagaccagct catctggtcc tctggttcaa atgccattta caggctgatg agtccccaga   69300
gaagggtcta gccccggccc agtgggctga gccacacacc cacccgcctg tgcactgacg   69360
ccaggccaga gcacaccact tcacgccacg ctgccgggca cccttcagcc tgcctcagga   69420
agccctccat gctcacagac actcggggca cacgccttca tgctgtcctt gaagttcctt   69480
tgctctcccc cgtgtccaat ctgtccaaag cttccatggcc ctacacagcc ccctgcaaaa   69540
agcctaagtg gggcccctca cctacctgtc agccccacgc cgcccctggt ctccgctcct   69600
caaagctgca cagcgggcct cccaaatccc tgccgggagc cctccggcgg cccccgcgtt   69660
ctcagatgga gtcccacagt ccctctaagg ccatcgcgtg tcctgcccac cctccccaca   69720 ccactcccc ccttcccaga aaagatctgc ccaggacggt ggcactggtc acatcacctg    69780
ccactggcag ggggaggcag ccaagagtcc agaaccagtg ttctgagaca cttaaagcaa   69840
agttctggaa agttcttaaa gttcccagaa aaaatggcca gagcagtcat aaataaacat   69900
gttttgttag agatacttga cttcaagaga aacaaagcag acacccgtgc acgaggggac   69960
gatctagcct gattcctaca aaaactgagt ttaccaatgc ctgcaaaacc ctgctaaaga   70020
aaacacggcc caagaatttt atgtccccaa aactagcaac tagcgttcaa acagattcca   70080
cacgtgcaca aagtcgggat tctctccttg agtccttcct tactgaataa actatatatg   70140
tacatattta tctatttatt ataagaaaaa caatttatct tcaatagcgt atattgtgca   70200
```

-continued

```
tactgaatac acatgaacac gtgcgtatat acacacacat actcaacgtg attgcatagt   70260
ctactgaaaa tcaaaattaa ttatttgaac aaagacaaat atccaaccaa gacaaaagag   70320
gaaagactcc gacacaaaag agacagccat ttaaagtaac acttaaaagc cgcaccgcag   70380
cacatgcggc tcccggaagc gggggagcac cggccccgct gcgcggaggc cctgtcgggc   70440
tgagcccgtt ctcggctcgg ctcaccagca ggaaggcggg ggggggcgc caggggcaaag   70500 ccaggcggag ggggagagag gctcaggtgt tgggggagtc tgacaagggc ccttgacggt   70560
ggtgcagaca gagccaggga accagtgctg tccccaggcc atcgcagctg agcctgaaga   70620
cgcagcgggg cgtcctgggc tgggctcggg aacagcgca cagaagtgct gcgggaggct   70680
cacggcagcg ggctgcccag gccagccacc cgagggccac acagccagca gccatgggat   70740
gcagaccgcc ccacccagcg acgagcgatg agcggggaag ggcggaaggg agcctccgat   70800
gcggaggcag aaacgtcctg cgttcaggca cacctcccca cacagcagtt tccccgatct   70860
tcccagaatc tgtgcagaag caaagtgtag accttttaa tgggaacttg cgctgtgtta   70920
tggaactgga aaacctgacc taagccccag aatccaaaac gtgtatgaag gggccagtat   70980 cacccccagcc ctgccagaac ggccgagtca gccggacaga gagaaaagca ccacctgaca   71040
tcactcgcag gtggggtctt caaaaatgcc gcagacgagc ttatttacaa aggagaaacc   71100
gcctcgcagg catggaacac acagtcatgg ttaccggggg aggggtggg gagggataga   71160 ctgggagttc gagatttgca gatcctgact actaggcata aaacagataa gcaagtttct   71220
tctgtagagc tcagggagct tttagtatct tctagtaact tgtactgaaa aagaatatga   71280
caaggaatgc acgtacgtac gtgtacgtgt gactgaagca cgatgccggc accagaaata   71340
attggcacga cactgtaaac tgactacacc tcaattaaag acaattaatt ttttagaaag   71400
aacagctgtt atgaaaaaga ccacaaggac gtgttggcga ggacgtggag aaaggggagc   71460
cctcgtgcac tgctggtggg aatgcagatt ggtgcagccg ctgtggaaaa cagtatggag   71520
gttcctcaaa atactgaaca cagagctgcc acgtgaccca gcccccccat tccccgggtat   71580 tcacccgaag aaaacaaaaa cattactgtg aaaacatgca cgcaccccgt gttcacagca   71640
gcactactta caacagccaa gacagggaag caacgcaagc gtccaacaag atggctggat   71700
agagacggcg tggcgtgtac gcaaatggaa tactcgtcag ccacagagca ggaacgctca   71760
cctgctgtga cgcacggatg gccctgggcg ttacgctgag cgaagcgagt caggcagaga   71820
gagaccagca ccacacggtc tcactcatac gtggaatctg aaaaaaaaga aaacaaaaat   71880
gaacaaacga aataaaacag aaacagactc cgatacagaa aacaaacagg aggtcgccag   71940
aggtggggag gggccggaca ggtgaagggg aattagggac acacctccag ccgcacgacg   72000
agtaggccac ggggatgtga agcgcagcac gaggagcccg ggcaggcacg ttgcagccac   72060
tttgccccag ggcggatggc tctgcgtcta ccgcggtgat catttcttaa tgtgcgtaaa   72120
cgtcgaattc ttgtgcagca cagcttccgc gcgccatctg tcagcgctgc ttcaacagta   72180
agtaaatgcg caaataagcc agcggcaggt gacggcaggc tgagcgggag gaagtgacgg   72240
acgccgcagg ggcaacggcg aggcccagca gcagcactgc aggaaacacg ctgtctgaaa   72300
aggaggatgt ctccttggag ttctggagtt tagcccttgt tttccaggac cagccggag   72360 ccagaatgaa ggcagtcgct cgggaagccc ttccgtgttg aggcggttca gagacgcagg   72420
cggcacgggg ccaggtaggg acgcagacgc accgcactgc cgctggacgc actctgtctt   72480
tgcggcgggg cgaatccaaa agccttcggg gtcacaacgc tcccgaggct gccctcctcc   72540
cgtcccaagg aatcgcctac aaacagcaag tcccgagggt tttgttcgtg aaacagtgag   72600
```

-continued

```
tcataagcct gaaccagagc agaactgatc aagaaaaacc agcagcgagat gcaccgcagg   72660 tgaacaccca ccagaaacac actagcgaag gatgaggaga gcgtcgcctg cacgggttga   72720
gaagatcacg ataacgataa cgaagcaact ggattcacaa aggaaagcac agctcccaag   72780
cgcaagggcg tgtagaagag accggccgct gccaggagga ggcggagggc ggcctggccg   72840
aactgcccac cgctagctcg gagccccag accagctgga accacaaggc tggcgatgcc   72900
cgaagcgtca cctggatgcc aaccaacccg agaaccgtgc accagcgggt cagacgcgcc   72960
gcagcacccc ccgcccccaa ggccttcaac accccttccc tgaaggccct cggggagttc   73020
gggcttggag cacgagcggc ccgctctcct agccaggcgc ctgcctttcc tccaccgcca   73080
ccggcatcag cagattgcct ttactgcacg cggacgcgca gactcgagtt tggttcagta   73140
acacgcgggg tcacgtgggg tcaaagtccc tgggagacaa ggaagtcccc ggcgtccaga   73200
cttggtgtgg gaatcattcc ataatgtgtg caaatgtcag ttcaccgtgc aacacagctg   73260
aagatgctgc cagtgggcgc agccggagtt ccaggccctt gtcccgtccc agaaagagtt   73320
cagagacaag acacagtggt taaaagagta aagtgaggat tgattaaagg ggggatggta   73380
cattctccag gccagagcgg gcaggctcag gggagcggct gccctgagtt tctttggcaa   73440
gttagctaca tagggtgtaa aaatgaatgg gcggaatatt cactggggag ggaagggttt   73500
ggggtcgtat tccctgctca tcatcccaac tccccttcc caaagggagg agggattttt   73560
gtccccactt agtctggagc agaagtgtca cgtctgtgct tgatggctac ttctgatccg   73620
caaggctgat tttattgaaa tgaggacata gtgagcaaaa ggtcacattc agacactgga   73680
gattcctgcc tttctcacct ttctttgttc ttctccaggc cacttgtcac cccaaaaagc   73740
gtgatccctt atcagcccag aggttcctgc ttttcctttg ctgcccaggg acccctgctg   73800
cccacgtgat gtgtgcttcc ctgcgtttgg cctgtgcccc tcctttccac ccagttcctg   73860
ccgtttggtc tgtgtccccc ttctctgctc acatctagct gtctgcctgc tccaacaaaa   73920
ctaacagaat cctgtgcagc aactttattt cagtaaagaa ataaatgggc caaaagcagc   73980
tgacactggg cagaggccac acgggaggaa gtgacagatg atctggaaca gtgggtcccg   74040
ggtgtcatgt tctgggtgga ttttctctgg ctcccgtgtt ccctgtcagg atgtggatac   74100
aactgaccaa gtgcacccct tgaaaaacca agtacccagg cagctgtctt ctgcagagag   74160
aaaggcttta ttgccgggca gccaagaaag gagacggggg acaatgctca gaagtaggag   74220
cagggccggg ggagggggtt gtgctgggaa tcgattggtg gaaagttaag gtacgtttca   74280
agagttctgt gcacagatac ggctgctcgt gccctgcatg ggccgtgtgt gcagtctggg   74340
ggagttctgt gtgttgcaca cagcggattt tcagcctctg acgtccaaag ttcatcatca   74400
atcatcctag tccctcaggg tgctgtgagg aaggggctga tctgtccaca tgttgtttcc   74460
agacctgagg tgttcggcaa agcaaacctg gggtctctgt taatcacctt gtttcccct   74520 aagggacttg agtgtgcaag ttgcagggtg tggtttcaca cccactcccc ctaaactgag   74580
ttcctctgcc aagcttgtga ctaatctctc tctccaaaac tttattccct ttcttgtccg   74640
acacctgtta ccactaagac tgagggtatc aaaggaaaca gaggatttaa accaagcagg   74700
accctgtggg gcctctgggt acaaaagcct ttccatgtcc cccgcttctc aattgcagga   74760
aaaaggcttc agactcctag accttccctg agttcctagc cagggaagtg aggggatgca   74820
gaaatgaagg aggagtcaag gaacagcaga gcagcaactg agcagggccc cggtctctcc   74880
tcaggggaga cacaggacgc tgtgcctttg agctcttctg caggaactca gccccaccgc   74940
```

-continued

```
ccaaggtgga ggatggtaac ttcgcaccga gcaccagctc tggaccccag gctggctgga  75000
accagaagcc tgatgagtga gacccctgga agaccaccct ggcacccca gcacccggtc  75060 aggggaaggg cacacaccct gcaggccagc cctccatctt cccataaaac tctccgctga  75120
agcccatcgg ggagtttgga cttttccaaag gcacccgtcc tcctcactcg gccctgcagt  75180 aaccccttcct ctgctccaga ctccgacatt tcagtttgtc tggactcact gtgcgtgggg  75240
cacacaaact tgggtttgac gacagattca tggagagtat tgccttattt caagatggag  75300
tttttgaatt ccactttaaa atatttttc tcgtccatta cttttggtag ctgattttgg  75360
aaagaattaa tttaggcagc attcaaaagt acaagtcatc aacaaggtgg aagtcaggct  75420
ggcctttgac ttcttaccag ctacatttaa caccagtgga cagtgaccag tgcccacagg  75480
accttccagg gaagacatga ggcccctggg agctgccatg caccagtctg tcctccgaga  75540
ataaaggcca ctggaccagg ggatgcaaac taagtgtcca tcggcgggtg aatggatgca  75600
gaatgcgtgg tatctatatg cagtggaata ttactcagcc atgagaaagg aagaaatcct  75660
gccattggtg acaacacggg tggaccctga aggcactatg ccaactgaga tgagtcaggc  75720
agagaaaaac agatgtgggg tcatctcaca aatgcatgga atctaaaaat ctgaatttgc  75780
agaaacagaa tagaaaggtg gttgggaggt gggcaaaatg gggagatgct atttaaggta  75840
cacacctgta ccttaaattc tggaaatctc agacacagca cagagattat aggcaacagt  75900
gatgtgtgta ttatagactt gagttatgct aggtcttaat tgttcccatc ataaaaaaaa  75960
agcaatgatg attatgtgag gtgatagacg tgtcagctaa aaccacagtg gtcatcattc  76020
tgcaacatat aaatgcacca gactagggga gggtgtagct cagtggtaga gcatgtgctt  76080
aacatgcaga agatcctgga ttcaataccc tgtacctcca ttaaaataag taaacctagt  76140
tacctccctc cacaaaaaca tacaaataaa taaataaaaa taaatgtacc aaatcaacaa  76200
gtgtgctcct taaactttac ataatattgt aaagtcaatt atatctcaat aaaaacaaag  76260
tgttttactg ctgtgagaat gtagtttggt gcagccatta tggaaaacac tatggagatt  76320
cctcaaaaat cttaaaacag acttaccctg tgatccagcg atcccactcc tgggcacata  76380
tccagaggga actaatttga aaagatacat gcaccccaat gttcatagca gcactgttta  76440
caacagctaa gacatggaag ccacctaaat gtccatggtg tatatagaca atggaatact  76500
actcagccat aaaaaagaat aaaataatgc catttgcagc aacatggatg ctcctagaga  76560
atgtcattct aagtgaagta agccagaaag agaaagaaaa ataccatatg agatggctca  76620
tatgtgaaat cttaaaaaaa aaagaaaaaa agagaacact gtgaactcat ctacaaagca  76680
gaaacagacg cacagacatt atcaatctta tggttaccag ggttgggagg ggataaattt  76740
gggagtttga gatttgcaaa tgttagccac tatatacaaa aatagattta aaaaacaagt  76800
atcttctgta gagcgcaggg aactatattg aatatcttgt aataaccttt aatgaaaaag  76860
aatatatgta tgtatgtatg catgtatatg tgtgactggg acgttgtgct gtacaccaga  76920
aattgacaca ctgtaactga ctgtacttca ataaaaaata ataataataa attttttaga  76980
aaagcaaagt gttttataaa aagtcataaa ggctaccgaa aacagtttga acaagcaaga  77040
atacaggaaa tatgtttcca taacgcccag catggtgcac ctgctagtgg aaagcttcag  77100
ctaccaacgt gccagggagg cggggccaag gttccaggga ggctggggcc tactgccagg  77160
gaggcggggc caaggttcca gggaggctgg ggcctactgc cagggaggcg gggccaaggt  77220
tccagggagg ctgggggccta ctgccaggga ggcgggggcca acgtgccagg gaggcggggc  77280
caacatgcca gggaggctgg ggccaaaggg cagccgtgga tgttcagcgc acttaactcc  77340
```

-continued

```
ctacagagca gaagcttcat aactgcccaa agctgggagg agggcagcaa acgtgggagt   77400
cagagcactg tgaactgctg cctcctgcta gcagctgggt gtccgaggac gtcagtaagg   77460
ccaagccaag gactgggagc tcagcgagcg agaccgcaca gcaaacacga agaacttgac   77520
tccagaggcc agagtctaca gtgggaggga aggaggacag gggaagaggg gggccccacc   77580
tgcttcacgc gtgtttcgga gagggccatg cgtgtgggtg aagaggcagc acagaggatg   77640
tcagggacac cctcgtggta aaggcgacca ctgcacacac agcagcaaag aaagacacct   77700
tgaaatgaaa acctgcttct gcaagtttaa aaaataggaa aatgcggcat aaaactgtaa   77760
accaggattg atgccaaata tatccacctg tcttaccaat aagtgtgagc agtctttaca   77820
tgcctgctaa aaggaacagc ctttcagact ggatcacaaa acaacagcca actctcccag   77880
cacgtgagag cttcacgcat cacacatcac acgagaagcg ctggcagacc tgactcgagg   77940
aatgccagga gatccagccg cttcctctgc gatacaatgt gaagctctgt gtccccggca   78000
gacgcctctc ttagatcggc ctcctgtccc cttggggaag gaaggctgtt agcaggtgcc   78060
aagtgccttt cgcaccaggt ccttcacttc ctttatctct taattctgcg agactgtggc   78120
aagcaagatg ctgttaccca catttttaca gatgagggaa tttgatgctc agagcattta   78180
agtggctttt caacgtaaca ctgacatcaa cgtggagcag actcacctag ggagccccga   78240
tccttccctg ctccaaggcg ggtgggtggg gtccacctac tgcagggggcc gctgggagct   78300 ggcgtggctc agagcagaca cagcaccgcc agcagaaaag cgattcacca caggggggctc   78360 attgcagtgg gccaaggact gtggggcagc gcgtctggat gggaaggcca gcgcatgtca   78420
agtcttcaga ggggggttct tcacgttctg gaagctgggg gaaccgtatt tcccgcttct   78480
gtccatccca aggcttcacc catggaacat ctacgaagtc cagcgctgtg tgggtggcca   78540
gacaggacag tggtcaccgg gagccttcca aggactctga gggcacttgg tgcttctgcc   78600 ttcccttttca ccacaggctg gaaactcatg acatggagaa aagctagcaa gctgcctcaa   78660
aatgcagagg gcttggtgat acaaacaaat gagtgaaaat aaattgtgca aataaatgtg   78720
cacaaataaa tgtgtgtaaa taaatgtgtg caaatgtatg tgtgcagcaa tgatggggcc   78780
gtctgtccgg tcctgtatga tgtgggtgaa tgcccagcgc tcttgccccg cctacggctg   78840
tggctcccct ccctggggac tgtcaaccaa gcattgacct tggcctgatt tactgtaacc   78900
ctagggcaaa ggaggggtga aggagatgtc atggtctcct gatcactgag gttctgttga   78960
acatccaggt cattatcctg aaggtgtcgt gaggaagaac aagatgggcc ccacattaga   79020
tctgctgttt tggctctcac cctctgctct gcttcctgtg ctcagtcagg ctggttctgc   79080
acctcttgtg aaagaatatt gcctggagcc tgaagtagac cggacagccc attctcaagg   79140
ctctgacttc taagagtata acccttccca ttcatataaa gacagcaagc tgaagaagag   79200
aaagtaacat ttgttctgtt ggaggtttgc agcgacaccg tgacctgacc cacgtggaca   79260
gctgcaagaa caaagggttc agacaccaag aaatttgcaa caaccaacca cagcccctcc   79320
cttttttagt ataaaaggag cctgaattct gactcaagga agatggttct ctgggacatg   79380
agtcgcccat cttctcgctc tgccagcttt ccacataaag tcgctcttcc ttgcccaac    79440 acctcgcctc ttgatttatt ggcctgttgc gcagcgagca gaacgagtct ggactgggta   79500
acaaggggac aggcatgtcc cactgtcaag gggatgcctc cctcaggatc tgaaccccaa   79560
gagttcctgc ttccatcact gaaaaccca ctgaggctgc tcaccccgt ccctgcagca     79620 ctgcccagga gccgccagtc taaaatgagg tgctcgtaca gcagctcagc ctccctcggt   79680
```

-continued

```
ctccgagagg aaggtgctcc cggggccgag ggacagcaca gccaggggag gcctgagatg   79740
gacacagcat cgttctggac gtggagacgt ggaatcagca ggcgcttccc ttcttccatg   79800
aagagccaga ctacagtgag attgcgtttg ctcctgcccc tcctttctgc ttccggccac   79860
agcagctact ctgccatcat gaaggaatgg ccaagacatc cccagagatg cagccaccac   79920
tccctgcccc ataacctcgt ccctgagcaa atccccgccc cacctcctca ccccgcgggg   79980
aggccagccg gccttggtgg ccccgttgaa gatcagacct tctgtcgcct ggagctggag   80040
gttctccttc gcacgggccc tgacaacacc ccagtcagtg tccttctccg gggacatggg   80100
gcacttagga gactcccgag agcttacacc cgctccaccc ctgcagaggg cggggggcag   80160
gcaccaggat cttttgttct tttttcgacc gttgtctttt gaaatgtatg gtgtgagttg   80220
gtgccacttt ttaaaaattt gcttgtgcgc tgtcatcttc ctttctggct ttcccatttt   80280
tgctcatgcc actgggtatg aagggtgggc accccgctcc tctcccttc ggtaacctct    80340 cacagccgct gctccacgac tgaagcagcc acgtgacctt gcattgcttc tgccctgaaa   80400
caagacgcgc tttttcctct tgcgtttgtg cccacaagga ccttccttct ggagtcaagt   80460
gcccagagac caggtccccg tcggtggagg ccagcagaag ccgagtctcg ggcacaaagc   80520
gctctcccct agaacacgag gatggttctc actacttgct gaagcacacc tgtgttctgg   80580
ccatctggtc taccactgcc ccagctctgg ggcaacggga ccctggagtg ggattcactt   80640
gccaagtcgt ggtggcactg caggttggag ggccgtggag ccccccaggcc cactagcagc   80700 ccctgccctt cgtcaaggcc tctgaccccc aggcagatgt tgggcgtcac ctctgactcg   80760
tccatctcct ggacgttgtg acccaggagt tcaaggagca gagtgaatgc tgctgccacc   80820
cgcctcccac cgtggcagac ctgagggcct ttccctctgg ctgctcagtc gcagctcact   80880
ggctattttc agcagcagct gcacggtgtg tgccgactct cacaaggcag ctgagtggcc   80940
agggcaccct ccctccctgc ctttagaagc tcagtcctca gctcaaatcc aagctctgct   81000
cagggaagcc aagccaagag acaccttccc ggtcacctgc tccagaggcg gtggggggtg   81060
ggggctgtga gaccacagca aaagccggga gaccaactcc acatggccgc ggggcccagt   81120
tctggccacc ccatacacag atccagatgc cacgccggca ctcactgggc acacaccagt   81180
aacatgcatg cccttcccct ggcatgtgct gtggtgggtg gaggcaggag cgagatccca   81240
gaactgggcc gtgggatgct gagacagcgg gaggggctg ccttgaggga gccctgccta    81300
caaactgtga gccgcccaca cagccccaga gggtcaggca gaggaaccgc actcccccag   81360
ggagcaggac ctcagcccac gaggcgaggg caggctcagg aggccatacc ccagtggtcc   81420 cacccaggt cttgccagct ctcaggccac agtcgctgct tcagagcaac agaccctgc     81480 tccttctcca cccctcccca tctcacctct cctcttctcc cccaatggcc tcctccgtgg   81540
gctcttctgg gcactcagtc cacagtgcag ccctcatagc tcaacgctgg ggtctcctct   81600
caccaccccg gacccagacg tgtccaccca ttgcccgtgg tcctggtgta tctgggggcc   81660
tcccagcacg cccgccggcc tgcctgaggc tgctgcgtct ggcatctccc cgcctctcct   81720
agacccaggc cggagctgtc ccaaatcctg aggcagctgc ctcgcagtca ccaccgctct   81780
tccagccctc tgtcccccat tcccccttcc tgcccactcc cctgtgggag cctccctgta   81840
cctgcaggct cacaaccctc tcccagcacc caggcttccg cctctgatgc cccaggccag   81900
cctgaatctg tcctccggcc tgccccagac agaagccgcc cttcctcagc ctctttgctg   81960
ggcacacagc ccccttaca tctagtcaca tcagaccacc taccattctc ctccaggcct     82020
aggacccagc ctctagatct cagcctcagc tggaatcaca cacacacaca cacacacaca   82080
```

-continued

```
cacacacact tcccctcccc cgggacccc aaggtctggg cgggtctggg cagggctccc  82140
ttagaccacc atgctccccc ctcgtaaccg cccccagcc cagggcatca aaagctgaga  82200
tccttcccaa aggacctgca gcccagggac agggcaggga cctgggactg tgggcacaca  82260
gtggcccgac actcggtgga cactcggtgc accctcagcc cctgggagcc cgacttccct  82320
ggaggactgt gaacacggag aagtaacaag gggctgctgc cggcaccaca gctgcgacca  82380
aagagagtcc cggacagacc ccacgggggc caggccgggg cagagcccgc cccccctggg  82440
gtcagcactg gcctgggccc ctgcccgctg ccctgcgggg gacacgacgc cagtgcaggt  82500
ggcctccaga cagccgggag gcacagtctg gaatttgctc ctatttctga aagaaaaagg  82560
cagccgtgca ggcagccttc aacgctttga ggattgttag cagatgactt gtagctggcc  82620
caggaatgcc tgtgagggcg ggcagggaga ggtctcccct gggctctgtg gcccacctgc  82680
cagcccttgg ggttttggct gagctgggaa ccgcagtgct aactggagcc acagtgactg  82740
acaactctac aaaaacttct ggccagagcc gccccagggc agccaggtcc ccgcccaag  82800 ggctcacggc caggtgcaca aggggtcag gtttccggtg gacaagagat ggttcacatc  82860
ccaggcaagg gactaggtcc ccggggctgg gggaaggggc cagtgcagca gcctgggccc  82920
caggtcgtgg ggagcccagc tgggatcagg gctgtggggt gagtggcgcc gagccttgga  82980 gcagcaggg ggcagggaaa gcgtggtctc gggggaccaa agcaagtcag gtgtcaggac  83040
gtccgaatcc ttggccagga atgatgtagg agggagccag cgggggcctct cctcaagcag  83100 agagcaggct tctggttccg ggggctcccg ggccccagct ccctgcacct gtgcttcccc  83160
cattgctggg gcacctgggc acctgggcac cgtgtcctca ggtgagccca gcgtccagtc  83220
tccagcctgg gggactgtgg gactggagtg ggctgagcca agcagtctgc tgtcccagac  83280
ttgggacagg aggtcagggg atggcaggag gtggggggac aggagaagca gcggggcaga  83340
ggccatgctg ctggaacctc gatcactggg gccaggcac ctggccactg tgtcctcagg  83400
tgagccttcc ctgcggctgc tctgcgtggg cgtccggcca ggtccctggg cagctccccg  83460
agcctgcctg cccgaggcct ggatgaggct gcggcccag gggacaggca ggcttctggc  83520
cccgttaggg gcagtccctc ggggctcaca gagctcctgg tggtgagcga gctcgtgaga  83580
gctgggctga gggaagcctg ggggacaggt gccggctggg aaggagaagt tgtgggcaga  83640
gcccagccag ggcccagctg ggggtttgtg cactgggggc caggcaagca gaccagtgtg  83700
gctacaggta tctcgaagtt tggggccagg gcaccctggt cactgtctcc tcaggtaagt  83760
acatcctttc cttcctccct catcgccctg ggatctgtgt ggccatggac agtgaggtct  83820
ggcccatcca aggggcccac gcaggtttat gtctggggga gagcagggac tatgtccctg  83880
tgcaatgctt tggacgcatg gggccagggg accctggtca ctgtctcctc aggtaagaca  83940
gctctctgcc ctcggtcctg ggctgggaag gacatttcca gagattcctg ggtctttgcg  84000
gggggcccag gggctgcttc tgaggcccta tggctgttgg tcctgggaga tggcgtctct  84060
ccagtggagc gcgggctggg cagagtgggc ccgtgtctga gccacagaga ccggggggcca  84120 gggctttgtg cggccaggtc gctgggcagg cggctcgggt ttttgcacag cacctaacgg  84180
ggcccgtggc gctgtgatga gtatgactac tggggccagg ggacccaggt caccgtctcc  84240
tcaggtgagt cttctcaagc ctctctcctt ggtctctccg agggtttttg ctgcgtttta  84300 gggggggaaat tagggtgtat gggtcttggc tctagagggc ctggagtctt aggaagaggg  84360
cctgggggcc ccaggctcac accaacaagg agagtccagg cgccctccct tcctgggctc  84420
```

-continued

```
tgcagccagg gccttctctg ctggtctcag ccacacttgg cctctgggag cccgaggtcc   84480
ccagccctgt aggccccgct aggtgtcata tgaggtggtc ccaagagctc agccggccac   84540
cagcatttgc ctggggtctt gacacagttg tcacaatgtg accccagtt tgaatactgg    84600 ggccagggca ccctggtcac tgtctcaggt aagattgctc tctgccctca gttctgggct    84660
gagaaagaaa tttccagaga ttccttggtt ttgtgggaga cgcggggagg ctgtttctga    84720
ggccgtttgt ctgtcggtcc tgaggagatg agtctctgcc ggtggagcgc gggctgggca    84780
gagtgggctc tgtaattgag ccacagagac cgagggccag ggctttgtgc gaccaggtca    84840 ctggagggg gctcgggttt ttgcacacca cctaacgggg cccgtggcgt tgtgctgact     84900
ttggttcctg gggccagggg acccaggtca ccgtctcctc gggtgagtcc tcatcccctc    84960
cccacttcca ctgcaactgg ggagagctgg ggtgtggggg tctcggtgtt agaggcacag    85020
gggcattttg gggctcagga aggggagtcg gggagaggct cctcgtgaac aggggctgga    85080
ggtgggcctc tctgccccag ggacgccctg gtgtggggc cgggcggagc ccttggctgc    85140
tctggccatt taattcgagc gttgccaggg gctcccgtca gcttttggcg gggtggccgc    85200
ttgagcttgg ctggatttcc gaggtggagt taggagtctg tgttttgtgg tcagatggcc    85260
caggcaggca gtggccgggc ttctgggggg ccagactgca acatggggtc tccagggcgg    85320
tcaggaggga gcggcgccaa cagagggttc tggggccctc tgggtttgtg actcagaggg    85380
tcacttgcat gtggtgccgg agacagtgtg ggtccccagg cagccgcggg gccgtgccag    85440
gcctccgagg tttttgtggg gtgaggctgg agcttccgcc attgtgatta ctacggcatg    85500
gactactggg gcaaagggac cctggtcacc gtctcctcag gtaagagtgg cccctccagg    85560
gcctttgtgt tcttctcctg tctgtggggt tttctgagca tcgatgtctg gtccttagga   85620
gggtccgtgt cccccaggtg gcctgggcag ggctgaccag gagaggatgg ggaccaggtt    85680
tcctggggat ttcagagtct ctggattttc tgacgccttt caaaaatcgg aatagtgcca    85740
gcattcaaga ggggtctcag gcaggaaggg ccaccgagag tgagccccag gacccccttg    85800
gtggccaggc ggtttggtct gtggcgggag agcttctgct gttgcggtca cagagtcggc    85860
tgagaggtgt gcccgacgcc agtgtttgca cacacagggc agagtggaat gctctctggg    85920
ctaggagctg cgctctgggc tagactgtac tgaaaattcc tcgttgcttg ggaagagaac    85980
agcctgggtg aggaaggaca ggcagagtct tgatcttggt gacagcaggg tgcctccctg    86040
aagcagagaa cttgggaggc tacagccgct gggctctgtg agaacagttt ctaagagaaa    86100
gggaggtgtt ccatcaacag gagtacttcc aaaatattaa aaggcaggat agctatgaag    86160
tggctcctga gacagatgat taagaaaatt gtgactttaa aatgtgagaa gttttcaagc    86220
agatgacttt ttttaatgtt taagtatttt aaattcttat cattcaatta acaaccatga    86280
accatgtctc tcgggagcca ttagttctga gttaggccca gagcagttgt gcggtgctgt    86340
tggcccctga tccagggctg agctttgagg ttaataaatt gagattatta ttctttaatt    86400
aattgatggt gttgagttag tcaagatggc cgcaggcaga gctggccacc tgcagcaggt    86460
ggcaggaagc ggcttcggcc gagtctattt taggaagtga gaaagcccga atggtaaatt    86520
tacagcttgc ggttgccagg gtggtttgcc cagcctcaca gcactgaaag tgctccacag    86580
agcaaaacaa cacctggata atttgcattt ctaaaatagg gcaaacatgc tgacagaaac    86640
agaaggttcc tgttttaact acttgaactg aactctcaga cttagcttat caactgctca    86700
cttatactca ttttccaagt aagaccttta agaaattgca tggcgaggtg cagcttggca    86760
atgcgttcct atcacttta aagcgtcagt ccttcacggt tgctcatcgc gagccgtccc     86820
```

-continued

```
ccagggtccc caaagcgctg ttttcacaag gactgtgttc agaggtcttg gctggtcgat   86880
cttctcttcg tgacgaagaa acgctctgct gttcagctgc agttgctttc gtctccgtgt   86940
tggtcaaggc cgctgctcag gtgtccacct gaggacgggc tttgggggaa acgtgtgtgt   87000
ccgtcgtgag ctgtttcggt cagacgtggg agctggtgca ttgagaggac gcccggtgag   87060
gttctgaatc agaagggcag gacaccctag aaggacagtc tgttctggaa ggtcgaccca   87120
gcgtctgagt tgaaggcgct ccggtggagg gccccagagc gggggccccg gcctcgccac   87180
agccggggct ctcctgggag ccccecggagc ggggagcggc aggtgcagtt tgtgccgccg   87240
ggcccctcgg ctgtccgtga atcagtcttc ttaatggacc tggaggaatc cttccatgcc   87300
agggacccca cggagcttgc caggggccag gcaccgagac ggtaagagag gcagccccac   87360
tgccagattt cctgctcggg acagcgcgta ggcggcgttt ctgctccact cggggggaggg   87420 cggtcttcaa cgcccgctcg gtgagacaga gactcgggtg aatccctcga ggggccgccg   87480
tccggctggg ccacgtctga ctttccctaa agaacaggcc aaggacagcg tggcgggggc   87540
tgctccacag ccccttaact actgccggcg tggctcccgc tgcttccaca gacccaaggc   87600
accccttacc acgtcctcgc ttaaatggac gcagtttaaa cgcagctttg ggtttaaggt   87660
ctttgccgtg tgtgtgaagg tggcccctgc cttctgcaga gtttatgata aagagcagaa   87720
ttgtgagtgg caacctcagg tacaatgcgt ttcctggtca tttttcaatga gggattttcc   87780 tagagggaat ttagtcaagt cgggactcac tttagactca ggagggagga actcgcgcca   87840
agggtaggtg cgcaggaagg cgaaggcagc cgggagacaa tccccggggc tctcctctcc   87900
gcgaagaagc catgctgcca gttccaggga gggacctttc cttctgacag tggccagtgc   87960
agctcctgaa caagatgtgc taaggagctg aaagcctccg ggcagcattt cattcagaca   88020
gcggaagggg ggtagcgact ggtgccgctc aggagccatg gccgctgggc ctgggcaggg   88080
atggaggagc tggggtaccc ggagtgaggg ggactccgag gaggagaagg aggaagggcc   88140
accaggaagg agttgaccct gcaccgagcc cagctgtgca ggactcctgg atgagatggc   88200
cttagctgag ccaggcgggt ctggcggccc caccctttct ggccagtacc atgagctatc   88260
aggacagaac cgggccgagc ctgagctgag atgaactaaa ctggattaaa ctgggcttcc   88320
tgagccgggc tggattaagc caggctgagc caaactgagc cgagctgagt cgggctgatc   88380
caggctgagc tggctgagcc aagttgagct gggctgagct gagctgagct gggctgagct   88440
gggctgagct gagctgagct gggctgagct gggctgagct gggctgaact gggctgagct   88500
gagctaggct gagcagggct gagctgagct gggctgagct gagctgggct aagctgggct   88560
gaactgggtt gagctgagct gggctgagct gggctgagct gggttgagct gagctgagct   88620
gggctgagct gagctgggct aagctggggt gagctgagct gggctaagtt gggctgagct   88680
gggctgaact ggtttgagct gagctgggct gagctgggtt gatctgggct gagctgggct   88740
gagctgggtt gatctgggct gagctgggct gagctgagat gggctagctg ggctgaactg   88800
ggttgagctg agctgagctg ggctgagctg ggctgagctg ggctgaactg ggctgggctg   88860
agcagggctg agccgtgctg gctcagctgg gctgaactgg gccgagctga gcttagctgg   88920
gctgagctga gctgggctaa gctacgctga gctgagctga gctgagatga gctgggctga   88980
gctgggctgg gctgagctga gctgagctgg gctgggctga actgagctga gctgagctga   89040
gctgggctca gctgaataga gttgggatga gctgggctga actgggctga gctcagctgg   89100
gctgggctga gctgagctga gttgggctga gctgagcttg gctaacctgg gctgagctgg   89160
```

-continued

```
gttgagctga gctgggctga gctgggctga gctgggttga gctgagctgg gctgagctgg    89220
gctgagctgg tttgagctga gctgggctga gctgggttga tctgggctga gctgggctga    89280
gctgagatgg gctagctggg ctgaactggg ttgagctggg ctcagctggg ctgagctgag    89340
ctgagctggg ttgagctgag ctgagctgag ctgggctgag ctgggctgag ctgggctgag    89400
ctgagctggg ctgagctggg ctgaactggg ctgggctgag cagggctgag ctatgctggg    89460
atgaactggg ctgagctggg ctgagctgag ctgggctgag ctgggctaaa cttggctggg    89520
ctgagcaggg ctgagccgtg ctgggctgaa ctgggctgaa ctgggccgag ctgagcttag    89580
ctgggctgag ctgagctggg ctaagctacg ctgagctgag ctgagctgag atgagctggg    89640
ctgagctggg ctgaacttgg ctgggctgag cagggctgag ccatgctggg ctgaactggg    89700
atgagctggg ctgaactggg atgtactggg ctgaactggg ccgagctgag cttagctggg    89760
cttagcttgg ctgagcttgt ctgagctggg ctgagctggg ctgagctgaa ctgagctgag    89820
ctgggctgaa ctgggctgag ctgaactgaa ttgggatgag ctgggctgaa ctgggttgag    89880
ctgagctgag ctgaactgtg ttgagctgag ctgggctaag ctgggctgag ctgggctaag    89940
ctgaactgag atgagctgag ctgagctgag ctgggctaag ctgggctgag ctgggctgag    90000
ttgggctgaa ctgggttgag ctgagctgag ctgagctggg ttgagctgag ctgagctggg    90060
ctgaactggg ttgagctggg ctgagctgag ctgtgctgag ctgagctgaa ctgggctggg    90120
ctgagcaggg ctgagccatg ctgggctgaa ctgggttcag ctgagcttag ctggcccgag    90180
ctgagctgag ctgggctgaa ctgggttgcg ttgagctggg ctgagttggc tgagccaggt    90240
tggattgagc tgagctgagc tgtgctgagt tgggctgagt tgggctgaac tgggttgggc    90300
tgagttggtc tgaactgggt tgagctgagc tgagctgggc tgagctgggc tgaactgggt    90360
tgagctgggc tgagctgagc tgagttgggc tgagctgggc tgagctgagc agggctgagc    90420
tgtgctgggc tgaactgggc tgagctgggc tgagctgagc tcggctgggt tgagctgagc    90480
tgagctgggc tgagctgggc tgagctgagc tgggctgaac tgggctgaac tggtccgagc    90540
tgagcttagc tgggctgagc cgggctgagc tgggctctac tgcgctgaac tgggctgagc    90600
tggactgaac tgggctgagc cgggctgagc caggctgggc tgaactgggc taagcagggc    90660
tgatttggtg agctgggctg aggtgggttg aactgggctg aactgaactg gaatgagccg    90720
ggttgacctg agctgggttg agctgagctg ggttgagctg agccaggctg agcttggctg    90780
agctgtgctg ggttgagctg ggctgaactg ggccgagctg agcttagctg ggctgagctg    90840
agctgggcta agctacgctg agctgagctg agctgagatg agctgggctg agctgggctg    90900
aacttggctg ggctgagcag ggctgagcca tgctgggctg aactgggatg agctgggctg    90960
aactgggatg tactgggctg aactgggccg agctgagctt agctgggctg agcttggctg    91020
agcttgtctg agctgggctg agctgggctg gcggagctgg gctgagctga gctgaactgt    91080
gttgtagaac tgggttgagc tgagctgggc tgagccaggc tgagttggtt tgagctgagc    91140
tgagcttggc tgagctgggc ttggctgagc tgggctgggc taggctgggc tgagctggct    91200
aagctgagct ttctgagttg gctgagctg agctggcgga gctgggctga gctgagctga    91260
actgtgttgt agaactgggt tgagctgagc tgggctgagc tgggcttagc tcggctgagc    91320
cgagctgggc tgaacttggt tgagctgaac tgagctgagc ttggctgagc cgctgggctg    91380
ggctgcaatg agccgagctg ggttgggctg gattgagctg agctgggatg agccggactg    91440
ggctgaactg ggctgagccg ggctgagctg ggctgagctg ggctgaactt ggctgggctg    91500
agccgggctg agccaggctg ggctgaactg ggctaagcag ggctgagccg ggctgagctg    91560
```

```
ggttgagctg ggctgaactg aactgcagtg agctgggttg aggtgagcca ggctgagctg   91620
ggttgagctg agcttggctg agctgtgctg ggttgagctg ggttgaactg ggctaagctg   91680
agctcagctg gcctgacctg gttaagctgg ctgagccgag ctgggctggg ctgcaatgag   91740
ccgagctggg ttgggctgga ttgagctgag ctgggatgag ccggactggg ctgaactggg   91800
ctgagccggg ctgagctggg ttgagctggg ctgaactgaa ctgcagtgag ctgggttgag   91860
gtgagccagg ctgagctggg ttgagctgag ctgggctgag ccaggctgag ttggtttgag   91920
ctgggctgag ctgggctgag ctgggctgag ctgggctgaa ctgtgttgta gaactgggtt   91980
gagctgagct gggctgagct gggcttagct cggctgagcc gagctgggct gaacttggtt   92040
gagctgaact gagctgagct tggctgagcc gagctgggct gggctgcaat gagccgagct   92100
gggttgggct ggattgagct gagctgggat gagccggact gggctgaact gggctgagcc   92160
gggctgagct gggttgagct gggctgaact gaactgcagt gagctgggtt gaggtgagcc   92220
aggctgagct gggttgagct gagctgggct gagccaggct gagtttggtt tgagctgagc   92280
tgagctgggc tgagctgggc tgagttaacc gtggtgaatg agatggatcc agtagaagtg   92340
ggctggctga gtccgcttga cctaaacaat atgacgcgct gcttcgggat ggttaaccgt   92400
ggctgaacca ggtgggtcta gctgggctga gctggccagg ctacaccgtc ctggctgaca   92460
ctgggctgac ctcagtgacc tgggcatgct gaggacaggc cgagctgagt ccgcgtcagt   92520
ctcgctgatg gcacgcacac ctttcctcca agcccaggca cccagggccc gactgcagtg   92580
tggctgagcc aggggcggaa gggctgggct ggcggggccg agagtgctgg catccgctgc   92640
atggcctcgg agggaaggca gggcgtgcaa ggacgtctct cacccctcc tcctcttctg   92700 ttccctcgcg ggtcctcaga gagctcgtct gccccgacac tcttcccct cgcctcctgt   92760 gagagccccg tgtccgacga gagcccagtg gccttgggct gcctagcccg ggacttcctg   92820
cctggctcca tcaccttctc ctggagctac ccggacggca tcgcggtcag tagccagagc   92880
atcaagacct tcccgtccgt cctgcgggag ggcaagtatg tggccacctc ccaggtgctc   92940
ctgccctccc agagcgccct ccaggggtca gagctgattt gcaaagtcca gcactccaag   93000
gggaactcgg acgtggttgt gacccccca ggtgagccgg gctcctccca ggctgggtgg   93060
caggggtggg agtaagccag cccacctgac gctctgtctt tccctgcagt gattttagat   93120 ctgccccca gcgtgacact cttcatgccc ccccgagacg gcttctctgg cacttccaaa   93180
cgcacgtcca agctcatctg tcaggccaca gacttcagcc ccaggagat ctccgtgtcc   93240 tggtttcgtg agggcaagcg gctggtgtct ggcttcatta cggaagatgt ggaagcctca   93300
aagtccaatc caggggacctt cagtgtcatc agcatgctga ccatcaccga cggcgactgg   93360
ttcagccagg ctgtgtacac ctgccaggtg gagcacagag ggatggtcat cgagaagaac   93420
gtgtcttccc agtgcaaccc cagtgagtgg tctggcccga gcacagcccc gggacagggg   93480
ggcccacaca cgcagtctgc agacatcacc ccagacctga ccagcagctc cctgagcctt   93540
ggcttcccag agcggccaag ggcagggagg gggctgtgca gggcagctcg gggagtgttt   93600
cagacatgcc cagtgtcctc ccccagcagg gcccggagtt cacgaggcac tcggcaaagt   93660
cagcccctgc tctttgggca gccctgtacc ttggcctgat ttcatgctaa ccaactgtct   93720
cctatctcca ggtccttccc ccggcatcga ggtcttcgcc attccccct ccttctccga   93780 catcttcctc aacaagtcag ccaagctcac ctgcctggtc acaggcctgg tcacctacga   93840
cagcctgaga atttcctgga cccgccaggg tgaaaaggct gtggattccc agatcattga   93900
```

-continued

```
ctccacgatc ctccccaacg gcaccttcag cgccacgtgt gtggcgtcag tctgcgtgga    93960
ggactgggag tcaggagaca ggttcacgtg cacggtgacc cacctggatc tgccctcacc    94020
cctgaagcgg agcatcttca agcccacagg taggccctgc actgcccctc ccctgccc     94080 gggactctcc ccaggctgcc tgggcctgca ggccccgtg ccccatgtcg tccgggatgg     94140
cccgcggccc gccccagctc accgctgtct gtcctcccgc agaagtgcac aagcacatgc    94200
cttccgtcta cgtgctgccg ccggcccggg agcagctgag cctgcgggag tcagcctcca    94260
tcacctgcct ggtgaagggc ttctcccctc cggacgtgtt tgtgcagtgg ctgaagaagg    94320
gggagcagga gccctgtcc cctgacaact acgtgaccag tgccccagtg cccgagccca     94380
acagcccggg ctactacttt gtccacagcg tcctgacggt gagcgagaag gactggagtg    94440
ccggggcgac ctacacctgc gtcgtgggcc atgaggccct gcccacttg gtgaccgaga     94500 ggaccgtgga caagtccacc ggtaaaccca ccctgtacaa cgtgtccctg gtcatgtccg    94560
acacggccag cacctgctac tgaccgcctg gccgcccact tgggcctggg ccagaggccc    94620
tgggtggccg tcgctgtgtg tgtgcacgcg ggcagactaa ccatgtcaat gattgggatg    94680 ttgcattta taaaaattag aaataaaaaa agaccattca aaagatgctg gttgtgagtg     94740
agcgatgctc tccctgctgg ggccatggct gtgctgcccc caccccgcag accgccctcc    94800 accacctcc cccccgcctc tcacccacag ctccgaccca cctctggaag ccctgcacc      94860 acttgccaga tgcccacagc aggccaagcc cacacttgct gctcctctgg cggcttccat    94920
ggcaacagag gcacaccagt gtgccacaca cacacacaca cacacacaca ctcgtaagca    94980
cacacacacc tgcacacgtg cagggacacg caggcatgtg ggcacacaca cacccagaga    95040
cacacggaca tgcgcactca cgcgggtaca cacggtccca ggcactcaca cagacacaca    95100
tgcacataca tgcacacacg tgcacgtgca cgtgcccgga caagacgtgg gcacaccgac    95160
agtgacgcat gcacacgcgt gagcacacgg gcacacgcac agggacacac agggatgctg    95220
atgccagcgc ttgcactccc acagtcacct agtgcccgct ggcggtgtcc ctctgcacca    95280
cgctggctgt ggggcttcac acccaagctc tgcctggcct gcctccgctt ggaggtgtgt    95340
ccgtgggccg gcccagctgg gacccctgcc gcagccacca tccccaggct cagggcgaag    95400
aactcggagg gtcaccctgg gcctggccag ctgcagctgc tcaggaacgc cccagcccgt    95460
gtccaggagg ggtgcccctc ccagcccagg ctctagttga aggtggcagt gcccccccacc    95520 cccagcccca cctgcgaaca gacgcagtca gggcatgtcc tgacagagca ggcagaaccc    95580
agcatcagcc tggaggcag ggaggctgtc tctggaggca cctccttgga gcaggacact     95640
cccgtgtgaa ccaggtctgc ccctgcaggc acccagcctg gaaatgtcgg gccctgaggt    95700 cccggagca gggagtgagg ggcatagagc ccagcgggca ggaggggagc aggggccagc     95760
ggggtctcct cttccgacaa gggcaccccc ccagctgcct cctaggccct ccaggagcca    95820
gagctccaga tgcccccaag gacccatcag tgtgcggtct gcagacccta ctggacgtcc    95880
tcagcctgtt catcccaaca tcactctctc tgggaccta ggtgtctgtc tgattccttg      95940
gtcccagagc catgggtcct ggtggggccg acaggccagc cagggcccct cccggcctct    96000
cacacgtgtt gtagctccaa gacggagaga gagaaagtga gggccctcgg gcacaggtgt    96060
ccgcctgccc cagggctggt cctcagaggc caagggcccc accaagctgc aggggacaag    96120
aggacccact ccctgcctct cagcccccag tggccctggt tgtgcccta catcctccag      96180 gagagtctgg ggtgctgggg gccattccgc tggggctccc gcctccgtgg ctggcagaga    96240
cccttcctga ccaagcccgg gagctcctgg ccccaccgca cacatacctt cctcctgctt    96300
```

-continued

```
gtttctgctg cccccacccc cagccctgcc ggggggggcag cacagccaag ggcccgaggg   96360
cgggctcggg tgatgggcag ctagggtggg ctttgctggg gctgcagcca cactgaccac   96420
tctgcgccat gtctcccaca gagggggagg tgagcgcgga tgaggaaggc ttcgagaacc   96480
tgaacaccat ggcctccacc ttcatcgtcc tcttcctcct gagcctcttc tacagcacca   96540
ccgtcaccct gttcaaggta gaccagcctg gccagcgggc gggggcccca tgacccttgg   96600 cacccccac cactcacgcc atccctgtcg cctgcaggtg aagtgaccca ccaagcaagg   96660
atgtgggaga ccagagacgg acaagacggg tgccgcccgg gggcctgggg tcccctgcct   96720
gcgtggccca tccacatgta ctcagacctt ccctgtgtcc ctctccagct tcaagcgcta   96780
agaaactggc ttctcccaac acggccaaat gccgtggcca agccgggtgc ccgcagccgt   96840
aggcccagcc cggccctgct ttgtgatgtc gctcttgtgg ccttgaaata aagacgtcag   96900
ttttatcttg tgaaactgct tcttcctgaa ggcttttctt ccccacacct cacttcggtg   96960
tgtcacacat cctgagagtt ggccctaatt ccaaagggct cgtgggcaag ggcaagagcc   97020
tgcggggctg tgctgggccg ggcacagccc tgctggagag gatccccctgc ctgggctccc   97080 agcacgccta agctggggggc cgggctcagg cctctgggct tctgcgtgcc atcggcgggg   97140
ccctgccata agcaccgcgc aatgcgttgt cactcggtca ccatccgcag caagcccagc   97200
cacagggagt tctgtccaac ctttggggca tgtactgtgt gtgccagtgg gactcaggag   97260
gtgcgctggg cgtgggtgca gccgcagtgc accctgcaga atcccggggg ggcggatagt   97320
gactaaggta tagaagcggg ttcagaagtt tctagtgaaa cagcctggag aatgcatggt   97380
ggggaggctg gggaaagggg aggcagtgcc aggcccagga tggtggcagg aggtgggggga   97440 gccgggccgc cctctggcga tcagtgctcc ctctgagaac agatcggcgc caggtgaagt   97500
aaggacacct gggggggcctc gctcaggctg tggagaagtt cagctgtggc agcaagggtc   97560
agggtggaca caggtgggag gagaggagag aaggcagaac ctggggccca gaggaggggc   97620
ccaggtgagg gctgctcttg tgagccgggc tcctgggggc ggcaatttca ggggactgga   97680
gagtggctgg gagacccccag gactgactct cctggggtgt ctggggcctg agcaccagcc   97740
tggccctgaa gaggtgcctg cccaagagag atttgtaact ggacatgggt cccaaatgga   97800
acccattccc tggctttggg ctcccagggg gtgtccagac cccggctttg ttcccattaa   97860
acggaccccc ttacaggccc aacctggcag gctggggaca ttcgacaagg ggtcccacaa   97920
agtgcaagac acctcgggca gggatggggg ctcccacgca ggctgtgggg ttgactgttc   97980
ggggccacac ctacacgagc gtcccagcag ggctggcagt catgacagaa ccacagacca   98040
gacttaaacg tcatgaattt attctccccc ggtctggagg ctggaaggaa agtcaaggcg   98100
tcagctacgc tggtttcttc tagggccatg ttggagggtc cggtcaatgc tgccttccta   98160
gcttccgggg gcggccagca cctcgttcct gtttaactac ttgaactgaa ctctcagact   98220
tagcttatca actgctcact tatactcatt ttccaagtaa gacctttaag aaattgcatg   98280
gcgaggtgca gctaggcaat gcgtccctat cacttttaaa gcgtcagtcc ttcacggttg   98340
ctcatcgcga gccgtccccc agggtccccg aagcgctgtt ttcacaagga ctgtgttcag   98400
aggtcttggc tggtcgatct tctcttcgtg acgaagaaac gctctgctgt tcagctgcag   98460
ttgctttcgt ctccgtgttg gtcaaggccg ctgctcaggt gtccacctga ggacgggctt   98520 tggggggaaac gtgtgtgtcc gtcgtgagct gtttcggtca gacgtgggag ctggtgcatt   98580
gagaggacgc ccggtgaggt tctgaatcag aagggcagga caccctagaa ggacagtctg   98640
```

-continued

```
ttctggaagg tcgacccagc gtctgagttg aaggcgctcc ggtggagggc cccagagcgg   98700
gggccccagc ctcgccacag ccggggctct cctgggagcc cccggagcgg ggagcggcag   98760
gtgcagtttg tgccgccggg cccctcggct gtccgtgaat cagtcttctt aatggacctg   98820
gaggaatcct tccatgccag ggaccccacg gagcttgcca ggggccaggc accgagacgg   98880
taagagaggc agccccactg ccagatttcc tgctcgggac agcgcgtagg cggcgtttct   98940
gctccactcg ggggagggcg gtcttcaacg cccgctcggt gagacagaga ctcgggtgaa   99000
tccctcgagg ggccgccgtc cggctgggcc acgtctgact ttccctaaag aacaggccaa   99060
ggacagcgtg gcgggggctg ctccacagcc ccttaactac tgccggcgtg gctcccgctg   99120
cttccacaga cccaaggcac cccttaccac gtcctcgctt aaatggacgc agtttaaacg   99180
cagctttggg tttaaggtct ttgccgtgtg tgtgaaggtg gcccctgcct tctgcagagt   99240
ttatgataaa gagcagaatt gtgagtggca acctcaggta caatgcgttt cctggtcatt   99300
ttcaatgagg gattttccta gagggaattt agtcaagtcg ggactcactt tagactcagg   99360
agggaggaac tcgcgccaag ggtaggtgcg caggaaggca aaggcagccg ggagacaatc   99420 cccgggggctc tcctctccgc gaagaagcca tgctgccagt tccagggagg gacctttcct   99480
tctgacagtg gccagtgcag ctcctgaaca agatgtgcta aggagctgaa agcctccggg   99540
cagcatttca ttcagacagc ggaagggggg tagcgactgg tgccgctcag gagccatggc   99600
cgctgggcct gggcagggat ggaggagctg gggtacccgg agtgagggggg actccgagga   99660 ggagaaggag gaagggccac caggaaggag ttgaccctgc accgagccca gctgtgcagg   99720
actcctggat gagatggcct tagctgagcc aggcgggtct ggcggcccca ccctttctgg   99780
ccagtaccat gagctatcag gacagaaccg ggccgagcct gagctgagat gaactaaact   99840
ggattaaact gggcttcctg agccgggctg gattaagcca ggctgagcca aactgagccg   99900
agctgagtcg ggctgatcca ggctgagctg gctgagccag gttgagctgg gctgagctga   99960
gctgagttgg gctgagctga tctgagctgg gctgagctgg gctgagcagg gctgagctga  100020
gctgggctga gctgggctga gctgggttga gctgagctga gctgggttga gctgagctgg  100080
gctgggctaa gctgggctga actgggttga gctgagctgg gctgagctgg gctgagctgg  100140
gctgagctga gctgggctaa gctgggctga gctgagttga gctgggctca gctgggctga  100200
gctgggctga gctgagatgg gctagctggg ctgaactggg ttgagctggg ctcagctggg  100260
ctgagctgag ctgagctggg ttaagctgag ctgagctggg ctcagctggg ctgagctgag  100320
cagggctgag ctgggctgag ctgagatggg ctagctgggc tgaactgggt tgagctgggc  100380
tcagctgggc tgagctgagc tgagctgggt taagctgagc tgagctgggc tcagctgggc  100440
tgagctgagc agggctgagc tgtgctgggc tgaactgggc tgagctgggc tgaactgggc  100500
tgggctgagc agggctgagc catgctggct cagctgggct gaactgggcc gagctgagct  100560
tagctgggct gagctgagct gggctatgct acgctgagct gagctgagct gagctgagct  100620
gggctgagct gggctgggct gagctgagct gagctgggct gggctgaact gagctgagct  100680
gagctgagct gagctgggct cagctgaata gagttgggat gagctgggct gaactgggct  100740
gagctgagct gggctgagct cagctgggct gggctgagct gagctgagtt gggctgagct  100800
gggctgagct gagcagggct gagctgtgct gggctgaact gggctgagct gggctgagct  100860
gggctgagct gagctcggct gggttgagct gagctgagct gggctgagct gggctgagct  100920
gagctgggct gagctgagct gggctgaact gggctgaact ggtccgagct gagcttagct  100980
gggctgagcc gggctgagct gggctctact gcgctgaact gggctgagct ggactgaact  101040
```

-continued

```
gggctgagcc gggctgagcc aggctgggct gaactgggct aagcaggggct gatttggtga 101100 gctgggctga ggtgggttga actgggctga actgaactgg aatgagccgg gttgacctga 101160
gctgggttga gctgagctgg gttgagctga gccaggctga gcttggctga gctgtgctgg 101220
gttgagctgg gctgaactgg gccgagctga gcttagctgg gctgagctga gctgggctaa 101280
gctacgctga gctgagctga gctgagatga gctgggctga gctgggctga acttggctgg 101340
gctgagcagg gctgagccat gctgggctga actgggatga gctgggctga actgggatgt 101400
actgggctga actgggccga gctgagctta gctgggctga gcttggctga gcttgtctga 101460
gctgggctga gctgggctgg cggagctggg ctgagctgag ctgaactgtg ttgtagaact 101520
gggttgagct gagctgggct gagctgggct tagctcggct gagccgagct gggctgggct 101580
gcaatgagcc gtgctgggtt gggctggatt gagctgagct gggatgagcc ggactgggct 101640
gaactgggct gagccgggct gagctgggct gagctgggct gaactaggct gggctgagca 101700
gggctgagcc atgctgggct gaactgggat gagctgggct gaactgggat gtactgggct 101760
gaactgggcc gagctgagct tagctgggct gagcttgtct gagctgggct gagctgggct 101820
gagctgaaat gagctgagct gggctgaact gggctgagct gggctgagct gggctgagct 101880
gagctcggct gggttgagct gagctgagct gggctgagct gggctgagct gagctgggct 101940
gaactgggct gaactggtcc gagctgagct tagctgggct gagccgggct gagctgggct 102000 ctactcgcgct gaactgggct gagctggact gaactgggct gagccgggct gagccaggct 102060
gggctgaact gggctaagca gggctgattt ggtgagctgg gctgaggtgg gttgaactgg 102120
gctgaactga actggaatga gccgggttga cctgagctgg gttgagctga gctgggttga 102180
gctgagctgg gttgagctga gctgagctga gctgggctga gctgaggtga actgggctgg 102240
gctgagcagg gctgagccat gctgggctga actgggatga gctgggctga actgggatgt 102300
actgggctga actgggccga gctgagctta gctgggctga gctgagctgg gctgagctgg 102360
gctgaacttg gctgggctga gcagggctga gccgtgctgg gctgaactgg gctgaactgg 102420
gccgagctga gcttagctgg gctgagctga gctgggctaa gctacgctga gctgagctga 102480
gatgagctgg gctgagctga gctgggctga acttggctgg gctgagcagg gctgagccat 102540
gctgggctga actgggatga gctgggctga actgggatgt actgggctga actgggccga 102600
gctgagctta gctgggctga gcttggctga gcttgtctga gctgggctga gctgggctgg 102660
cggagctggg ctgagctgag ctgaactgtg ttgtagaact gggttgagct gagctgggct 102720
gagccaggct gagttggttt gagctgagct gagcttggct gagctgggct tggctgagct 102780
gggctgggct aggctgggct gagctggcta agctgagctt tctgagttgg gctgagctga 102840
gctggcggag ctgggctgag ctgagctgaa ctgtgttgta gaactgggtt gagctgagct 102900
gggctgagct gggctaagct gagctcagct ggcctgacct ggttaagctg gctgagctga 102960
gctggttgaa gtgggttgaa gtgcgctgag ctgtgctgag ctgggctgag ttaaccgtgg 103020
tgaatgagat ggatccagta gaagtgggct ggctgagtcc gcttgaccta aacaatatga 103080
cgcgctgctt cgggatggtt aaccgtggct gaaccaggtg ggtctagctg ggctgagctg 103140
gccaggctac accgtcctgg ctgacactgg gctgacctca gtgacctggg catgctgagg 103200
acaggccgag ctgagtccgc gtcagtctcg ctggtggcac gcacaccttt cctccaagcc 103260
caggcaccca gggcccgact gcagtgtggc tgagccaggg gcggaagggc tgggctggcg 103320
gggccgagag tgctggcatc cgctgcatgg cctcggaggg aaggcagggc gtgcaaggac 103380
```

-continued

```
gtctctcacc ccctcctcct cttctgttcc ctcgcgggtc ctcagagagc tcgtctgccc 103440
cgacactctt cccccctcgcc tcctgtgaga gccccgtgtc cgacgagagc ccagtggcct 103500
tgggctgcct agcccgggac ttcctgcctg gctccatcac cttctcctgg agctacccgg 103560
acggcatcgc ggtcagtagc cagagcatca agaccttccc gtccgtcctg cgggagggca 103620
agtatgtggc cacctcccag gtgctcctgc cctcccagag cgccctccag gggtcagagc 103680
tgatttgcaa agtccagcac tccaagggga actcggacgt ggttgtgacc cccccaggtg 103740
agccgggctc ctcccgcgct gggtggcagg ggtggggcca agccacgccc ctacccccca 103800
cagattccct ctcttcccat ttacctgcag cccctcttgt tgtccataaa tgcaaccgtt 103860
gttctaggtc cttggctcgt cccagaaaga gttcagagac aaaacacagt ggttaaaaga 103920
gtaaagtgag gattgattaa aggggggatg gtacattctc caggccagag cgggcaggct 103980
caggggagcg gctgccctga gtttctttgg caagttagct acatagggtg taaaaatgaa 104040
tgggcggaat attcactggg gagggaaggg tttggggtcg tattccctgc tcatcatccc 104100 aactcccct tcccaaaggg aggagggatt tttgtcccca cttagtctgg agcagaagtg 104160
tcacggcgtc tgtgcttgat ggctacttct gatccgcaag gctgatttta ttgaaatgag 104220
gacatagtga gcaaaaggtc acattcagac actggagatt cctgcctttc tcacctttct 104280
ttgttcttct ccaggccact tgtcacccca aaaagcgtga tcccttatca gcccagaggt 104340
tcctgctttt cctttgctgc ccagggaccc ctgctgccca cgtgatgtgt gcttccctgc 104400
gtttggcctg tgcccctcct ttccacccag ttcctgccgt ttggtctgtg tccccttct 104460 ctgctcacat ctagctgtct gcctgctcta acgctcccac ccaggggaca gcacattctg 104520
accctcaact gctcactgcc cctctgatct cagcacctaa gcagaccatg accgctgtgt 104580
cggccctcac gtcgacccca tcagaggact gccccaaggc ccgcaccgcg atgaggaatc 104640
taggttagcg accccatcc gagcacaccc tcatctgcct gccgacccct cagctacctc 104700
cttcaggtag ccctttgtga cttctccaaa gagtcttcag gaaagtgggg cactgacctg 104760
aggggggcct actatgccca ggaggctggg cactggcaga tgccgcctca tgccctgtgc 104820
ggtcctcagc ctctctgaat gggtgacctg ccagtcacac cgcgaggagc acagtggaga 104880
gggaggcccg tggccagcac cggacccacc tggcccagtg gatcagctga gtcgtgagct 104940
tgtgaggaga ctcacatggg gacacattgc acaggcagcc agggatgcgg cgctgagccc 105000
tacaaccctc acggaaatat agggtgccac ccaaagggcc ggggagccac ggcggccaga 105060
cccaggagct ggccacggca ggacccccag gagtgagctg ccttcctgcc cctctgcctg 105120
gggcccaggg tcacacttca ccctgtcgcc gccctgggca gcgtgtcctc actctgagcc 105180
ttggaggctg aagcagctga cagagggag cagtcagacg gagagtagca gctccctcgc 105240
tggccttctg ggcactgaag ctcaaagaag ccgtggcctg ctcgggtgtc tctgtgggct 105300
tattggccag gatgctcacc cccccccca gccagaatct gctcccactg tgctcatccg 105360
gacactccag ccctgggctc ggggaggtct gctcaggcac acaaagcatg ggcgagtcaa 105420
gagacgccag ctctccaaag agatgccgtg gctcacctgc agcagggtgt gtgccaaacg 105480
caccccttcc ccggagtgct ggcagtcaga gttgactgtg acatctgcat ccagtcagcc 105540
acccagcagt tttgggaggg agcaggtgga gctccaggaa gacagattgg gccctccggc 105600
tctggggctg gactgccctc cagtggaaaa ggacccttct tagggcacgc ccaaggtggg 105660
ctgagcccat gagccaagcc ctcagaacag gcctgcacac cccaccccag gagggcccc 105720 caacccagac gtggcccagc tgtcacactg cccgctggcc agatgcagcc taagcctgct 105780
```

-continued

```
ctctagagcc tgggcccggc ctttgcagtt tcagaggagt ggacaaggag gaggaggagg 105840
ggtcagaaac cctgcgtagt tctaaagcct ggaatattta ctctctggca ctttacagaa 105900
aaagctggtt gacaggcggt ctgtcacaaa tttatggcct gataacatac tgtccattct 105960
cgccctaaac ccaagaggaa ggtccttggg cccttagcac agatactcgt gagcagtgag 106020
cagtcagggt cccaccagag ccaggaggca cactcaggga gcagtgacta ccagaagcca 106080
agctgccacc cctggggctg ggggccgggg gccggggggc catagccccc accttctaag 106140
gagcctagag gacaccctta gtcacccct ccccaacagt gccggccacc agccccacca 106200
gcccccagcc cccccagcca gaagcctgga tgctgggaag cccaaaagag gctgtcctca 106260
gaggtcagtc acttggggga ccgagctggg gagaagggtg gaggactttc aggggacacc 106320
agagagggcc tgggctgtga gaccccagcc tagtgatggg aggtcacctg ggaccacact 106380
tctggaagct ggggagaggg caggcctggg gttgggcagt gaccagaaac acccaggagg 106440
cgctggccag ccccaggacc accccctccc cccaccggca gggactccca tgcacccct 106500 ctgatcttac cccaccctg cggagtgtca gaaccacacc cgtccgccca gcctctgcct 106560
gctgcaccct cccctgcagg gcctctggct ccaggtcaag gccaccttca cctgcctggc 106620
gctaggggac aacctgcagg agaccattgt ccttggaggg ggccagggag cctcacagca 106680
ggctcccaaa ggaggcgcac gccaagcatg ccgaaggttc ccggagccag agcagccacg 106740
tggccctgcc cagggcctct tgggcagagg ggcctccgtc acctgcacct tgagcagccc 106800
tggcctgcag gccccagtga tttttggcagc acagagagaa cctggtgagg ccagctccca 106860
ggtcagaaga cagggtggcc acgggcccca ggcaccccac acctcaacca gcccagcagc 106920
tgctctggcc acctccttcc atgactgtcc tccggccacc agcttctccc agtgctccca 106980
gtgccacctg agcatgacca ggcttctccc tgcagctgcc ttggccccca gaaacctccc 107040
tgtccgcatc ctgaccacag ctgacccgct cacctctgcc aaggcaggct cctggctcct 107100
gtgtgaggtg tctggcttcc cgcccatgga catcttcctt gcctggctgg agggccagtg 107160
tgaagtgaac ccttcgtagt ttgccaccag gcgccccaca gcccagccca gcgggaatgc 107220
cgtgttcagc acctggagcg gcctgcgcgt cccggccacc cagggccact gggaggccag 107280
cctacacctg tgtggtcggg catgaggcct cctggactcc gctcagtgcc agctggaacc 107340
tggacactgg cggtgagtca gccccacaga cacagggctg gaggcagagg ggcagcaggg 107400
tggggctatg gccgagccca gccggtcctt ctctggaggg catgcttccc cgccctgggg 107460
cctctaggtg tctcaacagc taccctgccg acctgtcccc ctgtgcacac accgggctgg 107520
ccccggaagg gagggaggtg gtgccatgcc ccccaggccc caagaaccag ccattcccca 107580
caaggtgtgc ctgtcactgg gcacagagcc gggggcctcc cttgggctag gcatgagggc 107640
cgtcactcca gaaagccgct ctccaggggc atgcgagctt ccccagcccc caaggtctcc 107700
acccacccag gagcacaggc agcacctcgg aggccgatg cacctgggag tgagggctgg 107760
gtttgacagc gaccttgact gcaagccatc cagagggcag agggacaggc acctgcccga 107820
gaaggggctc tcgtcggggc ccagggctca ccctccctc tgaggcatcc tgccaggaca 107880
ccttgctgcc ccgctagagg gcaggaccca gaccagtgcc tctccctgcc cagcgcagca 107940
ccagtgagac agtggtggac acactgggtc gggcagggag caggacacac agcgcagcct 108000
gagctggagg gtggggtcca ggccccaggc caccaaagga gccaggcaga gggagatgcc 108060
cagtggggac cagagtcagc aaagtggggc gggctgtggg gggtgggcag gaagcctccg 108120
```

-continued

```
gctccaccgg ggtcagggat cttgcgtgca gccctgactg tcgccacggg cagtcccca 108180 gcagcagaga tgcccagaca gcagctccag ccccgctgcc tcccccgaca gcttggcacg 108240
gccacccgct gagcaacagt ccctccagcc ccgcagggtt ccccagagtg tggctgcccc 108300
tccgcacccc ggcccgcctg ggcccgacg ggtcttctcc tgaagctcca gccccgttcc 108360
tggctgccca ccgggggcca gggccgtttg tccacaatcc gcgttcacag cacagcccct 108420
cccaatccgg gcgccatctg tgctgggccg cctgccgggg ctcatgcccc tcaggcctgt 108480
ccgttccccg gtcgctgaag tggactcctg accgggccca cagtctgtcc gaaggaggac 108540
caccccctca agggctccct gagagccgag tcctcactga cccaacccc ggcctgccgt 108600 cctccacacc ccgcagacag gccgccccag gcacacagcc agctcttcca ggtctcaggt 108660
ccgggagggt ctggacgggc cgcctcccag gccttggccc aagactctcc catctcttgc 108720
aggggctaaa ggtatatcca cctgccaggg ccgcacactc tgaagacagt gcatagcaga 108780
agctgtaggc ggccaggcca gtccccaggg cctccaggag tgagggaagg aagccctcca 108840
cagaaggcca gagccacacc acccgcccca ggtctgagcc cagaggcgtg ctcaggaagg 108900
cagctggggc ttccctgcct ggacccctcc tccagacagg tggaggggtc cagaactgct 108960
ccctgcttag ggcagcctcg cccccgcccc acagccagtc ctccgtggcc tcagccccag 109020
ctggattgca gcctctgctt ccactgggcc agctgtccct gcagtggtga ctttgctgcc 109080
ttgggcagtc ctgtggcctt tccccgtcc tgcatccaca ggccacccc tccctctcca 109140 gtctagggtc agcccaccac tgtcccctgc agaacaagca tgccctctac ggttgtcatc 109200
gtggttaaac gtccctctgg cctggccgct cctcagccca cagccccacc tcatgagacg 109260
gccacctctg cccaggccca tggacaagcc aggacacctc accctccgt caccctcgca 109320 gctggcagcc ccccgactcc tgaatcctcc cgcttctctc cgtgggccct gcgccatttc 109380
tcccctccct gcaggtctcc cagccagtgt tgcctccttc actccgtggc cagggtgatc 109440
tttaaacccc atcagggctc tgcctccact taggatgcag tcagtagcaa gatagtcact 109500
caggcggcaa gaaaatgaca ccggcaaata aactgtagct gaagagctga gggcttggag 109560
atgtcgcact gacctagatt ctcaggggag aagaggcact tggccgcttt gtcctcaccg 109620
caaccgcagg aggacagagg cgtggctgtc cgtgacagga gggggtgtga gggagtcagc 109680
caggatctcg tgtctgcaga gctggcacaa ggcgggcgat actgatgagc cccagaaaaa 109740
tcccccccac ccactgaccg ccccacccgg gaccgtggct gggcgagcag cggctgggag 109800
cagagcgggg tggcagcaag ccgtctccag ccttgcacga agcttagagc ccaaagcccg 109860
accccacccg aaggcgtagt caggagccac ctctcctgcc acccagcccg accgaggcga 109920
gtggaagacg cgtgtgtaca tgcggcctca ggctcgctgt gtctgtgcac aacgtgcagc 109980
atccaatcaa aacttcaaga tgcaaataag cggaaagccc tcactcgtaa tccaaacaca 110040
atgtcagagt gagagcccgg ggacccgggt gctggagtca aacgcgatct ggtcatgtca 110100
ctgctccctc atctgaaacg ctcctcatgg cttccttgtg ccctaagaag aaattccagg 110160
ccctgcccca ggggttctgg gactgtgccc gagggactgc ccgccgacct gccctgtccc 110220
tctcaagagg cgtgaatggg gcatgacttc tcccacctac aattcttctc aatgccgcgt 110280
ctctcgtcca aagcctttcc gccttctcag ccagctgact tccgcttctc attcacacga 110340
gctcttctgt gtgtctgaga agacgccctg cccccccaggc ctgggtcacg ggggatccgt 110400
gcacctggcc tttacctggg cggagcacgt ccgtggggag ctgtccctgt gcttagctgt 110460
ctgacgggcc ccagacccct caccactgca ttccaagtgt ctagaacagg ctctttcaag 110520
```

-continued

```
ttctccatgc cacaggactg tggccttttt aattttttcc aattaatcat ggaccaatac 110580
cttcgtagag tacagtgggg attaattact agaaaaatga aacagaaaca aagacatgcc 110640
agtgttttct tattagagtc aacagactgc tgtaaaaagt tttctgatgc acacatcact 110700
tgcatactta cccccgtgc cctgtgacca gtggtcccca gctggcacca cccacggacc 110760
ccacctccag cagctgtggt caaacacaag gtggacccgc aaaaaccacg cacagaatga 110820
atacctggaa aactctatga cgtgtgacag gtcccaggac tcagcacctc ccacctgccc 110880
ataggccttc ccgccggatc gcggcgtgcg ctctgggcct ggacgcccgc acgtccctcc 110940
caccctgcct tgccctgcgc ccgctccagt ctccatcaga aatgacttcc tcttatacag 111000
gttggtcccg acgtgccctt gcttaaagcc cttggatggc tcctcaccac tctcaggaca 111060
aagtcaccag cggatcctgg gccctgctca gctctggcct ctcctccgcg gaacgctgag 111120 cacccgctg caggcgcccg gggctcctgt cactctcccc agccaggctc tcccgatacc 111180
gggcgttcat gatgccgata ccgggcgtcc gtgatgtcgc gccctctgct ctctgcctgg 111240
tgggcaccgt cagctctttc tttcaccctg gccagtgagg ctgccgctgc acagccggct 111300
gggccgcccc cgtgcgtccg cgtcttccct gcgccccgca cagcctggca gggagaaggc 111360
agttctcaga tgctggtcgg gggtggcagg gcacccctag cataggccct ggctgtcagc 111420
tgcctgccgt gtgctggggc gggcgcagga ccaatcttct caccagcgcc tgctcctccc 111480
cagatctggc ctcctggacc tcccagagcc acggcgagag tggcagtggc tattctggcc 111540
tggaggacac caaccgactg tggctaacct tcatggccct gctcctcgtg actctggtct 111600
acagcggctg catcgccttc attaaggtgg ggtgaggacc ccgcccgcac gggtgggcag 111660
ctccctcgcc cgccagccag cacccctgcg tccagggctg tggggacact ggagtccgcc 111720
cggggatcct gagggagcgg gaggaatact tgggccgttg gtgggccacc tggaccctct 111780
cagctgtagg gctgcaccct tccttccacc cgcagccccc ctagagaaga acaggcactc 111840
cacacccact cgcctgggat gggggccctg actcggctgg caggagggga ccagacatgg 111900
aagcttgcac cctgtcctcc aagagaagca aggccccagc tgtgccatgt gctccaggga 111960
ccctgctctc agtgcccccct ctcccgcagc ctgtacccac cagcccccttc ttgacactgg 112020 gctcttgcca tgggcaaagc tgccccagag agcagacgcc ggcaccgcgg agggaagctg 112080
ccagagggca gagggtccgg cctgcactct gtcctgtgca cggggccctt ccagccccgt 112140
cttgttcaca ccccgcctgc cctggctctc ctctgtccac gcagagccca gcccaccaga 112200
gaggaggctc tcccccccgga gtccccccag tcctgactat agccccccttg acttcccacc 112260 cacggtcctg ccccataaac agctttggct catctcacct gcctcctgtt tctctgtccc 112320
agcagtctgg ctcttcccag gtcagaggac caggaggctg aggacagaca tccaggggaa 112380
tccacacacg agcaagatag gttgccagca gggtcggaga agcagcgggg gcagccatgg 112440
tgcagaagcc agcagagctg agaggccctg ctccccacat caaacacagg caaacacagg 112500
ggcctgtgcc caagcacacc catgtgcagt ccgtgcccac acacgggcac gcacaccgca 112560
cacaacacac acacgagcac acgggcgctc acacagaagg cggcactgag tggtgagaca 112620
ggagcggctg ggcacacaga gtcctggggg ggtccagccc accctcact gtctgcacag 112680 ctgggcagcc cttgagaccc cccctcgcac ccactccctc catcagacag ggtgagagcc 112740
cccctcaggt agagtggggt gagcagttgg tgaagtgctg tctgaaggga cctggagaga 112800
ccctggcact ggtcactggt cagtgcctgg tcacttctgg cctcctgctg tccccagagc 112860
```

-continued

```
ccccacagcg ggccctggtc cactgcagtc tttcctctcc ctgccaggtg aggggccacc 112920
catgcacggg gaggccagcg aggagggcac cgtgcaggtg ccagccccgg gcggcctccc 112980
agcctccact ctgcagacca gtggtcggtg cccaggctgc tccctccgg cctgcccacc 113040 tcgcggactc cgggtcttac tcctagtctg gctccgatgc cacaccatcc ccccatcccc 113100
cagtccagcc ttgacccagc agcacctctt catggcttcc acgcccaccc catccctgaa 113160
tgtggccctt actccacatg ttggcctggg agggtggccg cacatctcac actcagcaca 113220
cccgcaactg accatccaga tggcaggctg aacgtggccg tgaggctgct gatctgatcc 113280
ctggagcctg caagtggcgc ccatgcagat gtgctcagcc cgggatcctg acacaacaag 113340
gagactctgg cttcttgggc tggcccagtg tcaccacaag gtcctcgcgg gagggaggca 113400
ggggaacccc ggcaaggaga agccaggcgg gtgacataga ggcaggaggc tacacttctg 113460
gctgcgaaga cggaggaccg cccacccgtg cttgaggtcc tgcgagactc gtgtcagact 113520
cctgcctcca ttcggtgaca aggcaagtgc ctgcggggat ctgctgcagt ggccgcaaca 113580
aggaaaacac cattggtccc tccagaagca gcccgtcccc tgcgtcctcc ccatcccagc 113640
aagagcgccc catccctccc acagctcagg tccagactct gaatggactc ccatctttct 113700
ctgcacctcg tcccagtcta gcagcggacc tgccccagct ctgcccactt tcctgggcct 113760
ggccgtgtct gcagggcctc agtcacatcc tccaggcctc ccatcccaac tcgcccgctg 113820
cggccttctc agccagcctg gcagtgaggt ggccctgtcg cgagatcgcc gatgagggct 113880
cagctcgccc gctgcccgaa agggcctcac attttatccg aaatttgtac atgggtccac 113940
accctgacct cccgtccttc catcgtcaga gcctccggcc tggctgtgcc ctggcagaga 114000
cctctctccc ggcctctgga cctgcactcc cagtccttca ctgcagcccg ccccgtggcc 114060
ctgcccagaa cgacggcgca ctgccctcat ccccccaccc ctgctccaag ttctctgctc 114120
tgccccttcc agcccttccc aagtttcaca tgcgcattgt gctagttggt catttctttc 114180
tcctcgtaga aacctagaaa gttaactcca agagcgcagg gtttttatctc cctgatgagc 114240 cccaacacgt ggaccagagc ccatgggcag tagtgccagc aaacactcac tgagcgacgg 114300
aggtcagggc cgcgcccgag tcccagggtc acgggccctc ccgggacagg caggcccagt 114360
ggagtgtgcc acgccacttc ccttctgaga gcaactcctg gcccactctg ccccatctca 114420
gtaagtgacc acctccagac tccaggctca cccactcccc agcccacagc caggggggtc 114480 tttaaaacc tgaatctgtc ctgggagtcc cagctcaaac ccaatgaaga gttcttgtta 114540
caagagtgaa atcaaaattt tcatgcctcc ccactgaccc agccaggccc agggcccaga 114600
tgggccccac caccctgctt atgacggtcc atgcttgctc cccactttcc acagtgtgtc 114660
actacctgtg gggccctggg tactgcctgc ctccagtcag gacctgaagt ccctcaagag 114720
cagcagctga aggaaggtgt gaaggaagga aggggtggcc tgcctcgggg gagaggcctc 114780
agagcctcca aggagagcat gcacagggcc ctcactgcag gagcccccga gcgatcgtca 114840
ctgttaccca gctatcccca agtccacagc cccaagggtt tgcactgtgg agtcctgtct 114900
gcaggcccca ggaggctggg agggaggcca gagggaggcc agacaccaaa gcctgcaggt 114960
tccctgagca tggaggtgc ctggtttggt ccaaggagcc tgtatttgag tttctttctg 115020
ctcaggaaac attttcacac aaagcacgag agccctcca accacagcca gggcctcagc 115080
ctgttgggtg gacgccgggc ccttcactca gttcttcaac aggaaaaccc aggggggcctt 115140 ccagcagacc ctctttttatc ttcaagaacc accagtctat ctctgccaga ggcgtgtgac 115200
agcccggggc cctggggcca gccatttccc ctcacaagac tgcttgtggc cttcctggca 115260
```

-continued

```
ccgcagccac tggcctccgc ccagccccgg gccgttggtc ctgcacgctc tgcagctcac 115320
ccgagtcacc acgatcccac ccgcctggca ccctcctctc ggggcagaaa catctgtttc 115380
cagctttggc gacaaacagg acgcacccgc ctcctacccc taagtcaagg cttgatgagc 115440
ccagtcccct ggtgtggagc ccacccccctg gccacctgtg tgaggcccga ctgaacgccc 115500
tccctcagtg tttgggggag gttccgagcc agccctgccc tctgaggctt gtggactgag 115560
gcttcccagg acccaggcag aaaccaggct gtgatctcca gccaaggaat gtgttcattc 115620
ctggtccaca gccgggcccg tgttgactga gttaattctg gaaggcatat ggctgggaca 115680
agacctcaaa agagagttgg gggacaggaa gatcagggac agcgtctctg ccctcacggt 115740
caggacaaga gtaaagtcgg aaccagcagc atgcaaatcg gtaagcaggc cagaggaagt 115800
tacgggaacc tgtctgcgtt ccattggggt gaatgagtgc tttctcagaa tgacaccaag 115860
gccaggaagt ttaaaagtga cattgagaga tttgcctaca gaaagaaaaa attttaaatc 115920
tatgaagata aagtctctac aaacaaaaag ttaaatgctg tgggagagag agtgggcaaa 115980
gtgagtaact tcaaaaagag tctgcagtag tcagggttct ccaagaatag atgtatgaga 116040
cagaaatgac agacagacag ataaacgtat gtgtgtatac tgatatatac atagagagaa 116100
agagagattt ttaaggaatt gggtcctgtg atcgtgaagg cttggagcat ccaaaatccg 116160
cagggcaggc cagcagtcca gagctccagg gaagagttga tgttacagtc tgagtccaaa 116220
ggccatctgc gggcagaatt ccctcttcct caggaaacct cactctttt tctcttaagg 116280 tcttcaactg aatagatgag gcctacccat gtagaacaat ctgctttacc caatgtctac 116340
tgctttaaat atcaacacat ttttcaaata ccttcactct ttggattagt gtttgaccaa 116400
atatctgggc actatatcct agccaagtta atccataaaa ttaaccatca gaaagcccaa 116460
ctaaatgagc gttggaaaaa atgcaatgaa tgggacaaat ctgacctata agaagttttt 116520
ggtggaagtg ggagtggagg gatcatttcc agtagtttgt aaacaacaaa tagccaataa 116580
aacatgaaat tgttagccat cacacataat caaagcagtg actttaaaca actgaccatc 116640
agttcaggtg acaactgttc atggcagcct accatgcgcc aagcaggcat ccaagtggga 116700
gtgtgcagtg tgactgctct gtggcaccac tgccctgatg ggagaggaac aacacaactg 116760
gacacagatc aaatgcccta ccaaagacaa ggaggccagg cgaggaccga cacctcactg 116820
ccaggtgctg tcctggcaga tgaagggcct gcaggcatcg gggaggcacg tccaggcaga 116880
aggagcagaa ggcagaaagg tcctgggtca gaaatgtgct ttacaagttc aaggagcagc 116940
aggaaggcta gtggggctgc atcagaagct gggagactgg ggaggaggag gtggggaaga 117000
taaagtgagg ccatacgagc ccgttcaagc ttcatgcttt gctctggggt gatgggatgc 117060
ccccaaaggc atttgggttg gggggttttc aattttgcac tggaaagtca gctgcactgg 117120
agggagggtt taagtcaagg gccctggaga tctgtgcagg agtccttctg ggggagtagc 117180
aggaggcaga gcaggggcag tggcagcaga gagaagggct cagatcatgc atgtgcctga 117240
aagtggagct gagggtctgc agagagaagt cgcacccacg agatcccctg catcacagca 117300
tgaatgcagt gccattcact gatctctggg gtcaacaact ctcccttcag tgtggccagt 117360
tcaagctgcc aattacatac acaggaatgg atgtgggagt ggatgctcct gttggacctg 117420
ggctctgggg cttaggaaga agtcactgga ggaggaggag taaatccagg actgcacatg 117480
gtgctgtggc tgatactccc aggactagca gggacaccaa gaaaggtgcg tggaagggag 117540
ccaaagtcaa tgtgtggcac caggtggagg ggaggacttg gaagccaggg tcagaggcag 117600
```

-continued

```
gagtcagaaa gatacagggc tagaaggagg acatcatgtg cagggacact ctgcacgtgg 117660
tgccaaggaa ggacttggtc cactgcatgc atgctccgga ggcgtgtctc caggaggctg 117720
acagggagca aggggtcctc tcaagagcag tctcaacagc aaggtggcca agacctggct 117780
agagtggcct caagaaggag gagggagggg tgagtggatg caaaagtcag ggcacaccag 117840
acctaggagc agagtccacc agcctggtca agccgacacc agcatcacag agcacgcaca 117900
tacatcgaac acaaacctgc ttgtgaagcc tgatgtccac tgcaccatcg ataaactgaa 117960
aaaaactaaa gtcatggtat caagatctcc aacagtgcag caaatgagag agacaaccat 118020
ggcgaagggg taaatgggct cctacacaca gctcacgggt caaatcagaa gagaagtcca 118080
tagccttaaa tgtctgtgag gcagaaagca ctgagttaat acagagccca aactgaaaag 118140
ttgggaaaag aacagcaaaa taaacacaaa aaaacggaaa taatcatata agccaaaaaa 118200
aatcaattac ttcaaaaaca cacctgcacc ccagtgttca tagcagcact atttacaaca 118260
gccaagacag cctaaatgtc catcaacaga tgactggata aagaagaaat ggtatgtttt 118320
tacaatggaa tactactcag ccataaaaaa atgacaacat aacgccattt gcagcaacat 118380
ggatgcccct ggagaatgtc attctaagtg aagtaagcca gaaagagaaa gaaaaatacc 118440
atatgagatc actcatatgt ggaatctaaa aaacatgaat ataaatacaa aacagaaaca 118500
gactcataga cacagaacac aaacttgtgg ttgccaaagg ggtgggggt gggaagggac 118560 agactgggtg gtcaaaatgt agaataaaca aggctatact gtatagcata ggcaaatata 118620
tgcaagatct tatagtagct tacagcgaaa aaatgtgaca atgaatgtat atatgttcat 118680
gtataactga aaaattgtgc tctaccctgg aatttgatgt aacattgtaa aatgacaata 118740
actcagtaaa aaatattttt taaaaactag ttattgatga aaaagtaata agaggaaata 118800
ataaataaat ttattccact agtatatagt aaaaatttta aatcccagga cagtatctta 118860
tcaaaaatga ctcaggaata gaaaagctca atagtaccat atttattaaa cttctttgtt 118920
ttatttatta cataaattaa agcagtagat ttaaatcttt tcaaataaaa ataccagggc 118980
catgtttcct gaagctctta aaaaaatgta ttattcaaat tttatttaaa aaactatcaa 119040
aaagtgaaga agaaggaata acacccaact cattctataa agccaatata acactgattg 119100
ggaatcagaa aaggaaagca tggaaaagaa aagctatggg acagtcttac tcatgaaaca 119160
gataaaaata ctccagagaa aatattaaca aataattttg aacctcatga aaaaacagat 119220
aattcactat gtccaagtca ggtttatccc aaaaatataa ggatagttta acctaatgaa 119280
atctattatt gtcattcaaa gcatgttcat aataaagaag aagaatttta agatcatctt 119340
aaaggcagag agaaaatgtt gaaagaatgt atactctttc aagatataaa acttttttgct 119400 aactaaaaca caatggaatt ctttgatctg acaaagttta tcaaccaaaa ttctttgaat 119460
tttttttctt agaggaaaat tggaagcaac tgtgtactag aagtcttgat gtattccata 119520
agaccaaaaa tatattaaaa catgataact ttctaagtag aaaaaatcca gaaaaatata 119580
taaaaataat aacaattaaa aataacaggt aacttgctac aataccaata tacagaaatc 119640
aagttttttg ctattaacca gtagcaaaca gaaagtcatt tttgtaaaga tgccagatgt 119700
ctgcttctgt taagggcata caggtaatgt ggcccaacct tcccattgag gaatactaga 119760
aaaagctgga aaagtacttt tagaatcttc ctgaaggtag tgacaagtta acaaagtcat 119820
gaataatcac gggattgaga gccagaggag actgaaattc agagattcaa acctggcagc 119880
cactttttcc ccaaagcctt ttactgattc tagaataaag ttgagacact gagcagcaat 119940
tttgacaatc ccataggggg agggagaaga aatttggaat tttagaacta atgtgtacaa 120000
```

```
ctgcatgaat taaggactca acagacagat ttagaagcag agttaacaca gctggagaat 120060
tagtaaacca gaagctgaaa caaaagaaag gagctataat gtagaccaga aaacaaaggc 120120
atgagttgaa agaagagtgg gtacactgac aaagtccaac gtgtaagtgc ttaaagccct 120180
agagaaagag agagagaaga gaagacacag tcataaagag gtaattgcag aaatctttcc 120240
aaacttaagg agaggtacca ccccttggtt caaacagaat aaaacacaca cacgcagaaa 120300
gtcacaccca tccataacat aaaactactg aatactaaag gagaaaatct tgaaggcagc 120360
tgaaggaatg gggaacctta cattatcttc aaaggagcaa caataagatg gacagctgat 120420
gtcacaacag aaggagaagc aaggagagtg atgctctgtc catagtgctg aataaaacca 120480
ccgataagcc agggaaacca tccttcagaa atgaagatga ccctgctttt cccttctcct 120540
tagctatagt ttcctgggac tgtgataaca aagtaccact aactgggtgg cttaaaacca 120600
ctctctcaca gttctggaag ctagagatct gaaaccagta tgccctcagg gctgtgctcc 120660
ctctgaagtc tctaggggag gagatttcct cgcttcttct agcctttgat ggttgccagc 120720
aatccttggc atccattggc ttgcagatgc accctccaat ctctgcctct accttcacat 120780
ggagttttcc ctgtctctgg gtctctgggt ctaaattttc ctcttcttat gaggatacta 120840
gtcatatcag atttagggcc caccttactc aagtacaacc acatcagaac ttggtgatag 120900
ctgcaaagac gctgttccaa atatggtcac agtcacaggt tccagatgga catgaatttg 120960
ggatgacact gcaaggccca gtatactttc ctttcctgtg caatttaggt gaagctctta 121020
ggtgagcaga tcaatgtgaa cgtgtgcacg gtggggttgg gagcggcaga ggcctggaat 121080
aggccctgtg tgggtgggga gggtggcctg atgcgcgaag taagatctgg agcaagatga 121140
gagggctcca cctggctgag ggtatagact agaatgacca gaatctcaga acctgaagtg 121200
agagaggaaa gcattatgtg gcacggaggg gaggttggta gctcacaagg gaactgatga 121260
aataagtgaa tatactgaga agcacagaca aaagagaaga gagttacgaa gatcaaaagg 121320
aagaaaacta gaatggatca tgtgatttgg agctggattg tatgcatctg tcagaattca 121380
cattttcaac acatgcagat acagagagag agagtaagta gtggccaaaa acttcccaaa 121440
tttgatgaaa tatatgaatc tgcacatcca agaagctt                            121478
```

<210> SEQ ID NO 33
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 33

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
            20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Thr Lys His Ser Gly Arg Arg Asp
                85                  90                  95
```

```
Gly Met Asp Tyr Trp Gly Lys Gly Thr Leu
            100                 105
```

<210> SEQ ID NO 34
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 34

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
            20                  25                  30

Gly Lys Glu Arg Glu Phe Val Ala Ala Ile Ser Trp Ser Gly Gly Ala
        35                  40                  45

Thr Arg Tyr Val Asp Ser Val Lys Gly Arg Phe Thr Ile Ser Arg Asp
    50                  55                  60

Asn Ala Lys Ser Thr Val Tyr Leu Gln Met Asn Ser Leu Lys Pro Glu
65                  70                  75                  80

Asp Thr Ala Val Tyr Tyr Cys Ala Thr Lys Asp Ser Gly Arg Arg Asp
                85                  90                  95

Gly Met Asp Tyr Trp Gly Lys Gly Thr Leu
            100                 105
```

<210> SEQ ID NO 35
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 35

```
Gly Leu Val Gln Pro Gly Asp Ser Leu Arg Leu Ser Cys Ala Thr Ser
1               5                   10                  15

Gly Arg Thr Val Ser Ser Asn Ala Met Gly Trp Phe Arg Gln Ala Pro
            20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Ser Ala Lys Ser Thr Val Tyr Leu Gln Met Asn Ser Leu Lys Pro Glu
65                  70                  75                  80

Asp Thr Ala Ile Tyr Tyr Cys Ser Thr Lys Asp Pro Gly Arg Arg Asp
                85                  90                  95

Gly Met Asp Tyr Trp Gly Lys Gly Thr Leu
            100                 105
```

<210> SEQ ID NO 36
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 36

```
Gly Leu Val Gln Ala Gly Asp Ser Leu Arg Leu Ser Cys Thr Ala Ser
1               5                   10                  15

Gly Arg Asn Leu Ser Ser Tyr Gly Met Gly Trp Phe Arg Gln Val Pro
            20                  25                  30

Gly Lys Glu Arg Glu Phe Val Ala Ala Ile Ser Trp Ser Gly Gly Ala
        35                  40                  45

Thr Lys Tyr Val Asp Ser Val Lys Gly Arg Phe Asn Ile Ser Arg Asp
    50                  55                  60

Asn Ala Lys Asn Thr Val Tyr Leu Gln Met Asn Arg Leu Lys Pro Glu
65                  70                  75                  80

Asp Thr Ala Val Tyr Tyr Cys Ala Thr Lys Asp Ser Gly Arg Arg Asp
                85                  90                  95

Gly Met Asp Tyr Trp Gly Lys Gly Thr Leu
            100                 105
```

```
<210> SEQ ID NO 37
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 37
```

```
Gly Leu Val Gln Ala Gly Asp Ser Leu Arg Leu Ser Cys Ser Ala Ser
1               5                   10                  15

Gly Arg Asn Leu Ser Ser Tyr Ala Met Gly Trp Phe Arg Gln Val Pro
            20                  25                  30

Gly Lys Glu Arg Glu Phe Val Ala Ala Ile Ser Trp Thr Gly Gly Ala
        35                  40                  45

Thr Lys Tyr Val Asp Ser Val Lys Gly Arg Phe Asn Ile Ser Arg Asp
    50                  55                  60

Asn Ala Lys Asn Thr Val Tyr Leu Gln Met Asn Arg Leu Lys Pro Glu
65                  70                  75                  80

Asp Thr Ala Val Tyr Tyr Cys Ala Thr Lys Asp Ser Gly Arg Arg Asp
                85                  90                  95

Gly Met Asp Tyr Trp Gly Lys Gly Thr Leu
            100                 105
```

```
<210> SEQ ID NO 38
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 38
```

```
Gly Leu Val Gln Ala Gly Gly Ser Leu Arg Leu Ser Cys Val Val Ser
1               5                   10                  15

Gly Arg Asn Phe Ser Asp Tyr Ala Met Gly Trp Phe Arg Gln Val Pro
            20                  25                  30

Gly Arg Glu Arg Glu Phe Val Gly Ala Ile Ser Leu Ser Gly Gly Ala
        35                  40                  45

Thr Arg Tyr Val Asp Ser Val Lys Gly Arg Phe Thr Ile Ser Arg Asp
    50                  55                  60

Asn Ala Lys Ser Thr Val Tyr Leu Gln Met Asn Ser Leu Lys Pro Glu
65                  70                  75                  80
```

-continued

```
Asp Thr Ala Val Tyr Tyr Cys Ala Thr Lys Asp Ser Gly Arg Arg Asp
                85                  90                  95

Gly Met Asp Tyr Trp Gly Lys Gly Thr Leu
            100                 105

<210> SEQ ID NO 39
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 39

Gly Leu Val Gln Ala Gly Gly Ser Leu Arg Leu Ser Cys Val Val Ser
1               5                   10                  15

Gly Arg Asn Phe Ser Asp Tyr Ala Met Gly Trp Phe Arg Gln Val Pro
                20                  25                  30

Gly Arg Glu Arg Glu Phe Val Gly Ala Ile Ser Trp Ser Gly Gly Ala
        35                  40                  45

Thr Arg Tyr Ala Gly Ser Val Lys Gly Arg Phe Thr Ile Ser Arg Asp
    50                  55                  60

Asn Ala Lys Ser Thr Val Tyr Leu Gln Met Asn Ser Leu Lys Pro Glu
65                  70                  75                  80

Asp Thr Ala Val Tyr Tyr Cys Ala Thr Arg Asp Pro Gly Arg Arg Asp
                85                  90                  95

Gly Met Asp Tyr Trp Gly Lys Gly Thr Leu
            100                 105

<210> SEQ ID NO 40
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 40

Gly Leu Val Gln Ala Gly Gly Ser Leu Arg Leu Ser Cys Val Val Ser
1               5                   10                  15

Gly Arg Asn Phe Ser Ser Phe Ala Met Asn Trp Phe Arg Gln Val Pro
                20                  25                  30

Gly Lys Glu Arg Glu Phe Val Gly Ala Ile Ser Leu Ser Arg Gly Ala
        35                  40                  45

Thr Arg Tyr Ala Gly Ser Val Lys Gly Arg Phe Thr Ile Ser Arg Asp
    50                  55                  60

Asn Ala Lys Ser Thr Val Tyr Leu Gln Met Asn Ser Leu Lys Pro Glu
65                  70                  75                  80

Asp Thr Ala Val Tyr Tyr Cys Ala Thr Lys Asp Ser Gly Arg Arg Asp
                85                  90                  95

Gly Met Asp Tyr Trp Gly Lys Gly Thr Leu
            100                 105

<210> SEQ ID NO 41
<211> LENGTH: 106
<212> TYPE: PRT
<213> ORGANISM: Artificial Sequence
<220> FEATURE:
<223> OTHER INFORMATION: mus musculus genetically modified to contain a
      rearrangeable camelid IgH locus
```

-continued

<400> SEQUENCE: 41

```
Gly Leu Val Gln Ala Gly Gly Ser Leu Arg Leu Ser Cys Ala Val Ser
1               5                   10                  15

Gly Arg Asn Phe Ser Ser Phe Ala Met Asn Trp Phe Arg Gln Val Pro
            20                  25                  30

Gly Lys Glu Arg Glu Phe Val Gly Ser Ile Ser Leu Ser Gly Gly Ala
        35                  40                  45

Thr Arg Tyr Val Gly Ser Val Lys Gly Arg Phe Thr Ile Ser Arg Asp
    50                  55                  60

Asp Ala Lys Asn Thr Val Tyr Leu Gln Met Asn Asp Leu Lys Pro Glu
65                  70                  75                  80

Asp Thr Ala Val Tyr Tyr Cys Ala Thr Lys Asp Pro Gly Arg Arg Asp
                85                  90                  95

Gly Met Glu Tyr Trp Gly Lys Gly Thr Leu
            100                 105
```

<210> SEQ ID NO 42
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 42

```
Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
            20                  25                  30

Gly Lys Gly Leu Glu Trp Val Ser Ala Ile Ser Trp Asn Gly Gly Asn
        35                  40                  45

Thr Tyr Tyr Ala Glu Ser Met Lys Gly Arg Phe Thr Ile Ser Arg Asp
    50                  55                  60

Asn Ala Lys Asn Thr Leu Tyr Leu Gln Met Asn Ser Leu Lys Ser Glu
65                  70                  75                  80

Asp Thr Ala Val Tyr Tyr Cys Ala Lys Glu Val Val Gly Gly Tyr Tyr
                85                  90                  95

Tyr Gly Met Asp Tyr Trp Gly Lys Gly Thr Leu
            100                 105
```

<210> SEQ ID NO 43
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 43

```
Gly Leu Val Gln Pro Gly Gly Ser Leu Arg Leu Ser Cys Glu Ala Ser
1               5                   10                  15

Gly Phe Thr Phe Asp Asp Tyr Ala Met Ser Trp Val Arg Gln Ala Pro
            20                  25                  30

Gly Lys Gly Leu Glu Trp Val Ser Ala Ile Ser Trp Asn Gly Gly Ser
        35                  40                  45

Thr Tyr Tyr Ala Glu Ser Met Lys Gly Arg Phe Thr Ile Ser Arg Asp
    50                  55                  60

Asn Ala Lys Asn Thr Leu Tyr Leu Gln Met Asn Ser Leu Lys Ser Glu
```

-continued

```
65                  70                  75                  80

Asp Thr Ala Val Tyr Tyr Cys Ala Lys Glu Val Val Ser Gly Tyr Tyr
                85                  90                  95

Tyr Gly Met Asp Tyr Trp Gly Lys Gly Thr Leu
            100                 105

<210> SEQ ID NO 44
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 44

Gly Leu Val Gln Pro Gly Gly Ser Leu Arg Leu Ser Cys Ala Ala Ser
1               5                   10                  15

Gly Phe Thr Phe Asp Asp His Ala Met Asn Trp Val Arg Gln Ala Pro
                20                  25                  30

Gly Lys Gly Leu Glu Trp Val Ser Ala Ile Ser Trp Asn Gly Gly Ser
            35                  40                  45

Thr Tyr Tyr Ala Glu Ser Met Lys Gly Arg Phe Thr Ile Ser Arg Asp
        50                  55                  60

Asn Ala Lys Asn Thr Leu Tyr Leu Gln Met Asn Ser Leu Lys Ser Glu
65                  70                  75                  80

Asp Thr Ala Val Tyr Tyr Cys Ala Lys Glu Val Val Thr Gly Tyr Tyr
                85                  90                  95

Tyr Gly Met Asp Tyr Trp Gly Lys Gly Thr Leu
            100                 105

<210> SEQ ID NO 45
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 45

Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
                20                  25                  30

Gly Lys Gly Leu Glu Trp Val Ala Ala Phe Ser Trp Asn Gly Tyr Ser
            35                  40                  45

Thr Tyr Tyr Ala Glu Ser Met Lys Gly Arg Phe Thr Ile Ser Arg Asp
        50                  55                  60

Asn Ala Lys Asn Thr Leu Tyr Leu Gln Met Asn Ser Leu Lys Ser Glu
65                  70                  75                  80

Asp Thr Ala Val Tyr Tyr Cys Ala Lys Glu Val Val Gly Gly Tyr Tyr
                85                  90                  95

Tyr Gly Met Asp Tyr Trp Gly Lys Gly Thr Leu
            100                 105

<210> SEQ ID NO 46
<211> LENGTH: 107
<212> TYPE: PRT
<213> ORGANISM: Artificial Sequence
<220> FEATURE:
<223> OTHER INFORMATION: mus musculus genetically modified to contain a
```

-continued rearrangeable camelid IgH locus

<400> SEQUENCE: 46

Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
            20                  25                  30

Gly Lys Gly Leu Glu Trp Val Ser Ala Ile Ser Trp Asn Gly Gly Asn
        35                  40                  45

Thr Tyr Tyr Ala Gly Ser Met Lys Gly Arg Phe Thr Ile Ser Arg Asp
    50                  55                  60

Asn Ala Glu Asn Thr Leu Tyr Leu Gln Met Asn Ser Leu Lys Ser Glu
65                  70                  75                  80

Asp Thr Ala Val Tyr Tyr Cys Ala Lys Glu Val Val Gly Gly Tyr Tyr
                85                  90                  95

Tyr Gly Met Asp Tyr Trp Gly Arg Gly Thr Leu
            100                 105

<210> SEQ ID NO 47
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 47

Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
            20                  25                  30

Gly Lys Gly Leu Glu Trp Val Ser Ala Ile Asn Trp Asn Gly Gly Gly
        35                  40                  45

Thr Tyr Tyr Ala Glu Ser Met Lys Gly Arg Phe Thr Ile Ser Arg Asp
    50                  55                  60

Asn Ala Lys Asn Thr Leu Tyr Leu Gln Met Asn Ser Leu Lys Ser Glu
65                  70                  75                  80

Asp Thr Ala Val Tyr Tyr Cys Ala Lys Glu Val Val Asp Gly Tyr Tyr
                85                  90                  95

Tyr Gly Met Asp Tyr Trp Gly Lys Gly Thr Leu
            100                 105

<210> SEQ ID NO 48
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 48

Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
            20                  25                  30

Gly Lys Gly Leu Glu Trp Val Ser Ala Ile Asn Trp Asn Gly Asp Ser
        35                  40                  45

Thr Tyr Tyr Ala Glu Ser Met Lys Gly Arg Phe Thr Ile Ser Arg Asp
    50                  55                  60

-continued

```
Asn Ala Lys Asn Thr Leu Tyr Leu Gln Met Asn Ser Leu Lys Ser Glu
65                  70                  75                  80

Asp Thr Ala Val Tyr Tyr Cys Ala Lys Glu Val Val Ala Gly Tyr Tyr
                85                  90                  95

His Gly Met Asp Tyr Trp Gly Lys Gly Thr Leu
            100                 105

<210> SEQ ID NO 49
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 49

Gly Leu Val Gln Pro Gly Gly Ser Leu Arg Leu Ser Cys Ala Ala Ser
1               5                   10                  15

Gly Phe Thr Phe Asp Asp Tyr Ala Met Ser Trp Val Arg Gln Ala Pro
                20                  25                  30

Gly Lys Gly Leu Glu Trp Val Ser Ala Ile Ser Trp Ser Gly Asp Ile
        35                  40                  45

Thr Tyr Tyr Ala Glu Ser Met Lys Gly Arg Ile Thr Ile Ser Arg Asp
    50                  55                  60

Ser Ala Lys Asn Lys Leu Tyr Leu Lys Met Asn Ser Leu Lys Ser Glu
65                  70                  75                  80

Asp Thr Ala Val Tyr Tyr Cys Ala Lys Glu Val Val Gly Arg Tyr Tyr
                85                  90                  95

Tyr Gly Met Asp Tyr Trp Gly Lys Gly Thr Leu
            100                 105

<210> SEQ ID NO 50
<211> LENGTH: 107
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 50

Gly Leu Val Gln Pro Gly Gly Ser Leu Thr Leu Ser Cys Ala Ala Ser
1               5                   10                  15

Gly Phe Thr Phe Asp Asp Phe Ala Met Asn Trp Val Arg Gln Ala Pro
                20                  25                  30

Gly Lys Gly Leu Glu Trp Val Ser Ala Ile Ser Trp Asn Gly Gly Gly
        35                  40                  45

Thr Tyr Tyr Ala Glu Ala Met Lys Gly Arg Phe Thr Ile Ser Arg Asp
    50                  55                  60

Asn Ala Asn Asn Met Val Tyr Leu His Met Ser Ser Leu Lys Ser Glu
65                  70                  75                  80

Asp Thr Ala Ile Tyr Tyr Cys Ala Lys Glu Val Val Ala Gly Tyr Tyr
                85                  90                  95

Tyr Gly Met Asp Tyr Trp Gly Lys Gly Thr Leu
            100                 105

<210> SEQ ID NO 51
<211> LENGTH: 109
<212> TYPE: PRT
<213> ORGANISM: Artificial Sequence
```

-continued

<220> FEATURE:
<223> OTHER INFORMATION: mus musculus genetically modified to contain a
      rearrangeable camelid IgH locus

<400> SEQUENCE: 51

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
            20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
            100                 105
```

<210> SEQ ID NO 52
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 52

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
            20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
            100                 105
```

<210> SEQ ID NO 53
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 53

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
            20                  25                  30

Gly Lys Glu Arg Glu Phe Val Ala Ala Ile Ser Trp Ser Gly Gly Ser
        35                  40                  45
```

-continued

```
Thr Tyr Tyr Ala Asp Ser Val Lys Gly Arg Phe Thr Ile Ser Arg Asp
    50                  55                  60

Asn Ala Lys Asn Thr Val Phe Leu His Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
                100                 105
```

```
<210> SEQ ID NO 54
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 54
```

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
                20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Asn Ala Lys Asn Thr Val Phe Leu His Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
                100                 105
```

```
<210> SEQ ID NO 55
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 55
```

```
Gly Leu Val Gln Ala Gly Gly Ser Leu Arg Leu Ser Cys Ala Ala Ser
1               5                   10                  15

Gly Arg Thr Phe Ser Ser Tyr Ala Met Gly Trp Phe Arg Gln Ala Pro
                20                  25                  30

Gly Lys Glu Arg Glu Phe Val Ala Ala Ile Ser Trp Ser Gly Gly Ser
        35                  40                  45

Thr Tyr Tyr Ala Asp Ser Val Lys Gly Arg Phe Thr Ile Ser Arg Asp
    50                  55                  60

Asn Ala Lys Asn Thr Val Phe Leu His Met Asn Ser Leu Lys Pro Glu
65                  70                  75                  80

Asp Thr Ala Val Tyr Phe Cys Ala Ala Gly Met Glu Ile Val Gly Arg
                85                  90                  95

Gly Tyr His Gly Met Asp Tyr Trp Gly Lys Gly Thr Leu
                100                 105
```

```
<210> SEQ ID NO 56
<211> LENGTH: 109
```

<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 56

Gly Leu Val Gln Ala Gly Gly Ser Leu Arg Leu Ser Cys Ala Ala Ser
1               5                   10                  15

Gly Arg Thr Leu Ser Asn Tyr Ala Met Gly Trp Phe Arg Gln Ala Pro
            20                  25                  30

Gly Lys Glu Arg Glu Phe Val Ala Gly Ile Asn Trp Ile Asn Asp Asn
        35                  40                  45

Thr Tyr Tyr Val Asp Ser Val Lys Gly Arg Phe Thr Ile Ser Arg Asp
    50                  55                  60

Asn Ala Lys Asn Thr Val Phe Leu His Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
            100                 105

<210> SEQ ID NO 57
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 57

Gly Leu Val Gln Ala Gly Gly Ser Leu Arg Leu Ser Cys Val Ala Ser
1               5                   10                  15

Gly Arg Thr Phe Ser Asn Tyr Ala Met Gly Trp Phe Arg Gln Ala Pro
            20                  25                  30

Gly Lys Glu Arg Glu Phe Val Ala Gly Ile Asn Trp Ile Asn Asp Asn
        35                  40                  45

Thr Tyr Tyr Ile Asp Ser Val Lys Gly Arg Phe Thr Ile Ser Arg Asp
    50                  55                  60

Asn Ala Lys Asn Thr Val Phe Leu His Met Asn Ser Leu Lys Pro Glu
65                  70                  75                  80

Asp Thr Ala Val Tyr Phe Cys Ala Ala Gly Met Glu Ile Leu Thr Arg
                85                  90                  95

Gly His Tyr Gly Met Asp Tyr Trp Gly Lys Gly Thr Leu
            100                 105

<210> SEQ ID NO 58
<211> LENGTH: 109
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 58

Gly Leu Val Gln Ala Gly Gly Ser Leu Arg Leu Ser Cys Ala Ala Ser
1               5                   10                  15

Gly Arg Thr Leu Ser Asn Tyr Ala Met Gly Trp Phe Arg Gln Gly Pro
            20                  25                  30

Gly Lys Glu Arg Glu Phe Val Ala Gly Ile Asn Trp Ile Asn Asp Asn

-continued

```
        35              40              45
Thr Tyr Tyr Glu Asp Ser Val Lys Gly Arg Phe Thr Ile Ser Arg Asp
    50              55              60

Asn Ala Lys Asn Thr Val Phe Leu His Met Asn Ser Leu Lys Pro Glu
65              70              75              80

Asp Thr Ala Val Tyr Phe Cys Ala Ala Gly Met Glu Ile Val Thr Arg
                85              90              95

Gly His Tyr Gly Met Asp His Trp Gly Lys Gly Thr Leu
            100             105

<210> SEQ ID NO 59
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 59

Gly Leu Val Gln Ala Gly Gly Ser Leu Arg Leu Ser Cys Ala Ala Ser
1               5               10              15

Gly Arg Thr Phe Ser Ser Tyr Ala Met Gly Trp Phe Arg Gln Ala Pro
            20              25              30

Gly Lys Glu Arg Glu Ile Val Ala Ser Ile Ser Trp Asn Gly Gly Ser
        35              40              45

Thr Asp Tyr Ala Asp Ser Val Lys Gly Arg Phe Thr Ile Ser Arg Asp
    50              55              60

Asn Ala Lys Asn Thr Val Tyr Leu Gln Met Asn Ser Leu Lys Pro Glu
65              70              75              80

Asp Thr Ala Val Tyr Tyr Cys Ala Ala Asp Ser Thr Asn Trp Val Phe
                85              90              95

Tyr Asp Tyr Trp Gly Gln Gly Thr Gln
            100             105

<210> SEQ ID NO 60
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 60

Gly Leu Val Gln Ala Gly Gly Ser Leu Arg Leu Ser Cys Ala Ala Ser
1               5               10              15

Gly Arg Thr Phe Ser Ser Tyr Ala Met Gly Trp Phe Arg Gln Ala Pro
            20              25              30

Gly Lys Glu Arg Glu Ile Val Ala Thr Ile Ser Trp Asn Gly Gly Thr
        35              40              45

Thr Asp Tyr Ala Asp Ser Val Lys Gly Arg Phe Thr Ile Ser Arg Asp
    50              55              60

Asn Ala Lys Asn Thr Val Tyr Leu Gln Met Asn Ser Leu Lys Pro Glu
65              70              75              80

Asp Thr Ala Val Tyr Tyr Cys Ala Ala Asp Ser Thr Asn Trp Val Phe
                85              90              95

Tyr Asp Tyr Trp Gly Gln Gly Thr Gln
            100             105
```

-continued

<210> SEQ ID NO 61
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 61

Gly Leu Val Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Ser Ile Ser Trp Asn Gly Gly Ser
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 62
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 62

Gly Leu Val Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Gly Thr
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 63
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 63

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

```
Gly Lys Glu Arg Glu Ile Val Ala Thr Ile Ser Trp Asn Gly Gly Thr
        35                  40                  45

Thr Asp Tyr Ala Asp Ser Val Lys Gly Arg Phe Thr Ile Ser Arg Asp
        50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 64
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 64

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Gly Ser
        35                  40                  45

Thr Asp Tyr Ala Asp Ser Val Lys Gly Arg Phe Thr Ile Ser Arg Asp
        50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 65
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 65

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Ser Ile Ser Trp Asn Gly Gly Ser
        35                  40                  45

Thr Asp Tyr Ala Asp Ser Val Lys Gly Arg Phe Thr Ile Ser Arg Asp
        50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105
```

-continued

```
<210> SEQ ID NO 66
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 66

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
                20                  25                  30

Gly Lys Glu Arg Glu Ile Val Ala Thr Ile Ser Trp Asn Gly Gly Ser
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 67
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 67

Gly Leu Ala Gln Ala Gly Gly Ser Leu Arg Leu Ser Cys Ala Ala Ser
1               5                   10                  15

Gly Arg Thr Phe Ser Ser Phe Ala Met Ala Trp Phe Arg Gln Ala Pro
                20                  25                  30

Gly Lys Glu Arg Glu Ile Val Ala Ser Ile Asn Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 68
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 68

Gly Leu Ala Gln Ala Gly Gly Ser Leu Arg Leu Ser Cys Ala Ala Ser
1               5                   10                  15
```

```
Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Gly Thr
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 69
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 69

Gly Leu Ala Gln Ala Gly Asp Ser Leu Arg Leu Ser Cys Ala Ala Ser
1               5                   10                  15

Gly Arg Pro Phe Asn Thr Tyr Thr Met Ala Trp Phe Arg Gln Ala Pro
            20                  25                  30

Gly Lys Glu Arg Glu Ile Val Ala Thr Ile Ser Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Asn Trp Val Phe
                85                  90                  95

Tyr Asp Tyr Trp Gly Gln Gly Thr Gln
            100                 105

<210> SEQ ID NO 70
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 70

Gly Leu Ala Gln Ala Gly Gly Ser Leu Arg Leu Ser Cys Ala Val Ser
1               5                   10                  15

Gly Arg Thr Phe Ser Ser Tyr Ala Met Ala Trp Phe Arg Gln Ala Pro
            20                  25                  30

Gly Lys Glu Arg Glu Ser Val Ala Thr Ile Ser Arg Asn Gly Asp Arg
        35                  40                  45

Thr Asp Tyr Val Asp Ser Val Lys Gly Arg Phe Thr Ile Ser Arg Asp
    50                  55                  60

Asn Ala Lys Asn Thr Val Tyr Leu Gln Met Asn Ser Leu Lys Pro Glu
65                  70                  75                  80

Asp Thr Ala Val Tyr Tyr Cys Ala Ala Asp Ser Thr Lys Trp Val Phe
                85                  90                  95
```

-continued

```
Tyr Asp Tyr Trp Gly Gln Gly Thr Gln
            100                 105

<210> SEQ ID NO 71
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 71

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Asp Thr
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Thr Pro Glu
65                  70                  75                  80

Asp Thr Ala Val Tyr Tyr Cys Ala Ala Asp Ser Thr Lys Trp Val Phe
            85                  90                  95

Tyr Asp Tyr Trp Gly Gln Gly Thr Gln
            100                 105

<210> SEQ ID NO 72
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 72

Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Asp Thr
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Thr Pro Glu
65                  70                  75                  80

Asp Thr Ala Val Tyr Tyr Cys Ala Ala Asp Ser Thr Lys Trp Val Phe
            85                  90                  95

Tyr Asp Tyr Trp Gly Gln Gly Thr Gln
            100                 105

<210> SEQ ID NO 73
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 73

Gly Leu Ala Gln Ala Gly Gly Ser Leu Arg Leu Ser Cys Val Val Ser
```

-continued

```
1               5               10              15

Gly Arg Thr Phe Ser Ser Tyr Ala Met Ala Trp Phe Arg Gln Ala Pro
            20              25              30

Gly Lys Glu Arg Glu Val Val Ala Thr Ile Ser Arg Asn Gly Asp Arg
        35              40              45

Thr Asp Tyr Val Asp Ser Val Lys Gly Arg Phe Thr Ile Ser Arg Asp
    50              55              60

Asn Ala Lys Asn Thr Val Tyr Leu Gln Met Asn Ser Leu Lys Pro Glu
65              70              75              80

Asp Thr Ala Val Tyr Tyr Cys Ala Ala Asp Ser Thr Lys Trp Val Phe
            85              90              95

Tyr Asp Tyr Trp Gly Gln Gly Thr Gln
            100             105

<210> SEQ ID NO 74
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 74

Gly Leu Ala Gln Ala Gly Gly Ser Leu Arg Leu Ser Cys Ala Ala Ser
1               5               10              15

Gly Arg Thr Phe Ser Ser Tyr Ala Met Ala Trp Phe Arg Gln Ala Pro
            20              25              30

Gly Lys Glu Arg Glu Ile Val Ala Ser Ile Ser Trp Asn Gly Asn Ser
        35              40              45

Thr Asp Tyr Ala Asp Ser Val Lys Gly Arg Phe Thr Ile Ser Arg Asp
    50              55              60

Asn Ala Lys Asn Thr Val Tyr Leu Gln Met Asn Ser Leu Lys Ala Glu
65              70              75              80

Asp Thr Ala Val Tyr Tyr Cys Ala Ala Asp Ser Thr Lys Trp Val Phe
            85              90              95

Tyr Asp Tyr Trp Gly Gln Gly Thr Gln
            100             105

<210> SEQ ID NO 75
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 75

Gly Leu Ala Gln Ala Gly Gly Ser Leu Arg Leu Ser Cys Ala Ala Ser
1               5               10              15

Gly Arg Thr Phe Ser Ser Phe Ala Met Ala Trp Phe Arg Gln Ala Pro
            20              25              30

Gly Lys Glu Arg Glu Ile Val Ala Thr Ile Asn Trp Asn Gly Gly Ser
        35              40              45

Thr Asp Tyr Thr Asp Ser Val Lys Gly Arg Phe Thr Ile Ser Arg Asp
    50              55              60

Asn Ala Lys Asn Thr Val Tyr Leu Gln Met Asn Ser Leu Lys Pro Glu
65              70              75              80

Asp Thr Ala Val Tyr Tyr Cys Ala Ala Asp Ser Thr Lys Trp Val Phe
```

-continued

```
                    85              90              95

Tyr Asp Tyr Trp Gly Gln Gly Thr Gln
            100             105

<210> SEQ ID NO 76
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 76

Gly Leu Ala Gln Ala Gly Gly Ser Leu Arg Leu Ser Cys Ala Ala Ser
1               5                   10                  15

Gly Arg Thr Phe Ser Ser Phe Ala Met Ala Trp Phe Arg Gln Ala Pro
            20                  25                  30

Gly Lys Glu Arg Glu Ile Val Ala Ser Ile Asn Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Ile Tyr Leu Gln Met Asn Ser Leu Lys Pro Glu
65                  70                  75                  80

Asp Thr Ala Val Tyr Tyr Cys Ala Ala Asp Ser Thr Lys Trp Val Phe
                85                  90                  95

Tyr Asp Tyr Trp Gly Gln Gly Thr Gln
            100             105

<210> SEQ ID NO 77
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 77

Gly Leu Ala Gln Ala Gly Gly Ser Leu Arg Leu Ser Cys Ala Ala Ser
1               5                   10                  15

Gly Arg Thr Phe Ser Ser Phe Ala Met Ala Trp Phe Arg Gln Ala Pro
            20                  25                  30

Gly Lys Glu Arg Glu Ile Val Ala Ser Ile Ser Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Val Phe Leu Gln Met Asn Ser Leu Lys Pro Glu
65                  70                  75                  80

Asp Thr Ala Val Tyr Tyr Cys Ala Ala Asp Ser Thr Lys Trp Val Phe
                85                  90                  95

Tyr Asp Tyr Trp Gly Gln Gly Thr Gln
            100             105

<210> SEQ ID NO 78
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 78
```

```
Gly Leu Ala Gln Ala Gly Gly Ser Leu Arg Leu Ser Cys Ala Ala Ser
1               5                   10                  15

Gly Arg Thr Phe Ser Ser Tyr Ala Met Ala Trp Phe Arg Gln Ala Pro
            20                  25                  30

Gly Lys Glu Arg Glu Ile Val Ala Thr Ile Ser Trp Asn Gly Asp Thr
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Glu Pro Glu
65                  70                  75                  80

Asp Thr Ala Val Tyr Tyr Cys Ala Ala Asp Ser Ser Arg Trp Val Phe
                85                  90                  95

Tyr Asp Tyr Trp Gly Gln Gly Thr Gln
            100                 105
```

<210> SEQ ID NO 79
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 79

```
Gly Leu Ala Gln Ala Gly Gly Ser Leu Arg Leu Ser Cys Ala Ala Ser
1               5                   10                  15

Gly Arg Thr Phe Ser Ser Phe Ala Met Ala Trp Phe Arg Gln Ala Pro
            20                  25                  30

Gly Lys Glu Arg Glu Ile Val Ala Ser Ile Asn Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Glu Pro Glu
65                  70                  75                  80

Asp Thr Ala Val Tyr Tyr Cys Ala Ala Asp Ser Ser Arg Trp Val Phe
                85                  90                  95

Tyr Asp Tyr Trp Gly Gln Gly Thr Gln
            100                 105
```

<210> SEQ ID NO 80
<211> LENGTH: 105
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 80

```
Gly Leu Ala Gln Ala Gly Gly Ser Leu Arg Leu Ser Cys Ala Ala Ser
1               5                   10                  15

Gly Arg Thr Phe Ser Ser Phe Ala Met Ala Trp Phe Arg Gln Ala Pro
            20                  25                  30

Gly Lys Glu Arg Glu Ile Val Ala Ser Ile Ser Trp Asn Gly Asp Ile
        35                  40                  45

Thr Asp Tyr Ala Asp Ser Val Lys Gly Arg Phe Thr Ile Ser Arg Asp
    50                  55                  60

Asn Ala Lys Asn Thr Val Tyr Leu Gln Met Asn Ser Leu Glu Pro Glu
65                  70                  75                  80
```

-continued

```
Asp Thr Ala Val Tyr Tyr Cys Ala Ala Asp Ser Ser Arg Trp Val Phe
                85                  90                  95

Tyr Asp Tyr Trp Gly Gln Gly Thr Gln
            100                 105

<210> SEQ ID NO 81
<211> LENGTH: 10
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 81

Lys Asp Asn Gly Ser Ser Pro Met Asp Tyr
1               5                   10

<210> SEQ ID NO 82
<211> LENGTH: 15
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 82

Ala Asp Val Arg Thr Val Val Ala Ala Asn Tyr Gly Met Asp Tyr
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 83

Ala Asp Ser Thr Asn Trp Val Phe Tyr Asp Tyr
1               5                   10

<210> SEQ ID NO 84
<211> LENGTH: 13
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 84

Lys Asp Arg Asp Tyr Ser Gly Ser Tyr Tyr Tyr Thr Asp
1               5                   10

<210> SEQ ID NO 85
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 85

Ala Asp Ser Thr Lys Trp Val Phe Tyr Asp Tyr
1               5                   10

<210> SEQ ID NO 86
```

<211> LENGTH: 10
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 86

Arg Tyr Tyr Ser Gly Ser Tyr Pro Asp Tyr
1               5                   10

<210> SEQ ID NO 87
<211> LENGTH: 5
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 87

Tyr Tyr Ser Gly Ser
1               5

<210> SEQ ID NO 88
<211> LENGTH: 8
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 88

Arg Arg Thr Tyr Gly Met Asp Tyr
1               5

<210> SEQ ID NO 89
<211> LENGTH: 5
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 89

Lys Gln Pro Asp Tyr
1               5

<210> SEQ ID NO 90
<211> LENGTH: 16
<212> TYPE: PRT
<213> ORGANISM: Artificial Sequence
<220> FEATURE:
<223> OTHER INFORMATION: Mus musculus genetically modified to contain
      the Llama IgH Locus

<400> SEQUENCE: 90

Ala Gly Tyr Gln Leu Leu Pro Tyr Gly Asn Tyr Tyr Gly Met Asp Tyr
1               5                   10                  15

<210> SEQ ID NO 91
<211> LENGTH: 12
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 91

```
Lys Gly Asn Ser Tyr Tyr Ser Tyr Gly Met Asp Tyr
1               5                   10

<210> SEQ ID NO 92
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 92

Ala Asp Ser Ser Arg Trp Val Phe Tyr Asp Tyr
1               5                   10

<210> SEQ ID NO 93
<211> LENGTH: 13
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 93

Lys Asp Arg Ser Tyr Ser Gly Ser Tyr Tyr Tyr Asp Tyr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 94

Ala Lys Asp Ala Pro Tyr Gly Ser Ser Trp Leu Asp Tyr
1               5                   10

<210> SEQ ID NO 95
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 95

Lys Gly Gly Val Trp Arg Asp Gly Met Asp Tyr
1               5                   10

<210> SEQ ID NO 96
<211> LENGTH: 13
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 96

Ala Asp Asp Gly Ser Ser Trp Tyr Gly Asp Phe Gly Ser
1               5                   10

<210> SEQ ID NO 97
<211> LENGTH: 12
<212> TYPE: PRT
<213> ORGANISM: Artificial Sequence
<220> FEATURE:
```

<223> OTHER INFORMATION: mus musculus genetically modified to contain a
      rearrangeable camelid IgH locus

<400> SEQUENCE: 97

Ala Ser Thr Val Val Ala Leu Tyr Gly Met Asp Tyr
1               5                   10

<210> SEQ ID NO 98
<211> LENGTH: 15
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 98

Ala Asp Gln Tyr Gly Ser Ser Trp Tyr Asp Tyr Gly Met Asp Tyr
1               5                   10                  15

<210> SEQ ID NO 99
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 99

Ala Ala Gly Ser Ser Trp Tyr Arg Tyr Asp Tyr
1               5                   10

<210> SEQ ID NO 100
<211> LENGTH: 14
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 100

Lys Thr Pro Gly Ser Ser Trp Tyr Arg Asp Gly Met Asp Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 101

Ala Asp Pro Tyr Gly Arg Tyr Glu Tyr Asp Tyr
1               5                   10

<210> SEQ ID NO 102
<211> LENGTH: 9
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 102

Leu Ala Gly Val Thr Asp Phe Gly Ser
1               5

-continued

```
<210> SEQ ID NO 103
<211> LENGTH: 12
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 103

Ala Gly Tyr Tyr Ser Gly Ser Tyr Arg Met Asp Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Mus musculus genetically modified to contain
      the Llama IgH Locus

<400> SEQUENCE: 104

Ala Gly Thr Val Val Ala Gly Thr Tyr Asp Tyr
1               5                   10

<210> SEQ ID NO 105
<211> LENGTH: 13
<212> TYPE: PRT
<213> ORGANISM: Artificial Sequence
<220> FEATURE:
<223> OTHER INFORMATION: mus musculus genetically modified to contain a
      rearrangeable camelid IgH locus

<400> SEQUENCE: 105

Lys Asp Arg Asp Tyr Ser Gly Ser Tyr Tyr Phe Asp Tyr
1               5                   10
```

VHH-CONTAINING HEAVY CHAIN ANTIBODY AND PRODUCTION THEREOF

CROSS-REFERENCE TO RELATED PATENT APPLICATIONS

This application is a national stage entry of International Application No. PCT/EP2017/082074, filed on Dec. 8, 2017, and claims priority to European Patent Application No. EP 16203240.3 filed Dec. 9, 2016, the contents of these applications are hereby incorporated by reference as if set forth in their entirety herein.

SEQUENCE LISTING

This application contains, as a separate part of the disclosure, a Sequence Listing in computer readable form (filename: 2022-06-09_166228-00016_ST25; Created: Jun. 6, 2022 and is 535,864 bytes in size), which is incorporated by reference in its entirety

FIELD OF THE INVENTION

The present invention describes isolated polynucleotides for the production of a VHH-containing heavy chain antibody in a mammal and vectors comprising said isolated polynucleotide. Moreover, the invention relates to a transgenic mammal comprising the vector for the production of a VHH-containing heavy chain antibody. Further, the invention relates to VHH-containing heavy chain antibodies as well as methods for the production and cloning of VHH-containing heavy chain antibodies.

BACKGROUND OF THE INVENTION

Monoclonal and recombinant antibodies are important tools in medicine and biotechnology. Llamas carry a variant immunoglobulin locus that permits the generation of unusual antibodies composed only of heavy chains. The single variable domain of these antibodies (designated VHH, sdAb, or nanobody) is the smallest antigen-binding domain generated by adaptive immune systems. With a long complementarity-determining region 3 (CDR3), VHHs can extend into crevices on proteins that are not accessible to conventional antibodies, including functionally interesting sites such as the active site of an enzyme or the receptor-binding canyon on a virus surface. VHHs offer numerous other advantages compared to conventional antibodies carrying variable domains (VH and VL) of conventional antibodies, including higher stability, solubility, expression yields, and refolding capacity, as well as better in vivo tissue penetration. Moreover, in contrast to the VH domains of conventional antibodies VHH do not display an intrinsic tendency to bind to light chains. This facilitates the induction of heavy chain antibodies in the presence of a functional light chain loci. Further, since VHH do not bind to VL domains, it is much easier to reformat of VHHs into bispecific antibody constructs than constructs containing conventional VH-VL pairs or single domains based on VH domains.

So far, heavy-chain antibodies are generated in camelids, such as llamas which have several disadvantages: camelids are expensive to maintain and are not suitable for straight forward genetic engineering resulting in a lack of gene-deficient camelids. Alternatively, conventional antibodies, or heavy-chain antibodies that are based on the human or mouse elements are expressed in transgenic mice.

Up to now, neither a genetic construct nor a transgenic animal that comprises the camelid VHH region, camelid D region, camelid J region and camelid constant heavy chain region which are not rearranged are available.

WO 02/085944 A2 relates to the generation of camelised heavy chain antibodies, wherein the VHH heavy chain locus does not comprise a functional CH4 domain. Due to the lack of the functional CH4 domain no functional IgM antibody can be produced, thereby the class switch from IgM to IgG is omitted which is disadvantageous, since the natural maturation process is thereby shortened.

Thus the invention combines unique functional and structural properties of llama antibodies, that not only lie in the lack of the light chain, but also further structural characteristics, such as the elongated CDR regions that can approach also deep crevices of the antigen, high solubility and high stability, with technologies of genetic modifications and improvements of rodents (e.g. the large repertoire of knock-out mice that is available).

In particular, the genetic construct and transgenic animals of the invention allow to exploit fully the natural maturation processes leading to highly efficiently target-specific VHH-containing heavy chain antibodies.

It is the goal of the present invention to provide an improved platform for antibody generation. In particular, it is the goal of the invention to provide VHH-containing heavy chain antibodies with unique functional and structural properties, transgenic mammals for producing VHH-containing heavy chain antibodies as well as the corresponding methods and constructs that allow to exploit the natural recombination and selection mechanism of the mammalian organism, as well as the combination with the genetic modification tools that are available.

SUMMARY OF THE INVENTION

Thus, a first aspect of the invention refers to an isolated polynucleotide for the production of a VHH-containing heavy chain antibody in a mammal, comprising:

a) a camelid VHH region,
b) a camelid D region,
c) a camelid J region,
d) a camelid constant heavy chain region, without a CH1 domain;

wherein the camelid VHH region, the camelid D region and the camelid J region are not rearranged.

Since the camelid sequences are optimized for the structure of VHH-containing heavy chain antibodies, it is advantageous that all elements including VHH region, D region, J region and constant heavy chain regions comprise structural characteristics of the camelid VHH-containing heavy chain antibody. When the elements in the polynucleotide are not rearranged, the rearrangement, somatic hypermutation and class switch can occur in the transgenic animal and thereby advantages of the natural immune system can be exploited.

In some embodiments, the camelid D region comprises at least two camelid D elements, preferably all camelid D elements. Preferably, the camelid J region comprises at least two camelid J elements, preferably all camelid J elements. Thereby the genetic variation is increased. Additionally, the polynucleotide may comprise at least one synthetic D element and/or at least one synthetic J element.

In a preferred embodiment the constant heavy chain region comprises an element encoding a CH4 domain.

The inventors found that, surprisingly, genetic construct and transgenic animals comprising an IgM region with a CH4 domain are advantageous, since they allow to produce efficiently target-specific VHH-containing heavy chain antibodies. The inventors assume that this could be due to the fact that extensive somatic hypermutation can already occur at the IgM stage and that a construct comprising a CH4 domain does not only allow to produce IgG but also IgM antibodies. Thereby the full maturation process in the organism including somatic hypermutation, selection of IgM antibodies followed by the class switch to IgG antibodies can be exploited. Thereby highly effective antibodies can be produced, since they passed through the complete maturation process.

Typically, the constant heavy chain region comprises elements encoding a) a CH2, a CH3 and a CH4 domain of an IgM, and/or b) a hinge, a CH2 domain and a CH3 domain of an IgG.

In a preferred embodiment, the constant heavy chain region comprises elements encoding a) a CH2, a CH3 and a CH4 domain of an IgM, and b) a hinge, a CH2 domain and a CH3 domain of an IgG.

In a preferred embodiment, the constant heavy chain region is lacking an IgD region.

Thus, in a particular embodiment the constant heavy chain region comprising elements encoding a) a CH2, a CH3 and a CH4 domain of an IgM, and b) a hinge, a CH2 domain and a CH3 domain of an IgG, wherein heavy chain region is lacking an IgD region.

So far neither a genetic construct nor a transgenic animal is available that comprises the camelid VHH region, camelid D region, and camelid J region which are not rearranged and a camelid constant heavy chain region without a functional CH1 domain and further contains a CH4 domain.

Moreover, the inventors found that, surprisingly, genetic construct and transgenic animals comprising an IgM region with a CH4 domain and lacking an IgD region are particularly advantageous. The camelid genomic IgD region has distinct features compared to the corresponding genomic region of other mammals (Achour et al. 2008). The coding region of the camelid IgD is non-functional, i.e. the exons do not encode a functional polypeptide. Moreover, unlike the IgD region of the mouse and human IgH-locus, the camelid IgD region contains an apparently intact upstream switch region that could cause class switch recombination of a rearranged V-D-J gene to the non-functional IgD gene. The inventors therefore assume that the deletion of the camelid IgD region including the associated upstream switch region has a beneficial effect on heavy chain antibody production since this precludes class switch recombination to a non-functional locus.

In some embodiments, the constant heavy chain region comprises an element which encodes at least one of the group consisting of camelid IgG2a, camelid IgG2b, camelid IgG2c, camelid IgG3 and camelid IgM. In particular embodiments, the constant heavy chain region does not comprise a δ region.

In preferred embodiments the constant heavy chain region comprises an element which encodes camelid IgM and at least one of the group consisting of camelid IgG2a, camelid IgG2b, camelid IgG2c, camelid IgG3. In more preferred embodiments the constant heavy chain region comprises an element which encodes camelid IgM and at least one of the group consisting of camelid IgG2a, camelid IgG2b, camelid IgG2c, camelid IgG3, does not comprise a δ region containing the IgD pseudogene and the upstream-switch region.

In a specific embodiment, the constant heavy chain region does not comprise a γ2a region.

Preferably, the polynucleotide comprises at least one enhancer specific for the mammal in which the VHH-containing heavy chain antibody is expressed or a related mammal.

In some embodiments, the camelid VHH region comprises at least 1 camelid VHH element.

Additionally, the polynucleotide may comprise at least one synthetic VHH element.

In some embodiments, the camelid VHH region may comprises at least one element encoding a shark VNAR or a synthetic VNAR-like variable domain.

In specific embodiments, the exons encoding the membrane proximal CH domain(s), transmembrane domain(s) and cytosolic domain(s) may be exchanged by the exons encoding the corresponding domains of the mammal in which the VHH-containing heavy chain antibody is expressed or a related mammal. In more specific embodiments, the exons encoding the membrane proximal CH domain(s), transmembrane domain(s) and cytosolic domain(s) may be exchanged by the exons encoding the corresponding murine domains.

The camelid may be of the family selected from *Lama, Vicugna* or *Camelus*. The camelid may be for example *Lama pacos, Lama guanicoe, Vicugna pacos, Camelos dromedaries Camelus bactrianus*. In one embodiment the camelid is selected from *Lama pacos* and *Lama glama*, preferably *Lama glama*.

In some embodiments, the polynucleotide is encoded by the sequence being at least 80% identical to SEQ ID NO.: 30. For example, the polynucleotide may be encoded by the sequence to SEQ ID NO.: 30 or fragments thereof.

Typically, the camelid VHH region, the camelid D region and the camelid J region are capable of rearranging to form a VDJ coding sequence.

Another aspect of the invention refers to a vector comprising the polynucleotide as described herein. In some embodiments the vector is a bacterial artificial chromosome, yeast artificial chromosome, human artificial chromosome, cosmide or synthetic DNA, preferably a bacterial artificial chromosome. Thereby a platform for site-specific improvement of the camelid derived gene locus, in particular the *Lama glama* derived IgH locus is provided.

Another aspect of the invention refers to a transgenic mammal comprising the isolated polynucleotide as described herein or a vector comprising the isolated polynucleotide as described herein. The polynucleotide is not endogenous but heterologous to the transgenic mammal. Preferably, the mammal is devoid of a functional endogenous IgH locus.

Typically, the transgenic mammal is a non-human mammal. The transgenic mammal may be for example a rodent, such as a mouse or rat. Thereby, it is possible to generate VHH-containing heavy chain antibodies in transgenic rodents, especially transgenic mice. This allows to generate VHH-containing heavy chain antibodies in the rodent genetic background, including the opportunity to immunize animals genetically deficient for the immunogen or its respective orthologue. In specific embodiments, the mammal is a mouse and the polynucleotide comprises a mouse Ig-alpha enhancer. Upon expression of a rearranged immunoglobulin encoded by the polynucleotide as defined herein, the mammal expresses VHH-containing heavy chain antibodies, thereby the mammal may be capable of generating B cells. In specific embodiments, the mammal expresses the VHH-containing heavy chain antibody as membrane bound and/or soluble version.

A further aspect of the invention refers to a VHH-containing heavy chain antibody which is encoded by a rearranged VHH-D-J sequence of the polynucleotide as described herein.

Another aspect of the invention refers to a method for the production of a VHH-containing heavy chain antibody in a mammal comprising the step of expressing a heterologous VHH-containing heavy chain antibody in that mammal, wherein the heterologous VHH-containing heavy chain antibody is encoded by a rearranged VHH-D-J sequence of the polynucleotide as defined herein.

Further, the invention relates to a method for cloning a VHH-containing heavy chain antibody from a mammal wherein the heterologous VHH-containing heavy chain antibody is encoded by a rearranged VHH-D-J sequence of the polynucleotide as defined herein.

Accordingly, the invention refers to a VHH-containing heavy chain antibody produced by the methods as described herein.

In summary, the platform of the invention is suitable for
    generating camelid-derived heavy chain only antibodies
        with the special properties of camelid elements, such as
        high solubility, high stability and extended CDR
        regions capable of approaching functional protein crevices,
    exploiting the natural rearrangement system of the
        immune system,
    exploiting in particular the IgM selection, somatic hypermutation and the class switch recombination from IgM
        to IgG of the immune system,
    generating VHH-containing heavy chain antibodies in
        transgenic mammals, in particular mammals lacking
        the endogenous target antigen,
    site-specific improvement of the *Lama glama* derived IgH
        locus.

BRIEF DESCRIPTION OF THE DRAWINGS

The present invention will hereafter be described with reference to the accompanying drawings, wherein like reference numerals denote like elements.

FIG. 1 is a schematic diagram of BACs V03 and F07 isolated from a *Lama glama* genomic library and of the genetic modifications made to generate BAC TE-01 as a basis for endowing transgenic mice with the capacity to produce llama-derived heavy chain only antibodies.

FIG. 2 is a Germline transmission of llama IgH transgene TE-01. (A) Schematic diagram of llama IgH transgene TE-01 and of the location of the PCR primers used for genotyping. (B) PCR genotyping of the offspring of a cross between a TE-01-carrying founder mice and a WT mouse.

FIG. 5 is an amino acid sequence alignment of a clone of VHH-IgM heavy chain antibodies obtained from the spleen of an immunized TE-01 transgenic mouse shows extensive somatic hypermutation. The figure shows an amino acid sequence alignment of nine members of a clone of VHH-IgM heavy chain-antibodies obtained from the spleen of an immunized TE-01 mouse three days after the final boost immunization. Amino-acid residues encoded by the D element in germline configuration in the rearranged clone are underlined. The junctions of the D element with the VHH and J genes show extensive N-junction nucleotide deletions and insertions. Residues in the VHH region that differ from the germline configuration due to somatic hypermutation are highlighted in grey. Similarly, variant residues in the CDR3 likely due to somatic mutation are also highlighted in grey. Numbering of amino acid residues on top corresponds to Kabat numbering of V domains (Kabat et al. (1991) Sequences of Proteins of Immunological Interest, 5th ed., NIH Publication No. 91-3242, Bethesda, MD, USA). The framework and complementarity determining regions (FR1-FR4, CDR1-CDR3) are indicated in brackets below the alignment. The two cysteine residues mediating the conserved canonical disulfide bridge are marked by asterisks and highlighted in grey. Sequences 5-1 to 5-9, SEQ ID NOs: 33-41, respectively.

FIG. 8 is a SDS-PAGE and Coomassie staining of proteins in the supernatants of transiently transfected HEK-6E cells reveals efficient production of chimeric VHH-rabbit IgG heavy chain antibodies. HEK-6E cells were transfected with expression vectors encoding individual heavy chain antibodies (VHH-rabbit IgG hinge-CH2-CH3) from immunized TE-01 mice. Cell supernatants were harvested six days after transfection and proteins in cell supernatants were analyzed by SDS-PAGE and Coomassie staining. Each lane was loaded with 10 µl cell supernatant. Bands at 40-45 kD correspond to reduced heavy chain antibodies. SM=molecular weight marker proteins containing BSA (1 µg, 64 kD), IgG heavy chain (500 ng, 50 kD), IgG light chain (250 ng, 25 kD), lysozyme (100 ng, 14 kD).

FIG. 10 is an amino acid sequence alignment of 22 members of a clone of AAV-specific VHH heavy chain antibodies obtained from an immunized TE-01 transgenic mouse three days after the final boost immunization. Amino-acid residues encoded by the D element in germline configuration in the rearranged clone are underlined. The junctions of the D element with the VHH and J genes show extensive N-junction nucleotide deletions and insertions. Residues in the VHH region that differ from the germline configuration due to somatic hypermutation are highlighted in grey. Similarly, variant residues in the CDR3 likely due to somatic mutation are also highlighted in grey. Numbering of amino acid residues on top corresponds to Kabat numbering of V domains (Kabat et al. (1991) Sequences of Proteins of Immunological Interest, 5th ed., NIH Publication No. 91-3242, Bethesda, MD, USA). The framework and complementarity determining regions (FR1-FR4, CDR1-CDR3) are indicated in brackets below the alignment. The two cysteine residues mediating the conserved canonical disulfide bridge are marked by asterisks and highlighted in grey. Sequences 10-01 to 10-22, SEQ ID NOs: 59-80, respectively.

DETAILED DESCRIPTION OF THE INVENTION

Figure 3:
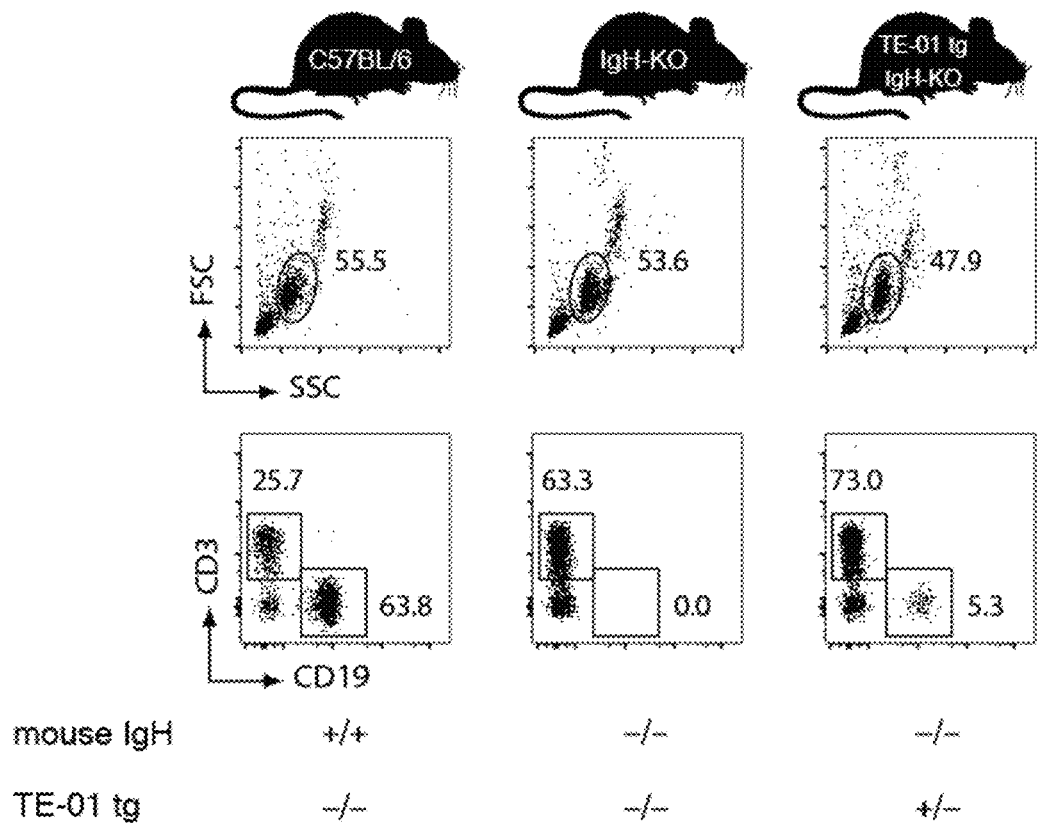
FIG. 3 is a B cell rescue by llama IgH transgene TE-01. Peripheral blood cells of 9-12 week old mice were stained with fluorochrome conjugated antibodies against CD3 (T cells) and CD19 (B cells) before analysis by flow cytometry. B cells do not develop in IgH-KO animals. Introduction of the TE-01 transgene rescues B cell development in IgH-KO animals.

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. Vice versa, where a plural of a noun is used, this includes also the singular noun, unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of +10%, and preferably of ±5%.

Technical terms are used by their common sense. If a specific meaning is conveyed to certain terms, definitions of terms will be given in the following in the context of which the terms are used.

The invention refers to an isolated polynucleotide for the production of a VHH-containing heavy chain antibody in a mammal, comprising:

a) a VHH region,
b) a D region,
c) a J region, d) a constant heavy chain region, without a functional CH1 domain; wherein the VHH region, the J region and the D region are not rearranged.

The invention also refers to an isolated polynucleotide for the production of a VHH-containing heavy chain antibody in a mammal, comprising:

a) a camelid VHH region, b) a D region, c) a J region, d) a constant heavy chain region, without a functional CH1 domain; wherein the camelid VHH region, the J region and the D region are not rearranged.

"A constant heavy chain region, without a functional CH1 domain" in the context of this invention means that the constant heavy chain region when expressed does not express a functional CH1 domain, i.e. it either lacks an exon encoding a CH1 domain or contains such an exon with one or more defective splice signals.

The term "VHH-containing heavy chain antibody" is also known as "VHH-containing heavy chain only antibody" refers to an antibody which is composed only of heavy chains and does not comprise any light chains. Typically, an IgG antibody comprises two heavy chains, a secretory IgM antibody comprises 5 antibody subunits and therefore comprises 10 heavy chains. Each heavy chain comprises a variable region (encoded by VHH, D and J elements) and a constant region. The constant region further comprises a number of CH (constant heavy chain) domains, advantageously it comprises three CH domains (CH2, CH3, CH4) encoded by a constant region gene for an IgM isotype and two CH domains: (CH2, CH3) for IgG and IgA isotypes. A VHH-containing heavy chain antibody as herein defined does not possess a functional CH1 domain. It is the lack of a functional CH1 domain (which in conventional antibodies possesses the anchoring place for the constant domain of the light chain) and the presence of a VHH domain instead of a VH domain which accounts for the inability of the heavy chain antibodies according to the present invention to associate with light chains and their inability to form conventional antibodies.

Each heavy chain comprises a variable region (encoded by a VHH element, a D element and a J element) and a constant region. The constant region comprises a number of constant region elements, each element encoding a constant region CH domain. The antibodies defined herein, do not possess a functional CH1 domain. The lack of a functional CH1 domain (which in conventional antibodies possesses the anchoring place for the constant domain of the light chain) accounts for the inability of the heavy chain antibodies according to the present invention to associate with light chains to form conventional antibodies.

In the context of the present invention, the term "heterologous" means that the polynucleotide as described herein is not endogenous to that mammal. For example, in the case where the mammal is a rodent, then the expression is of a D element which is normally not found within a rodent, such as the D element of a camelid is heterologous.

A "rearranged VHH-D-J region" according to the present invention is comprised of a "VHH element", a "D element", a "J element" and nucleotides added at the junctions during rearrangement. Preferably, the complete rearranged heavy chain nucleotide sequence comprises a VHH-D-J region and three "constant heavy chain elements" for an IgM isotype, two "constant heavy chain elements" for IgG or IgA isotypes and three "constant heavy chain elements" for an IgE isotype.

In particular, the present invention refers to an isolated polynucleotide for the production of a VHH-containing heavy chain antibody in a mammal, comprising:

a) a camelid VHH region, b) a camelid J region, c) a camelid D region, d) a camelid constant heavy chain region, without a functional CH1 domain; wherein the camelid VHH region, the camelid J region and the camelid D region are not rearranged.

A "camelid VHH region" relates to a sequence that comprises at least one camelid VHH element. The camelid VHH region is of camelid origin or is a synthetic DNA fragment comprising the features of a camelid VHH. Alternatively, sequences flanking the VHH element of the VHH region may be at least partially of a different origin than of camelid origin. The flanking sequences may be for example of the origin of the mammal in which the polynucleotide is expressed. The sequences flanking the VHH element(s) may comprise e.g. regulatory elements, such as enhancers, promoters or signal peptides directing localization such as secretion of the antibody. The VHH-flanking sequences preferably originate from the mammal in which the transgene is expressed or a closely related mammal, e.g. mouse flanking sequences for a transgenic rat.

In one embodiment the camelid VHH region comprises one camelid VHH element. Preferably, the camelid VHH region may comprise at least two camelid VHH elements, more preferably at least three camelid VHH elements, even more preferably at least 4 camelid elements, such as at least 5 camelid elements, most preferably at least 5 camelid VHH elements such as for the TE02 and the TE03 construct set out in the Examples. The "camelid VHH region" may comprise also synthetic VHH elements which comprise a polynucleotide sequence which is not of natural origin. Such synthetic VHH elements may be "humanized VHH elements" which comprise sequence stretches that are of camelid origin in combination with sequence stretches which are of an origin of a mammal different than camelid, in particular of human origin. In a particular preferred embodiment, the camelid VHH region comprises 5 camelid VHH elements and a humanized VHH element. An example for a synthetic VHH element is SEQ ID NO: 18. The synthetic VHH element may comprise a sequence which is at least 70%, at least 80%, at least 90%, at least 95%, at least 97% identical to SEQ ID NO: 18.

A "camelid VHH element" in the context of the present invention describes a naturally occurring VHH coding sequence found in camelids and any derivative or fragment thereof, as long as the resultant element recombines with a D element, a J element and a constant heavy chain region (which comprises several elements) according to the present invention to generate a VHH-containing heavy chain antibody as herein defined, when the polynucleotide is expressed. The camelid VHH element may be selected from the group consisting of SEQ ID NO: 15, SEQ ID NO: 16, SEQ ID NO: 17, SEQ ID NO: 19 and SEQ ID NO: 20. The camelid VHH element may comprise a sequence which is at least 70%, at least 80%, at least 90%, at least 95%, at least 97% identical to SEQ ID NO: 15. The camelid VHH element may comprise a sequence which is at least 70%, at least 80%, at least 90%, at least 95%, at least 97% identical to SEQ ID NO: 16. The camelid VHH element may comprise a sequence which is at least 70%, at least 80%, at least 90%, at least 95%, at least 97% identical to SEQ ID NO: 17. The camelid VHH element may comprise a sequence which is at least 70%, at least 80%, at least 90%, at least 95%, at least 97% identical to SEQ ID NO: 19. The camelid VHH element may comprise a sequence which is at least 70%, at least 80%, at least 90%, at least 95%, at least 97% identical to SEQ ID NO: 20. The VHH element is the sequence that encodes the polypeptide that forms part of the structure of the final mature antibody. That means that the VHH element does not contain sequences which are purely regulatory sequences or signal peptides that are not present in the structure of the final mature antibody.

In one embodiment, the VHH element may be selected from the group consisting of SEQ ID NO: 15, SEQ ID NO: 16, SEQ ID NO: 17, SEQ ID NO: 18, SEQ ID NO: 19 and SEQ ID NO: 20.

A "camelid D region" region refers to a sequence that comprises at least one camelid D element. The camelid D region may have the complete region of camelid origin. Alternatively, sequences flanking the D element of the D region may be at least partially of a different origin than of camelid origin. The flanking sequences may be for example of the origin of the mammal in which the polynucleotide is expressed or a related mammal. The sequences flanking the D element(s), may comprises e.g. regulatory elements, such as the 5' and 3' recombination signal sequences (RSS).

The term "camelid D element" refers to naturally occurring sequences of D elements which are found in camelids and derivatives, and fragments thereof as long as the resultant element can recombine to generate a heavy chain antibody as herein described. The D element may be derived from naturally occurring sources or they may be synthesized using methods familiar to those skilled in the art and described herein. The D element is the sequence that, together with nucleotides added at the junctions during rearrangement encodes the complementarity determining region 3 (CDR3) polypeptide that forms part of the structure of the final mature antibody. That means that the D element does not contain sequences which are purely regulatory sequences or signal peptides that are not present in the structure of the final mature antibody.

In a specific embodiment the camelid D region comprises at least two, at least three, at least 4, at least 5, at least 6, at least 7 camelid D elements. Preferably the camelid D region comprise all camelid D elements as described for example for *Lama pacos* in Achour et al. (2008) "Tetrameric and homodimeric camelid IgGs originate from the same IgH locus." J. Immunol. 181:2001-2009. In one embodiment the camelid D region may comprise all D elements from *Lama glama*. The D element may be selected from the group consisting of SEQ ID NO: 8, SEQ ID NO: 9, SEQ ID NO: 10, SEQ ID NO: 11, SEQ ID NO: 12, SEQ ID NO:13 and SEQ ID NO: 14. The D element may comprise a sequence which is at least 70%, at least 80%, at least 90%, at least 95%, at least 97% identical SEQ ID NO: 8. The D element may comprise a sequence which is at least 70%, at least 80%, at least 90%, at least 95%, at least 97% identical SEQ ID NO: 9. The D element may comprise a sequence which is at least 70%, at least 80%, at least 90%, at least 95%, at least 97% identical SEQ ID NO: 10. The D element may comprise a sequence which is at least 70%, at least 80%, at least 90%, at least 95%, at least 97% identical SEQ ID NO: 11. The D element may comprise a sequence which is at least 70%, at least 80%, at least 90%, at least 95%, at least 97% identical SEQ ID NO: 12. The D element may comprise a sequence which is at least 70%, at least 80%, at least 90%, at least 95%, at least 97% identical SEQ ID NO: 13. The D element may comprise a sequence which is at least 70%, at least 80%, at least 90%, at least 95%, at least 97% identical SEQ ID NO: 14. The polynucleotide may comprise additional D elements, for example homologous D elements from other animals such as rodents, horse, dog, cow, rabbit, shark, or different camelids or synthetic elements having a sequence that is not of natural origin. For example, the camelid D region may comprise D elements from *Lama* sp. and *Camelus* sp. In one embodiment the camelid D region may comprise all D elements from *Lama glama* and additional D elements. The polynucleotide may comprise D elements that encode structural domains not normally found in antibodies, for example contoxins or conotoxin-like peptides. Conotoxins are peptides consisting of 10-30 amino acid residues that typically have one or more disulfide bonds (PF07365). The polynucleotide may comprise D elements that encode a cysteine knot or a cysteine knot-like peptide. A cysteine knot is a protein structural motif containing three disulfide bridges (Pfam PF00007). Alternatively, the polynucleotide may comprise D elements encoding a fragment of a conotoxin-like or a cysteine-knot-like peptide, with the remaining fragments encoded by appropriately modified VHH and J elements.

Alternatively, the polynucleotide may comprise as D elements only synthetic D elements and as J element only synthetic J elements. Such synthetic DNA elements may encode domains such as a conotoxin or conotoxin-like peptide, or a cysteine-knot or a cysteine-knot-like peptide.

A "camelid J region" region refers to a sequence that comprises at least one J element. The camelid J region may have the complete region of camelid origin. Alternatively, sequences flanking the J element(s) of the J region may be at least partially of a different origin than of camelid origin. The flanking sequences may be for example of the origin of the mammal in which the polynucleotide is expressed or a related animal. The sequences flanking the J element(s) may comprise e.g. regulatory elements, such as a 5' recombination signal sequence (RSS) and a 3' donor-splice site.

The term "camelid J element" refers to naturally occurring sequences of J elements which are found in camelids and derivatives and fragments thereof as long as the resultant element can recombine to generate a heavy chain antibody as herein described. The J element may be derived from naturally occurring sources or they may be synthesized using methods familiar to those skilled in the art and described herein. The J element is the sequence that codes the polypeptide that forms part of the structure of the final mature antibody. That means that the J element does not contain sequences which are purely regulatory sequences or signal peptides that are not present in the structure of the final mature antibody.

In a specific embodiment the camelid J region comprises at least two, at least three, at least 4, at least 5, at least 6, at least 7 camelid J elements. Preferably the camelid J region comprise all camelid J elements as described for example for *Lama pacos* in Achour et al. (2008) "Tetrameric and homodimeric camelid IgGs originate from the same IgH locus." J. Immunol. 181:2001-2009. In one embodiment the camelid J region may comprise all J elements from *Lama glama*. The J element may be selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7. The J element may comprise a sequence which is at least 70%, at least 80%, at least 90%, at least 95%, at least 97% identical to one of the sequences set out in SEQ ID NO: 1. The J element may comprise a sequence which is at least 70%, at least 80%, at least 90%, at least 95%, at least 97% identical to one of the sequences set out in SEQ ID NO: 2. The J element may comprise a sequence which is at least 70%, at least 80%, at least 90%, at least 95%, at least 97% identical to one of the sequences set out in SEQ ID NO: 3. The J element may comprise a sequence which is at least 70%, at least 80%, at least 90%, at least 95%, at least 97% identical to one of the sequences set out in SEQ ID NO: 4. The J element may comprise a sequence which is at least 70%, at least 80%, at least 90%, at least 95%, at least 97% identical to one of the sequences set out in SEQ ID NO: 5. The J element may comprise a sequence which is at least 70%, at least 80%, at least 90%, at least 95%, at least 97% identical to one of the sequences set out in SEQ ID NO: 6. The J element may comprise a sequence which is at least 70%, at least 80%, at least 90%, at least 95%, at least 97% identical to one of the sequences set out in SEQ ID NO: 7. The polynucleotide may comprise additional J elements, for examples homologous J elements from other animals such as rodents, horse, dog, cow, rabbit, shark, or different camelids or synthetic elements having a sequence that is not of natural origin.

The term "camelid constant heavy chain region" refers to a sequence that comprises at least two camelid CH domains. The term may refer to a coding sequence for the constant region of the heavy chain found in camelids and any derivative or fragment thereof, as long as the resultant element recombines with a VHH element, D element and a J element according to the present invention to generate a VHH-containing heavy chain antibody as herein defined, when the polynucleotide is expressed. The camelid constant heavy chain region may have the complete region of camelid origin. Alternatively, sequences flanking the CH domain coding sequence of the camelid constant heavy chain region may be at least partially of a different origin than of camelid origin. The flanking sequences may be for example of the origin of the mammal in which the polynucleotide is expressed. In one embodiment, the exons encoding the membrane proximal CH domains, transmembrane domain and cytosolic domain are exchanged by the exons encoding the corresponding domains of the mammal in which the VHH-containing heavy chain antibody is expressed or a related mammal.

Generally, CH genes encode different domains of each constant heavy chain polypeptide, with generally three CH domains constituting a single IgM heavy chain antibody and two CH domains a single IgG heavy chain antibody as herein described. VHH-containing heavy chain antibodies do not possess a functional CH1 (containing the light chain domain anchoring region). Thus, the polynucleotide according to the present invention, in particular the constant heavy chain region does not contain an element encoding a functional CH1. Elements that are capable of expressing functional CH1 domains that are present in a sequence from which the polynucleotide of the invention derives from may be deleted by mutation, deletion substitution or other treatment of the CH1 element of the constant heavy region so that no functional CH1 domain can be expressed.

A "fragment" in the context of the invention means that the nucleotide sequence or the peptide sequence is shorter than the sequence it is derived of. The fragment may remain the functional characteristics of the sequence it is derived of. The fragment may be for example 1%, 3%, 5%, 6%, 8%, 10%, 12%, 15%, 20%, 30%, 40%, 50%, 60% shorter than the sequence it is derived from.

A "derivative" in the context of the invention means that the nucleotide sequence or the polypeptide sequence is modified. For example, a sequence may be humanized, murinized or camelized, meaning that the original sequence may be modified to include sequence motifs specific for human, mouse or camelid.

Each constant heavy chain region essentially comprises at least one constant region heavy chain gene. Preferably, the constant heavy chain region comprises a Cμ gene encoding for the constant region of an IgM antibody, so that generation of heavy chain IgM can occur. The constant heavy chain region may also comprise a Cγ gene encoding for the constant region of a IgG antibody. In other words, the constant heavy chain region comprises elements encoding a) a CH2, a CH3 and a CH4 domain of an IgM and/or b) a hinge, a CH2 domain and a CH3 domain of an IgG. In a specific embodiment the constant heavy chain region comprises elements encoding a) a CH2, a CH3 and a CH4 domain of an IgM and b) a hinge, a CH2 domain and a CH3 domain of an IgG.

In one embodiment the constant heavy chain region comprises an element which encodes at least one of the group consisting of camelid IgM, IgG2a, camelid IgG2b, camelid IgG2c, camelid IgG3, i.e. a μ, γ2a, γ2b, γ2c or γ3 element. In one embodiment the heavy chain region does not comprise a γ2a region.

In a preferred embodiment, the constant heavy chain region does not comprise a δ region with an associated switch region. Thereby, class switch to the IgD pseudogene can be avoided.

One skilled in the art will appreciate that the regions or elements may be derived from natural sources or may be synthesized using methods familiar to those skilled in the art.

The term "not rearranged" refers to nucleotide sequences in which the VHH region, D region, J region and constant heavy chain region are not rearranged to form a functional sequence that is capable to express a heavy chain antibody. That means that the VHH region, D region, J region and constant heavy chain region are separated by a nucleotide sequence and are capable to rearrange when introduced into the genome of the transgenic mammal as described herein. Thus the rearrangement of the VHH region, D region, J region and constant heavy chain region is carried out in the mammal in which the polynucleotide is introduced. This allows to exploit the natural recombination mechanism. The nucleotide separating the VHH region, D region, J region and constant heavy chain region may comprise several hundred to several thousand nucleotides. For example, in the naturally occurring gene locus of *Lama glama* the VHH elements are separated by sequence stretches of 5-20 kb. These sequence stretches can however be reduced to comprise for example less than 5000 bp, less than 3000 bp, less than 1000 bp. Typically, the separating sequences comprise more than 50 bp, more than 100 bp, more than 200 bp, more than 300 bp, more than 400 bp. In the naturally occurring clusters of D segments and J segments, the distance between the D segments or between the individual J segments may be of about 100 to 1000 bp, but can reach up to 20 kb. Preferably the sequences flanking the VHH, D, J and constant heavy chain regions are of camelid origin. Alternatively, these sequences may be specific for the mammal in which the VHH heavy chain antibody is expressed or a related mammal, e.g. mouse sequences in case of a transgenic rat.

As described above, the skilled person understands that the camelid VHH region, the camelid D region and the camelid J region according to the invention are capable of rearranging to form a VHH-D-J coding sequence.

Preferably, the polynucleotide comprises at least one enhancer or parts thereof. The at least one enhancer may be specific for the mammal in which the VHH heavy chain antibody is expressed or a related mammal. The enhancer may be an Ig-α or an Ig-μ enhancer or parts thereof, such as the sequences to which the corresponding transcription factors bind (e.g. HS3a, HS1,2, HS3b and HS4 for Ig-alpha). For example, if the VHH heavy chain antibody is expressed in a mouse, the polynucleotide may comprise a mouse Ig-alpha enhancer or a rat Ig-alpha enhancer. Accordingly, if the VHH heavy chain antibody is expressed in a rat, the polynucleotide may comprise a mouse Ig-alpha enhancer or a rat Ig-alpha enhancer.

The camelid may be of the family selected form *Lama, Vicugna* or *Camelus*. The camelid may be for example *Lama pacos, Lama guanicoe, Vicugna pacos, Camelos dromedaries*, or *Camelus bactrianus*. In one embodiment the camelid is selected from *Lama pacos* and *Lama glama*, preferably *Lama glama*.

An exemplary polynucleotide according to the invention is the llama IgH transgene TE-01 which is schematically depicted in FIG. 1. The sequence of TE-01 is set out in SEQ ID NO: 30. The invention therefore refers to polynucleotides which are at least 70%, at least 80%, at least 90%, at least 95%, at least 97% identical to SEQ ID NO: 30. For example, the polynucleotide is encoded by the sequence set out in SEQ ID NO: 30 or fragments thereof. Thus one embodiment of the invention refers to a polynucleotide encoding a camelid VHH element, 7 camelid D elements, 7 camelid J elements, camelid μ region lacking the CH1-encoding exon, camelid γ2b region and parts of a mouse α enhancer (HS3b und HS4). In particular, one embodiment of the invention refers to a polynucleotide encoding the VHH element set out in SEQ ID NO: 15, the camelid D elements set out in SEQ ID Nos: 8 to 14, the camelid J elements set out in SEQ ID Nos: 1 to 7, the camelid IgM CH2 domain set out in SEQ ID NO: 26, the camelid IgM CH3 domain set out in SEQ ID NO: 27, the camelid IgM CH4 domain set out in SEQ ID NO: 28, the camelid IgM transmembrane domain (TM) 1 domain set out in SEQ ID NO: 29, the camelid IgM TM2 domain having the sequence "GTGAAG", the camelid Ig2b hinge domain set out in SEQ ID NO: 21, the camelid IgM CH2 domain set out in SEQ ID NO: 22, the camelid Ig2b CH2 domain set out in SEQ ID NO: 23, the camelid Ig2b TM 1 domain set out in SEQ ID NO: 24 and the camelid Ig2b TM 2 domain set out in SEQ ID NO: 25.

The TE-01 construct is derived from the combination of the BAC F07 and the BAC V03 which are schematically depicted in FIG. 1. The sequence of F07 is set out in SEQ ID NO: 31 and the sequence of V03 is set out in SEQ ID NO: 32.

Figure 11:
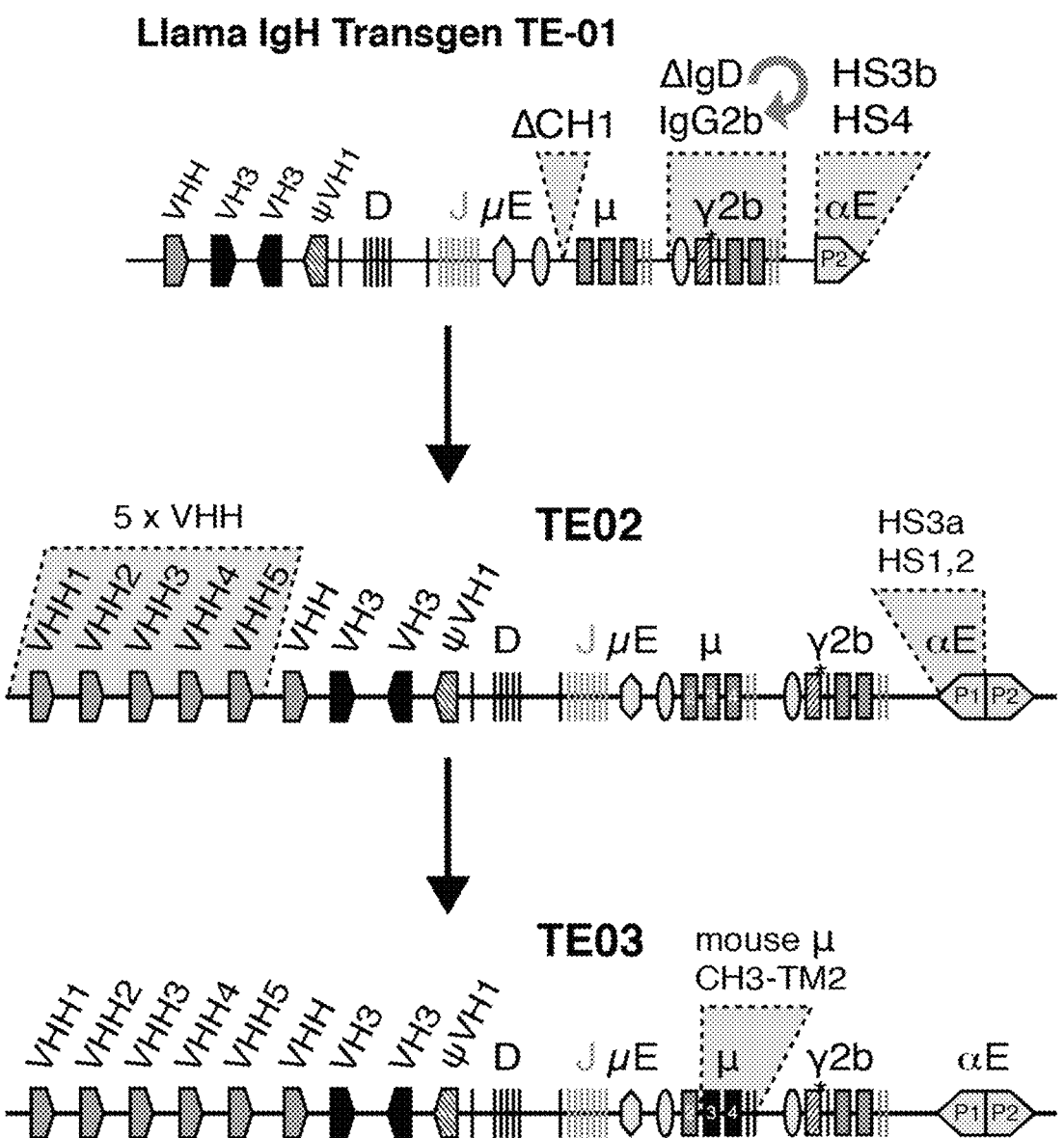
FIG. 11 is a schematic diagram of transgenes TE-02 and TE-03. Schematic diagram of BAC-recombineering used to generate llama IgH transgenes TE-02 and TE-03. A synthetic DNA cassette encoding 5 additional camelid or synthetic VHH genes was inserted at the 5' end of TE-01. Components HS3a and HS1,2 of the mouse 3' locus control region (αE=alpha enhancer) were inserted upstream of HS3b/HS4 (Pinaud et al., (2001) "Localization of the 3' IgH locus elements that effect long-distance regulation of class switch recombination" Immunity 15:187-199). Finally, to generate TE-03, the CH3-CH4-TM1-TM2 region of the llama IgM locus was replaced by the corresponding elements of mouse IgM.

Thus in one embodiment, the polynucleotide according to the invention is selected from the group consisting of the IgH transgenes TE-01, TE02 or TE03 which are schematically depicted in FIG. 11 and described herein. Preferably, the polynucleotide is the transgene TE02 or TE03 as depicted in FIG. 11. More preferably, the polynucleotide is the transgene TE03 as depicted in FIG. 11.

Another aspect of the invention refers to a vector comprising the polynucleotide according to any embodiments described above.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence (e.g., polynucleotide of the invention). The vector may be a plasmid, phagemid, cosmid, expression vector, retroviral vector, adenoviral vector, bacterial artificial chromosome (BAC), yeast artificial chromosome (YAC), human artificial chromosome (HAC), or synthetic DNA. Preferably, the vector is a BAC, YAC, HAC, cosmid or synthetic DNA, more preferably a BAC. Thereby a platform for site-specific improvement of the camelid derived gene locus, in particular the *Lama glama* derived IgH locus is provided. Methods to modify BACs are for example described in Parish et al. "BAC Modification through Serial or Simultaneous Use of Cre/Lox Technology" J. of Biomedicine and Biotechnology Volume 2011, pp. 1-12 (2010) and Warming et al. "Simple and highly efficient BAC recombineering using galK selection." Nucleic Acids Res. 33(4):e36 (2005).

Another aspect of the invention refers to a transgenic mammal comprising the isolated polynucleotide described herein or the vector described herein comprising the isolated polynucleotide. The polynucleotide according to the invention is not endogenous to the transgenic mammal, but is heterologous. The skilled person understands, that the transgenic mammal is a non-human mammal.

The transgenic mammal may be any mammal suitable to immunize with desired antigens, such as rodents (mice, rats, guinea pigs), lagomorpha (rabbits), camelids, goats, sheep, cats, dogs and other domestic or wild mammals. The transgenic mammal is advantageously smaller than a camelid and easier to maintain and immunize with desired antigens. In the context of the present invention, the mammal is not a human. Ideally, the transgenic mammal is a rodent, such as a guinea pig, rat or mouse or a lagomorph, such as a rabbit. Mouse and rat are especially preferred. Preferably, the mammal is genetically deficient for the immunogen for which the VHH-containing heavy chain antibody should be generated or its respective orthologue.

The invention therefore also relates to a transgenic mammal in which a VHH-containing heavy chain antibody which is encoded by a rearranged VHH-D-J sequence of the polynucleotide according to the invention. The skilled person understands, that in the context of the invention the rearrangement occurs in the transgenic mammal.

In a preferred embodiment the mammal is devoid of a functional endogenous IgH locus. The skilled person is aware of methods to achieve mammals lacking a functional endogenous IgH locus. Preferably the mammal is a mouse or rat devoid of a functional endogenous IgH locus as described in Gu et al. "Independent control of immunoglobulin switch recombination at individual switch regions evidenced through Cre-loxP-mediated gene targeting" Cell 73(6):1155-1164 (1993) or in Menoret et al. (2010) "Characterization of immunoglobulin heavy chain knockout rats" Eur. J. Immunol 40: 2932-2941.

When the polynucleotide according to the invention is expressed in the mammal, the transgenic mammal is capable of generating B cells. That means particularly that a mammal which is lacking a functional endogenous IgH locus and therefore is not able to generate B cells, said mammal after the introduction of the polynucleotide of the invention is capable to rescue the generation of B cells, meaning that the mammal is capable to generate B cells.

When the isolated polynucleotide is introduced to a mammal as described herein, the transgenic mammal expresses a VHH-containing heavy chain antibody. In a specific embodiment, the mammal expresses the VHH-containing heavy chain antibody as membrane bound and/or soluble version.

Another aspect of the invention refers to a method for the production of a VHH-containing heavy chain antibody in a mammal comprising the step of expressing a heterologous VHH-containing heavy chain antibody in that mammal, wherein the heterologous VHH-containing heavy chain antibody is encoded by a rearranged VHH-D-J sequence of the polynucleotide according to the invention. The skilled person understands, that in the context of the invention the rearrangement occurs in the transgenic mammal.

Moreover, the invention refers to a method for cloning a VHH-containing heavy chain antibody from a mammal wherein the heterologous VHH-containing heavy chain antibody is encoded by a rearranged VHH-D-J sequence of the polynucleotide according to the invention. The skilled person understands, that in the context of the invention the rearrangement occurs in the transgenic mammal. The method of cloning may comprise the steps of immunizing that mammal and immortalizing B cells expressing a VHH-containing heavy chain antibody from that mammal, for example by fusion to myeloma cells. Alternatively, the method may comprise the steps of immunizing that mammal and obtaining VHH-coding sequences from B cells of that mammal. The VHH coding sequences may be obtained by amplification techniques, such as PCR and selected by techniques such as phage display.

A further aspect of the invention refers to a VHH-containing heavy chain antibody produced by a method which is described in the above paragraphs.

Another aspect of the invention refers to VHH-containing heavy chain antibodies encoded by a rearranged VHH-D-J sequence of the polynucleotide according to the invention. The skilled person understands, that in the context of the invention the rearrangement occurs in the transgenic mammal.

In specific embodiments, the VHH-containing heavy chain antibody may comprise a sequence selected from the group of sequences as set out in SEQ ID NOs: 59 to 80 or fragments thereof.

The VHH-containing heavy chain antibody may be a camelid IgM and/or IgG, such as IgG2a, IgG2b, IgG2c, IgG3.

Also contemplated are fragments of the VHH-containing heavy chain antibodies as described herein, in particular nanobodies. The term "nanobody" refers to a molecule that comprises, typically consists of, a single rearranged VHH-D-J domain.

Methods:

Cloning of a *Lama glama* Genomic BAC-Library:

To clone the *Lama glama* IgH locus, genomic DNA was isolated from the liver of a llama and digested with HindIII resulting in DNA fragments with an average size of 150 kb. The fragments were cloned into the BAC vector pCC1 (Epicentre) and electroporated into *E. coli* DH10B cells to obtain a genomic library. Using probes specific for variable and constant domains, 17 BACs with insert sizes of 90-220 kb were isolated and verified by Southern blot analyses. The size of individual clones was determined using pulsed field gel electrophoresis (PFGE) of NotI-digested BACs. Two overlapping BACs (V03 and F07) carrying variable and/or constant segments of the immunoglobulin heavy chain gene locus were sheared into 5 kb fragments and sequenced by Sanger technology. Gaps were filled by primer-walking and full sequences were assembled using Lasergene software.

Generation of Llama IgH Transgene TE-10:

To promote expression of heavy chain only antibodies in mice, BAC V03 was genetically modified using BAC recombineering. Regions HS3b and HS4 of the mouse locus control region (LCR, alpha-enhancer) were inserted into the 3' end of BAC V03. For this, HS3b and HS4 were amplified from a plasmid (provided by Michel Cogné, Limoges, France) encoding the essential parts of the murine LCR (Pinaud et al., (2001) "Localization of the 3' IgH locus elements that effect long-distance regulation of class switch recombination" Immunity 15:187-199), using PCR primers with 50 bp overhangs homologous to the BAC insertion site. The insertion of the amplified construct into BAC V03 was carried out using the Red®/ET recombineering technology (GeneBridges).

The *Lama glama* Cδ pseudogene and the associated switch region was replaced by a spectinomycin resistance cassette. The selection cassette was PCR amplified with 50 bp overhangs homologous to the sequences flanking the *Lama glama* Cδ region. Exchange of the Cδ region by the amplified selection cassette was carried out using the Red®/ET recombineering technology.

To avoid pairing of heavy and light chains during B-cell development, the CH1 domain of the *Lama glama* Cμ locus was deleted in BAC V03. For this, the CH1 domain was replaced by an ampicilin resistance cassette flanked by the two loxP mutants lox71 and lox66 (Parrish et al. (2011) "BAC modification through serial or simultaneous use of CRE/Lox technology" J Miomed Biotechnol 2011:924068). This construct was synthesized with 50 bp overhangs homologous to sequences flanking the Cμ CH1 domain. Recombination was carried out using the recombineering strain *E. coli* SW106 (provided by Neal Copeland, Frederick, MD, USA) (Warming et al. (2005) "Simple and highly efficient BAC recombineering using galK selection" Nucleic Acids Res 24: 33(4):e36). The homologous recombination was followed by a Cre/loxP recombination to delete the ampicillin selection cassette from BAC V03.

To enable Class Switch Recombination (CSR) to a heavy chain only Cγ isotype, the previously inserted spectinomycin selection cassette at the position of the Cδ pseudogene was replaced by the *Lama glama* Cγ2b isotype obtained from BAC F07. For this, Cγ2b was cloned into the vector pBluescript II KS (+)/LIC. To equip the Cγ2b locus with homology arms, a gene synthesis construct with two homology regions each flanked by pBluescript II KS (+)/LIC compatible cloning sites (ClaI and BstZ17I) was designed. The 270 bp 3'-homology region was genetically fused to an ampicillin selection cassette flanked by the two loxP mutants lox71 and lox66. The construct was synthesized and cloned into the vector pUC57. The 285 bp 5' homology region was isolated by ClaI restriction digestion and cloned into the ClaI site upstream of the Cγ2b locus in pBluescript II KS (+)/LIC. The resulting plasmid was used as the target vector for the insertion of the 270 bp 3' homology arm fused to the ampicillin selection cassette. This construct was isolated by BstZ17I restriction digestion and cloned into the BstZ17I site downstream of the Cγ2b locus in pBluescript II KS (+)/LIC. A 5' homology arm of 285 bp size containing a NruI restriction site was synthezised as complementary primer sequences. Hybridization of the complementary single stranded DNA molecules led to a restriction site-specific overhang allowing site-specific insertion of the homology arm upstream of the Cγ2b locus. An ampicilin resistance cassette flanked by the two loxP mutants lox71 and lox66 fused to a 270 bp 3' homology arm containing a second NruI restriction site was synthesized as double stranded DNA and inserted downstream of the Cγ2b locus. The entire construct with both homology arms and the floxed ampicillin selection cassette was isolated using the blunt end NruI restriction sites encoded in the homology arms. Recombination was carried out using the recombineering strain *E. coli* SW106. The homologous recombination was followed by a Cre/loxP recombination to delete the ampicillin selection cassette downstream of the Cγ2b locus.

Derivation of Mice and Breeding:

The *Lama glama* IgH transgene TE-01 was purified using the PhasePrep BAC DNA Kit (Sigma-Aldrich) followed by a phenol/chloroform extraction and linearization with NotI. The linear construct was injected into fertilized oocytes of C57BL/6J×CBA mice with pronuclear injection as described by Nagy et al. (Manipulating the Mouse Embryo: A Laboratory Manual; Cold Spring Harbor Laboratory Press, New York, 2003). Founder mice were backcrossed to Ig-deficient JHT-mice (provided by Klaus Rajewsky) Gu et al. "Independent control of immunoglobulin switch recombination at individual switch regions evidenced through Cre-loxP-mediated gene targeting" Cell 73(6):1155-1164 (1993).

PCR Genotyping of Transgenic Mice:

Transgenic mice were identified by PCR from ear clip DNA using Platinum blue PCR super mix (Invitrogen). Pairs of PCR primers specific for the 5' and 3' transgene ends were used to verify germline transmission under the following conditions: 30× (95° C. 20 secs, 60° C. 30 secs, 72° C. 60 secs), 72° C. 10 mins (FIG. 2).

The knockout of the endogenous IgH locus (deletion of the J-elements and the μ-enhancer) of Ig-deficient JHT-mice was verified using the same PCR conditions. Primer pairs specific for the mutated region of the IgH locus are described in the technical support protocol of Stock No: 002438 (The Jackson Laboratory).

Flow Cytometry Analysis of Blood Lymphocytes:

To verify rescue of B-cell development by transgene TE-01, lymphocyte staining from blood of TE-01 transgenic, JHT and C57BL/6J mice was performed using fluorochrome conjugated antibodies specific for CD3 (Biolegend, Cat #100312) and CD19 (eBioscience, Cat #110193-85) (FIG. 3). A FACS Cantoll flow cytometer and FlowJo software (Becton Dickinson, Pont de Claix, France) were used for analysis.

Immunization of TE-01 Mice and Analysis of the Induced Heavy Chain Antibody Repertoire by Next Generation Sequencing To verify the capacity of TE-01 transgenic mice to produce functional IgM and IgG heavy chain antibodies, TE-01 transgenic mice were immunized with purified protein antigens. Mice received five immunizations in three week intervals. Three days after the final boost, mice were sacrificed and cells were isolated from spleen, lymph nodes and bone marrow. RNA was purified using the innuPREP RNA Mini Kit (analytik Jena) and transcribed into cDNA using reverse transcriptase (Gibco) and random hexamer primers (GE Healthcare).

Figure 4:
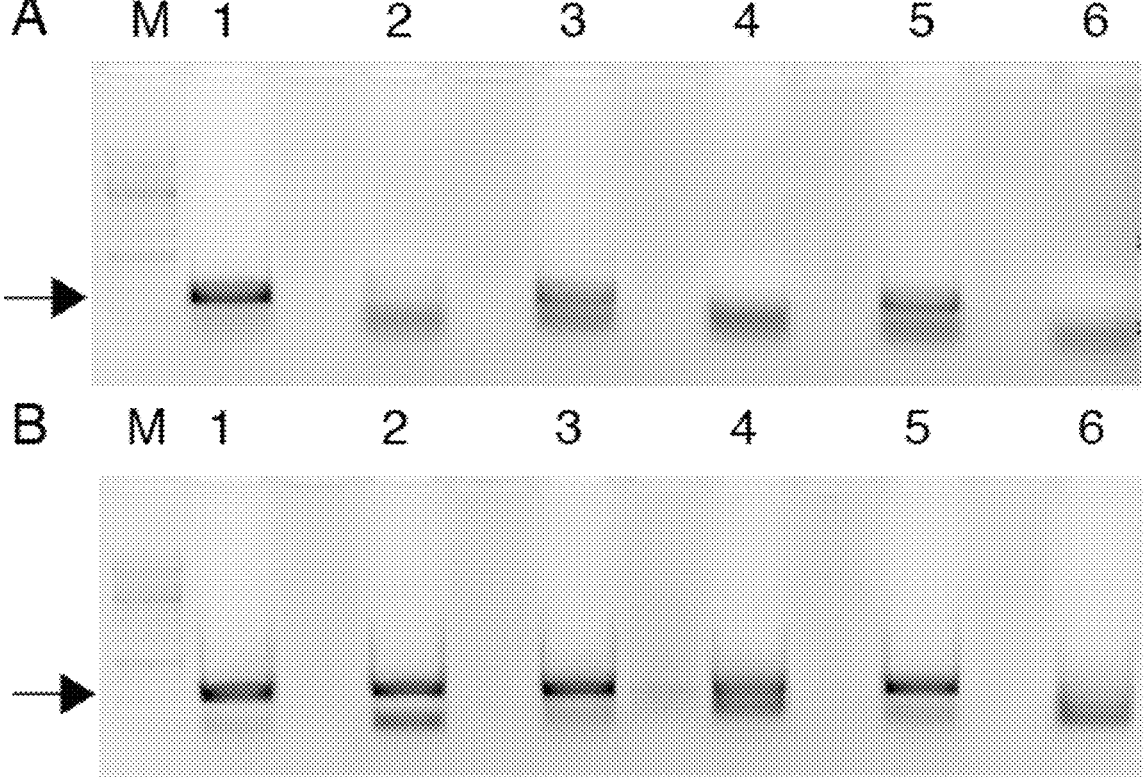
FIG. 4 is a PCR amplification of the IgM and IgG repertoires from spleen, lymph nodes and bone marrow of immunized TE-01 mice. A) cDNA was prepared from spleen (lanes 1, 2) lymph node (lanes 3, 4) or bone marrow (lanes 5, 6) three days after the final boost immunization. The VHH repertoire was PCR amplified with IgM-specific (lanes 1, 3, 5) or IgG-specific (lanes 2, 4, 6) primers. PCR products were size fractionated by agarose gel electrophoresis and stained with Roti-safe (Roth). B) Bands corresponding to IgM and IgG specific amplification products of the expected size were cut from the gel, purified, and subjected to a second round of PCR during which Illumina adapter sequences were extended.

The VHH repertoire was PCR amplified from cDNA (50 ng/reaction) using IgM-specific and IgG-specific primers (4 cycles: 98° C. 10 s, 55° C. 20 s, 72° 20 s, followed by 29 cycles 98° C. 10 s, 67° C. 20 s, 72° C. 20 s). PCR amplification products were analyzed by agarose gel electrophoresis (FIG. 4A). In case of IgM-specific primers, the results show distinct bands of the expected size in the first step PCR from spleen (lane 1), lymph nodes (lane 3) and bone marrow (lane 5). In case of IgG-specific primers, a specific band of the expected size is bearly detectable in the first step PCR from spleen (lane 2). PCR products were purified using the NucleoSpin® Gel Clean-up Kit (Macherey-Nagel, Düren, Germany) and subjected to a second PCR during which Illumina adapter sequences were extended and a sample-specific barcode was added (FIG. 4B). Distinct, prominent specific bands of the expected size were seen in the samples re-amplified from IgM-specific products from spleen, lymph node and bone marrow (lanes 1, 3, 5, respectively). In case of IgG-specific primers, specific bands of the expected size were detectable in samples re-amplified from IgG-specific products from spleen and lymph nodes (lanes 2 and 4). The final PCR product was size-separated with 1.5% agarose gel electrophoresis and amplicons were purified using the NucleoSpin® Gel and PCR Clean-up Kit (Macherey-Nagel, Düren, Germany). The concentration of the final PCR products was determined on a NanoDrop 2000 and amplicon purity was controlled on an Agilent 2100 Bioanalyzer (Agilent Technologies, Böblingen, Germany). NGS was performed on an Illumina MiSeq sequencer with 500 or 600 cycle single-indexed, paired-end runs.

Demultiplexing and Fastq formatted data output was generated by the MiSeq reporter. Raw sequences were processed to Ig V(D)J clonotypes based on the MiXCR analysis tool (Bolotin D A, et al. MiXCR: software for comprehensive adaptive immunity profiling. Nat Methods. 2015; 12(5):380-381) and sequence samples were compared using VDJ tools (Shugay M, et al. VDJtools: Unifying Post-analysis of T Cell Receptor Repertoires. PLoS Comput Biol. 2015; 11(11):e1004503).

Figure 6:
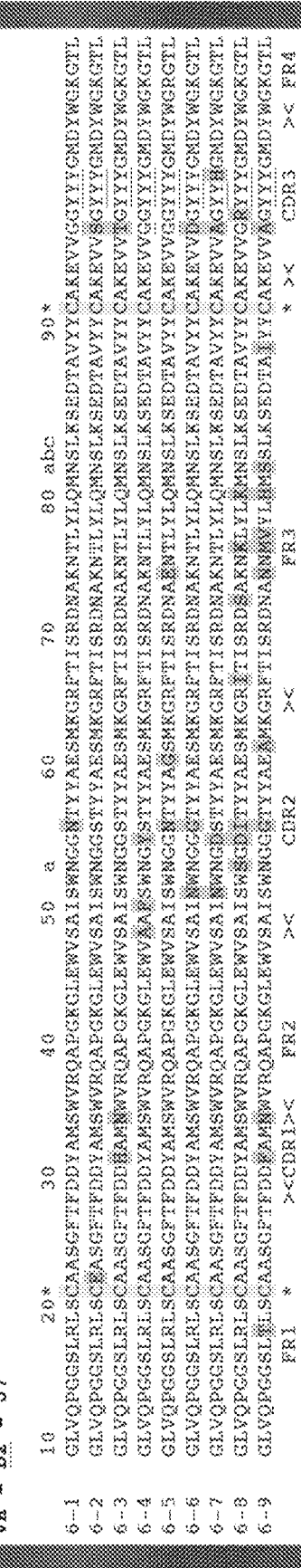
FIG. 6 is an amino acid sequence alignment of a clone of VH-IgM heavy chain antibodies obtained from the spleen of an immunized TE-01 transgenic mouse shows extensive somatic hypermutation. The figure shows an amino acid sequence alignment of nine members of a clone of VH-IgM heavy chain-antibodies obtained from the spleen of an immunized TE-01 mouse three days after the final boost immunization. Amino-acid residues encoded by the D element in germline configuration in the rearranged clone are underlined. The junctions of the D element with the VH and J genes show extensive N-junction nucleotide deletions and insertions. Residues in the VH region that differ from the germline configuration due to somatic hypermutation are highlighted in grey. Similarly, variant residues in the CDR3 likely due to somatic mutation are also highlighted in grey. Numbering of amino acid residues on top corresponds to Kabat numbering of V domains (Kabat et al. (1991) Sequences of Proteins of Immunological Interest, 5th ed., NIH Publication No. 91-3242, Bethesda, MD, USA). The framework and complementarity determining regions (FR1-FR4, CDR1-CDR3) are indicated in brackets below the alignment. The two cysteine residues mediating the conserved canonical disulfide bridge are marked by asterisks and highlighted in grey. Sequences 6-1 to 6-9, SEQ ID NOs: 42-50, respectively.
Figure 7:
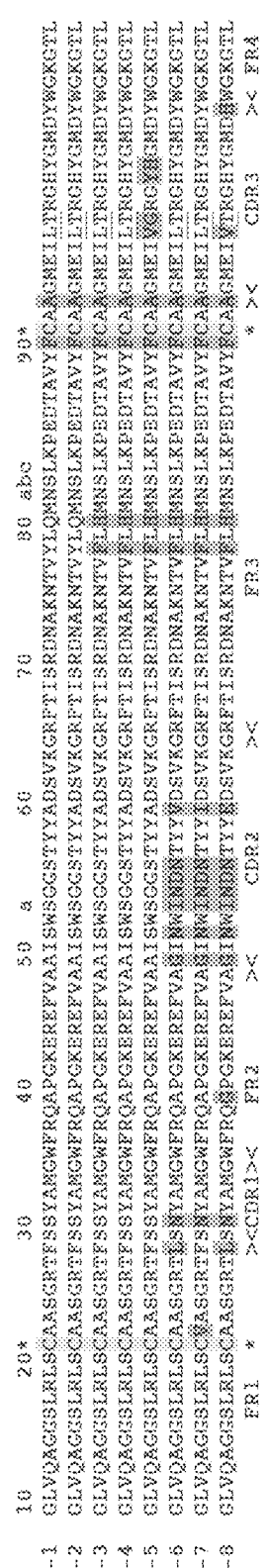
FIG. 7 is an amino acid sequence alignment of eight members of a clone of VHH-IgG heavy chain-antibodies obtained from the spleen of an immunized TE-01 mouse three days after the final boost immunization. Amino-acid residues encoded by the D element in germline configuration in the rearranged clone are underlined. The junctions of the D element with the VHH and J genes show extensive N-junction nucleotide deletions and insertions. Residues in the VHH region that differ from the germline configuration due to somatic hypermutation are highlighted in grey. Similarly, variant residues in the CDR3 likely due to somatic mutation are also highlighted in grey. Numbering of amino acid residues on top corresponds to Kabat numbering of V domains (Kabat et al. (1991) Sequences of Proteins of Immunological Interest, 5th ed., NIH Publication No. 91-3242, Bethesda, MD, USA). The framework and complementarity determining regions (FR1-FR4, CDR1-CDR3) are indicated in brackets below the alignment. The two cysteine residues mediating the conserved canonical disulfide bridge are marked by asterisks and highlighted in grey. Sequences 7-1 to 7-8, SEQ ID NOs: 51-58, respectively.

The results confirm efficient VHH-D-J and VH-D-J recombinations with extensive junctional nucleotide insertions and deletions (FIG. 5, Table 1). Moreover, the results reveal clonal expansion and extensive somatic hypermutation in IgM-producing clones carrying either a VHH or VH gene fragment (FIG. 5 Sequences 5-1 to 5-9, i.e. SEQ ID NOs: 33-41 and FIG. 6 Sequences 6-1 to 6-9 SEQ ID NOs: 42-50, respectively). Moreover, somatic hypermutation was observed also in IgG-producing clone families (FIG. 7 Sequences 7-1 to 7-8 SEQ ID NOs: 51-58). These results confirm functional class switch from IgM to IgG in the immunized mice.

TABLE 1

| clone | frequency | LN | spleen | BM | CDR3 | D |
|---|---|---|---|---|---|---|
| 1 | 14.118 | 318 | 12.848 | 952 | KDNGSSPMDY | D6 |
| 2 | 14.034 | 1.736 | 12.286 | 12 | ADVRTVVAANYGMDY | D6 |
| 3 | 11.875 | 8.390 | 1.858 | 1.627 | ADSTNWVFYDY | D3 |
| 4 | 8.844 | 363 | 8.469 | 12 | KDRDYSGSYYYTD | D2 |
| 5 | 8.198 | 7.700 | 498 | 0 | ADSTKWVFYDY | D3 |
| 6 | 7.919 | 7.824 | 3 | 92 | RYYSGSYPDY | D2 |
| 7 | 7.624 | 7.179 | 435 | 10 | YYSGS | D2 |

TABLE 1-continued

| clone | frequency | LN | spleen | BM | CDR3 | D |
|-------|-----------|-----|--------|-----|------|---|
| 8 | 6.436 | 1.025 | 3.958 | 1.453 | RRTYGMDY | D6 |
| 9 | 5.451 | 0 | 0 | 5.451 | KQPDY | D2 |
| 10 | 4.425 | 3.546 | 872 | 7 | AGYQLLPYGNYYGMDY | D6 |
| 11 | 3.549 | 1.557 | 1.973 | 19 | KGNSYYSYGMDY | D2 |
| 12 | 3.324 | 3.286 | 36 | 2 | ADSSRWVFYDY | D3 |
| 13 | 3.059 | 1.868 | 1.042 | 149 | KDRSYSGSYYYDY | D2 |
| 14 | 2.650 | 8 | 2.640 | 2 | AKDAPYGSSWLDY | D6 |
| 15 | 2.316 | 21 | 2.219 | 76 | KGGVWRDGMDY | D7 |
| 16 | 2.075 | 6 | 2.069 | 0 | ADDGSSWYGDFGS | D6 |
| 17 | 1.699 | 0 | 1.699 | 0 | ASTVVALYGMDY | D6 |
| 18 | 1.651 | 6 | 1.645 | 0 | ADQYGSSWYDYGMDY | D6 |
| 19 | 1.580 | 10 | 1.570 | 0 | AAGSSWYRYDY | D6 |
| 20 | 1.384 | 1.375 | 8 | 1 | KTPGSSWYRDGMDY | D6 |
| 21 | 1.283 | 1.280 | 0 | 3 | ADPYGRYEYDY | D6 |
| 22 | 1.261 | 5 | 1.255 | 1 | AGVTDFGS | D7 |
| 23 | 1.235 | 1.233 | 0 | 2 | AGYYSGSYRMDY | D2 |
| 24 | 1.141 | 48 | 1.093 | 0 | AGTVVAGTYDY | D6 |
| 25 | 1.136 | 21 | 1.114 | 1 | KDRDYSGSYYFDY | D2 |

Next generation sequencing of the VHH repertoire from lymph node, spleen and bone marrow confirms expansion of specific clones showing efficient VHH-D-J recombination with extensive junctional nucleotide insertions and deletions. The amino acid sequence of the CDR3 region and the D-element contained in the CDR3 is shown for each clone (i.e. SEQ ID NOs: 81 to 105). Amino acids encoded by the respective D element are underlined.

Figure 9:
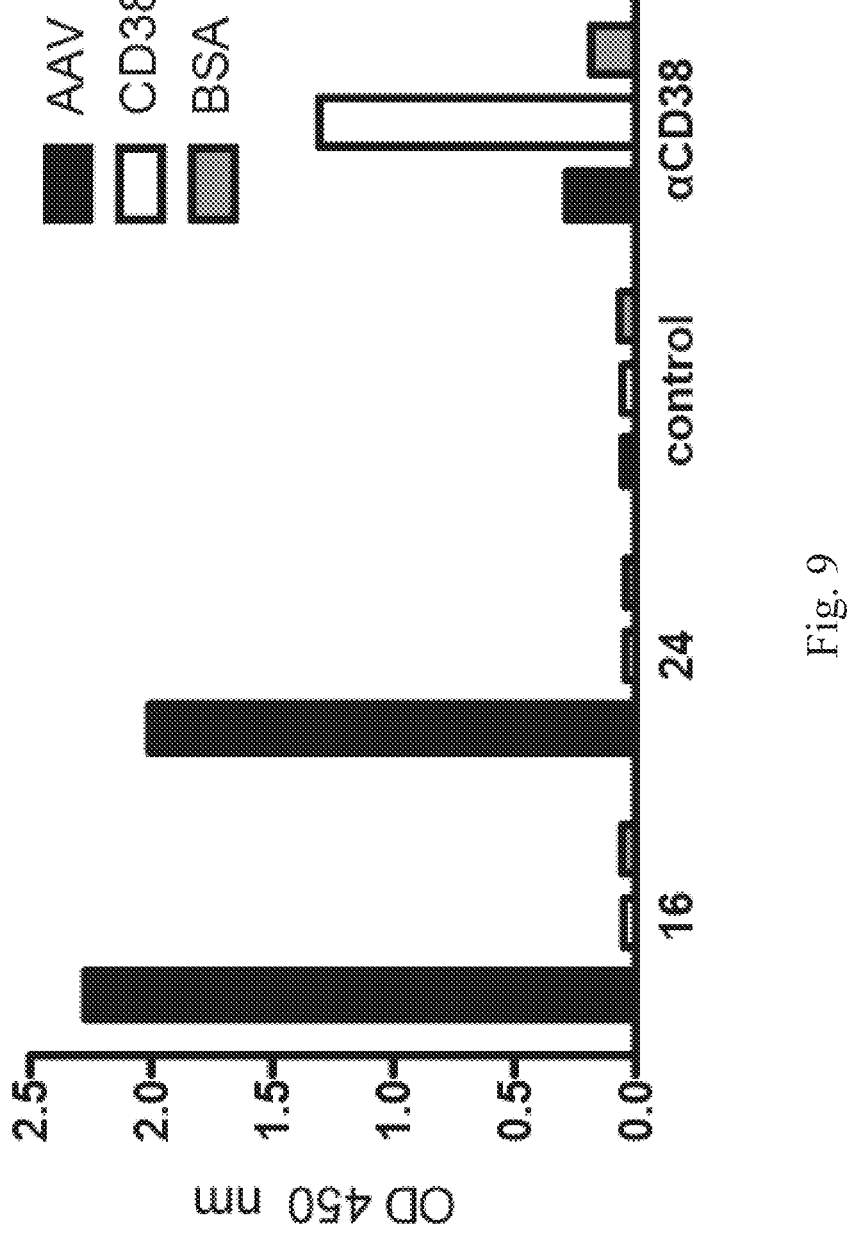
FIG. 9 is an ELISA analyses identifying antigen-specific VHH-rabbit IgG heavy chain antibodies. Specific binding of heavy chain antibodies to the antigen used for immunization (AAV1) was analyzed by ELISA. Wells were coated with the immunogen or with control antigens (BSA, CD38) overnight at 4° C. Wells were subsequently blocked with BSA. Wells were incubated for 60 min with HEK-6E cell supernatants containing individual Nb-rabbit IgG heavy chain antibodies (diluted 1:20 in PBS, 100 µl/well). Unbound proteins were removed by washing and bound heavy chain antibodies were detected with peroxidase-conjugated secondary antibodies (donkey anti-rabbit IgG, 1:5.000 in PBS, 100 µl/well) and TMB as substrate. The reaction was stopped after 15 min with 1M H2SO4 and absorption at 450 nm was measured with a plate reader (Victor, Perkin-Elmer Waltham, USA). An irrelevant Nb-rabbit IgG heavy chain antibody (s+16a) was used as negative control. A CD38-specific Nb-rabbit IgG heavy chain antibody was used as a positive control for wells coated with CD38.

Production of Chimeric Nanobody-Rabbit IgG Heavy Chain Antibodies and Identification of Antigen-Specific Binders:

In order to verify induction of an antigen-specific heavy chain IgM and IgG responses, the VHH coding region was PCR amplified and cloned into the pCSE2.5 expression vector (Schirrmann et al. "Transient Production of scFv-Fc Fusion Proteins in Mammalian Cells" in Antibody Engineering Vol. 2. (eds. R. Kontermann & S. Dubel) 387-398 (Springer-Verlag, Berlin Heidelberg; 2010)) upstream of a cassette encoding the hinge, CH2, and CH3 domains of rabbit IgG. Individual clones were sequenced and transiently transfected into HEK-6E cells (Zhang et al. "Production of chimeric heavy-chain antibodies" Methods Mol Biol 525, 323-336 (2009)). Cell supernatants were harvested 6 days after transfection. Proteins in cell supernatants were analyzed by SDS-PAGE and Coomassie staining (FIG. 8). The results reveal efficient production of heavy chain antibodies from the majority of IgM clones. In general, VHH-containing clones showed higher expression yields than VH-containing clones. Efficient production was also observed for most IgG clones. Cell supernatants were analyzed for antigen-specific heavy chain antibodies by ELISA. Wells were coated with the antigen used for immunization or an irrelevant control protein. Wells were blocked with albumin and were then incubated with individual HEK-6E cell supernatants containing Nb-rabbit IgG heavy chain antibodies (diluted 1:20 in PBS). Wells were washed and bound Nb-rabbit IgG heavy chain antibodies were detected with peroxidase-conjugated secondary antibodies (donkey-anti rabbit IgG, Dianova) and TMB as substrate (FIG. 9). A CD38-specific Nb-rabbit IgG heavy chain antibody and an ARTC2-specific Nb-rabbit IgG heavy chain antibody were used as controls. The results reveal that immunization of TE-01 transgenic mice induced distinct antigen-specific VHH-containing heavy chain antibodies from a B-cell clone with extensive somatic hypermutation (FIG. 10, Sequences 10-01 to 10-22; SEQ ID NOs: 59-80).

Generation of Llama IgH Transgene TE-02:

BAC recombineering was performed on BAC TE-01 as illustrated schematically in FIG. 11 to generate TE-02 and TE-03 llama IgH transgenic mice. Elements HS3a and HS1,2 (part 1; P1) of the mouse locus control region were inserted upstream of HS3b-HS4-cassette (part 2; P2) in BAC construct TE-01. For this, a DNA cassette containing an ampicillin selection cassette followed by elements HS3a and HS1,2 was used. The sequence of HS3a and HS1,2 was obtained from a plasmid encoding the essential parts of the murine LCR (Pinaud et al., (2001) "Localization of the 3' IgH locus elements that effect long-distance regulation of class switch recombination" Immunity 15:187-199). The selection cassette was flanked by the two loxP mutants lox71 and lox66. The whole construct was equipped with a 90 bp 5' homology arm and a 86 bp 3' homology arm homologous to the region to be modified on BAC TE-01. A blunt end SnaBI restriction cleavage site was placed at the outer ends of both homology arms. The construct was synthesized and cloned into vector pUC57. The DNA cassette was isolated by SnaBI restriction digestion. Recombination was carried out using the *E. coli* strain SW106. The homologous recombination was followed by a Cre/lox recombination to delete the ampicillin selection cassette upstream of the HS3a-HS1,2 cassette.

A synthetic DNA cassette with five additional VHH elements was inserted at the 5' end of BAC transgene TE-01. For this, 5 camelid VHH elements (SEQ ID NO:16, SEQ ID NO:17, SEQ ID NO:18, SEQ ID NO:19, SEQ ID NO:20) were flanked by mouse IgH-V locus sequences corresponding to the flanking sequences of frequently used mouse VH-elements. The leader peptide, the intron sequence between leader peptide and VHH exon and the RSS sequence at the 3' end of the VHH exon correspond to the camelid germline configuration. The selection cassette was flanked by the two loxP mutants lox71 and lox66 and the whole DNA cassette was equipped with two 390 bp homology arms homologous to the BAC insertion site. The construct was synthesized and cloned into the vector pUC57. The entire DNA cassette was isolated via NruI restriction sites encoded in the homology arms. Recombination was carried out using the *E. coli* strain SW106. The homologous recombination was followed by a Cre/lox recombination to delete the ampicillin selection cassette upstream of the 5 VHH elements.

Generation of Llama IgH Transgene TE-03:

The CH3-CH4-TM1-TM2 region of the *Lama glama* IgM locus in transgene TE02 was replaced by mouse sequences. For this, the genomic sequence of the mouse IgM locus from the CH3 domain to the transmembrane domain 2 (TM2) was flanked with 45 bp homology regions matching the corresponding sequence on the *Lama* IgM locus. An ampicillin selection cassette flanked by two loxP mutants (lox71 and lox66) was inserted into the intron sequence between exons CH4 and TM1. The outer end of each 45 bp homology region encoded for a SnaBI restriction cleavage site. The construct was synthesized and cloned into the vector pUC57. The DNA cassette was isolated with blunt ends via a SnaBI restriction digestion. Recombination was carried out using the *E. coli* strain SW106. The homologous recombination was followed by a Cre/lox recombination to delete the ampicillin selection cassette in the intron sequence between the CH4 and TM1 exons.

Figure 12:
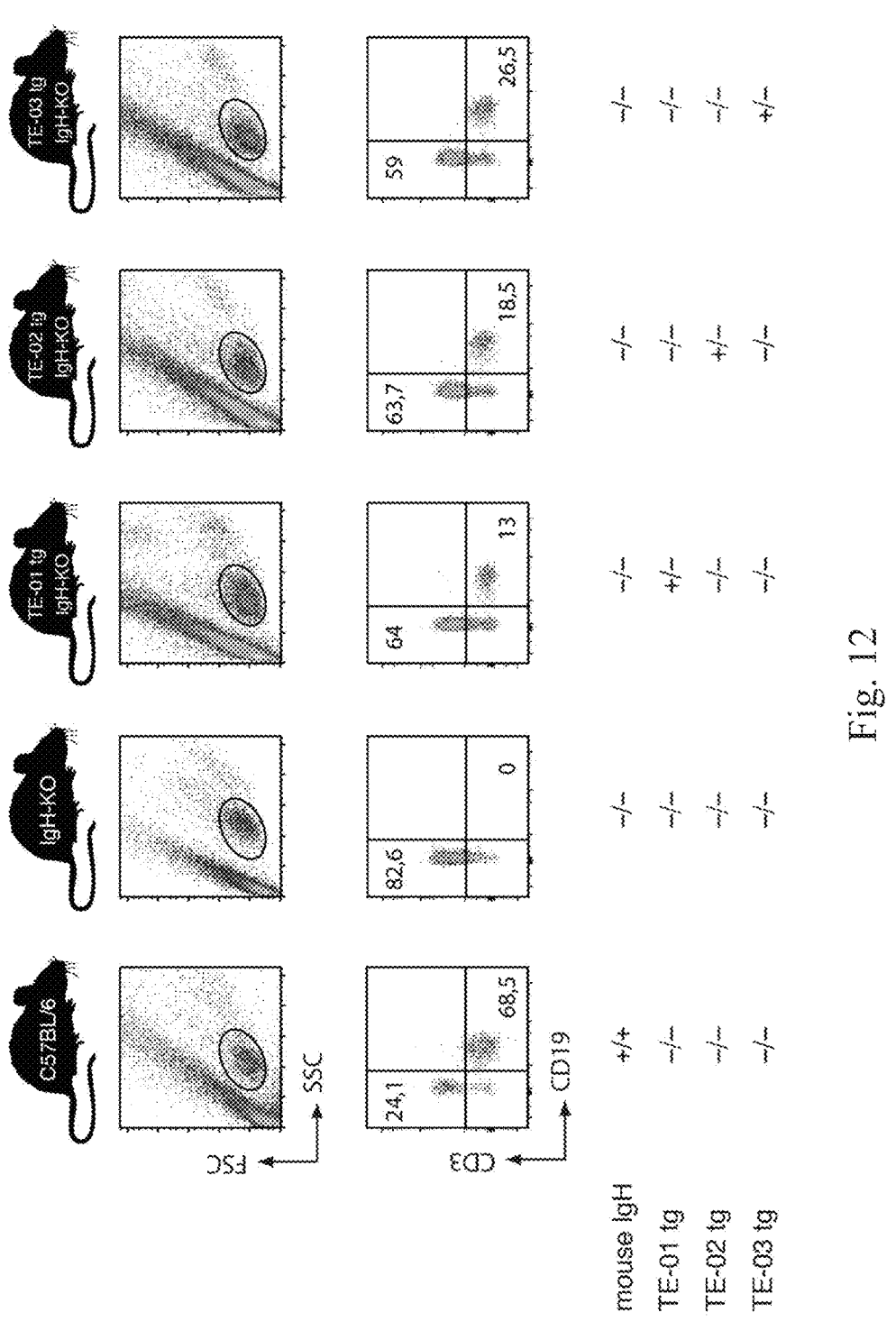
FIG. 12 is a B cell rescue by llama IgH transgenes TE-02 and TE-03. Peripheral blood cells of 9-12 week old mice were stained with fluorochrome conjugated antibodies against CD3 (T cells) and CD19 (B cells) before analysis by flow cytometry. B cells do not develop in IgH-KO animals. Introduction of either the TE-02 transgene or the TE-03 transgene rescues B cell development in IgH-KO animals.

Injection of BACs TE-02 and TE-03 into fertilized oocytes, verification of germline transmission animals by PCR, backcrossing to IgH-deficient mice, and flow cytometry analyses of peripheral blood lymphocytes were performed as described for TE-01. The results of flow cytometry analyses verify rescue of B cell development in murine IgH-deficient mice by both, *lama* IgH transgene TE-02 and *lama* IgH transgene TE-03 (FIG. 12).

The invention also comprises the following embodiments:

Embodiment 1: Isolated polynucleotide for the production of a VHH-containing heavy chain antibody in a mammal, comprising:
- a) a camelid VHH region,
- b) a camelid D region,
- c) a camelid J region,
- d) a camelid constant heavy chain region, without a CH1 domain; wherein the camelid VHH region, the camelid D region and the camelid J region are not rearranged.

Embodiment 2: Isolated polynucleotide according to embodiment 1, wherein the VHH-containing heavy chain antibody comprises an IgM constant heavy chain region with a functional CH4 domain.

Embodiment 3: Isolated polynucleotide according to embodiment 1 or 2, wherein the constant heavy chain region is lacking an IgD region.

Embodiment 4: Isolated polynucleotide according to any one of embodiments 1 to 3, wherein the camelid D region comprises at least two camelid D elements, preferably all camelid D elements.

Embodiment 5: Isolated polynucleotide according to embodiments 1 to 4, wherein the camelid J region comprises at least two camelid J elements, preferably all camelid J elements.

Embodiment 6: Isolated polynucleotide according to any one of embodiments 1 to 5, wherein the constant heavy chain region comprises elements encoding
- a) a hinge, a CH2 domain and a CH3 domain of an IgG, and/or
- b) a CH2, a CH3 and a CH4 domain of an IgM.

Embodiment 7: Isolated polynucleotide according to any one of embodiments 1 to 6, wherein the constant heavy chain region comprises an element which encodes at least one of the group consisting of camelid IgG2a, camelid IgG2b, camelid IgG2c, camelid IgG3 and camelid IgM.

Embodiment 8: Isolated polynucleotide according to any one of embodiments 1 to 7, wherein the constant heavy chain region does not comprise a δ region containing the IgD pseudogene and the associated switch region.

Embodiment 9: Isolated polynucleotide according to any one of embodiments 1 to 8, wherein the constant heavy chain region does not comprise a γ2a region.

Embodiment 10: Isolated polynucleotide according to any one of embodiments 1 to 9, wherein the polynucleotide comprises at least one enhancer specific for the mammal in which the VHH-containing heavy chain antibody is expressed or a related mammal.

Embodiment 11: Isolated polynucleotide according to any one of embodiments 1 to 10, wherein the camelid VHH region comprises at least one camelid VHH element.

Embodiment 12: Isolated polynucleotide according to any one of embodiments 1 to 11, wherein the polynucleotide further comprises at least one synthetic VHH element.

Embodiment 13: Isolated polynucleotide according to any one of embodiments 1 to 12, wherein the exons encoding the membrane proximal CH domains, transmembrane domain and cytosolic domain are exchanged by the exons encoding the corresponding domains of the mammal in which the VHH-containing heavy chain antibody is expressed or a related mammal.

Embodiment 14: Isolated polynucleotide according to any one of embodiments 1 to 13, wherein the camelid is *Lama* sp. preferably *Lama glama*.

Embodiment 15: Isolated polynucleotide according to any one of embodiments 1 to 14, wherein the polynucleotide is encoded by the sequence being at least 80% identical to SEQ ID NO.: 30.

Embodiment 16: Isolated polynucleotide according to any one of embodiments 1 to 14, wherein the polynucleotide is encoded by the sequence to SEQ ID NO.: 30 or fragments thereof.

Embodiment 17: Isolated polynucleotide according to any one of embodiments 1 to 15, wherein the camelid VHH region, the camelid J region and the camelid D region are capable of rearranging to form a VDJ coding sequence.

Embodiment 18: Vector comprising the polynucleotide according to any one of embodiments 1 to 17.

Embodiment 19: Vector according to embodiment 18, wherein the vector is a bacterial artificial chromosome, yeast artificial chromosome, human artificial chromosome, cosmid or synthetic DNA, preferably a bacterial artificial chromosome.

Embodiment 20: A transgenic mammal comprising the isolated polynucleotide of embodiments 1 to 17 or the vector of embodiment 18 and 19, wherein the polynucleotide is heterologous.

Embodiment 21: Transgenic mammal according to embodiment 20, in which a VHH-containing heavy chain antibody which is encoded by a rearranged VHH-D-J sequence and sequences encoding the constant domain of the polynucleotide of embodiments 1 to 17 is expressed.

Embodiment 22: Transgenic mammal according to embodiment 20 or 21, wherein the mammal is a rodent.

Embodiment 23: Transgenic mammal according to any one of embodiments 20 to 22, wherein the mammal is mouse or rat.

Embodiment 24: Transgenic mammal according to any one of embodiments 20 to 23, wherein the mammal is a mouse and the polynucleotide comprises a mouse Ig-alpha enhancer or fragments thereof.

Embodiment 25: Transgenic mammal according to any one of embodiments 20 to 24, wherein the mammal is devoid of a functional endogenous IgH locus.

Embodiment 26: Transgenic mammal according to any one of embodiments 20 to 25, wherein the mammal is capable of generating B cells upon expression of a rearranged immunoglobulin encoded by the polynucleotide as defined in embodiments 1 to 16.

Embodiment 27: Transgenic mammal according to any one of embodiments 20 to 26, wherein the mammal expresses a VHH-containing heavy chain antibody upon expression of the isolated gene sequence.

Embodiment 28: Transgenic mammal according to any one of embodiments 20 to 27, wherein the mammal expresses the VHH-containing heavy chain antibody as membrane bound and/or soluble version.

Embodiment 29: A method for the production of a VHH-containing heavy chain antibody in a mammal comprising the step of expressing a heterologous VHH-containing heavy chain antibody in that mammal, wherein the heterologous VHH-containing heavy chain antibody is encoded a rearranged VHH-D-J sequence of the polynucleotide as defined in embodiments 1 to 17.

Embodiment 30: A method for cloning a VHH-containing heavy chain antibody from a mammal wherein the heterologous VHH-containing heavy chain antibody is encoded a rearranged VHH-D-J sequence of the polynucleotide as defined in embodiments 1 to 17.

Embodiment 31: VHH-containing heavy chain antibodies, wherein the heterologous VHH-containing heavy chain antibody is encoded by a rearranged VHH-D-J sequence of the polynucleotide as defined in embodiments 1 to 17.

Embodiment 32: VHH-containing heavy chain antibody produced by the method according to embodiment 29.

---

We claim:

1. An isolated polynucleotide for the production of a VHH-containing heavy chain antibody in a mammal, wherein the polynucleotide comprises SEQ ID NO: 30.

2. A transgenic mouse or rat comprising the isolated polynucleotide of claim 1.

3. The transgenic mouse or rat of claim 2, wherein the transgenic mouse or rat expresses the VHH-containing heavy chain antibody as a membrane bound version.

4. A method for the production of a VHH-containing heavy chain antibody in a non-human mammal, the method comprising the step of expressing the polynucleotide of SEQ ID NO:30 in said non-human mammal.

5. A method for cloning a VHH-containing heavy chain antibody from a transgenic non-human mammal expressing the polynucleotide of SEQ ID NO:30, the method comprising the steps of:

(i) immunizing said transgenic non-human mammal expressing the polynucleotide of SEQ ID NO: 30, and immortalizing B cells expressing a heterologous VHH-containing heavy chain antibody from said transgenic non-human mammal, or (ii) immunizing said transgenic non-human mammal expressing the polynucleotide of SEQ ID NO: 30, and obtaining VHH-coding sequences for the heterologous VHH-containing heavy chain antibody from B cells of said transgenic non-human mammal, wherein the heterologous VHH-containing heavy chain antibody is encoded by the isolated polynucleotide of claim 1.

6. The transgenic mouse or rat of claim 2, wherein the transgenic mouse or rat expresses the VHH-containing heavy chain antibody as a soluble version.

* * * * *